US009585950B2

(12) United States Patent
Wacker et al.

(10) Patent No.: US 9,585,950 B2
(45) Date of Patent: Mar. 7, 2017

(54) CAPSULAR GRAM-POSITIVE BACTERIA BIOCONJUGATE VACCINES

(71) Applicant: GLYCOVAXYN AG, Schlieren (CH)

(72) Inventors: Michael Wacker, Unterengstringen (CH); Michael Kowarik, Zurich (CH); Michael Wetter, Zurich (CH)

(73) Assignee: GLYCOVAXYN AG (CH)

( * ) Notice: Subject to any disclaimer, the term of this patent is extended or adjusted under 35 U.S.C. 154(b) by 0 days.

(21) Appl. No.: 14/494,150

(22) Filed: Sep. 23, 2014

(65) Prior Publication Data

US 2015/0010592 A1 Jan. 8, 2015

Related U.S. Application Data

(62) Division of application No. 13/100,603, filed on May 4, 2011, now Pat. No. 8,871,491.

(60) Provisional application No. 61/332,170, filed on May 6, 2010.

(51) Int. Cl.

| | |
|---|---|
| ***A61K 39/085*** | (2006.01) |
| ***C12N 15/70*** | (2006.01) |
| ***C12N 15/74*** | (2006.01) |
| *A61K 39/00* | (2006.01) |

(52) U.S. Cl.

CPC ............ *A61K 39/085* (2013.01); *C12N 15/70* (2013.01); *C12N 15/74* (2013.01); *A61K 2039/6037* (2013.01); *A61K 2039/6087* (2013.01); *A61K 2039/64* (2013.01); *C07K 2319/034* (2013.01)

(58) Field of Classification Search

None

See application file for complete search history.

(56) References Cited

U.S. PATENT DOCUMENTS

| | | | |
|---|---|---|---|
| 5,643,758 | A | 7/1997 | Guan et al. |
| 2002/0019342 | A1 | 2/2002 | Bayer |
| 2004/0265954 | A1 | 12/2004 | Aebi et al. |
| 2005/0287628 | A1 | 12/2005 | Aebi et al. |
| 2011/0097357 | A1 | 4/2011 | Fernandez et al. |

FOREIGN PATENT DOCUMENTS

| | | |
|---|---|---|
| CA | 1340184 | 12/1998 |
| CA | 2360205 | 8/2000 |
| CA | 2477794 | 3/2003 |
| EP | 1481057 | 2/2006 |
| WO | WO 94/26906 | 11/1994 |
| WO | WO 00/52135 | 9/2000 |
| WO | WO 01/88117 | 11/2001 |
| WO | WO 02/00856 | 1/2002 |
| WO | WO 03/074687 | 9/2003 |
| WO | WO 2004/013151 A2 | 2/2004 |
| WO | WO 2005/116063 A1 | 12/2005 |
| WO | WO 2006/119987 A2 | 11/2006 |
| WO | WO 2007/113222 A2 | 10/2007 |
| WO | WO 2009/089396 A2 | 7/2009 |
| WO | WO 2009/104074 A2 | 8/2009 |

OTHER PUBLICATIONS

Abdian et al., 2000, "Identification of essential amino acids in the bacterial α-mannosyltransferase aceA", J Biol Chem; 275(51):40568-40575.

Aebi et al., 1996, "Cloning and characterization of the ALG3 gene of *Saccharomyces cerevisiae*", Glycobiology; 6:439-444.

Ahmed et al., 2006, "Safety and immunogenicity of *Escherichia coli* O157 O-specific polysaccharide conjugate vaccine in 2-5 year old children", J Infect Dis; 193(4):515-521.

Alaimo et al., 2006, "Two distinct but interchangeable mechanisms for flipping of lipid-linked oligosaccharides", Embo J; 25:967-976.

Alexander et al., 1994, "Role of the rfe gene in the biosynthesis of the *Escherichia coli* O7-specific lipopolysaccharide and other O-specific polysaccharides containing N-acetylglucosamine", J Bacteriol; 176:7079-7084.

Allard et al., 2001, "Epimerases:structure, function and mechanism", Cell Mol Life Sci; 58:1650-1665.

Altmann et al., 1999, "Insect cells as hosts for the expression of recombinant glycoproteins", Glycoconjugatc Journal; 16:109-123.

Amor et al., 1997, "Molecular and functional analysis of genes required for expression of group IB K antigens in *Escherichia coli*: characterization of the his-region containing gene clusters for multiple cell-surface polysaccharides", Mol Microbiol; 26:145-161.

Anderson, 1983, "Antibody responses to Haemophilus influenzae type b and diphtheria toxin induced by conjugates of oligosaccharides of the type b capsule with the nontoxic protein $CRM_{197}$", Infection and Immunity; 39(1):233-238.

Arbeit et al., 1984, "Predominance of two newly described capsular polysaccharide types among clinical isolates of *Staphylococcus aureus*", Diagn Microbiol Infect Dis; 2:85-91.

(Continued)

*Primary Examiner* — Jennifer Graser

(74) *Attorney, Agent, or Firm* — Jason C. Fedon; Edward R. Gimmi

(57) ABSTRACT

The present invention encompasses a novel *S. aureus* bioconjugate vaccine. More generally, the invention is directed to Gram-positive and other bioconjugate vaccines containing a protein carrier, at least one polysaccharide such as a capsular Gram-positive polysaccharide, and, optionally, an adjuvant or pharmaceutically acceptable carrier. The instant invention also includes methods of producing Gram-positive and other bioconjugate vaccines. An N-glycosylated protein is also provided that contains one or more polysaccharides such as Gram-positive polysaccharides. The invention is additionally directed to engineered prokaryotic organisms comprising nucleotide sequences encoding a glycosyltransferase of a first prokaryotic organism and a glycosyltransferase of a second prokaryotic organism. The invention further includes plasmids and prokaryotic cells transformed with plasmids encoding polysaccharides and enzymes which produce an N-glycosylated protein and/or bioconjugate vaccine. Further, the invention is directed to methods of inducing an immune response in a mammal comprising administering said bioconjugate vaccines.

25 Claims, 37 Drawing Sheets

(56) References Cited

OTHER PUBLICATIONS

Avery et al., 1929, "Chemo-immunological studies on conjugated carbohydrate-proteins. II Immunological specificity of synthetic sugar-protein antigens", J Exp Med; 50(4):533-550.
Baggett et al., 2004, "Community-onset methicillin-resistant *Staphylococcus aureus* associated with antibiotic use and the cytotoxin Panton-Valentine leukocidin during a furunculosis outbreak in rural Alaska", J Infect Dis; 189:1565-1573.
Baneyx et al., 1999, "Recombinant protein expression in *Escherichia coli*", Curr Opin Biotechnol; 10:411-421.
Baqar et al., 1995, "Safety and immunogenicity of a prototype oral whole-cell killed Campylobacter vaccine administered with a mucosal adjuvant in non-human primates", Vaccine; 13(1):22-28.
Bematchez et al., 2005, "A single bifunctional UDP-ClcNAc/Glc 4-epimerase supports the synthesis of three cell surface glycoconjugates in Campylobacter jejuni", J Biol Chem; 280:4792-4802.
Berg et al., 1997, "2-oxo acid dehydrogenase multienzyme complexes: the central role of the lipoyl domain", Biological Chemistry; 378:617-634.
Berg et al., 2001, "Sequence properties of the 1,2-diacylglycerol 3-glucosyltransferase from acholeplasma laidlawii membranes", J Biol Chem; 276(25):22056-22063.
Biiasin et al., 1998, "Identification of a gene essential for O-acetylation of the *Staphylococcus aureus* type 5 capsular polysaccharide", Mol Microbiol; 27:9-21.
Bigge et al., 1995, "Nonselective and efficient fluorescent labeling of glycans using 2-amino benzamide and anthranilic acid", Anal Biochem; 230(2):229-238.
Bill et al., 1995, "Expression and mutagenesis of recombinant human and murine erythropoietins in *Escherichia coli*", Biochimica et Biophysica Acta; 1261:35-43.
Billman-Jacobe, 1996, "Expression in bacteria other than *Escherichia coli*", Curr Opin Biotechnol; 7:500-504.
Bligh et al., 1959, "A rapid method of total lipid extraction and purification", Can J Biochem Physiol; 37(8):911-917.
Bourne et al., 2001, "Glycoside hydrolases and glycosyltransferases: families and functional modules", Current Opinion in Structural Biology; 11:593-600.
Branden et al., 1991, "Introduction to protein structure", Garland Publishing Inc., New York; pp. 247-268.
Breton et al., 1999, "Structure/function studies of glycosyltransferases", Current Opinion in Structural Biology; 9:563-571.
Bubeck Wardenburg ct al., 2008, "Panton-Valentine leukocidin is not a virulence determinant in murinc models of community-associated methicillin-resistant *Staphylococcus aureus* disease", J Infect Dis; 198:1166-1170.
Bugg et al., 1994, "From peptidoglycan to glycoproteins: common features of lipid-linked oligosaccharide biosynthesis", FEMS Microbiol Lett; 119:255-262.
Burda ct al., 1999, "The dolichol pathway of N-linked glycosylation", Biochimica et Biophysica Acta; 1426:239-257.
Burr et al., 2005, "Prevention of disease in ferrets fed an inactivated whole cell Campylobacter jejuni vaccine", Vaccine; 23:4315-4321.
Butzler, 2004, "Campylobacter, from obscurity to celebrity", Clinical Microbiology and Infection; pp. 868-876.
Campbell et al., 1997, "A classification of nucleotide-diphospho-sugar glycosyltransferases based on amino acid sequence similarities", Biochem J; 326:929-939.
Canals et al., 2006, "The UDP N-acetylgalactosamine 4-epimerase gene is essential for mesophilic Aeromaonas hydrophile serotype O34 virulence", Infect & Immun; 74(1):537-548.
Cardini et al., 1957, "Enzymatic formation of acetylgalactosamine", J Biol Chem; 225:317-327.
Casburn-Jones et al., 2004, "Traveler's diarrhea", Journal of Gastroenterology and Hepatology, 19:610-618.
CAZy (Carbohydrate-Active enZYmes) Database—GlycosylTransferase family classification (AFMB—CNRS—Universites Aix-Marseille I & II) last update: Oct. 25, 2010 at http://www.cazy.org/GlycosylTransferases.html.
CAZy (Carbohydrate-Active enZYmes) Database—Home (AFMB—CNRS—Universites Aix-Marseille I & II) last update: Oct. 25, 2010 at http://www.cazy.org.
Chang et al., 2003, "Infection with vancomycin-resistant *Staphylococcus aureus* containing the vanA resistance gene", New Engl J Med; 348:1342-1347.
Chart et al., 1991, "Serological identification of *Eschcrichia coli* O157:H7 infection in haemolytic uracmic syndrome", The Lancet; 337:138-140.
Choi et al., 2004, "Secretory and extracellular production of recombinant proteins using *Escherichia coli*", Appl Microbiol Biotechnol; 64:625-635.
Consortium for Functional Glycomics (CFG) Nature, Functional glycomics gateway—Nomenclature, last update: Apr. 28, 2010 at http://ww.functionalglycomics.org/static/consortium/Nomenclature.shtml.
Coutinho et al., 1999, "Life with no sugars?", J Mol Microbiol Biotech; 1(2):307-308.
Crooks et al., 2004, "WebLogo: A sequence logo generator", Genome Research; 14(6):1188-1190.
Cruezenet et al., 2000, "Expression, purification, and biochemical characterization of WbpP, a new UDP-GlcNAc C4 epimerase from Pseudomonas aeruginosa sertype O6", J Biol Chem; 275(25):19060-19067.
Crushell et al., 2004, "Enteric Campylobacter: purging its secrets?" Pediatric Research; 55(1):3-12.
Cunnion et al., 2001, "Capsule production and growth phase influence binding of complement to *Staphylococcus aureus*", Infect Immun; 69:6796-6803.
Datsenko et al., 2000, "One-step inactivation of chromosomal genes in *Escherichia coli* K-12 using PCR products", Proc Natl Acad Sci USA; 97:6640-6645.
Dean et al., 1999, "Characterization of the serogroup O11 O-antigen locus of Pseudomonas aeruginosa PA103", J Bacteriol; 181:4275-4284.
Dejonge et al., 2007, "Clinical trial of safety and efficacy of INH-A21 for the prevention of nosocomial staphylococcal bloodstream infection in premature infants", J Pediatr; 151:260-265.
Doig et al., 1996, "Characterization of a post-translational modification of Campylobacter flagellin: identification of a sero-specific glycosyl moiety", Molecular Microbiology; 19(2):379-387.
Dunphy et al., 1967, "The plurality of long chain isoprenoid alcohols (polyprenols) from natural sources", Biochim Biophys Acta; 136: 136-147.
Expression Library Screening (Procaryotic) Using AP-fusion proteins (last visited Nov. 1, 2010) at http://www.protocol-online.org/cgi-bin/prt/view_cache.cgi?ID=2752.
Fairweather et al, 1986, "Cloning, nucleotide sequencing, and expression of tetanus toxin fragment C in *Escherichia coli*", Journal of Bacteriology; 165(1):21-27.
Falt et al., 1996, "Construction of recombinant aroA *Salmonellae* stably producing the Shigella Sysenteriae sertype 1 O-antigen and structural characterization of the *Salmonella*/Shigella hybrid LPS", Microb Pathog; 20(1):11-30.
Faridmoayer et al., 2007, "Functional characterization of bacterial oligosaccharyltransferases involved in O-linked protein glycosylation", J Bacteriol; 189(22):8088-8098.
Fass et al., 1991, "Use of high densitycultures of *Escherichia coli* for high level production of recombinant Pseudomonas aeruginosa exotoxin A", Applied Microbiology and Biotechnolgy, 36(1):65-69.
Fattom et al., 1990, "Synthesis and immunologic properties in mice of vaccines composed of *Staphylococcus aureus* type 5 and type 8 capsular polusaccharides conjugated to Pseudomonas aeruginosa exotoxin A", Infect Immun; 58:2367-2374.
Fattom et al., 1993, "Laboratory and clinical evaluation of conjugate vaccines composed of *Staphylococcus aureus* type 5 and type 8 capsular polysaccharides bound to Pseudomonas aeruginosa recombinant exoprotein A", Infection and Immunity; 61(3):1023-1032.
Fattom et al., 1996, "A *Staphylococcus aureus* capsular polysaccharide (CP) vaccine and CP-specific antibodies protect mice against bacterial challenge", Infect Immun; 64:1659-1665.

(56) References Cited

OTHER PUBLICATIONS

Fattom et al., 1998, "Antigenic determinants of *S. aureus* type 5 and type 8 capsular polysaccharide vaccines", Infect Immun; 66:4588-4592.
Feldman et al., 2005, "Engineering N-liked protein glycosylation with diverse O antigen lipopolysaccharide structures in *Escherichia coli*", Proc Natl Acad Sci USA; 102:3016-3021.
Feng et al., 2005, "Structural and genetic characterization of the Shigella boydii type 18 O antigen", Gene; 355:79-86.
Field et al., 2003, "Structural and mechanistic basis of bacterial sugar nucleotide-modifying enzymes", Biochemistry; 42:7637-7647.
Foster et al., 1998, "Surface protein adhesins of *Staphylococcus aureus*", Trends Microbiol; 6:484-488.
Foster, 2005, "Immune evasion by staphylococci", Nature Reviews Microbiology; 3:948-958.
Francisco et al., 1992, "Transport and anchoring of β-lactamase to the external surface of *Escherichia coli*", Proc Natl Acad Sci USA: 89:2713-2717.
Fridkin et al., 2005, "Methicillin-resistant *Staphylococcus aureus* disease in three communities", N Engl J Med; 352:1436-1411.
Fry et al., 1998, "The lipopolysaccharide biosynthesis locus of Campylobacter jejuni 81116", Microbiology; 144:2049-2061.
Fujita et al., 2000, "Synthesis of neoglycoenzymes with homogenous N-linked oligosaccharides using immobilized endo-S-N-acetylglucosaminidase A", Biochmeical and Biophysical Research Communications, 267:134-138.
Gavel et al., 1990, "Sequence differences between glycosylated and non-glycosylated Asn-X-Thr/Ser acceptor sites: implications for protein engineering", Protein Eng; 3:433-442.
Gilbert et al., 2006, "Outbreak in Alberta of community-acquired (USA300) methicillin-resistant *Staphylococcus aureus* in people with a history of drug use, homelessness or incarceration", Canad Med Assoc J; 175:149-154.
Global Alliance for Vaccines and Immunization—Press releases (Mar. 11, 2006) at http://www.gavialliance.org/medi_centre/press_releases/2006_03_09_en_pr_queenrania_delhi.php.
Glover et al., 2005, "Chemoenzymatic synthesis of glycopeptides with PgIB, a bacterial oligosaccharyl transferase from Campylobacter jejuni", Chemistry & Biology; 12:1311-1316.
Glover et al., 2005, "In vitro assembly of the undecaprenylpyrophosphate-linked heptasaccharide for prokaryotic N-linked glycosylation", Proc Natl Acad Sci USA; 102(40):14255-14259.
"GlycoVaxyn AG appoints renowned vaccinologist Dr. Stanley Plotkin to supervisory board", Press Release (Oct. 6, 2009) available at http://www.glycovaxyn.com/content/news/releases/09%2010%2006.pdf.
"GlycoVaxyn AG completes CHF 11.5 million series A financing to advance novel conjugated vaccine pipeline towards clinic", Press Release (Jul. 16, 2007) available at http://www.glycovaxyn.com/content/news/releases/06%2010%2019.pdf.
"GlycoVaxyn AG raises CHF 25 million in financing led by Edmond de Rothschild Investment Partners", Press Release (Mar. 5, 2009) available at http://www.glycovaxyn.com/downloads/GlycoVaxyn%20Financing%20Release%2005-03-09.pdf.
"GlycoVaxyn and a Harvard University affiliated hospital receive USD 3.4 million NIH grant for *Staphylococcus aureus* vaccine development", Press Release (May 4, 2010) available at http://www.glycovaxyn.com/content/news/releases/10%2005%2004.pdf.
"GlycoVaxyn appoints Philippe Dro as CEO", Press Release (May 20, 2008) available at http://www.sofinnova.fr/glycovaxyn-appoints-phillippe-dro-as-ceo-actu-736.php.
"GlycoVaxyn opens to partnerships; series C financing round planned for 2011, CEO says mergermarket", pp. 1-2 (Nov. 25, 2009) at http://www.mergermarket.com/home/.
"GlycoVaxyn phase I clinical study shows positive data with Shigella dysenteriae vaccine candidate", (Oct. 8, 2010) available at http://www.glycovaxyn.com/content/news/releases/10%2010%2008.pdf.
"GlycoVaxyn winner of the life sciences prize 2006", Press Release (Oct. 19, 2006) available at http://www.glycovaxyn.com/content/news/releases/06%2010%2019.pdf.
"GlycoVaxyn's first clinical study with bioconjugate vaccine initiated", Press Release (Feb. 23, 2010) available at http://www.glycovaxyn.com/content/news/releases/10%2002%2023.pdf.
Goebel et al., 1929, "Chemo-immunological studies on conjugated carbohydrate-proteins" Journal of Experimental Medicine; 50(4):521-531.
Goldberg et al., 1992, "Cloning and surface expression of Pseudomonas aeruginosa O antigen in *Escherichia coli*", Proc Natl Acad Sci USA; 89(22):10716-10720.
Gordon et al., 1956, "Rapid paper chromatography of carbohydrates and related compounds", Anal Chem; 28:849-855.
Grabenhorst et al., 1999, "Genetic engineering of recombinant glycoproteins and the glycosylation pathway in mammalian host cells", Glycoconjugate Journal; 16:81-97.
Gray, 1979, "ELISA methodology for polysaccharide antigens: protein coupling of polysaccharides for adsorption to plastic tubes", J Immunol; 28:187-192.
Guan et al., 2005, "Extraction and identification by mass spectrometry of undecaprenyl diphosphate-MurNAc-pentapeptide-GlcNAc from *Escherichia coli*", Anal Biochem; 345:336-339.
Guerry et al., 1996, "Identification and characterization of genes required for post-translational modification of Campylobacter coli VC167 flagellin", Molecular Microbiology; 19(2):369-378.
Guo et al., 2007, "Three UDP-hexose 4-epimerases with overlapping substrate specificity coexist in *E. coli* O86:B7", Biochem Biophys Res Commun; 356:604-609.
Haberberger et al., 1994, "Prospects and problems for development of a vaccine against diarrhea caused by Campylobacter", Vaccine Research; 3:15-22.
Helenius et al., 2004, "Roles of N-linked glycans in the endopasmic reticulum", Annu Rev Biochem; 73:1019-1049.
Higgins et al., 2004, "Structure of the periplasmic component of a bacterial drug efflux pump", Proc Natl Acad Sci USA; 101:9994-9999.
Ho et al., 2006, "Preclinical laboratory evaluation of a bivalent *Staphylococcus aureus* saccharide-exotoxin A protein conjugate vaccine", Hum Vaccin; 2:89-98.
Hoffmeister et al., 2001, "Two sequence elements of glycosyltransferases involved in urdamycin biosynthesis are responsible for substrate specificity and enzymatic activity", Chem & Bio; 8:557-567.
Hofmann et al., 1993, "A database of membrane spanning protein segments", Biol Chem; 374:166 (abstract).
Hoiseth et al., 1981, "Aromatic-dependent *Salmonella typhimurium* are non-virulent and effective as live vaccines", Nature; 291:238-239.
Ihssen et al., 2010, "Production of glycoprotein vaccines in *Escherichia coli*", Microbial Cell Factories; 9(1):61.
Imperiali et al., 1991, "Differences between Asn-Xaa-Thr-containing peptides; a comparison of solution conformation and substrate behavior with oligosaccharyl-transferase", Biochemistry; 30:4374-4380.
International Search Report of International application No. PCT/CH03/00153, dated May 19, 2003.
International Search Report of International application No. PCT/EP2006/004397, dated Dec. 13, 2006.
International Search Report of International application No. PCT/EP2011/057111, dated Jul. 28, 2011.
Jeong et al., 2001, "Secretory production of human granulocyte colony-stimulating factor in *Escherichia coli*", Protein Expression and Purification; 23:211-318.
Johnson et al., 1999, "Alignment and structure prediction of divergent protein families: periplasmic and outer membrane proteins of bacterial efflux pumps", J Mol Biol; 287:695-715.
Johnson et al., 1999, "Synthesis of oligosaccharides by bacterial enzymes", Glycoconjugate Journal; 16:141-146.
Jones et al., 2005, "Revised structures for the capsular polysaccharides from *Staphylococcus aureus* types 5 and 8, components of novel glycoconjugate vaccines", Carbohydr Res; 340:1097-1106.

(56) References Cited

OTHER PUBLICATIONS

Josefsson et al., 2001, "Protection against experimental *Staphylococcus aureus* arthritis by vaccination with clumping factor A, a novel virulence determinant", Journal of Infectious Diseases; 184:1572-1580.

Jursch et al., 1994, "Histidine residues near the N terminus of staphylococcal alpha-toxin as reporters of regions that are critical for oligomerization and pore formation", Infect Immun; 62(6):2249-2256.

Kaniuk et al., 2004, "Investigation of the structural requirements in the lipopolysaccharide core acceptor for ligation of O antigens in the genus *Salmonella*: WaaL 'ligase' is not the sole determinant of acceptor specificity", J Biol Chem; 279:36470-36480.

Kapitonov et al., 1999, "Conserved domains of glycosyltransferases", Glycobiol; 9(10):961-978.

Karlyshev et al., 2004, "The Campylobacter jejuni general glycosylation system is important for attachment to human epithelial cells and in the colonization of chicks", Microbiology; 150; 1957-1964.

Kazakova et al., 2005, "A clone of methicillin-resistant *Staphylococcus aureus* among professional football players", N Engl J Med; 352:468-475.

Kean, 1966, "Separation of gluco- and galactocerebrosides by means of borate thin-layer chromatography", J Lipid Res; 7:449-452.

King et al., 2006, "Emergence of community-acquired methicillin-resistant *Staphylococcus aureus* USA 300 clone as the predominant cause of skin and soft-tissue infections", Ann Intern Med; 144:309-317.

Kiser et al., 1999, "*Staphylococcus aureus* cap5P encodes a UDP-N-acetylglucosamine 2-epimerase with functional redundancy", J Bacteriol; 181(16):4818-4824.

Klevens et al., 2007, "Invasive methicillin-resistant *Staphylococcus aureus* infections in the United States," Jama 298: 1763-71.

Knirel et al., 1988, "Somatic antigens of Shigella: structure of the O-specific polysaccharide chain of the Shigella dysenteriae type 7 lipoplysacharidc.".

Kollef eta l., 2005, "Epidemiology and outcomes of health-care associated pneumonia: results from a large US database of culture-positive pneumonia." Chest 128:3854-3862.

Konadu et al. 1998, "Investigational vaccine for *Escherichia coli* O157: phase 1 study of O157 O-specific polysaccharide-pseudomonas aeruginosa recombinant exoprotein A conjugates in adults", Journal of Infectious Diseases; 177(2):383-387.

Konadu et al., 1994, "Preparation, characterization, and immunological properties in mice of *Escherichia coli* O157 O-specific polysaccharide—protien conjugate vaccines", Infection and Immunity; 62(11):5048-5054.

Konadu et al., 1999, "Syntheses and immunologic properties of *Escherichia coli* O157 O-specific polysaccharide and shiga Toxin 1 B subunit conjugates in mice," Infection and Immunity; 67(11):6191-6193.

Kowarik et al., 2006, "N-Linked glycosylation of folded proteins by the bacterial oligosaccharvltransferase", Science; 314:1148-1150.

Kowarik et al., 2006, "Definition of the bacterial N-glycosylation site consensus sequence", Embo J; 25(9):1957-1966.

Kuwajima et al., 1986, "Nucleotide sequence of the hag gene encoding flagellin of *Escherichia coli*", J Bacteriol; 168(3):1479-1483.

Laemmill, 1970, "Cleavage of Structural Proteins during the Assembly of the Head of bacteriophage T4." Nature 227:680-685.

Law, 2000, "Virulence factors of *Escherichia coli* 0157 and other Shiga Toxin-producing *E-coli.*" J. App. Microbiol. 88:729-745.

Lee et al., 1997, "Protective efficacy of antibodies to the *Staphylococcus aureus* type 5 capsular polysaccharide in a modified model of endocarditis in rats." Infect Immun. 65:4146-51.

Lee et al., 1999, "Evaluation of a truncated recombinant flagellin subunit vaccine against Campy/obaeter jejuni", Infection and Immunity; 67(11):5799-5805.

Lefebre, 2002, "Construction and Evaluation of Plasmind vectors Optimized for Consitutive and Regulated Gene Expression in Burkholderia cepacia Complex Isolates," Appl. Environ Microbiol. 68:5956-5964.

Linton et al., 2002, "Identification of N-acetylgalactosamine-containing glycoproteins PEB3 and CgpA in Campylobacter jejuni", Molecular Microbiology; 43(2):497-508.

Linton et al., 2005, "Functional analysis of the Campylobacter jejuni N-linked protein glycoylation pathway", Molecular Microbiology; 55(6):1695-1703.

Liu et al., 2008, "Structure and genetics of Shigella O antigens." FEMS Microbiol. 32:627-653.

Lodish et al., 2000 "DNA Cloning with Plasmid vectors." Molec. Cell. Biology; 7.1 at http://www/ncbi.nlm.nih.gov/bookshelf/br.fcgi?book=mcb&part=A1582.

Lodish et al., 2000 "Protein Glycosylation in the ER and Golgi Complex"; 17.7 at http://www/ncbi.nlm.nih.gov/bookshelf/br.fcgi?book=mcb&part=A4816.

Lowy, 1998, "*Staphylococcus aureus* infections." New Eng. J Med. 339:520-32.

Lukac et al., 1988, "Toxoid of pseudomonas aeruginosa exotoxin A generated by deletion of an active-site residue", Infection and Immunity; 56(12):3095-3098.

Malissard et al., 1999, "The yeast expression system for recombinant glycosyltransferases", Glycoconjugate Journal; 16:125-139.

Maras et al., 1999, "Filamentous fungi as production organisms for glycoproteins of bio-medical interest", Glycoconjugate Journal; 16:99-107.

Marolda et al., 2006, "Interplay of the wzx translocase and the corresponding polymerase and chain length regulator proteins in the translocation and periplasmic assembly of lipopolysaccharide O antigen", Journal of Bacteriology; 188(14):5124-5135.

Marth et al., 1999, "Essentials of Glycobiology" Chapter 7 (Varki et al. eds.) available at http://www/ncbi.nlm.nih.gov/bookshelf/br.fcgi?book=glyco&part=A465.

McDevitt eta l., 1995, "Indentification of the ligand-binding domain of the surface-located fibrinogen receptor (clumping factor) of *Staphylococcus aureus*." Molecular Microbiology 16:895-907.

McDougal et al., 2003, "Pulsed-field gel electrophoresis typing of oxacillin-resistant *Staphylococcus aureus* isolates isolates from the United States; establishing a national database." J. Clin. Microbiol. 41:5113-20.

Meier-Dieter, 1990, "Biosyntehsis of enterobacterial common antigen in *Escherichia coli.*" J. Biol. Chem.; 265:13490-13497.

Menzies et al., 1996, "Passive immunization with antiserum to a nontoxic alpha-toxin mutant from *Staphylococcus aureus* is protective in a murine model." Infect Immun. 64:1839-41.

Merry et al., 2002, "Recovery of intact 2-aminobenzamide-labeled O-glycans released from glycoproteins by Hhydrazinolysis." Anal Biochem; 304(1):91-99.

Messner, 1997, "Bacterial glycoproteins," Glycoconjugate Journal 14:3-11.

Middlebrook et al., 1984, "Bacterial toxins: cellular mechanisms of action", Microbiological Reviews; 48(3): 199-221.

Mikusova et al., 2005, "Decaprenylphosphoryl Arabinofuranose, the Donor of the D-Arabinofuranosyl Residues of Mycobacterial Arabinan, is formed via a Two-Step Epimerization of Decaprenylphosphoryl Ribose." J. Bacteriol. 187:8020-8025.

Moreillon et al., 1995, "Role of *Staphylococcus aureus* coagulase and clumping factor in pathogenesis of experimental endocarditis." Infection & Immunity; 63:4738-43.

Muller et al., 2005, "An ATP-binding cassette-type cysteine transporter in Campylobacter jejuni inferred from the structure of an extracytoplasmic solute receptor protein", Mol Microbiol; 57:143-155.

Nairn et al., 1990, "Solutions, emulsions, suspensions and extracts", Remington's Pharmaceutical Sciences, 18th ed., Mack Publishing Co., Chapter 83, pp. 1519-1544.

Nanra et al, 2009, "Heterogenous in vivo expression of clumping factor A and capsular polysacchardie *Staphylococcus aureus*: Implications for vaccine design." Vaccine; 27:3276-80.

(56) References Cited

OTHER PUBLICATIONS

Nilsson et al.m, 1997, "The role of staphylococcal polysaccharide microcapsule expression in septicemia and septic arthritis." Infect Immun 65:4216-4221.
Nita-Lazar et al., 2005, "The N-X-S/T consensus sequence is required but not sufficient for bacterial N-linked protein glycosylation", Glycobiology; 15(4):361-367.
Notice of Abandonment of U.S. Appl. No. 10/506,917, dated Sep. 12, 2008.
Office Action of U.S. Appl. No. 10/506,917, dated Jan. 23, 2008.
Office Action of U.S. Appl. No. 10/506,917, dated May 9, 2007.
Office Action of U.S. Appl. No. 11/920,175, dated Nov. 9, 2011.
Office Action of U.S. Appl. No. 12/219,383, dated Jul. 23, 2009.
Office Action of U.S. Appl. No. 12/219,383, dated Mar. 20, 2009.
Office Action of U.S. Appl. No. 12/219,383, dated May 12, 2010.
Office Action of U.S. Appl. No. 12/219,383, dated Oct. 28, 2010 (Interview Summary).
Office Action of U.S. Appl. No. 12/219,383, dated Oct. 3, 2011.
O'Riordan et al., 2004, "*Staphylococcus aureus* capsular polysaccharides." Clin Microbiol Rev. 17(1):218-34.
Paetzel et al., 2002, "Signal peptidases", Chem Rev; 102:4549-4580.
Panina-Bordignon et al., 1989, "Universally immunogenic T cell epitopes: promiscuous binding to human MHC class II and promiscuous recognition by T cells" European Journal of Immunolgy; 19:2237-2242.
Parkhill et al., 2000, "The genome sequence of the food-borne pathogen Campylobacter jejuni reveals hypervariable sequences", Nature; 403:665-668.
Passwell et al., 2001, "Safety and immunogenicity of improved Shegella O-specific polysaccharide-protein conjugate vaccines in adults in Israel", Infection and Immunity, 69(3):1351-1357.
Paton & Paton, 1999, "Molecular Characterization of the Locus Encoding Biosynthesis of the Lipopolysaccharidc O Antigen of *Eschcrichia coli* Serotype O113," Infect & Immun 67(11): 5930-5937.
Pawlowski, 2000, "Preparation of pneumococcal capsular polysaccharide—protein conjugate vaccines utilizing new fragmentation and conjugation technologies." Vaccine 18:1873-1885.
Pearson et al., 2003, "Comparative genome analysis of Campylobacter jejuni using whole genome DNA microarrays", FEBS Letter; 554: 224-230, FEBS 27782.
Perry, 1986, "Structure of the O-chain polysaccharide of the phenol-phase soluble lipopolysaccharide of *Escherichia coli* 0:157:h7." Biochem. Cell Biol.; 64:21-28.
Petrescu et al., 2004, "Statistical analysis of the protein environment of N-glycosylation sites: implications for occupancy, structure, and folding", Glycobiology; 14(2):103-114.
Pozscay et al., 1999, "Protein conjugates of synthetic saccharides elicit higher levels of serum IgG lipopolysaccharide antibodies in mice than do those of the O-specific polysaccharide from Shigella dysenteriae type 1", Proc Natl Acad Sci USA; 96:5194-5197.
Pozsgay, 1998, "Synthesis of glycoconjugate vaccines again Shigella dysenteriae type 1", Journal of Organic—Chemistry; 63:5983-5999.
Qian et al., 2007, "Conjugating recombinant proteins to Psudomonas aeruginosa Exoprotein A: A strategy for enhancing immunogenicity to malaria vaccine candidates." Vaccine 25:3923-3933.
Raetz et al., 2002, "Lipopolysaccharide endotoxins", NIH-PA author manuscript, pp. 1-57, 19-25 (published in final edited form as: Annual Rev Biochem; 71:635-700, 2002.
Reeves et al., 1996, "Bacterial polysaccharide synthesis and gene nomenclature", Reviews, Elseview Science Ltd., pp. 495-503.
Robbins et al, 2009, "Synthesis, characterization, and immunogenicity in mice on Shigella sonnei O-specific oligosacchardie-core-protein conjugates." Proc. Natl. Acad Sci USA 106:7974-7978.
Royle et al., 2002, "An analytical and structural database provides a strategy for sequencing O-glycans from microgram quantities of glycoproteins." Anal Biochem; 304(1): 70-90.
Rubires, 1997, "A gene (wbbL) from Serratia marcesens N28b (O4) complements the rib-50 mutation of *Escherichia coli* K-12 derivatives" J Bacteriol 179(23):7581-7586.
Rudd et al., 1997, "Glycosylation: heterogeneity and the 3D structure of proteins", Crit Rev Biochem Mol Biol; 32:1-100.
Rush, 1997, "Polyisoprenyl phosphate specificity of UDP-GlcNAc: undecaprenyl phosphate N-acetylgluosaminyl 1-p transferase from *E. coli*" Glycobiology; 7:315-322.
Sambrook & Russell, "2006, Screening Bacterial Colonies by Hybridization: Small Numbers." Cold Spring Haab. Protoc; doi:10.1101/pdb.prot3925 at http://cshprotocols.cshIp.org/cgi/content/full/2006/2/pdb.prot3925.
Samuel, 2003, "Biosynthesis of O-antigens: genes and pathways involved in nucleotide sugar precursor synthesis and O-antigen assembly." Carbohydrate Res. 338: 2503-2519.
Sau et al., 1997, "The *Staphylococcus aureus* allelic genetic loci for serotype 5 and 8 capsule expression contain the type-specific genes flanked by common genes." Microbiology 143: 2395-405.
Schaad et al., 1991, "Safety and immunogenicity of Pseudomonas aeruginosa conjugate A vaccine in cystic fibrosis", The Lancet; 338:1236-1237.
Schaffer et al, 2008, "Vaccination and passive immunisation against *Staphylococcus aureus*" Ing J Antimicrob Agents 32 Suppl. 1:S71-78.
Schneerson et al., 1991, "Preparation, characterization, and immunogenicity of Haemophilus influenzae type B polysaccharide-proteins conjugates", Journal of Experimental Medicine; 152:361-376.
Schultz et al., 1998, "Prototype of a heme chaperone essential for cytochrome c maturation", Science; 281:1197-1200.
Schwimmer et al., 1956, "Reagent for Differentiation on 1,4- and 1,6-Linked Glucosaccharides." Science; 123:543-544.
Scott, 1997, "Vaccines against Campylobacter jejuni", Journal of Infectious Diseases; 176(Suppl. 2):5183-S188.
Seffernick et al., 2001, "Melamine deaminase and atrazine chlorohydrolase: 98 percent identical but functionally different", J Bacteriol; 183(8):2405-2410.
Shorr, 2007, "Epidemiology and economic impact of meticillin-resistant *Staphylococcus aureus*: review and analysis of the literature." Phamacoeconomis 25: 751-68.
Simons et al., 1984, "High-level expression of human interferon gamma in *Escherichia coli* under control of the $p_L$ promoter of bacteriophage lambda", Gene; 28:55-64.
Spears et al., 2006, "A comparison of enterphathogenic *Escherichia coli* pathogenesis," FEMS Microbiol. Lett 255:187-202.
Spirig et al., 1997, "The STT3 protein is a component of the yast oligosaccharyltransferase complex." Mol. Gen Genet 356:628-637.
Stenutz, 2006, "The structures of *Escherichia coli* O-polysaccharide antigens." FEMS Microbiol. Rev. 30: 382-403.
Stephan et al., 2004, "First isolation and further characterization of enteropathogenic *Escherichia coli* (EPC) O 157:H45 strains from cattle" BMC Microbiol. 4:10.
Stevenson, 1994, "Structure of the O Antigen of *Escherichia coli* K-12 and the Sequence of rfb Gene Cluster." J Bacteriol.; 176:4144-4156.
Sullam, 1996, "Diminished platelet binding in vitro by *Staphylococcus areus* is associated reduced virulence in a rabbit model of infective endocarditis." Infection & lmmun. 66:5183-5189.
Szu et al., 1994, "Laboratory and preliminary clinical characterization of Vi capsular polysaccharide-protein conjugate vaccines", Infection and Immunity; 62(10):4440-4444.
Szymanski et al., 1999, "Evidence for a system of general protein glycosylation in Campylobacter jejuni", Molecular Microbiology; 32(5):1022-1030.
Szymanski ct al., 2002, "Campylobacter protein glycosyation affects host cell interactions", Infection and Immunity; 70(4):2242-2244.
Szymanski et al., 2005, "Protein glycosylation in bacterial mucosal pathogens", Nature Reviews, Microbiology; 3:225-237.

(56) References Cited

OTHER PUBLICATIONS

Taylor et al., 1993, "Synthesis, characterization and clinical evaluation of conjugate vaccines composed of the O-specific polysaccharides of Shigella dysenteriae type 1, Shigella flexneri type 2a, and Shigella sonnei (Plesiomonas shigelloides) bound to bacterial toxoids", Infection and Immunity; 61(9):3678-3687.

Thakker et al., 1998, "*Staphylococcus aureus* serotype 5 capsular polysaccharide is antiphagocytic and enhances bacterial virulence in a murine bactermia model." Infect Immun. 66:5183-5189.

Thibault et al., 2001, "Identification of the carbohydrate moieties and glycosylation motifs in Campylobactor jejuni flagellin", J Biol Chem; 276(37):34862-34870.

Tsai et al., 1982, "A sensitive silver stain for detecting lipopolysaccharides in polyacrylamide gels." Anal Biochem. 119:115-119.

Tuchscherr, 2008, "Antibodies to capsular polysaccharide and clumping factor A prevent mastitis and the emergence of uncapsulated and small-colony variants of *Staphylococcus aureus* in mice." Infect Immun 76:5738-44.

Unligil et al., 2000, "Glycosyltransferase structre and mechanism." Curr. Op. Struct. Bio. 10:510-517.

Valvano, 2003, "Export of O-specific lipopolysaccharide", Front Biosci; 8:s452-471.

Vanbleu et al., 2004, "Genetic and physical map of the pLAFR1 vector DNA seq." 15(3): 225-227.

Vandaux et al, 1995, "Use of adhesion-defective mutants of *Staphylococcus aureus* to define the role of specific plasma proteins in promoting bacterial adhesion to canine arteriovenous shuts." Infect & Immunity 63:585-90.

Varki et al., 1999, "Essentials of Glycobiology", Cold Spring Harbor Laboratory Press; Cold Spring Harbor, New York pp. 85-100.

Vernachio et al., 2003, "Anti-clumping factor A immunoglobulin reduces the duration of methicillin-resistant *Staphylococcus aureus* bacteremia in an experimental model of infective endocarditis," Antimicrobial Agents & Chemotherapy, 47:3400-3406.

Wacheter et al., 1976, "Lipid Intermediates Involved in the Assembly of Membrane-Associated Glycoproteins in Calf Brain White Matter." Arch Biochem Biophys.; 174:726-737.

Wacker et al., 2001, "PgIB, an oligosaccharyltransferase in the eubacterium Campylobacter jejuni?", Glycobiology; 11:871.

Wacker et al., 2002, "N-linked glycosylation in Campylobacter jejuni and its functional transfer into *E. coli*", Science; 298:1790-1793.

Wacker et al., 2006, "Substrate specificity of bacterial oligosaccharyltransferase suggests a common transfer mechanism for the bacterial and eukaryotic systems", Proc Natl Acad Sci; 103:7088-7093.

Waechter et al., 1977, "Evidence for the Enzymatic Transfer of N-Acetylglucosamine form UDP-N-Acetylglucosamine into Dolichol Derivates and glycoproteins by Calf Brain Membrane." Arch. Biochem. Biophys. 181:185-198.

Wang et al., 2002, "The O-Antigen gene Cluster of *Escherichia coli* O55:H7 and Identification of a New UDP-GlcNAc C4 Epimerase Gene." J Bacteriol 184:2620-2625.

Wang et al.,1998, "Organization of *Escherichia coli* O157 O Antigen Gene cluster and Identification of its specific genes." Infect. Immune 66:3545-3551.

Watts et al., 2005, "*Staphylococcus aureus* strains that express serotype 5 of srotype 8 capsular polysaccharides differ in virulence," Infect Immun. 73:3502-11.

Wernerus et al., 2004, "Biotechnological applications for surface-engineered bacteria", Biotechnol Appl Biochem; 40:209-228.

Whisstock et al., 2003, "Prediction of protein function from protein sequence and structure", Q Rev Biophys; 36(3):307-340.

Whitfield et al., 1999, "Structure, assembly and regulation of express of capsules in *Escherichia coli*", Molecular Microbiology; 31(5):1307-1319.

Whitfield et al., 2006, "Biosynthesis and Assembly of Capsular Polysaccharides in *Escherichia coli*." Annu Rev. Biochem. 75:39-68.

Witkowski et al., 1999, "Conversion of a beta-ketoacyl synthase to a malonyl decarboxylase by replacement of the active-site cysteine with glutamine", Biochemistry; 38(36):11643-11650.

Wolfe et al., 1993, "Reactions adding Sugar Units to Proteins in the ER and Golgi Complex, Molecular and Cellular Biology." Wadsworth Publishing Co., CA 873-75.

Wyszynska et al., 2004, "Oral immunization of chickens with avirlent *Salmonella* vaccine strain carrying C. jejuni 72Dz/92 cjaA gene elicits specific humoral immune response associated with protection against challenge with wild-type Campylobacter", Vaccine; 22:1379-1389.

Yao et al., 1994, "Isolation of motile and non-motile insertional mutants of Campylobacter jejuni: the role of motility in adherance and invasion of eukaryotic cells", Molecular Microbiology; 14(5):883-893.

Young et al., 2002,"Structure of the N-linked glycan present on multiple glycoproteins in the gramnegative bacterium, Campylobacter jejuni", J Biol Chem; 277(45):42530-42539.

Zhang et al., 1997, "Molecular and chemical characterization of the lipopolysaccharide O-antigen and its role in the virulence of Yersinia enterocolitica serotype O:8." Mol. Microbiol. 23:63-76.

Zufferey eta 1., 1995, "STT3, a highly conserved protein required for yeast oligosaccharyl transferase activity in vivo." The EMBO Journal 14(20):4949-4960.

Fattom, A. et al., Synthesis and immunologic properties in mice of vaccines composed of *Staphylococcus aureus* type 5 and type 8 capsular polysaccharides conjugated to Pseudomonas aeruginosa exotoxin A., Infect. Immun., 1990, vol. 58 No. 7, pp. 2367-2374.

Mario F Feldman et al., "Engineering N-linked protein glycosylation with diverse O antigen lipopolysaccharide structures in *Escherichia coli*", Proceedings of the National Academy of Sciences, National Academy of Sciences, Washington, DC; US, vol. 102, No. 8, doi:DOI:10.1073/PNAS.0500044102, ISSN 0027-8424, (Feb. 22, 2005), pp. 3016-3021. Feb. 9, 2005.

Jones, C., Revised structures for the capsular polysaccharides from *Staphylococcus aureus* Types 5 and 8, components of novel glycoconjugate vaccines., Carbohydrate Res., 2005, vol. 340 No. 6, pp. 1097-1106.

Sau, S. et al., The *Staphylococcus aureus* allelic genetic loci for serotype 5 and 8 capsule expression contain the type-specific genes flanked by common genes., Microbiology, 1997, vol. 143 No. 7, pp. 2395-2405.

Chris Whitfield, Biosynthesis and assembly of capsular polysaccharides in *Escherichia coli*., Annu. Rev. Biothem., 75:39-68, Feb. 27, 2006.

Chris Whitfield, et al., Biosynthesis and assemably of Group 1, Carbohydrate Research, 338(2003) :2491-2502.

Press Release, GlycoVaxyn and a Harvard University affiliated hospital receive USD 3.4 million NIH grant for *Staphylococcus aureus* vaccine development., GlycoVaxyn [online], May 4, 2010, pp. 1-2, <https://web.archive.org/web/20110626233433/http://www.glycovaxyn.com/content/news/releases/10%2005%2004.pdf> [retrieved on Jun. 16, 2015].

| pLAFR | O11 *wbjA*::Tn50<*dhfr-1*>*wzy*::*cat* | | | | |
|---|---|---|---|---|---|
| pEXT22 | - | wbjA | Cap 8H* | Cap 5I* | Cap 5I |
| lane | 1 | 2 | 3 | 4 | 5 |

| pLAFR | O11 Δ*wbjA* Δ*wzy*O11* | | | | | | |
|---|---|---|---|---|---|---|---|
| pEXT22 | Cap5IJH | | Cap5IJ | | | | |
| pACT3 | - | | Cap5H | | - | | |
| IPTG conc. mM | 1 | 0.1 | 1 | 0.1 | 1 | 0.1 | |
| Expression Temperature | 37°C | | | | | | 30°C |
| lane | 1 | 2 | 3 | 4 | 5 | 6 | 7 |

| pLAFR Selection | | Tet | Kan | Kan | Tet | Tet |
|---|---|---|---|---|---|---|
| CP5 genes in O11 cluster | | HIJ | HIJK | | | |
| Strain | | W3110ΔwecA | | | | |

| CP5 Genes in O11 cluster | HIJ | HIJK | HIJ | KHIJ | HIJK | HIJ | KHIJ | HIJK |
|---|---|---|---|---|---|---|---|---|
| Promoter | *wzz/wzx* | | - | | | PO121 | | |
| Strain | W3110 Δ*wecA* | | | | | | | |

| Plasmid No. | 3 | 2 |
|---|---|---|

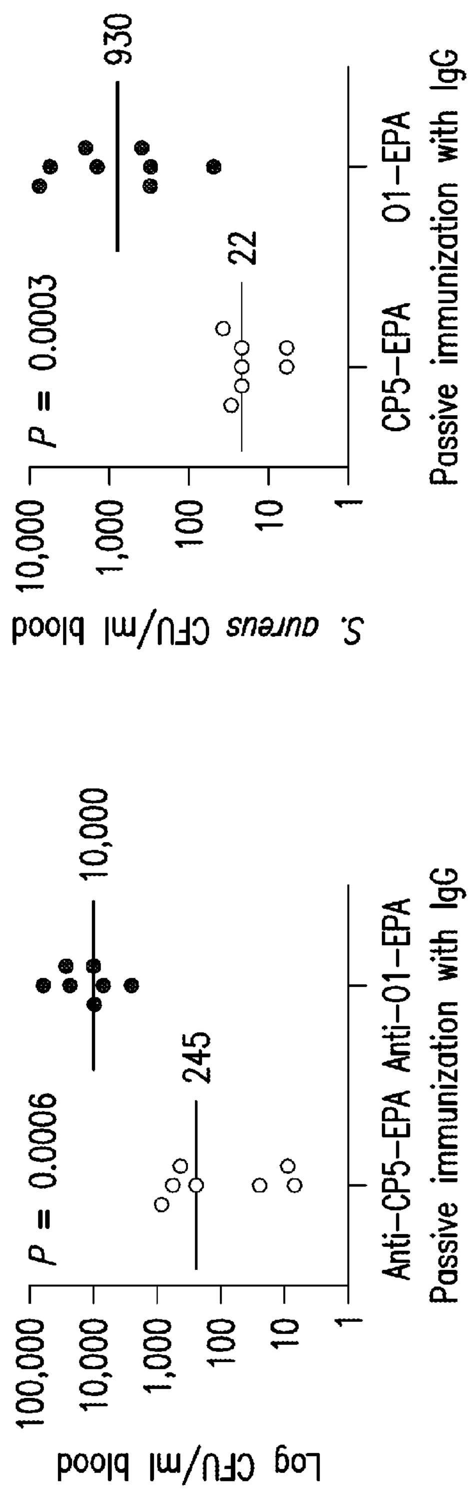
FIG.17A
FIG.17B
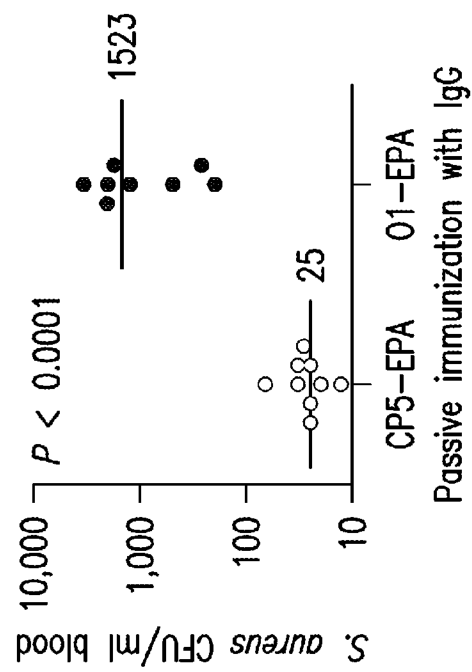
FIG.17C

```
                              SEQUENCE LISTING


<160> NUMBER OF SEQ ID NOS: 27

<210> SEQ ID NO 1
<211> LENGTH: 13369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

aattcacatg ttgcccatcc acgaaaccac cttatcgccg tggaacgcac ctggatcgac      60

agccccagca aagcagtcgc ttcctggtcc ggcaccggaa acatcgtacg gagaaaacaa     120

aaaaggccgc taggcggcct tttccggaga acgatgactc agggttctcg ccgcctctgg     180

cgatagatcc agtcgacgat ttcaccgtca ggcgcatagc cgctgacggt ttcccgcagc     240

aactggcgaa cccgcgagta gtcgtccttc tccacggcgg ccagcaactg ctccagcacg     300

accttgaagg cctcccagct caggtgttcc tcgttggccc gcatgatcat cggatggtcg     360

gtgggattca cgttgtcacc gatcagcagc tcttcgtaga gcttctcgcc aggacgcagg     420

ccactgaact cgatggcgat gtcaccatgg ggcgaacgct cggaacgcac gctcaggccg     480

gacaggtgga tcatcttctc ggcgagctcc aggatcttca ccggcggccc catgtccagc     540

acgaatacat ctccgccctg ccccatcgaa ccggcctgga tgaccaactg cgccgcctcg     600

ggaatggtca tgaagtaacg ggtgatgctc gggtgggtga ccgtcaccgg gccgccgcgc     660

ttgatctgct cgcggaacag cggaatgacc gaaccggacg aaccgaggac gttgccgaag     720

cggaccatgg tgaaacgggt cttgttgacg tgatgcacgt ccttccggtc gccgaacagc     780

accggcgccg attcgttgct gagcgcctga aggaccattt ccgccaggcg cttggtgctg     840

cccatcacat tggtcggccg caccgccttg tcggtggaaa tcagcacgaa gttctgcacg     900

ccgacctgca ccgcggcctg caccgcatgc aaggtgccta tcacgttgtt gagaacgccc     960

tcggcgatgt tgtgctcgac gatcggcaca tgcttgtagg ccgccgcatg gtagacggta    1020

ttgaccttcc aggtacgcat cacgtccacc aggcgctcgg gattgcgcac cgaaccgagg    1080

atcggcaaca ggttcaccga aagcgactcg cgcttgatcc gacgctccag ttcctgatgg    1140

atgctataga ggttgtattc gctgtgttcg aacaggatca gcacgctagg cgaacaactc    1200

atgatctgcc gacagagttc cgaaccgata gagccgcccg ccccggtcac catcaccacc    1260

tgaccgcgga tgcaccgttc cagcagctcc ttgcgcggtg cgacgctgtc gcgccccagc    1320

aggtcagcga tgtccacctc ctgcaggtca tccaccttga cccggccgct ggccaggtcc    1380

atgaagccgg gcatgctgcg cacgtgcagc gggaacggct ccagggactc gagaatctct    1440

cggcgccggg cccgagtggc ggaaggaatc gccaggagaa cctcctgcgc gcccgtctcg    1500

tcgatcatct ggcggatatg cttggcggta tagacccgca gaccggcaat gacccggttg    1560

gcgatctgct tgtcgtcatc gatgaacgcc accggacgca tcgcccgacc gagacgcaac    1620

gccgcaacca actggttgcc ggccgccccc gccccataga taaccaccct gggcaggcca    1680

tcctggcggt tgagaaatgg taccgactgc acagcagagt accagtcgcc catgaaatac    1740

tggcgcatgg ccagacgcaa gccgccgatc agcagcatgc tcaaccacca gtagttgaac    1800
```

```
accagggaac gcggcaccgg cgccggcgcg ccacgatacc agtacaccac cagcgacagc   1860
accagagccg agatggtcac cgccttggcg atggcgatca atgcgtcgtt accgagatag   1920
cgcatcaccg cgcgatacat gccgaagcga atgaatagtg gaatggcgat gaccggcgca   1980
gtgatgaaaa gccatgcatg ctcgccgaac acgtcgatca tatcgtctgt gcctagacgg   2040
accacaaaag cgagccacag agacagccat accagaagga tatccgtagc cacttgaagc   2100
aaacgtttcc agcgacgagg catggataac aactttactc ttaaacgatc tagcattccc   2160
ctactccttt aggcctgagc ggacgactct agcttacccg ccttgaacct cactgccaga   2220
aaaacgagag ggacgtaggc tatgacgatg cccatcaaag gctctagaga cccactcccg   2280
accaacaagg ctatagggag gagccagatg acgttcaatg ccgtgacgcc aatcgtaaca   2340
ggagcatgct ttccatagta tcggcttgcg tattgatagg catggcttcg atgagcctca   2400
tacaccttgt cccctctcag caagcgacga atcagggtat aggtcgcatc gacgatgaaa   2460
acgcctaaca ggaccaacca tgcccagaaa aaattcgtat tcatccacat ggcatgaatg   2520
gaaagaattc ctaaaacaat ccccagaaga ccactacccg catctcccat gaaaattttt   2580
gggggtggaa aattccagaa caagaatcca aaaacggcaa aagctagcga taaggggagc   2640
aaagcctgcg tcagttggcc attcagccag tataataatg ccccaccaac acagacaaaa   2700
atggcctgaa ggctagcaag tccatcgatc ccatccatga agttatagag attcagcaac   2760
cacacgagat agaaagcaaa gagaagtcct ccgaaccacc ccaggtccca actgacacca   2820
acaatctgaa atggtggtat gccattcaaa aagtacaatg agaccaaggc tgcactaaaa   2880
tgtcccagca gacgccagcg tgcggcgata tgaccgtgat catccatgaa tccaataatg   2940
gcaaccccgc cgccagcgag aagtaaagcc caggacacgg cccatgagat atttcccagt   3000
acagcccaaa taggcagcat gagacaaaaa gtaactacaa tggcgacccc tcctccgcgt   3060
ggagtgggaa cgacatggga acttcgagag ttaggggtgt caagtaagct cctcgctaag   3120
gcataacgac gcaagaggcc tgtaagcagt cccgaaaccc cagctgcagc gagtaacaaa   3180
taccattctt ccatttataa atttatcccc aaaaatactc tcaccccttc aacagggttc   3240
tattcgattg ttctgcgtgg tacgccatgc tagtagcaaa gcgcctgcag ataatcattc   3300
agtacgtttg acatatattc taccaacatc ttccaacgcg gaaagggtgc tcttgcgggg   3360
ttcccaacca agcaaaagcc tgcctttcga cgagtcgacc tctagtgagc agcataactg   3420
agtgtataac ccaccctttc ctactaattt aagaaacctc agaataaacc taggaacagg   3480
ccacatgatg gggcgacgcc ccattcccgc agcaagcgca gtcaccagtt gcttggtaga   3540
aatctcctga ccatcggata ccaaaaacag ttcgccggca gcagaagggt gcgtcataca   3600
gcaagctaga aagtcaacta aattatccag agaaacaaaa cttcgtcggt tatctatgca   3660
accaaatgga agaggaagtc ccgaagcaac cagcttcaac aatcgcgaga aatttccagg   3720
agctttccag tcgtaaacga gtggaggcct gacgataaca agttctgttg aggaatgctt   3780
gaaaagctcc cgaagcgcta cttcagcctc aaactttgaa atcgcatatt ctgcatgagg   3840
agccggcttg gagttctcat cgaagggctt ttctttggtt aaagcgccat ttacaccaat   3900
agaactaaca aaaatgaaac gctttacaga tgcttcgatc gcctgccgag caagcgccag   3960
agtagcatcg cgattcacct tccgaaaaat atctagtgaa tcacgctgcc ttccaaagat   4020
atgggctcgt ccagctagat gaactacaca ttcaacaccc cgcagcgcag catcaagctt   4080
agtgctctct ttcagctccg ctcgaacata ctcaaccccc gtaacgggat tgtacaggga   4140
```

```
tcgtacttgt ccgacaacct gaaagggggc ggcagcaagc gacctgcaaa gcgcactccc   4200
gacaaaaccg ctagccccgg ttaccagcac cttcatcata ttttcgactc agacagaagc   4260
ggtcgaacac aggcagcgaa tttttccaat gaaatatatt cagaataatt ttgctgaagg   4320
acactccgcg ggactccgcc taaactagac aagtcgagtt cacaaatctc atcgatcaat   4380
cttgccaaag caaccggatc attcggcgga cagttccaac cgattccggt ctcatctatt   4440
atacgggaga tttcagcccc tttttccatg acagctagaa tcggtttgtc tgctgccatg   4500
gagaaatatg ccttgctggg aaccccaagc ccgaacattc cttcttctaa ggtaactaag   4560
gcaacgtcac aggcagccaa accaaaattc ttttcggcta atggcagcct tccaaaatac   4620
ctcaaccgag cacactgatc ttccagcgcg tgttttttta cactgtcgac caaggcacca   4680
tctccaataa aagcaaaagc cgccttctcg tttttaacca actgaatagc agaaagtatg   4740
ttttctatac cttgtaatcg accgacatta ccaaaaaatt ggaaaaccct tttacctttc   4800
cattcaggaa tattgataaa aggagcatcc tctctcggta ctgggaaaac ctctttctca   4860
caggcccaat tcgaaataaa gaccaaagat cgcgggtcat tcaccttctc tttcataaga   4920
gcttccatat cgcgccctat tacgactaga cgatcagcgg atgagtaaat gaaagaaaag   4980
agacgacgta gaagccggta ggcaatacta tctttcttca gaacgcccgc cggcaccaag   5040
ttctcgggaa acacatcatg caccagcagc acccacttga aaccgagggc ataccttagc   5100
aagggaaacg tcatcagtag aagagcaggg ttggttccac tcaataccac atctcctcgt   5160
ctggcacgag aagtcaattt tactgagaac agaaacgcct gaaaaatctg cgccaatcct   5220
ctagaaagga gcctattctt attgctcctc ggaaacttaa agcattcttg ctcaacggaa   5280
ggtgaaacca caggcggggt ttcacctgcg gtcagcggga aaattacggt tagcccacca   5340
aactcccgct gcatctttcc tattatcttc tcccaatagt atcccgtgga gttctgattg   5400
gcaccgacat actcagaaac cacaaatatc cttgccatca actccacgcc tcaagttaat   5460
attttttcca gacagttcgc atgacatagt cccgatagct atgaactatg cgaacaatct   5520
tttcagaaac gttgggcatg ctatagtcag cgaccaagcg taacatgcgc tctgcgtcgc   5580
gcctctgtcc ctccaacacc tcgagtgctt gtagtactcg atccgaatcc agtccgacca   5640
tcatcaccac agcctcttcc atgccttctg ggcgttcatg agcctcacga atattcaaag   5700
cgggaaaatt cagtattgaa gactcctcac tgatggtccc actgtcagaa ataactgcct   5760
tggctgtaat ttgcagttta ttgtaatcct taaagccgag ggtttcagc agtttaatac   5820
cctcgtgaaa ctttgcctcc gtcgcctcaa ttctcttttt tgttctaggg tgagttgata   5880
cgatgacggg cagcgagtac ttttctgcca cagcgttgag catagaaacc aacttcaaga   5940
aattcttatc cgaatctatg ttttcctctc ggtgcgcact cacgacaaag aaccgctctg   6000
ttttcaaccc gagcctttca agaatatcgg aggactcgat cccgtcacga tagtgctcga   6060
gaacttcgaa catagggcta ccagtcttga taaccatgtc tggagaaagt ccttcacgca   6120
agagataatc acgcgcaatt gtactatagg tcaaatttac atcagctgta tgatcgacaa   6180
tgcgccgatt tatctcttca ggcacacgca tatcgaaaca gcgattgcct gcttccatat   6240
gaaaggtcgg tatcttacgc cgttttgcag gcagtaccgc catacaacta ttggtatcac   6300
ccagcacgag cagcgcatcg ggatctattt cgcccagaac acgatcgact gcgattatta   6360
cattccctat cgtttcagcc ccggaagacc cggcggcgtt tagaaaataa tccggctttc   6420
ttataccgag gtcctgaaaa aatatttcat taagttcgta atcataattc tgtccagtat   6480
ggacaagtac atgatcgcag tactgatcaa gcttcgccat gaccctagac aagcgaataa   6540
```

```
tctcaggacg agttccaaca accgtaacga cttttagctt ctgcattgtt atctcactat   6600
accttacgca ccttcgccta ctgaacaagc gtaggtatcc ggattttccc gatcaaatac   6660
ttcgttagcc cacaacatga ctaccatatc gtcagttccg acattagtaa tgtcatgagt   6720
ccatccaggt actgtttcga caatttctgc cttttcacca ttagtgcaaa tttcgtaaaa   6780
tgccccggtc aggatgtttc taaacttgaa acgtgccatc cctttgataa ccagaaactt   6840
ttcggttttc gagtgatggt aatgcccgcc cctggtaaca cctggatgag ccgtaaaaaa   6900
cgagaactgg ccagagtccg cggtcttcag catctcgacg aatgtgccac gcggatccga   6960
atgcattggc acgtcgtaac taaaactatc ttctggcaag aaacttagat aagtcgagta   7020
caaggcgcgc gtcaatcccg agccaaccct tgcggtagtc agtgactttc gactattacg   7080
aaactcatac aattgttctg cgagctcacc aacagaaatc tgatactggg gctcgacctg   7140
tagtgaaact gcattggata gcttcccatc catgactttc atgaaggtgc gaaccacatc   7200
atctatgtat acaagagtga tctctgccga ggaattgtta atttgaatcg gaatatctcg   7260
aataatatta tgacaaaaag tcgcaaccgc tgaattataa ttcggacgcg accatttacc   7320
gaatacatta ggaaggcgaa atatgtagac aggacaacca atatcctcac ctagcacttg   7380
gagatgctct tctgcggctc gcttgcttaa accgtactca ttatccacct cagcctgaat   7440
ggatgaagta taaagaagtg gtatggctcg tccattggac cttaccgcct cacacagagc   7500
atacgtgagt tcggaattcc cgatcttaaa ctcttctggt tttccggac gattgacccc    7560
ggcaagatga aaaataaaat cgacggaacg aattagctca ggcaaattac caacactact   7620
ctcgcgggtg aatggcacca cctcgatacc accccgctct gcaagatgag cgcacagatt   7680
ccttccaaca aatccattcg cgccagttac aagaactttc atcgtttatt cctctggact   7740
ggcactctcg ccacgctgaa tagcacgaat gaaatccaac ttcagcaaca gctttttcat   7800
tccttcgata tccagacgtt tggtattatg agaattatag tcctctgtat gagtaatttt   7860
ttcctcgcct tgctccacaa acttactata gttcagatca cgcaaatctg gggggatacg   7920
ataatagtca cccatgtctt cagcacaggc catttcctct cgactaagaa gcgcctcata   7980
aagcttctct ccatgacgcg tacctattac attgatagga taaccattct tgccaagcaa   8040
ttgagtaagc gcatgagcca gcacctcgat ggttgcagcc ggtgctttct gtacaaaaag   8100
atctccattg gtaccatgct cgaaagcata aagcacaagg tctacggcat ccgtaagcgt   8160
catcatgaaa cgtgtcatgt ttggatcagt gattgtgaga ggctggcctg atcgcatttg   8220
ctcgataaag agaggaatga ccgagcccct tgaagccatg acgttaccat aacgggtgcc   8280
acaaattacg gtaggagtgc gttccaggtt tcgagacttg gcgaccatga ccttttccat   8340
catggccttt gaaataccca tggcattgat tgggtaaact gccttatccg tactcagaca   8400
aacgactttt ttgacgccat tctggatagc agattcgagg acattttccg ttccgatgac   8460
attggtcttc acagcctcca tcgggtagaa ctcacaagag ggaacctgtt tcaatgcagc   8520
cgcatggaaa atgtagtcca caccgcgagt agcattcaga gtgctttgat agtcgcggac   8580
atctccaata taaaacctca acttggggtg agcatagcac ttacgcatat catcttgctt   8640
cttctcatcc cgactgaata cacgtatttc accaatatct gtatccagaa aacgcttcaa   8700
aacggcattt ccaaaggaac cagttccacc ggtaattaac agaacagagt tcttatccat   8760
acaccacctc tttactaatg tgttcaacgt cccttttccg cctcaaaata taaagaaagc   8820
gaaaaacaac gagccagaac aatgcagccc ctaccggatg gaaaagccca ccgccgctaa   8880
```

```
agacataatt aacgaaccag attataaatg cagagcataa gaagcctaac tctgtacaag   8940
ctgtttttct tcgccggaag acaagcaaaa atacagagta gacaaaaagc aacaatagca   9000
aaagaacagc caagccacca aaaatgaaac catagatgca aagcagctcg acaataccat   9060
tgtgcgccat tggatattgc gcataccta gaaccccccc tcccccaaaa acgcccgcgc   9120
ccaaaacaag tatctcgcta ccgtagaaag acaatgtttc caaaggcagt gcagttaccc   9180
gatcgaatat ggattcgaag aatggaacat cttgcgagac tgaggaatcg gaggtgagga   9240
gcccgacaat cagtcgatgc acggtttcca gactgccagc cccgaagtct gcaaggaaaa   9300
atacagataa acccagccct gcaagaagga aggtgaaaaa caagtatgtc tttttgatca   9360
gttttagcca ataggcaaag aataagacaa tgacgatatt ggccagagca gctttctgca   9420
gcgacagcat cgcccccaag caaagaagaa ggaaacatac cacgcgcgcc caaccottta   9480
gataaaagag tgaagcaagt gcgggaactc ccaccataac accatatgcg gtcaaacttc   9540
ctaccaatga tgcaaaacgg gcgcccccag cacgctcact ggcttcagcg aaccattcta   9600
taggtccaaa tacatactgc cagagaaaag aaagagccgc cagactgaag aaaaatgaaa   9660
taagttgcat gggcactttt agattatctc tggcaagaac catagcaaca aagagaagag   9720
gtaatgatgc ccacaacctg aaaatcccta tggaatagtc tccatataga tcgaaccata   9780
acaccgaaac gagcgaggca tacgtccaga agaaaataac aaatatacct aatgcgctat   9840
atttaatatc cctccagtta ttaataaata agagaaaaaa cagcccacaa aacccagcaa   9900
gaactaaata atacgcaccg gatagattcc ggagaatatg aaagagaaac acaaaaagga   9960
gaaccagagc aacgcttctc tgcttcatga gtaccaccca tctttgtttg ctttctcttt  10020
ggaaagtttc gactttctat cgagaacccc cttccgatag gatgaggcca aaacgagcct  10080
ataagcagct ctagagtaga gccatcgaat agagtccgtt ttctctagag aatgaataag  10140
aatatttgaa aactttgact ccagcgcaag acacagcact gctctgaata gactctgaaa  10200
cttgcttgac aaagcaaagc ccggctccat ccatcgtata ggaccaagag tctcaaggtc  10260
atcagttgtt gcaactttca tgaattccgg cattccgtca cgggcggcat gatagtactt  10320
gcgacagaac ttcgaaatac tgccttccgg ttcgacatgc tcgatttcag cccgacaagg  10380
aagaacagaa taaccaagct tgccaaccct taacccaaac tccgtatctt caaagccgta  10440
cccaacaaat cgctcatcaa aaagagcatt atcttggagc agaatatccc tctcagcgag  10500
catattcatg gtaacaatag ttttataccc caaggagttg ggcagcggct tgtcagcaga  10560
gaagtgacaa ctatccctat agcgatagta attactcgtc gacaccaatg agcaagaaaa  10620
tctgacacca ccgcaccaga taacgcgttc ccccctcga gagttagcag cgttcagaaa  10680
attcgagaga tgagcaggat ctggcacaca atcatcatca agaagcacta cgtagcgccc  10740
cttcgctaaa cgaacgcctt tatttcgttt tgcactagcc gaattcagct cggcctgctc  10800
aagacggacg ttgaagccct gaaccgcttc gaactcgcgg accacatcgg gtgtttcatc  10860
accactatta ctgtcgacaa caataacttc aaaatcctta aaagccagag actgcgctac  10920
aaggccggcc aggaccaatt ttagttcctt gggacgacgc caagtactaa cgacgacact  10980
caacaacatc aaagtcccct tttctctctc aacttaaccg tggccaggaa aaacattccc  11040
atccccaaag agacctctgt aacgaccagc gtccacgctc caaaaagctc atccccccaa  11100
agcgccaaga ggataaatgt taataccccg cccaattccg caaaaaaaat tgctcgcaaa  11160
tatacaccat catacccaga aggaacaaga gtcaaccctc catacagaac accaatacaa  11220
gcaaacactg gcactatcga aaacattctt attacaacag ttagacctct ggactgttcc  11280
```

```
gggaatagga gatatgaaat gtattcagaa aataagaaaa gaaataaaca actaggaata  11340
gctattagta acatcagacc tagcgctttc cttcttaaac tgccgactgc cgggtcggca  11400
ctcgcataca tcctgctaaa agtcggaaat agagcgctag ctatgggtga agtagcagcc  11460
gcgatcccgc gaaggaattt atccgcagta gaaagcactc cggccgcgga ggctccacca  11520
acaacaccaa ccgccgcaac gagcacttgc atgtgcaagc taagaaaagc cagagaaaga  11580
aaagatcgag caccgtcacg caatatatcg agaattctgt ctttctcgag aaccgggcgc  11640
caccgtattc ccatagaaaa taaaatacaa cagagagcac ttccacctat gacataggaa  11700
aaaccaaacc ccaacgaagc cagcacaagg tcagaatcct tcgtgacaaa aaaaacgacc  11760
aataggaaat aaaatacctt agacaaaaaa ttggtaagcg ccaaccatcc aaacagcgct  11820
cttccctgaa agaaccatac tgcttgaaga taatttccaa ctactgccgg aagagcagcc  11880
gcaaccaata caagcaaggg gattggtaaa atagaagata cagccaaaat ggccagcact  11940
aaaagtgaaa gcagcaacaa taagaatcta gcactctgta caacagaaaa gaaactagac  12000
agttcaactt tgttatcgat aatggcagcc tttcttgatc ctgccagaat aaatccaaag  12060
tctaccagtt gacatagaat gacagccacg gcctgggcaa tcaccaattg gccaaacgct  12120
tcgcttgaca atgttctcgt gagaaaagga atcgcagcaa gaggcaaaag atagttgctg  12180
cccatggata taccggagta gaaaacgccc cgccttattg acattctact cgataccccc  12240
taatacaatt caacaactac aacaagtaag ccctgatgcc agtaagtggc atcagggttt  12300
agatcaaaac ttagcgaaga gagccatcgc tacgaagctt ccttataaaa ccagcgagca  12360
ctgcgagtag aattccaatt atcaatcctg ccaaagtacc tatagtaact ataagaatct  12420
tcttcggctt aatgggttga tttgaaaaag agagtccctc gtcttccttg tagacagcca  12480
ccgcatcaga atccacagac aaactggagt tccaagatag tttctcttgg agagttctca  12540
actcaggaat gaatggagca tctacactac gcgactcaag attgttgatt tcagcgcgca  12600
gcgccttagc tcctcgcatg tacatcaagt caccatccat gatcgaggag agttgttgct  12660
cggacgcccc ttctattaat ggcgggccat ctatcttgag cgactccgca atcagcaatg  12720
cctccttcaa acgtgcaatt ctatcatcac ggcggccctt cgccatattc tgcagcacgg  12780
ttatgcggct ctgcattgca gcatttctta cctggaaatc tctacctgca ctatcaataa  12840
cctcatgcac ggcccgatcc gcagccaaac gcacgaaagc ttgtgcccat gtagcaagaa  12900
cctctcgctt cgtgccctcc acaattaccg tataacggtc tgcatctggc ttgttagcag  12960
gatcaatctt tacctctttg gagaacttct tataaaactc ctcctgctca tcttcgcttt  13020
ccgctccctc acccacctgg ggaaggtata tcttatagaa gaactctttt ttattctcat  13080
ccgaaagcag attgcgcgaa aagatcgcat agatacttct aacagtatat gcatctaggc  13140
cattctccct tctaccaaca ttgaaacctt cgatagaccc aagagcagga ggcactactg  13200
caaccctata ttcatataca ggcttactca gatacgcata ggtaaaagac ccgattaatg  13260
caagaagagt agtcagaaga atcagaacct tgttaaccca aagctccttg accagcttca  13320
ccaggtcaac ctcaccatca gccgtcatca aagaagaatt gcctcaggg             13369
```

<210> SEQ ID NO 2
<211> LENGTH: 15244
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
aattcacatg ttgcccatcc acgaaaccac cttatcgccg tggaacgcac ctggatcgac     60
agccccagca aagcagtcgc ttcctggtcc ggcaccggaa acatcgtacg gagaaaacaa    120
aaaaggccgc taggcggcct tttccggaga acgatgactc agggttctcg ccgcctctgg    180
cgatagatcc agtcgacgat ttcaccgtca ggcgcatagc cgctgacggt ttcccgcagc    240
aactggcgaa cccgcgagta gtcgtccttc tccacggcgg ccagcaactg ctccagcacg    300
accttgaagg cctcccagct caggtgttcc tcgttggccc gcatgatcat cggatggtcg    360
gtgggattca cgttgtcacc gatcagcagc tcttcgtaga gcttctcgcc aggacgcagg    420
ccactgaact cgatggcgat gtcaccatgg ggcgaacgct cggaacgcac gctcaggccg    480
gacaggtgga tcatcttctc ggcgagctcc aggatcttca ccggcggccc catgtccagc    540
acgaatacat ctccgccctg ccccatcgaa ccggcctgga tgaccaactg cgccgcctcg    600
ggaatggtca tgaagtaacg ggtgatgctc gggtgggtga ccgtcaccgg gccgccgcgc    660
ttgatctgct cgcggaacag cggaatgacc gaaccggacg aaccgaggac gttgccgaag    720
cggaccatgg tgaaacgggt cttgttgacg tgatgcacgt ccttccggtc gccgaacagc    780
accggcgccg attcgttgct gagcgcctga aggaccattt ccgccaggcg cttggtgctg    840
cccatcacat tggtcggccg caccgccttg tcggtggaaa tcagcacgaa gttctgcacg    900
ccgacctgca ccgcggcctg caccgcatgc aaggtgccta tcacgttgtt gagaacgccc    960
tcggcgatgt tgtgctcgac gatcggcaca tgcttgtagg ccgccgcatg gtagacggta   1020
ttgaccttcc aggtacgcat cacgtccacc aggcgctcgg gattgcgcac cgaaccgagg   1080
atcggcaaca ggttcaccga aagcgactcg cgcttgatcc gacgctccag ttcctgatgg   1140
atgctataga ggttgtattc gctgtgttcg aacaggatca gcacgctagg cgaacaactc   1200
atgatctgcc gacagagttc cgaaccgata gagccgcccg ccccggtcac catcaccacc   1260
tgaccgcgga tgcaccgttc cagcagctcc ttgcgcggtg cgacgctgtc gcgccccagc   1320
aggtcagcga tgtccacctc ctgcaggtca tccaccttga cccggccgct ggccaggtcc   1380
atgaagccgg gcatgctgcg cacgtgcagc gggaacggct ccagggactc gagaatctct   1440
cggcgccggg cccgagtggc ggaaggaatc gccaggagaa cctcctgcgc gcccgtctcg   1500
tcgatcatct ggcggatatg cttggcggta tagacccgca gaccggcaat gacccggttg   1560
gcgatctgct tgtcgtcatc gatgaacgcc accggacgca tcgcccgacc gagacgcaac   1620
gccgcaacca actggttgcc ggccgccccc gccccataga taaccaccct gggcaggcca   1680
tcctggcggt tgagaaatgg taccgactgc acagcagagt accagtcgcc catgaaatac   1740
tggcgcatgg ccagacgcaa gccgccgatc agcagcatgc tcaaccacca gtagttgaac   1800
accagggaac gcggcaccgg cgccggcgcg ccacgatacc agtacaccac cagcgacagc   1860
accagagccg agatggtcac cgccttggcg atggcgatca atgcgtcgtt accgagatag   1920
cgcatcaccg cgcgatacat gccgaagcga atgaatagtg gaatggcgat gaccggcgca   1980
gtgatgaaaa gccatgcatg ctcgccgaac acgtcgatca tatcgtctgt gcctagacgg   2040
accacaaaag cgagccacag agacagccat accagaagga tatccgtagc cacttgaagc   2100
aaacgtttcc agcgacgagg catggataac aactttactc ttaaacgatc tagcattccc   2160
ctactccttt aggcctgagc ggacgactct agcttacccg ccttgaacct cactgccaga   2220
aaaacgagag ggacgtaggc tatgacgatg cccatcaaag gctctagaga cccactcccg   2280
```

-continued

```
accaacaagg ctatagggag gagccagatg acgttcaatg ccgtgacgcc aatcgtaaca   2340
ggagcatgct ttccatagta tcggcttgcg tattgatagg catggcttcg atgagcctca   2400
tacaccttgt cccctctcag caagcgacga atcagggtat aggtcgcatc gacgatgaaa   2460
acgcctaaca ggaccaacca tgcccagaaa aaattcgtat tcatccacat ggcatgaatg   2520
gaaagaattc ctaaaacaat ccccagaaga ccactacccg catctcccat gaaaattttt   2580
gggggtggaa aattccagaa caagaatcca aaaacggcaa aagctagcga taaggggagc   2640
aaagcctgcg tcagttggcc attcagccag tataataatg ccccaccaac acagacaaaa   2700
atggcctgaa ggctagcaag tccatcgatc ccatccatga agttatagag attcagcaac   2760
cacacgagat agaaagcaaa gagaagtcct ccgaaccacc ccaggtccca actgacacca   2820
acaatctgaa atggtggtat gccattcaaa aagtacaatg agaccaaggc tgcactaaaa   2880
tgtcccagca gacgccagcg tgcggcgata tgaccgtgat catccatgaa tccaataatg   2940
gcaaccccgc cgccagcgag aagtaaagcc caggacacgg cccatgagat atttcccagt   3000
acagcccaaa taggcagcat gagacaaaaa gtaactacaa tggcgacccc tcctccgcgt   3060
ggagtgggaa cgacatggga acttcgagag ttaggggtgt caagtaagct cctcgctaag   3120
gcataacgac gcaagaggcc tgtaagcagt cccgaaaccc cagctgcagc gagtaacaaa   3180
taccattctt ccatttataa atttatcccc aaaaatactc tcaccccttc aacagggttc   3240
tattcgattg ttctgcgtgg tacgccatgc tagtagcaaa gcgcctgcag ataatcattc   3300
agtacgtttg acatatattc taccaacatc ttccaacgcg gaaagggtgc tcttgcgggg   3360
ttcccaacca agcaaaagcc tgcctttcga cgagtcgacc tctagtgagc agcataactg   3420
agtgtataac ccaccctttc ctactaattt aagaaacctc agaataaacc taggaacagg   3480
ccacatgatg gggcgacgcc ccattcccgc agcaagcgca gtcaccagtt gcttggtaga   3540
aatctcctga ccatcggata ccaaaaacag ttcgccggca gcagaagggt gcgtcataca   3600
gcaagctaga aagtcaacta aattatccag agaaacaaaa cttcgtcggt tatctatgca   3660
accaaatgga agaggaagtc ccgaagcaac cagcttcaac aatcgcgaga aatttccagg   3720
agctttccag tcgtaaacga gtggaggcct gacgataaca agttctgttg aggaatgctt   3780
gaaaagctcc cgaagcgcta cttcagcctc aaactttgaa atcgcatatt ctgcatgagg   3840
agccggcttg gagttctcat cgaagggctt ttctttggtt aaagcgccat ttacaccaat   3900
agaactaaca aaaatgaaac gctttacaga tgcttcgatc gcctgccgag caagcgccag   3960
agtagcatcg cgattcacct tccgaaaaat atctagtgaa tcacgctgcc ttccaaagat   4020
atgggctcgt ccagctagat gaactacaca ttcaacaccc cgcagcgcag catcaagctt   4080
agtgctctct ttcagctccg ctcgaacata ctcaaccccc gtaacgggat tgtacaggga   4140
tcgtacttgt ccgacaacct gaaagggggc ggcagcaagc gacctgcaaa gcgcactccc   4200
gacaaaaccg ctagccccgg ttaccagcac cttcatcata ttttcgactc agacagaagc   4260
ggtcgaacac aggcagcgaa tttttccaat gaaatatatt cagaataatt ttgctgaagg   4320
acactccgcg ggactccgcc taaactagac aagtcgagtt cacaaatctc atcgatcaat   4380
cttgccaaag caaccggatc attcggcgga cagttccaac cgattccggt ctcatctatt   4440
atacgggaga tttcagcccc tttttccatg acagctagaa tcggtttgtc tgctgccatg   4500
gagaaatatg ccttgctggg aaccccaagc ccgaacattc cttcttctaa ggtaactaag   4560
gcaacgtcac aggcagccaa accaaaattc ttttcggcta atggcagcct tccaaaatac   4620
ctcaaccgag cacactgatc ttccagcgcg tgttttttta cactgtcgac caaggcacca   4680
```

```
tctccaataa aagcaaaagc cgccttctcg tttttaacca actgaatagc agaaagtatg   4740
ttttctatac cttgtaatcg accgacatta ccaaaaaatt ggaaaaccct tttacctttc   4800
cattcaggaa tattgataaa aggagcatcc tctctcggta ctgggaaaac ctctttctca   4860
caggcccaat tcgaaataaa gaccaaagat cgcgggtcat tcaccttctc tttcataaga   4920
gcttccatat cgcgccctat tacgactaga cgatcagcgg atgagtaaat gaaagaaaag   4980
agacgacgta gaagccggta ggcaatacta tctttcttca gaacgcccgc cggcaccaag   5040
ttctcgggaa acacatcatg caccagcagc acccacttga aaccgagggc ataccttagc   5100
aagggaaacg tcatcagtag aagagcaggg ttggttccac tcaataccac atctcctcgt   5160
ctggcacgag aagtcaattt tactgagaac agaaacgcct gaaaaatctg cgccaatcct   5220
ctagaaagga gcctattctt attgctcctc ggaaacttaa agcattcttg ctcaacggaa   5280
ggtgaaacca caggcggggt ttcacctgcg gtcagcggga aaattacggt tagcccacca   5340
aactcccgct gcatctttcc tattatcttc tcccaatagt atcccgtgga gttctgattg   5400
gcaccgacat actcagaaac cacaaatatc cttgccatca actccacgcc tcaagttaat   5460
attttttcca gacagttcgc atgacatagt cccgatagct atgaactatg cgaacaatct   5520
tttcagaaac gttgggcatg ctatagtcag cgaccaagcg taacatgcgc tctgcgtcgc   5580
gcctctgtcc ctccaacacc tcgagtgctt gtagtactcg atccgaatcc agtccgacca   5640
tcatcaccac agcctcttcc atgccttctg ggcgttcatg agcctcacga atattcaaag   5700
cgggaaaatt cagtattgaa gactcctcac tgatggtccc actgtcagaa ataactgcct   5760
tggctgtaat ttgcagttta ttgtaatcct taaagccgag ggtttcagc agtttaatac    5820
cctcgtgaaa ctttgcctcc gtcgcctcaa ttctcttttt tgttctaggg tgagttgata   5880
cgatgacggg cagcgagtac ttttctgcca cagcgttgag catagaaacc aacttcaaga   5940
aattcttatc cgaatctatg ttttcctctc ggtgcgcact cacgacaaag aaccgctctg   6000
ttttcaaccc gagcctttca agaatatcgg aggactcgat cccgtcacga tagtgctcga   6060
gaacttcgaa catagggcta ccagtcttga taaccatgtc tggagaaagt ccttcacgca   6120
agagataatc acgcgcaatt gtactatagg tcaaatttac atcagctgta tgatcgacaa   6180
tgcgccgatt tatctcttca ggcacacgca tatcgaaaca gcgattgcct gcttccatat   6240
gaaaggtcgg tatcttacgc cgttttgcag gcagtaccgc catacaacta ttggtatcac   6300
ccagcacgag cagcgcatcg ggatctattt cgcccagaac acgatcgact gcgattatta   6360
cattccctat cgtttcagcc ccggaagacc cggcggcgtt tagaaaataa tccggctttc   6420
ttataccgag gtcctgaaaa aatatttcat taagttcgta atcataattc tgtccagtat   6480
ggacaagtac atgatcgcag tactgatcaa gcttcgccat gaccctagac aagcgaataa   6540
tctcaggacg agttccaaca accgtaacga cttttagctt ctgcattgtt atctcactat   6600
accttacgca ccttcgccta ctgaacaagc gtaggtatcc ggattttccc gatcaaatac   6660
ttcgttagcc cacaacatga ctaccatatc gtcagttccg acattagtaa tgtcatgagt   6720
ccatccaggt actgtttcga caatttctgc cttttcacca ttagtgcaaa tttcgtaaaa   6780
tgccccggtc aggatgtttc taaacttgaa acgtgccatc cctttgataa ccagaaactt   6840
ttcggttttc gagtgatggt aatgcccgcc cctggtaaca cctggatgag ccgtaaaaaa   6900
cgagaactgg ccagagtccg cggtcttcag catctcgacg aatgtgccac gcggatccga   6960
atgcattggc acgtcgtaac taaaactatc ttctggcaag aaacttagat aagtcgagta   7020
```

```
caaggcgcgc gtcaatcccg agccaaccct tgcggtagtc agtgactttc gactattacg   7080
aaactcatac aattgttctg cgagctcacc aacagaaatc tgatactggg gctcgacctg   7140
tagtgaaact gcattggata gcttcccatc catgactttc atgaaggtgc gaaccacatc   7200
atctatgtat acaagagtga tctctgccga ggaattgtta atttgaatcg gaatatctcg   7260
aataatatta tgacaaaaag tcgcaaccgc tgaattataa ttcggacgcg accatttacc   7320
gaatacatta ggaaggcgaa atatgtagac aggacaacca atatcctcac ctagcacttg   7380
gagatgctct tctgcggctc gcttgcttaa accgtactca ttatccacct cagcctgaat   7440
ggatgaagta taaagaagtg gtatggctcg tccattggac cttaccgcct cacacagagc   7500
atacgtgagt tcggaattcc cgatcttaaa ctcttctggt tttccggac gattgacccc   7560
ggcaagatga aaaataaaat cgacggaacg aattagctca ggcaaattac caacactact   7620
ctcgcgggtg aatggcacca cctcgatacc accccgctct gcaagatgag cgcacagatt   7680
ccttccaaca aatccattcg cgccagttac aagaactttc atcgtttatt cctctggact   7740
ggcactctcg ccacgctgaa tagcacgaat gaaatccaac ttcagcaaca gctttttcat   7800
tccttcgata tccagacgtt tggtattatg agaattatag tcctctgtat gagtaatttt   7860
ttcctcgcct tgctccacaa acttactata gttcagatca cgcaaatctg gggggatacg   7920
ataatagtca cccatgtctt cagcacaggc catttcctct cgactaagaa gcgcctcata   7980
aagcttctct ccatgacgcg tacctattac attgatagga taaccattct tgccaagcaa   8040
ttgagtaagc gcatgagcca gcacctcgat ggttgcagcc ggtgctttct gtacaaaaag   8100
atctccattg gtaccatgct cgaaagcata aagcacaagg tctacggcat ccgtaagcgt   8160
catcatgaaa cgtgtcatgt ttggatcagt gattgtgaga ggctggcctg atcgcatttg   8220
ctcgataaag agaggaatga ccgagcccct tgaagccatg acgttaccat aacgggtgcc   8280
acaaattacg gtaggagtgc gttccaggtt tcgagacttg gcgaccatga ccttttccat   8340
catggccttt gaaataccca tggcattgat tgggtaaact gccttatccg tactcagaca   8400
aacgactttt ttgacgccat tctggatagc agattcgagg acattttccg ttccgatgac   8460
attggtcttc acagcctcca tcgggtagaa ctcacaagag ggaacctgtt tcaatgcagc   8520
cgcatggaaa atgtagtcca caccgcgagt agcattcaga gtgctttgat agtcgcggac   8580
atctccaata taaaacctca acttggggtg agcatagcac ttacgcatat catcttgctt   8640
cttctcatcc cgactgaata cacgtatttc accaatatct gtatccagaa aacgcttcaa   8700
aacggcattt ccaaaggaac cagttccacc ggtaattaac agaacagagt tcttatccat   8760
acaccacctc tttacgtgta ggctggagct gcttcgaagt tcctatactt tctagagaat   8820
aggaacttcg gaataggaac ttcatttaaa tggcgcgcct tacgccccgc cctgccactc   8880
atcgcagtac tgttgtattc attaagcatc tgccgacatg gaagccatca caaacggcat   8940
gatgaacctg aatcgccagc ggcatcagca ccttgtcgcc ttgcgtataa tatttgccca   9000
tggtgaaaac gggggcgaag aagttgtcca tattggccac gtttaaatca aaactggtga   9060
aactcaccca gggattggct gagacgaaaa acatattctc aataaaccct ttagggaaat   9120
aggccaggtt ttcaccgtaa cacgccacat cttgcgaata tatgtgtaga aactgccgga   9180
aatcgtcgtg gtattcactc cagagcgatg aaaacgtttc agtttgctca tggaaaacgg   9240
tgtaacaagg gtgaacacta tcccatatca ccagctcacc gtctttcatt gccatacgta   9300
attccggatg agcattcatc aggcgggcaa gaatgtgaat aaaggccgga taaaacttgt   9360
gcttattttt ctttacggtc tttaaaaagg ccgtaatatc cagctgaacg gtctggttat   9420
```

```
aggtacattg agcaactgac tgaaatgcct caaaatgttc tttacgatgc cattgggata   9480
tatcaacggt ggtatatcca gtgatttttt tctccatttt agcttcctta gctcctgaaa   9540
atctcgacaa ctcaaaaaat acgcccggta gtgatcttat ttcattatgg tgaaagttgg   9600
aacctcttac gtgccgatca acgtctcatt ttcgccaaaa gttggcccag ggcttcccgg   9660
tatcaacagg gacaccagga tttatttatt ctgcgaagtg atcttccgtc acaggtaggc   9720
gcgccgaagt tcctatactt tctagagaat aggaacttcg gaataggaac taaggaggat   9780
attcatatgg tgcacggaag tttaaactta tttatcatca tcatctttat aatcaccatg   9840
atgacgccgt ccttttgtaa taaaatagaa caacacaaac caaaattcac ttacaactaa   9900
ataatttgaa ctaaacatta ataatgtgat tggatagatt gctataaaca taacgagtaa   9960
atctatagtg tttggatcat agttcctaat cattttataa actagtagca aaatgcaaat  10020
cattatgata aaaaacccta ataagccaaa tgatagaatc aactcaataa tgatgttatg  10080
tggtatattt ccgattagtt tataatagtt aaatggccca tagcctaata acggactttg  10140
ttgaataaag taaatacctt tttcataaat cggtcctctt ccagaagtac cttctaaatt  10200
aagtgttcca ccttgtagat atgaaaatgt tctagtattc gaaccttttg taaaaagaaa  10260
gtaaatcaat acactagata tgcttaatgc aaaaatatac ataatgcttt ttactgcaat  10320
aggtattcct cttttaaacg taataagtat aaatgcaaat aagccgtaaa gaattaataa  10380
aatagcacct ccacgccctc ctggtataaa cacaataggg atatcaatta ttgtaaatag  10440
aacatatatc cacttatgtt tcactgaacc tttcataatg aaataaatgc ctaatccggc  10500
agtaaatgct gaaaggtacg aagcgttttg atagttcata agtccaaaat tgatatagct  10560
aggtatctca cctgtaagtt ttggtattaa aattacaaaa ataaatgaaa tagaaaatat  10620
gaaaaatact aatttaaaaa atctttctac cgtagccttg tttatatatt taatataaat  10680
accactaatt gccgctggaa ctgcccatgt taaaaagaat agaatattat ttttagctag  10740
tttctcttcc ttatctggtg aaaaataata aaaagctaga taaagcaaac atatagcaat  10800
taataatatt aaccctcgcg gaatttcttg cgtgacaatt atcttataaa tagcaaacac  10860
cgtagtaatt aatgctatac caaccatggt tgagtaatac accggctcta tagggaaccc  10920
taatacttct ttagtaaatg tagagattac tataaatatg ttcatgctga taattgcaca  10980
aagtacaaaa aatttcatag ttcctcctgc tagaggatcc ccgggtcctt acagatcctc  11040
ttctgagatg agtttttgtt caaatttata taattctact aatcgttcac tttctatttg  11100
ccaattcaaa attttagacg ccttaattgc attttgacgt aaatgattaa acaaatcgtg  11160
attatctctt aattttctaa ccgccttttc aatttctaac ggcgtaactt cctttaaaac  11220
aatgccaaat ttatattttt cattgagata aatatgctct ttgacaggag ataaaattac  11280
tggtaaacca gcatgtatac attcaaaaat tttattagat actgtatatt caaaattaat  11340
agatacaggt ttcgtcaaga taacaccaac attactttct gctaacttat caaccaattc  11400
ttttacttca actggtttat ccaacctaat attttccgag ttataactaa tcagttcttt  11460
tatcacttct tcatgcggac caaaccctcg aattatgaat gaaggagcat tttgtttaaa  11520
agctgatgaa gcaataataa actcttcata tcctctgtcc attacaattt gaccttgata  11580
tacgatttct ttaaagtttt cgatttcttt aaattctctg ctatcattta aaataggtgc  11640
attcgtaata acattcgctt ccttcttata tcctttagat tgataatatt cttttgctgc  11700
atgacttact gttacgaagg cattaacacg atgttttact atgtgttttt ctatactttc  11760
```

```
tacaaacttt gaaataagtg gaactttatt aataaaggca tttttcgcat atatttcatg  11820
cgcatcataa acaatattag ctttttttata attgcttaaa tagaccatta ataatacgtc  11880
gaaatcattt gcatgaatca cgtcaggttt aaaagcttta atttctcgga taacacctgt  11940
tgcaaatctt atacgcttaa ttaatttaga aagaatattt ttgggatcta ccttgctacc  12000
taacaaacga taattacaat ctaaattttc caatcgccta ttagtagctt gtgaattatt  12060
cattccaaca attttataat cattcgtaac gcctttaatt gtttctattt gtttaagtac  12120
ccttgggtct tgaacaatat tactcgatac aatatttaaa attctcattg tacacctcct  12180
gctcattgta cacctcctgt tacgcataat ccggcacatc atacggataa ctagtatcct  12240
ttttatttaa atattcaacc gaaaatcctt ttagtttgtc aggcgttttc tcccaccact  12300
tgctttccaa aagtttttca attgttttat tgtcaaatcg cttcttaatc acttttgcag  12360
gaaccccacc aacaacctca tatgctccta catttttagt aacaactgag ccggctgcta  12420
tgactgcacc agtatttatt gttaatccat ccataataat tacatttgca ccaatccaca  12480
catcattttt aattgttgta cggcttggtt ggtcattaaa gtctataaac ttttgcttta  12540
tgttaaatgg attattatta gaataaaaaa tcggtgatga gctaaaaaag tgtgtaggat  12600
gttttcctaa cccaattttt acatccgaag atatcgaaca atatcttcct acttctacat  12660
tattaaaatc actaccaaat ccaatataac tgtattcacc aatgtgagaa ttcctgattt  12720
tacaccatct atctatatag ttattgccat caaattttga gtttgtaata tacgccaagc  12780
gatgaatctt aacattcgat tctttagagg actggttttt cagcaaacca attatctttt  12840
caatcgctat cctcatctta agatcaaagt ccccttttct ctctcaactt aaccgtggcc  12900
aggaaaaaca ttcccatccc caaagagacc tctgtaacga ccagcgtcca cgctccaaaa  12960
agctcatccc cccaaagcgc caagaggata aatgttaata ccccgcccaa ttccgcaaaa  13020
aaaattgctc gcaaatatac accatcatac ccagaaggaa caagagtcaa ccctccatac  13080
agaacaccaa tacaagcaaa cactggcact atcgaaaaca ttcttattac aacagttaga  13140
cctctggact gttccgggaa taggagatat gaaatgtatt cagaaaataa gaaaagaaat  13200
aaacaactag gaatagctat tagtaacatc agacctagcg ctttccttct taaactgccg  13260
actgccgggt cggcactcgc atacatcctg ctaaaagtcg gaaatagagc gctagctatg  13320
ggtgaagtag cagccgcgat cccgcgaagg aatttatccg cagtagaaag cactccggcc  13380
gcggaggctc caccaacaac accaaccgcc gcaacgagca cttgcatgtg caagctaaga  13440
aaagccagag aaagaaaaga tcgagcaccg tcacgcaata tatcgagaat tctgtctttc  13500
tcgagaaccg ggcgccaccg tattcccata gaaaataaaa tacaacagag agcacttcca  13560
cctatgacat aggaaaaacc aaaccccaac gaagccagca caaggtcaga atccttcgtg  13620
acaaaaaaaa cgaccaatag gaaataaaat accttagaca aaaaattggt aagcgccaac  13680
catccaaaca gcgctcttcc ctgaaagaac catactgctt gaagataatt tccaactact  13740
gccggaagag cagccgcaac caatacaagc aaggggattg gtaaaataga agatacagcc  13800
aaaatggcca gcactaaaag tgaaagcagc aacaataaga atctagcact ctgtacaaca  13860
gaaaagaaac tagacagttc aactttgtta tcgataatgg cagcctttct tgatcctgcc  13920
agaataaatc caaagtctac cagttgacat agaatgacag ccacggcctg ggcaatcacc  13980
aattggccaa acgcttcgct tgacaatgtt ctcgtgagaa aaggaatcgc agcaagaggc  14040
aaaagatagt tgctgcccat ggatataccg gagtagaaaa cgccccgcct tattgacatt  14100
ctactcgata ccccctaata caattcaaca actacaacaa gtaagccctg atgccagtaa  14160
```

```
gtggcatcag ggtttagatc aaaacttagc gaagagagcc atcgctacga agcttcctta  14220

taaaaccagc gagcactgcg agtagaattc caattatcaa tcctgccaaa gtacctatag  14280

taactataag aatcttcttc ggcttaatgg gttgatttga aaaagagagt ccctcgtctt  14340

ccttgtagac agccaccgca tcagaatcca cagacaaact ggagttccaa gatagtttct  14400

cttggagagt tctcaactca ggaatgaatg gagcatctac actacgcgac tcaagattgt  14460

tgatttcagc gcgcagcgcc ttagctcctc gcatgtacat caagtcacca tccatgatcg  14520

aggagagttg ttgctcggac gccccttcta ttaatggcgg gccatctatc ttgagcgact  14580

ccgcaatcag caatgcctcc ttcaaacgtg caattctatc atcacggcgg cccttcgcca  14640

tattctgcag cacggttatg cggctctgca ttgcagcatt tcttacctgg aaatctctac  14700

ctgcactatc aataacctca tgcacggccc gatccgcagc caaacgcacg aaagcttgtg  14760

cccatgtagc aagaacctct cgcttcgtgc cctccacaat taccgtataa cggtctgcat  14820

ctggcttgtt agcaggatca atctttacct ctttggagaa cttcttataa aactcctcct  14880

gctcatcttc gctttccgct ccctcaccca cctggggaag gtatatctta tagaagaact  14940

ctttttttatt ctcatccgaa agcagattgc gcgaaaagat cgcatagata cttctaacag  15000

tatatgcatc taggccattc tcccttctac caacattgaa accttcgata gacccaagag  15060

caggaggcac tactgcaacc ctatattcat atacaggctt actcagatac gcataggtaa  15120

aagacccgat taatgcaaga agagtagtca gaagaatcag aaccttgtta acccaaagct  15180

ccttgaccag cttcaccagg tcaacctcac catcagccgt catcaaagaa gaattgcctc  15240

aggg                                                               15244
```

```
<210> SEQ ID NO 3
<211> LENGTH: 16483
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

tcacatgttg cccatccacg aaaccacctt atcgccgtgg aacgcacctg gatcgacagc     60

cccagcaaag cagtcgcttc ctggtccggc accggaaaca tcgtacggag aaaacaaaaa    120

aggccgctag gcggcctttt ccggagaacg atgactcagg gttctcgccg cctctggcga    180

tagatccagt cgacgatttc accgtcaggc gcatagccgc tgacggtttc ccgcagcaac    240

tggcgaaccc gcgagtagtc gtccttctcc acggcggcca gcaactgctc cagcacgacc    300

ttgaaggcct cccagctcag gtgttcctcg ttggcccgca tgatcatcgg atggtcggtg    360

ggattcacgt tgtcaccgat cagcagctct tcgtagagct tctcgccagg acgcaggcca    420

ctgaactcga tggcgatgtc accatggggc gaacgctcgg aacgcacgct caggccggac    480

aggtggatca tcttctcggc gagctccagg atcttcaccg gcggccccat gtccagcacg    540

aatacatctc cgccctgccc catcgaaccg gcctggatga ccaactgcgc cgcctcggga    600

atggtcatga agtaacgggt gatgctcggg tgggtgaccg tcaccgggcc gccgcgcttg    660

atctgctcgc ggaacagcgg aatgaccgaa ccggacgaac cgaggacgtt gccgaagcgg    720

accatggtga aacgggtctt gttgacgtga tgcacgtcct tccggtcgcc gaacagcacc    780

ggcgccgatt cgttgctgag cgcctgaagg accatttccg ccaggcgctt ggtgctgccc    840

atcacattgg tcggccgcac cgccttgtcg gtggaaatca gcacgaagtt ctgcacgccg    900
```

```
acctgcaccg cggcctgcac cgcatgcaag gtgcctatca cgttgttgag aacgccctcg    960
gcgatgttgt gctcgacgat cggcacatgc ttgtaggccg ccgcatggta gacggtattg   1020
accttccagg tacgcatcac gtccaccagg cgctcgggat tgcgcaccga accgaggatc   1080
ggcaacaggt tcaccgaaag cgactcgcgc ttgatccgac gctccagttc ctgatggatg   1140
ctatagaggt tgtattcgct gtgttcgaac aggatcagca cgctaggcga acaactcatg   1200
atctgccgac agagttccga accgatagag ccgcccgccc cggtcaccat caccacctga   1260
ccgcggatgc accgttccag cagctccttg cgcggtgcga cgctgtcgcg ccccagcagg   1320
tcagcgatgt ccacctcctg caggtcatcc accttgaccc ggccgctggc caggtccatg   1380
aagccgggca tgctgcgcac gtgcagcggg aacggctcca gggactcgag aatctctcgg   1440
cgccgggccc gagtggcgga aggaatcgcc aggagaacct cctgcgcgcc cgtctcgtcg   1500
atcatctggc ggatatgctt ggcggtatag acccgcagac cggcaatgac ccggttggcg   1560
atctgcttgt cgtcatcgat gaacgccacc ggacgcatcg cccgaccgag acgcaacgcc   1620
gcaaccaact ggttgccggc cgccccgcc ccatagataa ccaccctggg caggccatcc    1680
tggcggttga gaaatggtac cgactgcaca gcagagtacc agtcgcccat gaaatactgg   1740
cgcatggcca gacgcaagcc gccgatcagc agcatgctca accaccagta gttgaacacc   1800
agggaacgcg gcaccggcgc cggcgcgcca cgataccagt acaccaccag cgacagcacc   1860
agagccgaga tggtcaccgc cttggcgatg gcgatcaatg cgtcgttacc gagatagcgc   1920
atcaccgcgc gatacatgcc gaagcgaatg aatagtggaa tggcgatgac cggcgcagtg   1980
atgaaaagcc atgcatgctc gccgaacacg tcgatcatat cgtctgtgcc tagacggacc   2040
acaaaagcga gccacagaga cagccatacc agaaggatat ccgtagccac ttgaagcaaa   2100
cgtttccagc gacgaggcat ggataacaac tttactctta aacgatctag cattccccta   2160
ctcctttagg cctgagcgga cgactctagc ttacccgcct tgaacctcac tgccagaaaa   2220
acgagaggga cgtaggctat gacgatgccc atcaaaggct ctagagaccc actcccgacc   2280
aacaaggcta tagggaggag ccagatgacg ttcaatgccg tgacgccaat cgtaacagga   2340
gcatgctttc catagtatcg gcttgcgtat tgataggcat ggcttcgatg agcctcatac   2400
accttgtccc ctctcagcaa gcgacgaatc agggtatagg tcgcatcgac gatgaaaacg   2460
cctaacagga ccaaccatgc ccagaaaaaa ttcgtattca tccacatggc atgaatggaa   2520
agaattccta aaacaatccc cagaagacca ctacccgcat ctcccatgaa aatttttggg   2580
ggtggaaaat tccagaacaa gaatccaaaa acggcaaaag ctagcgataa ggggagcaaa   2640
gcctgcgtca gttggccatt cagccagtat aataatgccc caccaacaca gacaaaaatg   2700
gcctgaaggc tagcaagtcc atcgatccca tccatgaagt tatagagatt cagcaaccac   2760
acgagataga aagcaaagag aagtcctccg aaccacccca ggtcccaact gacaccaaca   2820
atctgaaatg gtggtatgcc attcaaaaag tacaatgaga ccaaggctgc actaaaatgt   2880
cccagcagac gccagcgtgc ggcgatatga ccgtgatcat ccatgaatcc aataatggca   2940
accccgccgc cagcgagaag taaagcccag gacacggccc atgagatatt tcccagtaca   3000
gcccaaatag gcagcatgag acaaaaagta actacaatgg cgacccctcc tccgcgtgga   3060
gtgggaacga catgggaact tcgagagtta ggggtgtcaa gtaagctcct cgctaaggca   3120
taacgacgca agaggcctgt aagcagtccc gaaaccccag ctgcagcgag taacaaatac   3180
cattcttcca tttataaatt tatccccaaa aatactctca cccctcaac agggttctat    3240
```

```
tcgattgttc tgcgtggtac gccatgctag tagcaaagcg cctgcagata atcattcagt   3300
acgtttgaca tatattctac caacatcttc caacgcggaa agggtgctct tgcggggttc   3360
ccaaccaagc aaaagcctgc ctttcgacga gtcgacctct agtgagcagc ataactgagt   3420
gtataaccca ccctttccta ctaatttaag aaacctcaga ataaacctag gaacaggcca   3480
catgatgggg cgacgcccca ttcccgcagc aagcgcagtc accagttgct tggtagaaat   3540
ctcctgacca tcggatacca aaaacagttc gccggcagca gaagggtgcg tcatacagca   3600
agctagaaag tcaactaaat tatccagaga aacaaaactt cgtcggttat ctatgcaacc   3660
aaatggaaga ggaagtcccg aagcaaccag cttcaacaat cgcgagaaat ttccaggagc   3720
tttccagtcg taaacgagtg gaggcctgac gataacaagt tctgttgagg aatgcttgaa   3780
aagctcccga agcgctactt cagcctcaaa ctttgaaatc gcatattctg catgaggagc   3840
cggcttggag ttctcatcga agggcttttc tttggttaaa gcgccattta caccaataga   3900
actaacaaaa atgaaacgct ttacagatgc ttcgatcgcc tgccgagcaa gcgccagagt   3960
agcatcgcga ttcaccttcc gaaaaatatc tagtgaatca cgctgccttc caaagatatg   4020
ggctcgtcca gctagatgaa ctacacattc aacaccccgc agcgcagcat caagcttagt   4080
gctctctttc agctccgctc gaacatactc aaccccccgta acgggattgt acagggatcg   4140
tacttgtccg acaacctgaa agggggcggc agcaagcgac ctgcaaagcg cactcccgac   4200
aaaaccgcta gccccggtta ccagcacctt catcatattt tcgactcaga cagaagcggt   4260
cgaacacagg cagcgaattt ttccaatgaa atatattcag aataattttg ctgaaggaca   4320
ctccgcggga ctccgcctaa actagacaag tcgagttcac aaatctcatc gatcaatctt   4380
gccaaagcaa ccggatcatt cggcggacag ttccaaccga ttccggtctc atctattata   4440
cgggagattt cagccccttt ttccatgaca gctagaatcg gtttgtctgc tgccatggag   4500
aaatatgcct tgctgggaac cccaagcccg aacattcctt cttctaaggt aactaaggca   4560
acgtcacagg cagccaaacc aaaattcttt tcggctaatg gcagccttcc aaaatacctc   4620
aaccgagcac actgatcttc cagcgcgtgt ttttttacac tgtcgaccaa ggcaccatct   4680
ccaataaaag caaaagccgc cttctcgttt ttaaccaact gaatagcaga aagtatgttt   4740
tctatacctt gtaatcgacc gacattacca aaaaattgga aaccctttt acctttccat   4800
tcaggaatat tgataaaagg agcatcctct ctcggtactg ggaaaacctc tttctcacag   4860
gcccaattcg aaataaagac caaagatcgc gggtcattca ccttctcttt cataagagct   4920
tccatatcgc gccctattac gactagacga tcagcggatg agtaaatgaa agaaaagaga   4980
cgacgtagaa gccggtaggc aatactatct ttcttcagaa cgcccgccgg caccaagttc   5040
tcgggaaaca catcatgcac cagcagcacc cacttgaaac cgagggcata ccttagcaag   5100
ggaaacgtca tcagtagaag agcagggttg gttccactca ataccacatc tcctcgtctg   5160
gcacgagaag tcaattttac tgagaacaga aacgcctgaa aaatctgcgc caatcctcta   5220
gaaaggagcc tattcttatt gctcctcgga aacttaaagc attcttgctc aacggaaggt   5280
gaaaccacag gcggggtttc acctgcggtc agcgggaaaa ttacggttag cccaccaaac   5340
tcccgctgca tctttcctat tatcttctcc caatagtatc ccgtggagtt ctgattggca   5400
ccgacatact cagaaaccac aaatatcctt gccatcaact ccacgcctca agttaatatt   5460
ttttccagac agttcgcatg acatagtccc gatagctatg aactatgcga acaatctttt   5520
cagaaacgtt gggcatgcta tagtcagcga ccaagcgtaa catgcgctct gcgtcgcgcc   5580
tctgtccctc caacacctcg agtgcttgta gtactcgatc cgaatccagt ccgaccatca   5640
```

```
tcaccacagc ctcttccatg ccttctgggc gttcatgagc ctcacgaata ttcaaagcgg   5700
gaaaattcag tattgaagac tcctcactga tggtcccact gtcagaaata actgccttgg   5760
ctgtaatttg cagtttattg taatccttaa agccgagggg tttcagcagt ttaataccct   5820
cgtgaaactt tgcctccgtc gcctcaattc tctttttgt tctagggtga gttgatacga    5880
tgacgggcag cgagtacttt tctgccacag cgttgagcat agaaaccaac ttcaagaaat   5940
tcttatccga atctatgttt tcctctcggt gcgcactcac gacaaagaac cgctctgttt   6000
tcaacccgag cctttcaaga atatcggagg actcgatccc gtcacgatag tgctcgagaa   6060
cttcgaacat agggctacca gtcttgataa ccatgtctgg agaaagtcct tcacgcaaga   6120
gataatcacg cgcaattgta ctataggtca aatttacatc agctgtatga tcgacaatgc   6180
gccgatttat ctcttcaggc acacgcatat cgaaacagcg attgcctgct tccatatgaa   6240
aggtcggtat cttacgccgt tttgcaggca gtaccgccat acaactattg gtatcaccca   6300
gcacgagcag cgcatcggga tctatttcgc ccagaacacg atcgactgcg attattacat   6360
tccctatcgt ttcagccccg gaagacccgg cggcgtttag aaaataatcc ggctttctta   6420
taccgaggtc ctgaaaaaat atttcattaa gttcgtaatc ataattctgt ccagtatgga   6480
caagtacatg atcgcagtac tgatcaagct tcgccatgac cctagacaag cgaataatct   6540
caggacgagt tccaacaacc gtaacgactt ttagcttctg cattgttatc tcactatacc   6600
ttacgcacct tcgcctactg aacaagcgta ggtatccgga ttttcccgat caaatacttc   6660
gttagcccac aacatgacta ccatatcgtc agttccgaca ttagtaatgt catgagtcca   6720
tccaggtact gtttcgacaa tttctgcctt ttcaccatta gtgcaaattt cgtaaaatgc   6780
cccggtcagg atgtttctaa acttgaaacg tgccatccct ttgataacca gaaacttttc   6840
ggttttcgag tgatggtaat gcccgcccct ggtaacacct ggatgagccg taaaaaacga   6900
gaactggcca gagtccgcgg tcttcagcat ctcgacgaat gtgccacgcg gatccgaatg   6960
cattggcacg tcgtaactaa aactatcttc tggcaagaaa cttagataag tcgagtacaa   7020
ggcgcgcgtc aatcccgagc caacccttgc ggtagtcagt gactttcgac tattacgaaa   7080
ctcatacaat tgttctgcga gctcaccaac agaaatctga tactggggct cgacctgtag   7140
tgaaactgca ttggatagct tcccatccat gactttcatg aaggtgcgaa ccacatcatc   7200
tatgtataca agagtgatct ctgccgagga attgttaatt tgaatcggaa tatctcgaat   7260
aatattatga caaaaagtcg caaccgctga attataattc ggacgcgacc atttaccgaa   7320
tacattagga aggcgaaata tgtagacagg acaaccaata tcctcaccta gcacttggag   7380
atgctcttct gcggctcgct tgcttaaacc gtactcatta tccacctcag cctgaatgga   7440
tgaagtataa agaagtggta tggctcgtcc attggacctt accgcctcac acagagcata   7500
cgtgagttcg gaattcccga tcttaaactc ttctggtttt tccggacgat tgaccccggc   7560
aagatgaaaa ataaaatcga cggaacgaat tagctcaggc aaattaccaa cactactctc   7620
gcgggtgaat ggcaccacct cgataccacc ccgctctgca agatgagcgc acagattcct   7680
tccaacaaat ccattcgcgc cagttacaag aactttcatc gtttattcct ctggactggc   7740
actctcgcca cgctgaatag cacgaatgaa atccaacttc agcaacagct tttcattcc    7800
ttcgatatcc agacgtttgg tattatgaga attatagtcc tctgtatgag taattttttc   7860
ctcgccttgc tccacaaact tactatagtt cagatcacgc aaatctgggg ggatacgata   7920
atagtcaccc atgtcttcag cacaggccat ttcctctcga ctaagaagcg cctcataaag   7980
```

```
cttctctcca tgacgcgtac ctattacatt gataggataa ccattcttgc caagcaattg   8040
agtaagcgca tgagccagca cctcgatggt tgcagccggt gctttctgta caaaaagatc   8100
tccattggta ccatgctcga aagcataaag cacaaggtct acggcatccg taagcgtcat   8160
catgaaacgt gtcatgtttg gatcagtgat tgtgagaggc tggcctgatc gcatttgctc   8220
gataaagaga ggaatgaccg agccccttga agccatgacg ttaccataac gggtgccaca   8280
aattacggta ggagtgcgtt ccaggtttcg agacttggcg accatgacct tttccatcat   8340
ggcctttgaa atacccatgg cattgattgg gtaaactgcc ttatccgtac tcagacaaac   8400
gactttttg acgccattct ggatagcaga ttcgaggaca ttttccgttc cgatgacatt   8460
ggtcttcaca gcctccatcg ggtagaactc acaagaggga acctgtttca atgcagccgc   8520
atggaaaatg tagtccacac cgcgagtagc attcagagtg ctttgatagt cgcggacatc   8580
tccaatataa aacctcaact tggggtgagc atagcactta cgcatatcat cttgcttctt   8640
ctcatcccga ctgaatacac gtatttcacc aatatctgta tccagaaaac gcttcaaaac   8700
ggcatttcca aaggaaccag ttccaccggt aattaacaga acagagttct tatccataca   8760
ccacctcttt acgtgtaggc tggagctgct tcgaagttcc tatactttct agagaatagg   8820
aacttcggaa taggaacttc atttaaatgg cgcgccttac gccccgccct gccactcatc   8880
gcagtactgt tgtattcatt aagcatctgc cgacatggaa gccatcacaa acggcatgat   8940
gaacctgaat cgccagcggc atcagcacct tgtcgccttg cgtataatat ttgcccatgg   9000
tgaaaacggg ggcgaagaag ttgtccatat tggccacgtt taaatcaaaa ctggtgaaac   9060
tcacccaggg attggctgag acgaaaaaca tattctcaat aaaccctta gggaaatagg   9120
ccaggttttc accgtaacac gccacatctt gcgaatatat gtgtagaaac tgccggaaat   9180
cgtcgtggta ttcactccag agcgatgaaa acgtttcagt ttgctcatgg aaaacggtgt   9240
aacaagggtg aacactatcc catatcacca gctcaccgtc tttcattgcc atacgtaatt   9300
ccggatgagc attcatcagg cgggcaagaa tgtgaataaa ggccggataa aacttgtgct   9360
tatttttctt tacggtcttt aaaaaggccg taatatccag ctgaacggtc tggttatagg   9420
tacattgagc aactgactga aatgcctcaa aatgttcttt acgatgccat tgggatatat   9480
caacggtggt atatccagtg atttttttct ccattttagc ttccttagct cctgaaaatc   9540
tcgacaactc aaaaaatacg cccggtagtg atcttatttc attatggtga aagttggaac   9600
ctcttacgtg ccgatcaacg tctcattttc gccaaaagtt ggcccagggc ttcccggtat   9660
caacagggac accaggattt atttattctg cgaagtgatc ttccgtcaca ggtaggcgcg   9720
ccgaagttcc tatactttct agagaatagg aacttcggaa taggaactaa ggaggatatt   9780
catatggtgc acttacgcat aatccggcac atcatacgga taactatcga cgtccttttt   9840
attaatgaat ttagacttta aacctataat atttaaaatc acatacttaa taatgttgct   9900
gaacagcgtt gtccaaaaga atccatttag accaaacgca attgtcatta aaatagttat   9960
gaatataaat gtaatcgtgt gaagcgtcat ataattcgct tgtaatgtta ttgatgcgtg  10020
ttttgtattt aaagtttgga tcataatact cactgcattg aataaaacac ctatattacc  10080
taaaataata aacttcgaat ataaacttga atcaatgtta tacagtaaag agacaataat  10140
taatgtaatt ggataacata taatcatgac taaacatagt gcagctatag caaatagatt  10200
agttttcaaa tattgcttct ttatattgtc gctttcattt acagaaatat atgaaagtac  10260
tacattatta atcggataca gaaatgtagc taacattttc ccaataaatg ttgaaagaaa  10320
tgatatagtt acagctgttc cacctataat tggtaataag attaatctat ctaagtagag  10380
```

```
attcaaatta ttaaggctat ttgtactcag tagcatcaca taatctttga ccacattatt  10440
atcttcactt tgatactcgc ctatagttaa tccccgtaat ttaaccaatg tatatatcgt  10500
tgcaaacaat tcactggtaa taaaacaaac aatccagttt tggattaaat aatatagaaa  10560
tagtcctatc agcaaaccta aaaattgaat aagagcaata tacaaaatct gattatattt  10620
taaagtcatc ctaaaaaata cattcagata aatccttaaa cacattaaaa tattaagtag  10680
aattaaaaag ataatatcga tggtgttcaa attaaaaaag taaagaaata caataattaa  10740
agctatactc tcaatcagaa ttgaaattaa aagtatcgac acaaatttcc agtagtaatg  10800
attggatttg tatagattca tattaattaa tcgtatattg ttaagcgtat tgcctaatac  10860
aacactcgtg attgttatta ttgtataaat cgttaaaata gaaccaaacg cttcattacc  10920
tactcgttga ttaataattg gataagctaa aaattgtaat cctaaagcta taagcaacgt  10980
accaattatt gtctttacgc tatccataat aaaaactttc ttaaccatga tgcctcctgt  11040
ttaaacttat ttatcatcat catctttata atcaccatga tgacgccgtc cttttgtaat  11100
aaaatagaac aacacaaacc aaaattcact tacaactaaa taatttgaac taaacattaa  11160
taatgtgatt ggatagattg ctataaacat aacgagtaaa tctatagtgt ttggatcata  11220
gttcctaatc attttataaa ctagtagcaa aatgcaaatc attatgataa aaaaccctaa  11280
taagccaaat gatagaatca actcaataat gatgttatgt ggtatatttc cgattagttt  11340
ataatagtta aatggcccat agcctaataa cggactttgt tgaataaagt aaataccttt  11400
ttcataaatc ggtcctcttc cagaagtacc ttctaaatta agtgttccac cttgtagata  11460
tgaaaatgtt ctagtattcg aaccttttgt aaaaagaaag taaatcaata cactagatat  11520
gcttaatgca aaaatataca taatgctttt tactgcaata ggtattcctc ttttaaacgt  11580
aataagtata aatgcaaata agccgtaaag aattaataaa atagcacctc cacgccctcc  11640
tggtataaac acaataggga tatcaattat tgtaaataga acatatatcc acttatgttt  11700
cactgaacct ttcataatga aataaatgcc taatccggca gtaaatgctg aaaggtacga  11760
agcgttttga tagttcataa gtccaaaatt gatatagcta ggtatctcac ctgtaagttt  11820
tggtattaaa attacaaaaa taaatgaaat agaaaatatg aaaaatacta atttaaaaaa  11880
tctttctacc gtagccttgt ttatatattt aatataaata ccactaattg ccgctggaac  11940
tgcccatgtt aaaaagaata gaatattatt tttagctagt ttctcttcct tatctggtga  12000
aaaataataa aaagctagat aaagcaaaca tatagcaatt aataatatta accctcgcgg  12060
aatttcttgc gtgacaatta tcttataaat agcaaacacc gtagtaatta atgctatacc  12120
aaccatggtt gagtaataca ccggctctat agggaaccct aatacttctt tagtaaatgt  12180
agagattact ataaatatgt tcatgctgat aattgcacaa agtacaaaaa atttcatagt  12240
tcctcctgct agaggatccc cgggtcctta cagatcctct tctgagatga gtttttgttc  12300
aaatttatat aattctacta atcgttcact ttctatttgc caattcaaaa ttttagacgc  12360
cttaattgca ttttgacgta aatgattaaa caaatcgtga ttatctctta attttctaac  12420
cgccttttca atttctaacg gcgtaacttc ctttaaaaca atgccaaatt tatatttttc  12480
attgagataa atatgctctt tgacaggaga taaaattact ggtaaaccag catgtataca  12540
ttcaaaaatt ttattagata ctgtatattc aaaattaata gatacaggtt tcgtcaagat  12600
aacaccaaca ttactttctg ctaacttatc aaccaattct tttacttcaa ctggtttatc  12660
caacctaata ttttccgagt tataactaat cagttctttt atcacttctt catgcggacc  12720
```

```
aaaccctcga attatgaatg aaggagcatt ttgtttaaaa gctgatgaag caataataaa 12780
ctcttcatat cctctgtcca ttacaatttg accttgatat acgatttctt taaagttttc 12840
gatttcttta aattctctgc tatcatttaa aataggtgca ttcgtaataa cattcgcttc 12900
cttcttatat cctttagatt gataatattc ttttgctgca tgacttactg ttacgaaggc 12960
attaacacga tgttttacta tgtgtttttc tatactttct acaaactttg aaataagtgg 13020
aactttatta ataaaggcat ttttcgcata tatttcatgc gcatcataaa caatattagc 13080
tttttataa ttgcttaaat agaccattaa taatacgtcg aaatcatttg catgaatcac 13140
gtcaggttta aaagctttaa tttctcggat aacacctgtt gcaaatctta tacgcttaat 13200
taatttagaa agaatatttt tgggatctac cttgctacct aacaaacgat aattacaatc 13260
taaattttcc aatcgcctat tagtagcttg tgaattattc attccaacaa ttttataatc 13320
attcgtaacg cctttaattg tttctatttg tttaagtacc cttgggtctt gaacaatatt 13380
actcgataca atatttaaaa ttctcattgt acacctcctg ctcattgtac acctcctgtt 13440
acgcataatc cggcacatca tacggataac tagtatcctt tttatttaaa tattcaaccg 13500
aaaatccttt tagtttgtca ggcgttttct cccaccactt gctttccaaa agtttttcaa 13560
ttgttttatt gtcaaatcgc ttcttaatca cttttgcagg aaccccacca acaacctcat 13620
atgctcctac atttttagta acaactgagc cggctgctat gactgcacca gtatttattg 13680
ttaatccatc cataataatt acatttgcac caatccacac atcattttta attgttgtac 13740
ggcttggttg gtcattaaag tctataaact tttgctttat gttaaatgga ttattattag 13800
aataaaaaat cggtgatgag ctaaaaaagt gtgtaggatg ttttcctaac ccaattttta 13860
catccgaaga tatcgaacaa tatcttccta cttctacatt attaaaatca ctaccaaatc 13920
caatataact gtattcacca atgtgagaat tcctgatttt acaccatcta tctatatagt 13980
tattgccatc aaattttgag tttgtaatat acgccaagcg atgaatctta acattcgatt 14040
ctttagagga ctggtttttc agcaaaccaa ttatcttttc aatcgctatc ctcatcttaa 14100
gatcaaagtc cccttttctc tctcaactta accgtggcca ggaaaaacat tcccatcccc 14160
aaagagacct ctgtaacgac cagcgtccac gctccaaaaa gctcatcccc ccaaagcgcc 14220
aagaggataa atgttaatac cccgcccaat tccgcaaaaa aaattgctcg caaatataca 14280
ccatcatacc cagaaggaac aagagtcaac cctccataca gaacaccaat acaagcaaac 14340
actggcacta tcgaaaacat tcttattaca acagttagac ctctggactg ttccgggaat 14400
aggagatatg aaatgtattc agaaaataag aaaagaaata aacaactagg aatagctatt 14460
agtaacatca gacctagcgc tttccttctt aaactgccga ctgccgggtc ggcactcgca 14520
tacatcctgc taaaagtcgg aaatagagcg ctagctatgg gtgaagtagc agccgcgatc 14580
ccgcgaagga atttatccgc agtagaaagc actccggccg cggaggctcc accaacaaca 14640
ccaaccgccg caacgagcac ttgcatgtgc aagctaagaa aagccagaga aagaaaagat 14700
cgagcaccgt cacgcaatat atcgagaatt ctgtctttct cgagaaccgg gcgccaccgt 14760
attcccatag aaaataaaat acaacagaga gcacttccac ctatgacata ggaaaaacca 14820
aaccccaacg aagccagcac aaggtcagaa tccttcgtga caaaaaaaac gaccaatagg 14880
aaataaaata ccttagacaa aaaattggta agcgccaacc atccaaacag cgctcttccc 14940
tgaaagaacc atactgcttg aagataattt ccaactactg ccggaagagc agccgcaacc 15000
aatacaagca aggggattgg taaaatagaa gatacagcca aaatggccag cactaaaagt 15060
gaaagcagca acaataagaa tctagcactc tgtacaacag aaaagaaact agacagttca 15120
```

```
actttgttat cgataatggc agcctttctt gatcctgcca gaataaatcc aaagtctacc  15180

agttgacata gaatgacagc cacggcctgg gcaatcacca attggccaaa cgcttcgctt  15240

gacaatgttc tcgtgagaaa aggaatcgca gcaagaggca aaagatagtt gctgcccatg  15300

gatataccgg agtagaaaac gccccgcctt attgacattc tactcgatac cccctaatac  15360

aattcaacaa ctacaacaag taagccctga tgccagtaag tggcatcagg gtttagatca  15420

aaacttagcg aagagagcca tcgctacgaa gcttccttat aaaaccagcg agcactgcga  15480

gtagaattcc aattatcaat cctgccaaag tacctatagt aactataaga atcttcttcg  15540

gcttaatggg ttgatttgaa aaagagagtc cctcgtcttc cttgtagaca gccaccgcat  15600

cagaatccac agacaaactg gagttccaag atagtttctc ttggagagtt ctcaactcag  15660

gaatgaatgg agcatctaca ctacgcgact caagattgtt gatttcagcg cgcagcgcct  15720

tagctcctcg catgtacatc aagtcaccat ccatgatcga ggagagttgt tgctcggacg  15780

ccccttctat taatggcggg ccatctatct tgagcgactc cgcaatcagc aatgcctcct  15840

tcaaacgtgc aattctatca tcacggcggc ccttcgccat attctgcagc acggttatgc  15900

ggctctgcat tgcagcattt cttacctgga aatctctacc tgcactatca ataacctcat  15960

gcacggcccg atccgcagcc aaacgcacga aagcttgtgc ccatgtagca agaacctctc  16020

gcttcgtgcc ctccacaatt accgtataac ggtctgcatc tggcttgtta gcaggatcaa  16080

tctttacctc tttggagaac ttcttataaa actcctcctg ctcatcttcg ctttccgctc  16140

cctcacccac ctggggaagg tatatcttat agaagaactc tttttattc tcatccgaaa  16200

gcagattgcg cgaaaagatc gcatagatac ttctaacagt atatgcatct aggccattct  16260

cccttctacc aacattgaaa ccttcgatag acccaagagc aggaggcact actgcaaccc  16320

tatattcata tacaggctta ctcagatacg cataggtaaa agacccgatt aatgcaagaa  16380

gagtagtcag aagaatcaga accttgttaa cccaaagctc cttgaccagc ttcaccaggt  16440

caacctcacc atcagccgtc atcaaagaag aattgcctca ggg                   16483
```

<210> SEQ ID NO 4
<211> LENGTH: 16660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
aattccctga ggcaattctt ctttgatgac ggctgatggt gaggttgacc tggtgaagct     60

ggtcaaggag ctttgggtta acaaggttct gattcttctg actactcttc ttgcattaat    120

cgggtctttt acctatgcgt atctgagtaa gcctgtatat gaatataggg ttgcagtagt    180

gcctcctgct cttgggtcta tcgaaggttt caatgttggt agaagggaga atggcctaga    240

tgcatatact gttagaagta tctatgcgat cttttcgcgc aatctgcttt cggatgagaa    300

taaaaaagag ttcttctata agatatacct tccccaggtg ggtgagggag cggaaagcga    360

agatgagcag gaggagtttt ataagaagtt ctccaaagag gtaaagattg atcctgctaa    420

caagccagat gcagaccgtt atacggtaat tgtggagggc acgaagcgag aggttcttgc    480

tacatgggca caagctttcg tgcgtttggc tgcggatcgg gccgtgcatg aggttattga    540

tagtgcaggt agagatttcc aggtaagaaa tgctgcaatg cagagccgca taaccgtgct    600

gcagaatatg gcgaagggcc gccgtgatga tagaattgca cgtttgaagg aggcattgct    660
```

```
gattgcggag tcgctcaaga tagatggccc gccattaata gaaggggcgt ccgagcaaca    720
actctcctcg atcatggatg gtgacttgat gtacatgcga ggagctaagg cgctgcgcgc    780
tgaaatcaac aatcttgagt cgcgtagtgt agatgctcca ttcattcctg agttgagaac    840
tctccaagag aaactatctt ggaactccag tttgtctgtg gattctgatg cggtggctgt    900
ctacaaggaa gacgagggac tctcttttc aaatcaaccc attaagccga agaagattct    960
tatagttact ataggtactt tggcaggatt gataattgga attctactcg cagtgctcgc   1020
tggttttata aggaagcttc gtagcgatgg ctctcttcgc taagttttga tctaaaccct   1080
gatgccactt actggcatca gggcttactt gttgtagttg ttgaattgta ttagggggta   1140
tcgagtagaa tgtcaataag gcggggcgtt ttctactccg gtatatccat gggcagcaac   1200
tatcttttgc ctcttgctgc gattcctttt ctcacgagaa cattgtcaag cgaagcgttt   1260
ggccaattgg tgattgccca ggccgtggct gtcattctat gtcaactggt agactttgga   1320
tttattctgg caggatcaag aaaggctgcc attatcgata acaaagttga actgtctagt   1380
ttcttttctg ttgtacagag tgctagattc ttattgttgc tgctttcact tttagtgctg   1440
gccattttgg ctgtatcttc tattttacca atccccttgc ttgtattggt tgcggctgct   1500
cttccggcag tagttggaaa ttatcttcaa gcagtatggt tctttcaggg aagagcgctg   1560
tttggatggt tggcgcttac caatttttttg tctaaggtat tttatttcct attggtcgtt   1620
ttttttgtca cgaaggattc tgaccttgtg ctggcttcgt tggggtttgg tttttcctat   1680
gtcataggtg gaagtgctct ctgttgtatt ttattttcta tgggaatacg gtggcgcccg   1740
gttctcgaga aagacagaat tctcgatata ttgcgtgacg gtgctcgatc ttttctttct   1800
ctggcttttc ttagcttgca catgcaagtg ctcgttgcgg cggttggtgt tgttggtgga   1860
gcctccgcgg ccggagtgct ttctactgcg gataaattcc ttcgcgggat cgcggctgct   1920
acttcaccca tagctagcgc tctatttccg actttagca ggatgtatgc gagtgccgac   1980
ccggcagtcg gcagtttaag aaggaaagcg ctaggtctga tgttactaat agctattcct   2040
agttgtttat ttcttttctt attttctgaa tacatttcat atctcctatt cccggaacag   2100
tccagaggtc taactgttgt aataagaatg ttttcgatag tgccagtgtt tgcttgtatt   2160
ggtgttctgt atggagggtt gactcttgtt ccttctgggt atgatggtgt atatttgcga   2220
gcaatttttt ttgcggaatt gggcggggta ttaacattta tcctcttggc gctttggggg   2280
gatgagcttt ttggagcgtg gacgctggtc gttacagagg tctctttggg gatgggaatg   2340
tttttcctgg ccacggttaa gttgagagag aaaaggggac tttgatctta aggcgatcgc   2400
taggaggaca gctatgcgta ttgcgattct gggcgcgacc aacattaaac atatgagcct   2460
gctgagccat tatctgaacc atattgatct gaacattaac gaagtggata ttatttatac   2520
cgataaatat gatattgaag aacatattca gggcatcaac aactactaca aatacaaagt   2580
ggatatcaaa gaagattgga ccttcatcaa gaaagcgatt gcgtattatc gttttcgtcc   2640
gtatgcgatg aaaattctga aagaaaaccg ttatgatttt gtgattgtgt ggggcagcta   2700
caccggccat ctgttcaaaa gctttctgga aaaacattac aaaaacaaat tcatcctgaa   2760
catccgtgat tactttttcg aaaacaacaa actgattaaa tatcgtatga agaaaatcgt   2820
ggatgcgagc cgtgtgacca ccctgagcag cgaaggcttt ctgaaattcc tgccgaaaag   2880
cgaaaaatac cgtatcatct acagctacaa catgagcatc atccgtgaaa gcaacgtgac   2940
cgatggcttt aaaaaacgtt ggccgattaa cattggcttt attggcaacg tgcgttttaa   3000
```

```
cgaaattaac cagaaactga ttaaagaact ggcgaacgat agccgttttc atatgcagta   3060
ttttggcacc ggcagcgaaa aactggaagt gtttgcgcgt gaaaacttta ttaacaacat   3120
tacctttagc ggcggctttg atctgaaaga aaccccgaaa tatctgaacg aaattgatat   3180
tctgaacaac ctgtttggca accagaacat tgcgctggat accgcgctga gcattcgtat   3240
gtattatgcg ctgtttctga acaaaccgat tattaccacc gatgatacct ttaccgcgac   3300
cgaagcgaac aaatttggcc tgggctttag cattaacccg gaaaacctga aaggcattgg   3360
cgatgaactg atggattggt ataacaacct ggatgtgatg gatattaacc ataaacgtga   3420
agcgtatcgt aacgatgtga ttgaaaacaa caaacagttt tatcaggaaa ttggccgtat   3480
ttttaacgaa gaacagaaac tgattagcga agaagatctg taacgtttaa acaggaggac   3540
agctatgaac aaaatttata acgtgaccag ctatgtgatt gcgattctga tgtttccgtg   3600
cctgatgctg ggcgataaac cgctgctgtt tctggcgccg attagctatg gcgtgggcaa   3660
actgttcatc agcttcagca acaacccgaa cttcaaattc agcaaaatcg tgtacgatgt   3720
gctgggcttt ctgcgtctgg tgtttattcc ggcgatgatt gtgtttttcc aggatagcac   3780
cattgataac ctgccgctgg gccaggcgta ttttaaccag gcggtgattt atatgagcgt   3840
ggaatttatt attggcagcc tgtttattct gattctgagc aaactgttca agcatgaagt   3900
tgtgagccgt aacagcttta ccctgagcgg cagcagcatt tattatattg tgtttggcct   3960
ggtgatttgc ggcatttttg tggcgtttcc ggaagtgcgt aaaaacatta gctttctgat   4020
tattaaaacc gatgcgatgg gccgtggcac cgaagcgacc agcggcctga acgtgctgtt   4080
tgtgatgctg tttcagctgg cgctggcgct gctgtttctg atcatcgcgt acgcgagcta   4140
caaaaaatac aaagaaaacc cgaaaatcat ctacgtggtg ctgccgctgg cgattggcat   4200
tctgaacatt agcctgattg tgggcgaacg tcgtagctat cagctgtata ccatggtggc   4260
ggtgctgacc gttgtgagca tcctgtttag caaacataaa cgtcgtatca acatcatcat   4320
catcagcgtg ggcatcttcg tgctggcgct gatgaccctg tataaagaac tgtatgtgtt   4380
taactatagc agctatagcg aagcgctgaa cagcaccagc gtgagcaacc tgaaaattgt   4440
ggataccctg cagagctatt tttatggccc gagcaacatt gcggcgagca ttgattatct   4500
gaactattat aacggcagct ttaaacagta tctgtttgat aacacccgtg cggtgtttgg   4560
ctttaacttt ttcctggata aaaaacagct gattaccagc cagctgttta accagctgat   4620
ttatggcagc aaacagctga ccggccatct gattagcagc gcgggctatg gcattattta   4680
ttttggcccg ctgtttttct acctgaacct gattgcgaac atctttttcg cgtttctgag   4740
cgaatacatc atccgtaaaa gccatagcct ggaagtgatc ttcatcggca cctacatcta   4800
catgcgtctg attaccagca tttttagcca tccgaccccg ctgattaccc tgattagcat   4860
gattctggtg gtgtatgtga ttgcgatcat cccgggcatc atcatcaaga aattcaccaa   4920
aaaagtgggc atcgaagatt acaaagatga tgatgataaa taacgtttaa acaggaggac   4980
agctatgatt gtgaaaacct ttatgaaaag caaaattttt cgtctgatga acaccccgct   5040
gctgctgttt tataaaaaag aatatctgac cggctattat tttgaaaaca aagtggcggg   5100
ctggctgtgg gcgtggaaag cggtgccatt caagctgctg ggcattaaca ccagcctgcc   5160
gtttccggcg gatattaccg tgcgtatgca taacccgaac aacattgtgt ttgataaaaa   5220
cgatattcat atttttcaga gcccgggcac ctattttaac aactttagcg cggtgattta   5280
tattggccgt ggcgtgtata ttgcgccgaa cgtgggcatt attaccgcga accataacat   5340
taaaaacctg aaaagccatg cgccgggcga agatgtgaaa attggcaact atagctggat   5400
```

```
tggcatgaac agcgtgattc tgccgggcgt ggaactgggc gaacatacca ttgtgggcgc   5460
gggcagcgtg gtgaccaaaa gctttccgga aggcaacgtg gtgattggcg gcaacccggc   5520
gaaaattatt aagaaaatca gctatccgta tgatgtgccg gattatgcgt aattaattaa   5580
ccaggtgcac gaagaaaatt atgagattaa ataaatttat tggcgattcg tttttaatga   5640
ttttaagcag tggcatcgct caagtcatat taatcatcac taccccaatt attacaagac   5700
tatattcacc tacagaattt ggtgagttta caatttttc aaatatcgca atgattttaa   5760
taccaataat aaatgcaaga tacgatttgt tgattgtgaa taccaaaaat gaccgtagtg   5820
ctaatatact ttcacaaatc agtttttga tatcattgct tattttatta atactgatac   5880
caatatttgc gattagtgca tgtttatacc caaactttat attagatttt attttcatta   5940
ttattatgtt gtttttggta agtttaacaa acatttttac aaattatcta aataaggaaa   6000
gaaagtataa agtgttaagt ttgattaatg tgtttagagc tggatcaatg gctttacttc   6060
aaatcatttt cggactttta gcattaggaa gtttaggatt aattattggt ttttcattat   6120
cctatatcgc aggcattaca ctaggatata aaacgtttaa aaagcacttt aatattgtga   6180
gagataaaga agaaactaaa gcattatttt tagaaaataa aaatcagtta gtttattcaa   6240
caccatcaat attattaaat agtttgtctt tctcggttgt tgtgttcttt ataggtattt   6300
tgtataccaa tacagaagtg ggtatttatg gtatggccat aagagtacta ggcataccag   6360
tgacaattat ttcattaggg ttatcaaaaa tatttatgca acaagccaat gactattata   6420
ttgaacatgg taacttccga aatttattac ttaaatttag ttccatactg gttatagttt   6480
ctataattct ttatgtgcca ctttatttgt tcagtgaaga attagtcaat atattattag   6540
gacatagctg ggttgacgca attacagtta taaaaattgt tatcccatta tttgttataa   6600
ggctgattgt atcaacggta tcactttctg tgattgtatt acaaaaacaa cagttagaat   6660
taatactaca agcgttattt ttaataggta ctactgcaac atttgttata tcaaaaatgc   6720
ttaatttaac ttttttaaac tttgtatcta ttaatacaat tgttttaatc gtatcgtaca   6780
tgatattttt catagcactc tattattttg ctaaaaataa acagttcaaa aattctagtt   6840
atccgtatga tgtgccggat tatgcgtaag tgcaccatat gaatatcctc cttagttcct   6900
attccgaagt tcctattctc tagaaagtat aggaacttcg gcgcgcctac ctgtgacgga   6960
agatcacttc gcagaataaa taaatcctgg tgtccctgtt gataccggga agccctgggc   7020
caacttttgg cgaaaatgag acgttgatcg gcacgtaaga ggttccaact ttcaccataa   7080
tgaaataaga tcactaccgg gcgtattttt tgagttgtcg agattttcag gagctaagga   7140
agctaaaatg gagaaaaaaa tcactggata taccaccgtt gatatatccc aatggcatcg   7200
taaagaacat tttgaggcat ttcagtcagt tgctcaatgt acctataacc agaccgttca   7260
gctggatatt acggcctttt taaagaccgt aaagaaaaat aagcacaagt tttatccggc   7320
ctttattcac attcttgccc gcctgatgaa tgctcatccg gaattacgta tggcaatgaa   7380
agacggtgag ctggtgatat gggatagtgt tcacccttgt tacaccgttt tccatgagca   7440
aactgaaacg ttttcatcgc tctggagtga ataccacgac gatttccggc agtttctaca   7500
catatattcg caagatgtgg cgtgttacgg tgaaaacctg gcctatttcc ctaaagggtt   7560
tattgagaat atgtttttcg tctcagccaa tccctgggtg agtttcacca gttttgattt   7620
aaacgtggcc aatatggaca acttcttcgc ccccgttttc accatgggca aatattatac   7680
gcaaggcgac aaggtgctga tgccgctggc gattcaggtt catcatgccg tttgtgatgg   7740
```

```
cttccatgtc ggcagatgct taatgaatac aacagtactg cgatgagtgg cagggcgggg   7800

cgtaaggcgc gccatttaaa tgaagttcct attccgaagt tcctattctc tagaaagtat   7860

aggaacttcg aagcagctcc agcctacacg taaagaggtg gtgtatggat aagaactctg   7920

ttctgttaat taccggtgga actggttcct ttggaaatgc cgttttgaag cgttttctgg   7980

atacagatat tggtgaaata cgtgtattca gtcgggatga gaagaagcaa gatgatatgc   8040

gtaagtgcta tgctcacccc aagttgaggt tttatattgg agatgtccgc gactatcaaa   8100

gcactctgaa tgctactcgc ggtgtggact acattttcca tgcggctgca ttgaaacagg   8160

ttccctcttg tgagttctac ccgatggagg ctgtgaagac caatgtcatc ggaacggaaa   8220

atgtcctcga atctgctatc cagaatggcg tcaaaaaagt cgtttgtctg agtacggata   8280

aggcagttta cccaatcaat gccatgggta tttcaaaggc catgatggaa aaggtcatgg   8340

tcgccaagtc tcgaaacctg gaacgcactc ctaccgtaat ttgtggcacc cgttatggta   8400

acgtcatggc ttcaaggggc tcggtcattc ctctctttat cgagcaaatg cgatcaggcc   8460

agcctctcac aatcactgat ccaaacatga cacgtttcat gatgacgctt acggatgccg   8520

tagaccttgt gctttatgct ttcgagcatg gtaccaatgg agatcttttt gtacagaaag   8580

caccggctgc aaccatcgag gtgctggctc atgcgcttac tcaattgctt ggcaagaatg   8640

gttatcctat caatgtaata ggtacgcgtc atggagagaa gctttatgag gcgcttctta   8700

gtcgagagga aatggcctgt gctgaagaca tgggtgacta ttatcgtatc cccccagatt   8760

tgcgtgatct gaactatagt aagtttgtgg agcaaggcga ggaaaaaatt actcatacag   8820

aggactataa ttctcataat accaaacgtc tggatatcga aggaatgaaa aagctgttgc   8880

tgaagttgga tttcattcgt gctattcagc gtggcgagag tgccagtcca gaggaataaa   8940

cgatgaaagt tcttgtaact ggcgcgaatg gatttgttgg aaggaatctg tgcgctcatc   9000

ttgcagagcg gggtggtatc gaggtggtgc cattcacccg cgagagtagt gttggtaatt   9060

tgcctgagct aattcgttcc gtcgatttta tttttcatct tgccggggtc aatcgtccgg   9120

aaaaaccaga agagtttaag atcgggaatt ccgaactcac gtatgctctg tgtgaggcgg   9180

taaggtccaa tggacgagcc ataccacttc tttatacttc atccattcag gctgaggtgg   9240

ataatgagta cggtttaagc aagcgagccg cagaagagca tctccaagtg ctaggtgagg   9300

atattggttg tcctgtctac atatttcgcc ttcctaatgt attcggtaaa tggtcgcgtc   9360

cgaattataa ttcagcggtt gcgacttttt gtcataatat tattcgagat attccgattc   9420

aaattaacaa ttcctcggca gagatcactc ttgtatacat agatgatgtg gttcgcacct   9480

tcatgaaagt catggatggg aagctatcca atgcagtttc actacaggtc gagccccagt   9540

atcagatttc tgttggtgag ctcgcagaac aattgtatga gtttcgtaat agtcgaaagt   9600

cactgactac cgcaagggtt ggctcgggat tgacgcgcgc cttgtactcg acttatctaa   9660

gtttcttgcc agaagatagt tttagttacg acgtgccaat gcattcggat ccgcgtggca   9720

cattcgtcga gatgctgaag accgcggact ctggccagtt ctcgtttttt acggctcatc   9780

caggtgttac caggggcggg cattaccatc actcgaaaac cgaaaagttt ctggttatca   9840

aagggatggc acgtttcaag tttagaaaca tcctgaccgg ggcattttac gaaatttgca   9900

ctaatggtga aaaggcagaa attgtcgaaa cagtacctgg atggactcat gacattacta   9960

atgtcggaac tgacgatatg gtagtcatgt tgtgggctaa cgaagtattt gatcgggaaa  10020

atccggatac ctacgcttgt tcagtaggcg aaggtgcgta aggtatagtg agataacaat  10080

gcagaagcta aaagtcgtta cggttgttgg aactcgtcct gagattattc gcttgtctag  10140
```

```
ggtcatggcg aagcttgatc agtactgcga tcatgtactt gtccatactg gacagaatta  10200
tgattacgaa cttaatgaaa tattttttca ggacctcggt ataagaaagc cggattattt  10260
tctaaacgcc gccgggtctt ccggggctga aacgataggg aatgtaataa tcgcagtcga  10320
tcgtgttctg ggcgaaatag atcccgatgc gctgctcgtg ctgggtgata ccaatagttg  10380
tatggcggta ctgcctgcaa aacggcgtaa gataccgacc tttcatatgg aagcaggcaa  10440
tcgctgtttc gatatgcgtg tgcctgaaga gataaatcgg cgcattgtcg atcatacagc  10500
tgatgtaaat ttgacctata gtacaattgc gcgtgattat ctcttgcgtg aaggactttc  10560
tccagacatg gttatcaaga ctggtagccc tatgttcgaa gttctcgagc actatcgtga  10620
cgggatcgag tcctccgata ttcttgaaag gctcgggttg aaaacagagc ggttctttgt  10680
cgtgagtgcg caccgagagg aaaacataga ttcggataag aatttcttga agttggtttc  10740
tatgctcaac gctgtggcag aaaagtactc gctgcccgtc atcgtatcaa ctcaccctag  10800
aacaaaaaag agaattgagg cgacggaggc aaagtttcac gagggtatta aactgctgaa  10860
acccctcggc tttaaggatt acaataaact gcaaattaca gccaaggcag ttatttctga  10920
cagtgggacc atcagtgagg agtcttcaat actgaatttt cccgctttga atattcgtga  10980
ggctcatgaa cgcccagaag gcatggaaga ggctgtggtg atgatggtcg gactggattc  11040
ggatcgagta ctacaagcac tcgaggtgtt ggagggacag aggcgcgacg cagagcgcat  11100
gttacgcttg gtcgctgact atagcatgcc caacgtttct gaaaagattg ttcgcatagt  11160
tcatagctat cgggactatg tcatgcgaac tgtctggaaa aaatattaac ttgaggcgtg  11220
gagttgatgg caaggatatt tgtggtttct gagtatgtcg gtgccaatca gaactccacg  11280
ggatactatt gggagaagat aataggaaag atgcagcggg agtttggtgg gctaaccgta  11340
attttcccgc tgaccgcagg tgaaaccccg cctgtggttt caccttccgt tgagcaagaa  11400
tgctttaagt ttccgaggag caataagaat aggctccttt ctagaggatt ggcgcagatt  11460
tttcaggcgt ttctgttctc agtaaaattg acttctcgtg ccagacgagg agatgtggta  11520
ttgagtggaa ccaaccctgc tcttctactg atgacgtttc ccttgctaag gtatgccctc  11580
ggtttcaagt gggtgctgct ggtgcatgat gtgtttcccg agaacttggt gccggcgggc  11640
gttctgaaga aagatagtat tgcctaccgg cttctacgtc gtctcttttc tttcatttac  11700
tcatccgctg atcgtctagt cgtaataggg cgcgatatgg aagctcttat gaaagagaag  11760
gtgaatgacc cgcgatcttt ggtctttatt tcgaattggg cctgtgagaa agaggttttc  11820
ccagtaccga gagaggatgc tccttttatc aatattcctg aatggaaagg taaaagggtt  11880
ttccaatttt ttggtaatgt cggtcgatta caaggtatag aaaacatact ttctgctatt  11940
cagttggtta aaaacgagaa ggcggctttt gcttttattg gagatggtgc cttggtcgac  12000
agtgtaaaaa aacacgcgct ggaagatcag tgtgctcggt tgaggtattt tggaaggctg  12060
ccattagccg aaaagaattt tggtttggct gcctgtgacg ttgccttagt taccttagaa  12120
gaaggaatgt tcgggcttgg ggttcccagc aaggcatatt tctccatggc agcagacaaa  12180
ccgattctag ctgtcatgga aaaaggggct gaaatctccc gtataataga tgagaccgga  12240
atcggttgga actgtccgcc gaatgatccg gttgctttgg caagattgat cgatgagatt  12300
tgtgaactcg acttgtctag tttaggcgga gtcccgcgga gtgtccttca gcaaaattat  12360
tctgaatata tttcattgga aaaattcgct gcctgtgttc gaccgcttct gtctgagtcg  12420
aaaatatgat gaaggtgctg gtaaccgggg ctagcggttt tgtcgggagt gcgctttgca  12480
```

```
ggtcgcttgc tgccgccccc tttcaggttg tcggacaagt acgatccctg tacaatcccg  12540
ttacgggggt tgagtatgtt cgagcggagc tgaaagagag cactaagctt gatgctgcgc  12600
tgcggggtgt tgaatgtgta gttcatctag ctggacgagc ccatatcttt ggaaggcagc  12660
gtgattcact agatattttt cggaaggtga atcgcgatgc tactctggcg cttgctcggc  12720
aggcgatcga agcatctgta aagcgtttca tttttgttag ttctattggt gtaaatggcg  12780
ctttaaccaa agaaaagccc ttcgatgaga actccaagcc ggctcctcat gcagaatatg  12840
cgatttcaaa gtttgaggct gaagtagcgc ttcgggagct tttcaagcat tcctcaacag  12900
aacttgttat cgtcaggcct ccactcgttt acgactggaa agctcctgga aatttctcgc  12960
gattgttgaa gctggttgct tcgggacttc ctcttccatt tggttgcata gataaccgac  13020
gaagttttgt ttctctggat aatttagttg actttctagc ttgctgtatg acgcaccctt  13080
ctgctgccgg cgaactgttt ttggtatccg atggtcagga gatttctacc aagcaactgg  13140
tgactgcgct tgctgcggga atggggcgtc gccccatcat gtggcctgtt cctaggttta  13200
ttctgaggtt tcttaaatta gtaggaaagg gtgggttata cactcagtta tgctgctcac  13260
tagaggtcga ctcgtcgaaa ggcaggcttt tgcttggttg ggaacccccgc aagagcaccc  13320
tttccgcgtt ggaagatgtt ggtagaatat atgtcaaacg tactgaatga ttatctgcag  13380
gcgctttgct actagcatgg cgtaccacgc agaacaatcg aatagaaccc tgttgaaggg  13440
gtgagagtat ttttggggat aaatttataa atggaagaat ggtatttgtt actcgctgca  13500
gctggggttt cgggactgct tacaggcctc ttgcgtcgtt atgccttagc gaggagctta  13560
cttgacaccc ctaactctcg aagttcccat gtcgttccca ctccacgcgg aggaggggtc  13620
gccattgtag ttactttttg tctcatgctg cctatttggg ctgtactggg aaatatctca  13680
tgggccgtgt cctgggcttt acttctcgct ggcggcgggg ttgccattat tggattcatg  13740
gatgatcacg gtcatatcgc cgcacgctgg cgtctgctgg gacattttag tgcagccttg  13800
gtctcattgt actttttgaa tggcatacca ccatttcaga ttgttggtgt cagttgggac  13860
ctggggtggt tcggaggact tctctttgct ttctatctcg tgtggttgct gaatctctat  13920
aacttcatgg atgggatcga tggacttgct agccttcagg ccatttttgt ctgtgttggt  13980
ggggcattat tatactggct gaatggccaa ctgacgcagg ctttgctccc cttatcgcta  14040
gcttttgccg tttttggatt cttgttctgg aattttccac ccccaaaaat tttcatggga  14100
gatgcgggta gtggtcttct ggggattgtt ttaggaattc tttccattca tgccatgtgg  14160
atgaatacga attttttctg ggcatggttg gtcctgttag gcgttttcat cgtcgatgcg  14220
acctataccc tgattcgtcg cttgctgaga ggggacaagg tgtatgaggc tcatcgaagc  14280
catgcctatc aatacgcaag ccgatactat ggaaagcatg ctcctgttac gattggcgtc  14340
acggcattga acgtcatctg gctcctccct atagccttgt tggtcgggag tgggtctcta  14400
gagcctttga tgggcatcgt catagcctac gtccctctcg tttttctggc agtgaggttc  14460
aaggcgggta agctagagtc gtccgctcag gcctaaagga gtaggggaat gctagatcgt  14520
ttaagagtaa agttgttatc catgcctcgt cgctggaaac gtttgcttca agtggctacg  14580
gatatccttc tggtatggct gtctctgtgg ctcgcttttg tggtccgtct aggcacagac  14640
gatatgatcg acgtgttcgg cgagcatgca tggcttttca tcactgcgcc ggtcatcgcc  14700
attccactat tcattcgctt cggcatgtat cgcgcggtga tgcgctatct cggtaacgac  14760
gcattgatcg ccatcgccaa ggcggtgacc atctcggctc tggtgctgtc gctggtggtg  14820
tactggtatc gtggcgcgcc ggcgccggtg ccgcgttccc tggtgttcaa ctactggtgg  14880
```

```
ttgagcatgc tgctgatcgg cggcttgcgt ctggccatgc gccagtattt catgggcgac  14940

tggtactctg ctgtgcagtc ggtaccattt ctcaaccgcc aggatggcct gcccagggtg  15000

gttatctatg gggcgggggc ggccggcaac cagttggttg cggcgttgcg tctcggtcgg  15060

gcgatgcgtc cggtggcgtt catcgatgac gacaagcaga tcgccaaccg ggtcattgcc  15120

ggtctgcggg tctataccgc caagcatatc cgccagatga tcgacgagac gggcgcgcag  15180

gaggttctcc tggcgattcc ttccgccact cgggcccggc gccgagagat tctcgagtcc  15240

ctggagccgt tcccgctgca cgtgcgcagc atgcccggct tcatggacct ggccagcggc  15300

cgggtcaagg tggatgacct gcaggaggtg gacatcgctg acctgctggg gcgcgacagc  15360

gtcgcaccgc gcaaggagct gctggaacgg tgcatccgcg gtcaggtggt gatggtgacc  15420

ggggcgggcg gctctatcgg ttcggaactc tgtcggcaga tcatgagttg ttcgcctagc  15480

gtgctgatcc tgttcgaaca cagcgaatac aacctctata gcatccatca ggaactggag  15540

cgtcggatca agcgcgagtc gctttcggtg aacctgttgc cgatcctcgg ttcggtgcgc  15600

aatcccgagc gcctggtgga cgtgatgcgt acctggaagg tcaataccgt ctaccatgcg  15660

gcggcctaca agcatgtgcc gatcgtcgag cacaacatcg ccgagggcgt tctcaacaac  15720

gtgataggca ccttgcatgc ggtgcaggcc gcggtgcagg tcggcgtgca gaacttcgtg  15780

ctgatttcca ccgacaaggc ggtgcggccg accaatgtga tgggcagcac caagcgcctg  15840

gcggaaatgg tccttcaggc gctcagcaac gaatcggcgc cggtgctgtt cggcgaccgg  15900

aaggacgtgc atcacgtcaa caagacccgt ttcaccatgg tccgcttcgg caacgtcctc  15960

ggttcgtccg gttcggtcat tccgctgttc cgcgagcaga tcaagcgcgg cggcccggtg  16020

acggtcaccc acccgagcat cacccgttac ttcatgacca ttcccgaggc ggcgcagttg  16080

gtcatccagg ccggttcgat ggggcagggc ggagatgtat tcgtgctgga catggggccg  16140

ccggtgaaga tcctggagct cgccgagaag atgatccacc tgtccggcct gagcgtgcgt  16200

tccgagcgtt cgccccatgg tgacatcgcc atcgagttca gtggcctgcg tcctggcgag  16260

aagctctacg aagagctgct gatcggtgac aacgtgaatc ccaccgacca tccgatgatc  16320

atgcgggcca acgaggaaca cctgagctgg gaggccttca aggtcgtgct ggagcagttg  16380

ctggccgccg tggagaagga cgactactcg cgggttcgcc agttgctgcg ggaaaccgtc  16440

agcggctatg cgcctgacgg tgaaatcgtc gactggatct atcgccagag gcggcgagaa  16500

ccctgagtca tcgttctccg gaaaaggccg cctagcggcc ttttttgttt tctccgtacg  16560

atgtttccgg tgccggacca ggaagcgact gctttgctgg ggctgtcgat ccaggtgcgt  16620

tccacggcga taaggtggtt tcgtggatgg gcaacatgtg                        16660
```

<210> SEQ ID NO 5
<211> LENGTH: 972
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

```
catatgaaga aaatctggct ggcgctggcg ggcctggtgc tggcgtttag cgctagcgcg     60

gcggatagcg atattaacat taaaaccggc accaccgata ttggcagcaa caccaccgtg    120

aaaaccggcg atctggtgac ctatgataaa gaaaacggca tgctgaaaaa agtgttttat    180

agcttcatcg atgataaaaa ccataacaaa aaactgctgg tgatccgtac caaaggcacc    240
```

```
attgcgggcc agtatcgtgt gtatagcgaa gaaggcgcga acaaaagcgg cctggcgtgg    300

ccgagcgcgt ttaaagtgca gctgcagctg ccggataacg aagtggcgca gattagcgat    360

tattatccgc gtaacagcat tgataccaaa gaatatatga gcaccctgac ctatggcttt    420

aacggcaacg tgaccggcga tgataccggc aaaattggtg gactgattgg cgcgaacgtg    480

agcattggcc ataccctgaa atatgtgcag ccggatttta aaaccattct ggaaagcccg    540

accgataaaa aagtgggctg gaaagtgatt tttaacaaca tggtgaacca gaactggggc    600

ccgtatgatc gtgatagctg gaacccggtg tatggcaacc agctgtttat gaaaacccgt    660

aacggcagca tgaaagcggc ggataacttt ctggatccga acaaagcgag cagcctgctg    720

agcagcggct ttagcccgga ttttgcgacc gtgattacca tggatcgtaa agcgagcaaa    780

cagcagacca acattgatgt gatttatgaa cgtgtgcgtg atgattatca gctgcattgg    840

accagcacca actggaaagg caccaacacc aaagataaat ggattgatcg tagcagcgaa    900

cgttataaaa ttgattggga aaaagaagaa atgaccaacg gcagccatca tcatcatcat    960

cattaggtcg ac                                                         972
```

<210> SEQ ID NO 6
<211> LENGTH: 990
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
catatgaaga aaatctggct ggcgctggcg ggcctggtgc tggcgtttag cgctagcgcg     60

gcggatagcg atattaacat taaaaccggc accaccgata ttggcagcaa caccaccgtg    120

aaaaccggcg atctggtgac ctatgataaa gaaaacggca tgctgaaaaa agtgttttat    180

agcttcatcg atgataaaaa ccataacaaa aaactgctgg tgatccgtac caaaggcacc    240

attgcgggcc agtatcgtgt gtatagcgaa gaaggcgcga acaaaagcgg cctggcgtgg    300

ccgagcgcgt ttaaagtgca gctgcagctg ccggataacg aagtggcgca gattagcgat    360

tattatccgc gtaacagcat tgataccaaa gaatatatga gcaccctgac ctatggcttt    420

aacggcaacg tgaccggcga tgataccggc aaaattggtg gactgattgg cgcgaacgtg    480

agcattggcc ataccctgaa atatgtgcag ccggatttta aaaccattct ggaaagcccg    540

accgataaaa aagtgggctg gaaagtgatt tttaacaaca tggtgaacca gaactggggc    600

ccgtatgatc gtgatagctg gaacccggtg tatggcaacc agctgtttat gaaaacccgt    660

aacggcaaag atcaaaatag aactaaaatg aaagcggcgg ataactttct ggatccgaac    720

aaagcgagca gcctgctgag cagcggcttt agcccggatt ttgcgaccgt gattaccatg    780

gatcgtaaag cgagcaaaca gcagaccaac attgatgtga tttatgaacg tgtgcgtgat    840

gattatcagc tgcattggac cagcaccaac tggaaaggca ccaacaccaa agataaatgg    900

attgatcgta gcagcgaacg ttataaaatt gattgggaaa aagaagaaat gaccaacggc    960

agccatcatc atcatcatca ttaagtcgac                                     990
```

<210> SEQ ID NO 7
<211> LENGTH: 990
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
catatgaaga aaatctggct ggcgctggcg ggcctggtgc tggcgtttag cgctagcgcg     60
gcggatagcg atattaacat taaaaccggc accaccgata ttggcagcaa caccaccgtg    120
aaaaccggcg atctggtgac ctatgataaa gaaaacggca tgctgaaaaa agtgttttat    180
agcttcatcg atgataaaaa ccataacaaa aaactgctgg tgatccgtac caaaggcacc    240
attgcgggcc agtatcgtgt gtatagcgaa gaaggcgcga acaaaagcgg cctggcgtgg    300
ccgagcgcgt ttaaagtgca gctgcagctg ccggataacg aagtggcgca gattagcgat    360
tattatccgc gtaacagcat tgataccaaa gaatatatga gcaccctgac ctatggcttt    420
aacggcaacg tgaccggcga tgataccggc aaaattggtg gactgattgg cgcgaacgtg    480
agcattggcc ataccctgaa atatgtgcag ccggatttta aaaccattct ggaaagcccg    540
accgataaaa aagtgggctg gaaagtgatt tttaacaaca tggtgaacca gaactggggc    600
ccgtatgatc gtgatagctg gaacccggtg tatggcaacc agctgtttat gaaaacccgt    660
aacggcagca tgaaagcggc ggataacttt ctggatccga acaaagcgag cagcctgctg    720
agcagcggct ttagcccgga ttttgcgacc gtgattacca tggatcgtaa agcgaaagat    780
caaaatagaa ctaaaaaaca gcagaccaac attgatgtga tttatgaacg tgtgcgtgat    840
gattatcagc tgcattggac cagcaccaac tggaaaggca ccaacaccaa agataaatgg    900
attgatcgta gcagcgaacg ttataaaatt gattgggaaa aagaagaaat gaccaacggc    960
agccatcatc atcatcatca ttaagtcgac                                     990
```

<210> SEQ ID NO 8
<211> LENGTH: 990
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 8

```
catatgaaga aaatctggct ggcgctggcg ggcctggtgc tggcgtttag cgctagcgcg     60
gcggatagcg atattaacat taaaaccggc accaccgata ttggcagcaa caccaccgtg    120
aaaaccggcg atctggtgac ctatgataaa gaaaacggca tgctgaaaaa agtgttttat    180
agcttcatcg atgataaaaa ccataacaaa aaactgctgg tgatccgtac caaaggcacc    240
attgcgggcc agtatcgtgt gtatagcgaa gaaggcgcga acaaaagcgg cctggcgtgg    300
ccgagcgcgt ttaaagtgca gctgcagctg ccggataacg aagtggcgca gattagcgat    360
tattatccgc gtaacagcat tgataccaaa gaatatatga gcaccctgac ctatggcttt    420
aacggcaacg tgaccggcga tgataccggc aaaattggtg gactgattgg cgcgaacgtg    480
agcattggcc ataccctgaa atatgtgcag ccggatttta aaaccattct ggaaagcccg    540
accgataaaa aagtgggctg gaaagtgatt tttaacaaca tggtgaacca gaactggggc    600
ccgtatgatc gtgatagctg gaacccggtg tatggcaacc agctgtttat gaaaacccgt    660
aacggcagca tgaaagcggc ggataacttt ctggatccga acaaagcgag cagcctgctg    720
agcagcggct ttagcccgga ttttgcgacc gtgattacca tggatcgtaa agcgagcaaa    780
cagcagacca acattgatgt gatttatgaa cgtgtgcgtg atgattatca gctgcattgg    840
accagcacca actggaaagg caccaacacc aaagataaag atcaaaatag aactaaatgg    900
```

attgatcgta gcagcgaacg ttataaaatt gattgggaaa aagaagaaat gaccaacggc 960
agccatcatc atcatcatca ttaagtcgac 990

<210> SEQ ID NO 9
<211> LENGTH: 1659
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9
catatgaaga aaatctggct ggcgctggcg ggcctggtgc tggcgtttag cgctagcgcc 60
gcgagcgaaa acagcgtgac ccagagcgat agcgcgagca acgaaagcaa aagcaacgat 120
agcagcagcg tgagcgcggc gccgaaaacc gatgatacca acgtgagcga taccaaaacc 180
agcagcaaca ccaacaacgg cgaaaccagc gtggcgcaga acccggcgca gcaggaaacc 240
acccagagca gcagcaccaa cgcgaccacc gaagaaaccc cggtgaccgg tgaagccacc 300
accaccacca ccaaccaggc caacaccccg gcgaccaccc agagcagcaa caccaacgcg 360
gaagaactgg tgaaccagac cagcaacgaa accaccttta acgataccaa caccgtgagc 420
agcgtgaaca gcccgcagaa cagcaccaac gcggaaaacg tgagcaccac ccaggatacc 480
agcaccgaag cgaccccgag caacaacgaa agcgcgccgc agagcaccga tgcgagcaac 540
aaagatgtgg tgaatcaggc cgttaatacc agcgcgccgc gtatgcgtgc ctttagcctg 600
gcggccgtgg ccgccgatgc tccagcagca ggtaccgata ttaccaacca gctgaccaac 660
gtgaccgtgg gcattgatag cggcaccacc gtgtatccgc atcaggcagg ttatgtgaaa 720
ctgaactatg gctttagcgt gccgaacagc gcggtgaaag gcgatacctt taaaattacc 780
gtgccgaaag aactgaacct gaacggcgtg accagcaccg cgaaagtgcc gccgattatg 840
gcaggtgatc aggtgctggc gaacggcgtg attgatagcg atggcaacgt gatttatacc 900
tttaccgatt atgtgaacac caaagatgat gtgaaagcga ccctgaccat gccagcatat 960
attgatccgg aaaacgtgaa gaaaaccggc aacgtgaccc tggcgaccgg cattggcagc 1020
accaccgcga acaaaaccgt tctggtggat tatgaaaaat acggcaaatt ctacaacctg 1080
agcatcaaag gcaccatcga tcagatcgat aaaaccaaca acacctatcg tcagaccatt 1140
tatgtgaacc cgagcggcga taacgtgatt gcgccggtgc tgaccggcaa cctgaaaccg 1200
aacaccgata gcaacgcgct gattgatcag cagaacacca gcattaaagt gtataaagtg 1260
gataacgcgg cggatctgag cgaaagctat tttgtgaacc cggaaaactt tgaagatgtg 1320
accaacagcg tgaacattac ctttccgaac ccgaaccagt ataaagtgga atttaacacc 1380
ccggatgatc agattaccac cccgtatatt gtggtggtga acggccatat tgatccgaac 1440
agcaaaggcg atctggcgct gcgtagcacc ctgtatggct ataacagcaa cattatttgg 1500
cgtagcatga gctgggataa cgaagtggcg tttaacaacg gcagcggcag cggcgatggc 1560
attgataaac cggtggtgcc ggaacagccg gatgaaccgg gcgaaattga accgattccg 1620
gaagatggca gccatcatca tcatcatcat taggtcgac 1659

<210> SEQ ID NO 10
<211> LENGTH: 1677
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
catatgaaga aaatctggct ggcgctggcg ggcctggtgc tggcgtttag cgctagcgcc     60
gcgagcgaaa acagcgtgac ccagagcgat agcgcgagca acgaaagcaa aagcaacgat    120
agcagcagcg tgagcgcggc gccgaaaacc gatgatacca acgtgagcga taccaaaacc    180
agcagcaaca ccaacaacgg cgaaaccagc gtggcgcaga acccggcgca gcaggaaacc    240
acccagagca gcagcaccaa cgcgaccacc gaagaaaccc cggtgaccgg tgaagccacc    300
accaccacca ccaaccaggc caacaccccg gcgaccaccc agagcagcaa caccaacgcg    360
gaagaactgg tgaaccagac cagcaacgaa accaccttta acgataccaa caccgtgagc    420
agcgtgaaca gcccgcagaa cagcaccaac gcggaaaacg tgagcaccac ccaggatacc    480
agcaccgaag cgaccccgag caacaacgaa agcgcgccgc agagcaccga tgcgagcaac    540
aaagatgtgg tgaatcaggc cgttaatacc agcgcgccgc gtatgcgtgc ctttagcctg    600
gcggccgtgg ccgccgatgc tccagcagca ggtaccgata ttaccaacca gctgaccaac    660
gtgaccgtgg gcattgatag cggcaccacc gtgtatccgc atcaggcagg ttatgtgaaa    720
ctgaactatg gctttagcgt gccgaacagc gcggtgaaag gcgatacctt taaaattacc    780
gtgccgaaag aactgaacct gaacggcgtg accagcaaag atcaaaatag aactaaagcg    840
aaagtgccgc cgattatggc aggtgatcag gtgctggcga acggcgtgat tgatagcgat    900
ggcaacgtga tttatacctt taccgattat gtgaacacca aagatgatgt gaaagcgacc    960
ctgaccatgc cagcatatat tgatccggaa aacgtgaaga aaaccggcaa cgtgaccctg   1020
gcgaccggca ttggcagcac caccgcgaac aaaaccgttc tggtggatta tgaaaaatac   1080
ggcaaattct acaacctgag catcaaaggc accatcgatc agatcgataa aaccaacaac   1140
acctatcgtc agaccattta tgtgaacccg agcggcgata acgtgattgc gccggtgctg   1200
accggcaacc tgaaaccgaa caccgatagc aacgcgctga ttgatcagca gaacaccagc   1260
attaaagtgt ataaagtgga taacgcggcg gatctgagcg aaagctattt tgtgaacccg   1320
gaaaactttg aagatgtgac caacagcgtg aacattacct ttccgaaccc gaaccagtat   1380
aaagtggaat ttaacacccc ggatgatcag attaccaccc cgtatattgt ggtggtgaac   1440
ggccatattg atccgaacag caaaggcgat ctggcgctgc gtagcaccct gtatggctat   1500
aacagcaaca ttatttggcg tagcatgagc tgggataacg aagtggcgtt taacaacggc   1560
agcggcagcg gcgatggcat tgataaaccg gtggtgccgg aacagccgga tgaaccgggc   1620
gaaattgaac cgattccgga agatggcagc catcatcatc atcatcatta agtcgac      1677
```

<210> SEQ ID NO 11
<211> LENGTH: 1677
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

```
catatgaaga aaatctggct ggcgctggcg ggcctggtgc tggcgtttag cgctagcgcc     60
gcgagcgaaa acagcgtgac ccagagcgat agcgcgagca acgaaagcaa aagcaacgat    120
agcagcagcg tgagcgcggc gccgaaaacc gatgatacca acgtgagcga taccaaaacc    180
agcagcaaca ccaacaacgg cgaaaccagc gtggcgcaga acccggcgca gcaggaaacc    240
acccagagca gcagcaccaa cgcgaccacc gaagaaaccc cggtgaccgg tgaagccacc    300
```

```
accaccacca ccaaccaggc caacaccccg gcgaccaccc agagcagcaa caccaacgcg    360

gaagaactgg tgaaccagac cagcaacgaa accaccttta acgataccaa caccgtgagc    420

agcgtgaaca gcccgcagaa cagcaccaac gcggaaaacg tgagcaccac ccaggatacc    480

agcaccgaag cgaccccgag caacaacgaa agcgcgccgc agagcaccga tgcgagcaac    540

aaagatgtgg tgaatcaggc cgttaatacc agcgcgccgc gtatgcgtgc ctttagcctg    600

gcggccgtgg ccgccgatgc tccagcagca ggtaccgata ttaccaacca gctgaccaac    660

gtgaccgtgg gcattgatag cggcaccacc gtgtatccgc atcaggcagg ttatgtgaaa    720

ctgaactatg gctttagcgt gccgaacagc gcggtgaaag gcgatacctt taaaattacc    780

gtgccgaaag aactgaacct gaacggcgtg accagcaccg cgaaagtgcc gccgattatg    840

gcaggtgatc aggtgctggc gaacggcgtg attgatagcg atggcaacgt gatttatacc    900

tttaccgatt atgtgaacac caaagataaa gatcaaaata gaactaaagt gaaagcgacc    960

ctgaccatgc cagcatatat tgatccggaa aacgtgaaga aaaccggcaa cgtgaccctg   1020

gcgaccggca ttggcagcac caccgcgaac aaaaccgttc tggtggatta tgaaaaatac   1080

ggcaaattct acaacctgag catcaaaggc accatcgatc agatcgataa aaccaacaac   1140

acctatcgtc agaccattta tgtgaacccg agcggcgata acgtgattgc gccggtgctg   1200

accggcaacc tgaaaccgaa caccgatagc aacgcgctga ttgatcagca gaacaccagc   1260

attaaagtgt ataaagtgga taacgcggcg gatctgagcg aaagctattt tgtgaacccg   1320

gaaaactttg aagatgtgac caacagcgtg aacattacct ttccgaaccc gaaccagtat   1380

aaagtggaat ttaacacccc ggatgatcag attaccaccc cgtatattgt ggtggtgaac   1440

ggccatattg atccgaacag caaaggcgat ctggcgctgc gtagcaccct gtatggctat   1500

aacagcaaca ttatttggcg tagcatgagc tgggataacg aagtggcgtt taacaacggc   1560

agcggcagcg gcgatggcat tgataaaccg gtggtgccgg aacagccgga tgaaccgggc   1620

gaaattgaac cgattccgga agatggcagc catcatcatc atcatcatta agtcgac      1677
```

<210> SEQ ID NO 12
<211> LENGTH: 1677
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
catatgaaga aaatctggct ggcgctggcg ggcctggtgc tggcgtttag cgctagcgcc     60

gcgagcgaaa acagcgtgac ccagagcgat agcgcgagca acgaaagcaa aagcaacgat    120

agcagcagcg tgagcgcggc gccgaaaacc gatgatacca acgtgagcga taccaaaacc    180

agcagcaaca ccaacaacgg cgaaaccagc gtggcgcaga acccggcgca gcaggaaacc    240

acccagagca gcagcaccaa cgcgaccacc gaagaaaccc cggtgaccgg tgaagccacc    300

accaccacca ccaaccaggc caacaccccg gcgaccaccc agagcagcaa caccaacgcg    360

gaagaactgg tgaaccagac cagcaacgaa accaccttta acgataccaa caccgtgagc    420

agcgtgaaca gcccgcagaa cagcaccaac gcggaaaacg tgagcaccac ccaggatacc    480

agcaccgaag cgaccccgag caacaacgaa agcgcgccgc agagcaccga tgcgagcaac    540

aaagatgtgg tgaatcaggc cgttaatacc agcgcgccgc gtatgcgtgc ctttagcctg    600

gcggccgtgg ccgccgatgc tccagcagca ggtaccgata ttaccaacca gctgaccaac    660
```

```
gtgaccgtgg gcattgatag cggcaccacc gtgtatccgc atcaggcagg ttatgtgaaa    720

ctgaactatg gctttagcgt gccgaacagc gcggtgaaag gcgatacctt taaaattacc    780

gtgccgaaag aactgaacct gaacggcgtg accagcaccg cgaaagtgcc gccgattatg    840

gcaggtgatc aggtgctggc gaacggcgtg attgatagcg atggcaacgt gatttatacc    900

tttaccgatt atgtgaacac caaagatgat gtgaaagcga ccctgaccat gccagcatat    960

attgatccgg aaaacgtgaa gaaaaccggc aacgtgaccc tggcgaccgg cattggcagc   1020

accaccgcga acaaaaccgt tctggtggat tatgaaaaat acggcaaatt ctacaacctg   1080

agcatcaaag gcaccatcga tcagatcgat aaaaccaaca acacctatcg tcagaccatt   1140

tatgtgaacc cgagcggcga taacgtgatt gcgccggtgc tgaccggcaa cctgaaaccg   1200

aacaccgata gcaacgcgct gattgatcag cagaacacca gcattaaagt gtataaagtg   1260

gataacgcgg cggatctgag cgaaagctat tttgtgaacc cggaaaactt tgaagatgtg   1320

accaacagcg tgaacattac ctttccgaac ccgaaccagt ataaagtgga atttaacacc   1380

ccggatgatc agattaccac cccgtatatt gtggtggtga acggccatat tgatccgaac   1440

agcaaaggcg atctggcgct gcgtagcacc ctgtatggct ataacagcaa cattatttgg   1500

cgtagcatga gctgggataa cgaagtggcg tttaacaacg gcaaagatca aaatagaact   1560

aaaggcagcg gcgatggcat tgataaaccg gtggtgccgg aacagccgga tgaaccgggc   1620

gaaattgaac cgattccgga agatggcagc catcatcatc atcatcatta agtcgac      1677
```

```
<210> SEQ ID NO 13
<211> LENGTH: 643
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Lys Lys Ile Trp Leu Ala Leu Ala Gly Leu Val Leu Ala Phe Ser
1               5                   10                  15

Ala Ser Ala Ala Glu Glu Ala Phe Asp Leu Trp Asn Glu Cys Ala Lys
            20                  25                  30

Ala Cys Val Leu Asp Leu Lys Asp Gly Val Arg Ser Ser Arg Met Ser
        35                  40                  45

Val Asp Pro Ala Ile Ala Asp Thr Asn Gly Gln Gly Val Leu His Tyr
    50                  55                  60

Ser Met Val Leu Glu Gly Gly Asn Asp Ala Leu Lys Leu Ala Ile Asp
65                  70                  75                  80

Asn Ala Leu Ser Ile Thr Ser Asp Gly Leu Thr Ile Arg Leu Glu Gly
                85                  90                  95

Gly Val Glu Pro Asn Lys Pro Val Arg Tyr Ser Tyr Thr Arg Gln Ala
            100                 105                 110

Arg Gly Ser Trp Ser Leu Asn Trp Leu Val Pro Ile Gly His Glu Lys
        115                 120                 125

Pro Ser Asn Ile Lys Val Phe Ile His Glu Leu Asn Ala Gly Asn Gln
    130                 135                 140

Leu Ser His Met Ser Pro Ile Tyr Thr Ile Glu Met Gly Asp Glu Leu
145                 150                 155                 160

Leu Ala Lys Leu Ala Arg Asp Ala Thr Phe Phe Val Arg Ala His Glu
                165                 170                 175
```

```
Ser Asn Glu Met Gln Pro Thr Leu Ala Ile Ser His Ala Gly Val Ser
            180                 185                 190

Val Val Met Ala Gln Ala Gln Pro Arg Arg Glu Lys Arg Trp Ser Glu
        195                 200                 205

Trp Ala Ser Gly Lys Val Leu Cys Leu Leu Asp Pro Leu Asp Gly Val
    210                 215                 220

Tyr Asn Tyr Leu Ala Gln Gln Arg Cys Asn Leu Asp Asp Thr Trp Glu
225                 230                 235                 240

Gly Lys Ile Tyr Arg Val Leu Ala Gly Asn Pro Ala Lys His Asp Leu
                245                 250                 255

Asp Ile Lys Asp Asn Asn Asn Ser Thr Pro Thr Val Ile Ser His Arg
            260                 265                 270

Leu His Phe Pro Glu Gly Gly Ser Leu Ala Ala Leu Thr Ala His Gln
        275                 280                 285

Ala Cys His Leu Pro Leu Glu Ala Phe Thr Arg His Arg Gln Pro Arg
    290                 295                 300

Gly Trp Glu Gln Leu Glu Gln Cys Gly Tyr Pro Val Gln Arg Leu Val
305                 310                 315                 320

Ala Leu Tyr Leu Ala Ala Arg Leu Ser Trp Asn Gln Val Asp Gln Val
                325                 330                 335

Ile Arg Asn Ala Leu Ala Ser Pro Gly Ser Gly Gly Asp Leu Gly Glu
            340                 345                 350

Ala Ile Arg Glu Gln Pro Glu Gln Ala Arg Leu Ala Leu Thr Leu Ala
        355                 360                 365

Ala Ala Glu Ser Glu Arg Phe Val Arg Gln Gly Thr Gly Asn Asp Glu
    370                 375                 380

Ala Gly Ala Ala Ser Ala Asp Val Val Ser Leu Thr Cys Pro Val Ala
385                 390                 395                 400

Lys Asp Gln Asn Arg Thr Lys Gly Glu Cys Ala Gly Pro Ala Asp Ser
                405                 410                 415

Gly Asp Ala Leu Leu Glu Arg Asn Tyr Pro Thr Gly Ala Glu Phe Leu
            420                 425                 430

Gly Asp Gly Gly Asp Val Ser Phe Ser Thr Arg Gly Thr Gln Asn Trp
        435                 440                 445

Thr Val Glu Arg Leu Leu Gln Ala His Arg Gln Leu Glu Glu Arg Gly
    450                 455                 460

Tyr Val Phe Val Gly Tyr His Gly Thr Phe Leu Glu Ala Ala Gln Ser
465                 470                 475                 480

Ile Val Phe Gly Gly Val Arg Ala Arg Ser Gln Asp Leu Asp Ala Ile
                485                 490                 495

Trp Arg Gly Phe Tyr Ile Ala Gly Asp Pro Ala Leu Ala Tyr Gly Tyr
            500                 505                 510

Ala Gln Asp Gln Glu Pro Asp Ala Arg Gly Arg Ile Arg Asn Gly Ala
        515                 520                 525

Leu Leu Arg Val Tyr Val Pro Arg Trp Ser Leu Pro Gly Phe Tyr Arg
    530                 535                 540

Thr Gly Leu Thr Leu Ala Ala Pro Glu Ala Ala Gly Glu Val Glu Arg
545                 550                 555                 560

Leu Ile Gly His Pro Leu Pro Leu Arg Leu Asp Ala Ile Thr Gly Pro
                565                 570                 575

Glu Glu Glu Gly Gly Arg Val Thr Ile Leu Gly Trp Pro Leu Ala Glu
            580                 585                 590

Arg Thr Val Val Ile Pro Ser Ala Ile Pro Thr Asp Pro Arg Asn Val
```

```
        595                 600                 605

Gly Gly Asp Leu Asp Pro Ser Ser Ile Pro Asp Lys Glu Gln Ala Ile
    610                 615                 620

Ser Ala Leu Pro Asp Tyr Ala Ser Gln Pro Gly Lys Pro Pro Arg Glu
625                 630                 635                 640

Asp Leu Lys


<210> SEQ ID NO 14
<211> LENGTH: 624
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Ala Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Asp Asn Asn Asn Ser Thr Pro Thr Val Ile Ser His Arg Leu His Phe
                245                 250                 255

Pro Glu Gly Gly Ser Leu Ala Ala Leu Thr Ala His Gln Ala Cys His
            260                 265                 270

Leu Pro Leu Glu Ala Phe Thr Arg His Arg Gln Pro Arg Gly Trp Glu
        275                 280                 285

Gln Leu Glu Gln Cys Gly Tyr Pro Val Gln Arg Leu Val Ala Leu Tyr
    290                 295                 300

Leu Ala Ala Arg Leu Ser Trp Asn Gln Val Asp Gln Val Ile Arg Asn
```

```
305                 310                 315                 320

Ala Leu Ala Ser Pro Gly Ser Gly Gly Asp Leu Gly Glu Ala Ile Arg
                325                 330                 335

Glu Gln Pro Glu Gln Ala Arg Leu Ala Leu Thr Leu Ala Ala Ala Glu
            340                 345                 350

Ser Glu Arg Phe Val Arg Gln Gly Thr Gly Asn Asp Glu Ala Gly Ala
        355                 360                 365

Ala Ser Ala Asp Val Val Ser Leu Thr Cys Pro Val Ala Lys Asp Gln
    370                 375                 380

Asn Arg Thr Lys Gly Glu Cys Ala Gly Pro Ala Asp Ser Gly Asp Ala
385                 390                 395                 400

Leu Leu Glu Arg Asn Tyr Pro Thr Gly Ala Glu Phe Leu Gly Asp Gly
                405                 410                 415

Gly Asp Val Ser Phe Ser Thr Arg Gly Thr Gln Asn Trp Thr Val Glu
            420                 425                 430

Arg Leu Leu Gln Ala His Arg Gln Leu Glu Glu Arg Gly Tyr Val Phe
        435                 440                 445

Val Gly Tyr His Gly Thr Phe Leu Glu Ala Ala Gln Ser Ile Val Phe
    450                 455                 460

Gly Gly Val Arg Ala Arg Ser Gln Asp Leu Asp Ala Ile Trp Arg Gly
465                 470                 475                 480

Phe Tyr Ile Ala Gly Asp Pro Ala Leu Ala Tyr Gly Tyr Ala Gln Asp
                485                 490                 495

Gln Glu Pro Asp Ala Arg Gly Arg Ile Arg Asn Gly Ala Leu Leu Arg
            500                 505                 510

Val Tyr Val Pro Arg Trp Ser Leu Pro Gly Phe Tyr Arg Thr Gly Leu
        515                 520                 525

Thr Leu Ala Ala Pro Glu Ala Ala Gly Glu Val Glu Arg Leu Ile Gly
    530                 535                 540

His Pro Leu Pro Leu Arg Leu Asp Ala Ile Thr Gly Pro Glu Glu Glu
545                 550                 555                 560

Gly Gly Arg Val Thr Ile Leu Gly Trp Pro Leu Ala Glu Arg Thr Val
                565                 570                 575

Val Ile Pro Ser Ala Ile Pro Thr Asp Pro Arg Asn Val Gly Gly Asp
            580                 585                 590

Leu Asp Pro Ser Ser Ile Pro Asp Lys Glu Gln Ala Ile Ser Ala Leu
        595                 600                 605

Pro Asp Tyr Ala Ser Gln Pro Gly Lys Pro Pro Arg Glu Asp Leu Lys
    610                 615                 620
```

<210> SEQ ID NO 15
<211> LENGTH: 1148
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

```
taatgaaata cctgctgccg accgctgctg ctggtctgct gctcctcgct gcccagccgg     60

cgatggccat gcatatgagc aaagaagaag caccaaaaat acaaatgccg cctcaacctg    120

taacaaccat gagtgctaaa tctgaagatt taccacttag ttttacttac cctgctaaac    180

ttgtcagtga ttatgatgtc attataaaac ctcaagttag cggcgtaata gtaaataaac    240

tttttaaagc tggagataag gtaaaaaaag gacaaacatt atttattata gaacaagata    300
```

```
aatttaaagc tagtgttgat tcagcttacg gacaagcttt aatggctaag gcaactttcg    360
aaaatgcaag caaggatttt aatcgttcta aagctctttt tagcaaaagt gcaatctctc    420
aaaaagaata cgactcttct cttgctacat ttaacaattc aaaagctagt ctagcaagtg    480
ctagagcaca gcttgcaaat gcaagaattg atctagatca taccgagata aaagctcctt    540
ttgatggtac tataggagat gctttagtta atataggaga ttatgtaagt gcttcaacaa    600
ctgaactagt tagagttaca aatttaaatc ctatttacgc agatttcttt atttcagata    660
cagataaact aaatttagtc cgcaatactc aaagtggaaa atgggattta gacagcattc    720
atgcaaattt aaatcttaat ggagaaaccg ttcaaggcaa actttatttt attgattcgg    780
ttatagatgc taatagtgga acagtaaaag ccaaagccgt atttgataac aataactcaa    840
cacttttacc gggtgctttt gcaacaatta cttcagaagg ttttatacaa aaaaatggct    900
ttaaagtgcc tcaaataggt gttaaacaag atcaaaatga tgtttatgtt cttcttgtta    960
aaaatggaaa agtagaaaaa tcttctgtac atataagcta ccaaaacaat gaatacgcca   1020
ttattgacaa aggattgcaa aatggcgata aaatcatttt agataacttt aaaaaaattc   1080
aagttggtag cgaagttaaa gaaattggag cacaactcga gcaccaccac caccaccact   1140
gagtcgac                                                            1148
```

<210> SEQ ID NO 16
<211> LENGTH: 990
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

```
catatgaaga aaatctggct ggcgctggcg ggcctggtgc tggcgtttag cgctagcgcg     60
gcggatagcg atattaacat taaaaccggc accaccgata ttggcagcaa caccaccgtg    120
aaaaccggcg atctggtgac ctatgataaa gaaaacggca tgctgaaaaa agtgttttat    180
agcttcatcg atgataaaaa ccataacaaa aaactgctgg tgatccgtac caaaggcacc    240
attgcgggcc agtatcgtgt gtatagcgaa gaaggcgcga acaaaagcgg cctggcgtgg    300
ccgagcgcgt ttaaagtgca gctgcagctg ccggataacg aagtggcgca gattagcgat    360
tattatccgc gtaacagcat tgataccaaa gaatatatga gcaccctgac ctatggcttt    420
aacggcaacg tgaccggcga tgataccggc aaagatcaaa atagaactaa aattggtgga    480
ctgattggcg cgaacgtgag cattggccat accctgaaat atgtgcagcc ggattttaaa    540
accattctgg aaagcccgac cgataaaaaa gtgggctgga aagtgatttt taacaacatg    600
gtgaaccaga actggggccc gtatgatcgt gatagctgga acccggtgta tggcaaccag    660
ctgtttatga aaacccgtaa cggcagcatg aaagcggcgg ataactttct ggatccgaac    720
aaagcgagca gcctgctgag cagcggcttt agcccggatt ttgcgaccgt gattaccatg    780
gatcgtaaag cgagcaaaca gcagaccaac attgatgtga tttatgaacg tgtgcgtgat    840
gattatcagc tgcattggac cagcaccaac tggaaaggca ccaacaccaa agataaatgg    900
attgatcgta gcagcgaacg ttataaaatt gattgggaaa aagaagaaat gaccaacggc    960
agccatcatc atcatcatca ttaagtcgac                                     990
```

<210> SEQ ID NO 17
<211> LENGTH: 19442

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
gaattccctg aggcaattct tctttgatga cggctgatgg tgaggttgac ctggtgaagc     60

tggtcaagga gctttgggtt aacaaggttc tgattcttct gactactctt cttgcattaa    120

tcgggtcttt tacctatgcg tatctgagta agcctgtata tgaatatagg gttgcagtag    180

tgcctcctgc tcttgggtct atcgaaggtt tcaatgttgg tagaagggag aatggcctag    240

atgcatatac tgttagaagt atctatgcga tcttttcgcg caatctgctt tcggatgaga    300

ataaaaaaga gttcttctat aagatatacc ttccccaggt gggtgaggga gcggaaagcg    360

aagatgagca ggaggagttt tataagaagt tctccaaaga ggtaaagatt gatcctgcta    420

acaagccaga tgcagaccgt tatacggtaa ttgtggaggg cacgaagcga gaggttcttg    480

ctacatgggc acaagctttc gtgcgtttgg ctgcggatcg ggccgtgcat gaggttattg    540

atagtgcagg tagagatttc caggtaagaa atgctgcaat gcagagccgc ataaccgtgc    600

tgcagaatat ggcgaagggc cgccgtgatg atagaattgc acgtttgaag gaggcattgc    660

tgattgcgga gtcgctcaag atagatggcc cgccattaat agaaggggcg tccgagcaac    720

aactctcctc gatcatggat ggtgacttga tgtacatgcg aggagctaag gcgctgcgcg    780

ctgaaatcaa caatcttgag tcgcgtagtg tagatgctcc attcattcct gagttgagaa    840

ctctccaaga gaaactatct tggaactcca gtttgtctgt ggattctgat gcggtggctg    900

tctacaagga agacgaggga ctctcttttt caaatcaacc cattaagccg aagaagattc    960

ttatagttac tataggtact ttggcaggat tgataattgg aattctactc gcagtgctcg   1020

ctggttttat aaggaagctt cgtagcgatg gctctcttcg ctaagttttg atctaaaccc   1080

tgatgccact tactggcatc agggcttact tgttgtagtt gttgaattgt attagggggt   1140

atcgagtaga atgtcaataa ggcggggcgt tttctactcc ggtatatcca tgggcagcaa   1200

ctatcttttg cctcttgctg cgattccttt tctcacgaga acattgtcaa gcgaagcgtt   1260

tggccaattg gtgattgccc aggccgtggc tgtcattcta tgtcaactgg tagactttgg   1320

atttattctg gcaggatcaa gaaaggctgc cattatcgat aacaaagttg aactgtctag   1380

tttcttttct gttgtacaga gtgctagatt cttattgttg ctgctttcac ttttagtgct   1440

ggccattttg gctgtatctt ctattttacc aatccccttg cttgtattgg ttgcggctgc   1500

tcttccggca gtagttggaa attatcttca agcagtatgg ttctttcagg gaagagcgct   1560

gtttggatgg ttggcgctta ccaatttttt gtctaaggta ttttatttcc tattggtcgt   1620

tttttttgtc acgaaggatt ctgaccttgt gctggcttcg ttggggtttg gtttttccta   1680

tgtcataggt ggaagtgctc tctgttgtat tttattttct atgggaatac ggtggcgccc   1740

ggttctcgag aaagacagaa ttctcgatat attgcgtgac ggtgctcgat cttttctttc   1800

tctggctttt cttagcttgc acatgcaagt gctcgttgcg gcggttggtg ttgttggtgg   1860

agcctccgcg gccggagtgc tttctactgc ggataaattc cttcgcggga tcgcggctgc   1920

tacttcaccc atagctagcg ctctatttcc gacttttagc aggatgtatg cgagtgccga   1980

cccggcagtc ggcagtttaa gaaggaaagc gctaggtctg atgttactaa tagctattcc   2040

tagttgttta tttcttttct tattttctga atacatttca tatctcctat tcccggaaca   2100

gtccagaggt ctaactgttg taataagaat gttttcgata gtgccagtgt ttgcttgtat   2160
```

```
tggtgttctg tatggagggt tgactcttgt tccttctggg tatgatggtg tatatttgcg   2220
agcaattttt tttgcggaat tgggcggggt attaacattt atcctcttgg cgctttgggg   2280
ggatgagctt tttggagcgt ggacgctggt cgttacagag gtctctttgg ggatgggaat   2340
gtttttcctg gccacggtta agttgagaga gaaaagggga ctttgatctt aagatgagga   2400
tagcgattga aaagataatt ggtttgctga aaaaccagtc ctctaaagaa tcgaatgtta   2460
agattcatcg cttggcgtat attacaaact caaaatttga tggcaataac tatatagata   2520
gatggtgtaa aatcaggaat tctcacattg gtgaatacag ttatattgga tttggtagtg   2580
attttaataa tgtagaagta ggaagatatt gttcgatatc ttcggatgta aaaattgggt   2640
taggaaaaca tcctacacac ttttttagct catcaccgat tttttattct aataataatc   2700
catttaacat aaagcaaaag tttatagact ttaatgacca accaagccgt acaacaatta   2760
aaaatgatgt gtggattggt gcaaatgtaa ttattatgga tggattaaca ataaatactg   2820
gtgcagtcat agcagccggc tcagttgtta ctaaaaatgt aggagcatat gaggttgttg   2880
gtggggttcc tgcaaaagtg attaagaagc gatttgacaa taaaacaatt gaaaaacttt   2940
tggaaagcaa gtggtgggag aaaacgcctg acaaactaaa aggattttcg gttgaatatt   3000
taaataaaaa ggatactagt tatccgtatg atgtgccgga ttatgcgtaa caggaggtgt   3060
acaatgagca ggaggtgtac aatgagaatt ttaaatattg tatcgagtaa tattgttcaa   3120
gacccaaggg tacttaaaca aatagaaaca attaaaggcg ttacgaatga ttataaaatt   3180
gttggaatga ataattcaca agctactaat aggcgattgg aaaatttaga ttgtaattat   3240
cgtttgttag gtagcaaggt agatcccaaa aatattcttt ctaaattaat taagcgtata   3300
agatttgcaa caggtgttat ccgagaaatt aaagctttta aacctgacgt gattcatgca   3360
aatgatttcg acgtattatt aatggtctat ttaagcaatt ataaaaaagc taatattgtt   3420
tatgatgcgc atgaaatata tgcgaaaaat gcctttatta ataaagttcc acttatttca   3480
aagtttgtag aaagtataga aaaacacata gtaaaacatc gtgttaatgc cttcgtaaca   3540
gtaagtcatg cagcaaaaga atattatcaa tctaaaggat ataagaagga agcgaatgtt   3600
attacgaatg cacctatttt aaatgatagc agagaattta aagaaatcga aaactttaaa   3660
gaaatcgtat atcaaggtca aattgtaatg gacagaggat atgaagagtt tattattgct   3720
tcatcagctt ttaaacaaaa tgctccttca ttcataattc gagggtttgg tccgcatgaa   3780
gaagtgataa aagaactgat tagttataac tcggaaaata ttaggttgga taaaccagtt   3840
gaagtaaaag aattggttga taagttagca gaaagtaatg ttggtgttat cttgacgaaa   3900
cctgtatcta ttaattttga atatacagta tctaataaaa tttttgaatg tatacatgct   3960
ggtttaccag taattttatc tcctgtcaaa gagcatattt atctcaatga aaaatataaa   4020
tttggcattg ttttaaagga agttacgccg ttagaaattg aaaaggcggt tagaaaatta   4080
agagataatc acgatttgtt taatcattta cgtcaaaatg caattaaggc gtctaaaatt   4140
ttgaattggc aaatagaaag tgaacgatta gtagaattat ataaatttga acaaaaactc   4200
atctcagaag aggatctgta aggacccggg gatcctctag caggaggaac tatgaaattt   4260
tttgtacttt gtgcaattat cagcatgaac atatttatag taatctctac atttactaaa   4320
gaagtattag ggttccctat agagccggtg tattactcaa ccatggttgg tatagcatta   4380
attactacgg tgtttgctat ttataagata attgtcacgc aagaaattcc gcgagggtta   4440
atattattaa ttgctatatg tttgctttat ctagcttttt attatttttc accagataag   4500
```

```
gaagagaaac tagctaaaaa taatattcta ttctttttaa catgggcagt tccagcggca   4560
attagtggta tttatattaa atatataaac aaggctacgg tagaaagatt ttttaaatta   4620
gtatttttca tattttctat ttcatttatt tttgtaattt taataccaaa acttacaggt   4680
gagataccta gctatatcaa ttttggactt atgaactatc aaaacgcttc gtacctttca   4740
gcatttactg ccggattagg catttatttc attatgaaag gttcagtgaa acataagtgg   4800
atatatgttc tatttacaat aattgatatc cctattgtgt ttataccagg agggcgtgga   4860
ggtgctattt tattaattct ttacggctta tttgcattta tacttattac gtttaaaaga   4920
ggaataccta ttgcagtaaa aagcattatg tatatttttg cattaagcat atctagtgta   4980
ttgatttact ttctttttac aaaaggttcg aatactagaa cattttcata tctacaaggt   5040
ggaacactta atttagaagg tacttctgga agaggaccga tttatgaaaa aggtatttac   5100
tttattcaac aaagtccgtt attaggctat gggccattta actattataa actaatcgga   5160
aatataccac ataacatcat tattgagttg attctatcat ttggcttatt agggtttttt   5220
atcataatga tttgcatttt gctactagtt tataaaatga ttaggaacta tgatccaaac   5280
actatagatt tactcgttat gtttatagca atctatccaa tcacattatt aatgtttagt   5340
tcaaattatt tagttgtaag tgaattttgg tttgtgttgt tctattttat tacaaaagga   5400
cggcgtcatc atggtgatta taaagatgat gatgataaat aagtttaaac aggaggcatc   5460
atggttaaga aagtttttat tatggatagc gtaaagacaa taattggtac gttgcttata   5520
gctttaggat tacaattttt agcttatcca attattaatc aacgagtagg taatgaagcg   5580
tttggttcta ttttaacgat ttatacaata ataacaatca cgagtgttgt attaggcaat   5640
acgcttaaca atatacgatt aattaatatg aatctataca aatccaatca ttactactgg   5700
aaatttgtgt cgatactttt aatttcaatt ctgattgaga gtatagcttt aattattgta   5760
tttctttact tttttaattt gaacaccatc gatattatct ttttaattct acttaatatt   5820
ttaatgtgtt taaggattta tctgaatgta tttttttagga tgactttaaa atataatcag   5880
attttgtata ttgctcttat tcaattttta ggtttgctga taggactatt tctatattat   5940
ttaatccaaa actggattgt ttgttttatt accagtgaat tgtttgcaac gatatataca   6000
ttggttaaat tacggggatt aactataggc gagtatcaaa gtgaagataa taatgtggtc   6060
aaagattatg tgatgctact gagtacaaat agccttaata atttgaatct ctacttagat   6120
agattaatct tattaccaat tataggtgga acagctgtaa ctatatcatt tctttcaaca   6180
tttattggga aaatgttagc tacatttctg tatccgatta ataatgtagt actttcatat   6240
atttctgtaa atgaaagcga caatataaag aagcaatatt tgaaaactaa tctatttgct   6300
atagctgcac tatgtttagt catgattata tgttatccaa ttacattaat tattgtctct   6360
ttactgtata acattgattc aagtttatat tcgaagttta ttattttagg taatataggt   6420
gttttattca atgcagtgag tattatgatc caaactttaa atacaaaaca cgcatcaata   6480
acattacaag cgaattatat gacgcttcac acgattacat ttatattcat aactatttta   6540
atgacaattg cgtttggtct aaatggattc ttttggacaa cgctgttcag caacattatt   6600
aagtatgtga ttttaaatat tataggttta aagtctaaat tcattaataa aaaggacgtc   6660
gatagttatc cgtatgatgt gccggattat gcgtaagtgc accatatgaa tatcctcctt   6720
agttcctatt ccgaagttcc tattctctag aaagtatagg aacttcggcg cgcctacctg   6780
tgacggaaga tcacttcgca gaataaataa atcctggtgt ccctgttgat accgggaagc   6840
cctgggccaa cttttggcga aaatgagacg ttgatcggca cgtaagaggt tccaactttc   6900
```

```
accataatga aataagatca ctaccgggcg tattttttga gttgtcgaga ttttcaggag   6960
ctaaggaagc taaaatggag aaaaaaatca ctggatatac caccgttgat atatcccaat   7020
ggcatcgtaa agaacatttt gaggcatttc agtcagttgc tcaatgtacc tataaccaga   7080
ccgttcagct ggatattacg gcctttttaa agaccgtaaa gaaaaataag cacaagtttt   7140
atccggcctt tattcacatt cttgcccgcc tgatgaatgc tcatccggaa ttacgtatgg   7200
caatgaaaga cggtgagctg gtgatatggg atagtgttca cccttgttac accgttttcc   7260
atgagcaaac tgaaacgttt tcatcgctct ggagtgaata ccacgacgat ttccggcagt   7320
ttctacacat atattcgcaa gatgtggcgt gttacggtga aaacctggcc tatttcccta   7380
aagggtttat tgagaatatg tttttcgtct cagccaatcc ctgggtgagt ttcaccagtt   7440
ttgatttaaa cgtggccaat atggacaact tcttcgcccc cgttttcacc atgggcaaat   7500
attatacgca aggcgacaag gtgctgatgc cgctggcgat tcaggttcat catgccgttt   7560
gtgatggctt ccatgtcggc agatgcttaa tgaatacaac agtactgcga tgagtggcag   7620
ggcggggcgt aaggcgcgcc atttaaatga agttcctatt ccgaagttcc tattctctag   7680
aaagtatagg aacttcgaag cagctccagc ctacacgtaa agaggtggtg tatggataag   7740
aactctgttc tgttaattac cggtggaact ggttcctttg gaaatgccgt tttgaagcgt   7800
tttctggata cagatattgg tgaaatacgt gtattcagtc gggatgagaa gaagcaagat   7860
gatatgcgta agtgctatgc tcaccccaag ttgaggtttt atattggaga tgtccgcgac   7920
tatcaaagca ctctgaatgc tactcgcggt gtggactaca ttttccatgc ggctgcattg   7980
aaacaggttc cctcttgtga gttctacccg atggaggctg tgaagaccaa tgtcatcgga   8040
acggaaaatg tcctcgaatc tgctatccag aatggcgtca aaaaagtcgt ttgtctgagt   8100
acggataagg cagtttaccc aatcaatgcc atgggtattt caaaggccat gatggaaaag   8160
gtcatggtcg ccaagtctcg aaacctggaa cgcactccta ccgtaatttg tggcacccgt   8220
tatggtaacg tcatggcttc aaggggctcg gtcattcctc tctttatcga gcaaatgcga   8280
tcaggccagc ctctcacaat cactgatcca aacatgacac gtttcatgat gacgcttacg   8340
gatgccgtag accttgtgct ttatgctttc gagcatggta ccaatggaga tctttttgta   8400
cagaaagcac cggctgcaac catcgaggtg ctggctcatg cgcttactca attgcttggc   8460
aagaatggtt atcctatcaa tgtaataggt acgcgtcatg gagagaagct ttatgaggcg   8520
cttcttagtc gagaggaaat ggcctgtgct gaagacatgg gtgactatta tcgtatcccc   8580
ccagatttgc gtgatctgaa ctatagtaag tttgtggagc aaggcgagga aaaaattact   8640
catacagagg actataattc tcataatacc aaacgtctgg atatcgaagg aatgaaaaag   8700
ctgttgctga agttggattt cattcgtgct attcagcgtg gcgagagtgc cagtccagag   8760
gaataaacga tgaaagttct tgtaactggc gcgaatggat ttgttggaag gaatctgtgc   8820
gctcatcttg cagagcgggg tggtatcgag gtggtgccat tcacccgcga gagtagtgtt   8880
ggtaatttgc ctgagctaat tcgttccgtc gattttattt ttcatcttgc cggggtcaat   8940
cgtccggaaa aaccagaaga gtttaagatc gggaattccg aactcacgta tgctctgtgt   9000
gaggcggtaa ggtccaatgg acgagccata ccacttcttt atacttcatc cattcaggct   9060
gaggtggata atgagtacgg tttaagcaag cgagccgcag aagagcatct ccaagtgcta   9120
ggtgaggata ttggttgtcc tgtctacata tttcgccttc ctaatgtatt cggtaaatgg   9180
tcgcgtccga attataattc agcggttgcg actttttgtc ataatattat tcgagatatt   9240
```

```
ccgattcaaa ttaacaattc ctcggcagag atcactcttg tatacataga tgatgtggtt   9300
cgcaccttca tgaaagtcat ggatgggaag ctatccaatg cagtttcact acaggtcgag   9360
ccccagtatc agatttctgt tggtgagctc gcagaacaat tgtatgagtt tcgtaatagt   9420
cgaaagtcac tgactaccgc aagggttggc tcgggattga cgcgcgcctt gtactcgact   9480
tatctaagtt tcttgccaga agatagtttt agttacgacg tgccaatgca ttcggatccg   9540
cgtggcacat tcgtcgagat gctgaagacc gcggactctg gccagttctc gtttttttacg   9600
gctcatccag gtgttaccag ggcgggcat taccatcact cgaaaaccga aaagtttctg   9660
gttatcaaag ggatggcacg tttcaagttt agaaacatcc tgaccggggc attttacgaa   9720
atttgcacta atggtgaaaa ggcagaaatt gtcgaaacag tacctggatg gactcatgac   9780
attactaatg tcggaactga cgatatggta gtcatgttgt gggctaacga agtatttgat   9840
cgggaaaatc cggataccta cgcttgttca gtaggcgaag gtgcgtaagg tatagtgaga   9900
taacaatgca gaagctaaaa gtcgttacgg ttgttggaac tcgtcctgag attattcgct   9960
tgtctagggt catggcgaag cttgatcagt actgcgatca tgtacttgtc catactggac  10020
agaattatga ttacgaactt aatgaaatat tttttcagga cctcggtata agaaagccgg  10080
attattttct aaacgccgcc gggtcttccg gggctgaaac gatagggaat gtaataatcg  10140
cagtcgatcg tgttctgggc gaaatagatc ccgatgcgct gctcgtgctg ggtgatacca  10200
atagttgtat ggcggtactg cctgcaaaac ggcgtaagat accgaccttt catatggaag  10260
caggcaatcg ctgtttcgat atgcgtgtgc ctgaagagat aaatcggcgc attgtcgatc  10320
atacagctga tgtaaatttg acctatagta caattgcgcg tgattatctc ttgcgtgaag  10380
gactttctcc agacatggtt atcaagactg gtagccctat gttcgaagtt ctcgagcact  10440
atcgtgacgg gatcgagtcc tccgatattc ttgaaaggct cgggttgaaa acagagcggt  10500
tctttgtcgt gagtgcgcac cgagaggaaa acatagattc ggataagaat ttcttgaagt  10560
tggtttctat gctcaacgct gtggcagaaa agtactcgct gcccgtcatc gtatcaactc  10620
accctagaac aaaaaagaga attgaggcga cggaggcaaa gtttcacgag ggtattaaac  10680
tgctgaaacc cctcggcttt aaggattaca ataaactgca aattacagcc aaggcagtta  10740
tttctgacag tgggaccatc agtgaggagt cttcaatact gaattttccc gctttgaata  10800
ttcgtgaggc tcatgaacgc ccagaaggca tggaagaggc tgtggtgatg atggtcggac  10860
tggattcgga tcgagtacta caagcactcg aggtgttgga gggacagagg cgcgacgcag  10920
agcgcatgtt acgcttggtc gctgactata gcatgcccaa cgtttctgaa aagattgttc  10980
gcatagttca tagctatcgg gactatgtca tgcgaactgt ctggaaaaaa tattaacttg  11040
aggcgtggag ttgatggcaa ggatatttgt ggtttctgag tatgtcggtg ccaatcagaa  11100
ctccacggga tactattggg agaagataat aggaaagatg cagcgggagt ttggtgggct  11160
aaccgtaatt ttcccgctga ccgcaggtga aaccccgcct gtggtttcac cttccgttga  11220
gcaagaatgc tttaagtttc cgaggagcaa taagaatagg ctcctttcta gaggattggc  11280
gcagattttt caggcgtttc tgttctcagt aaaattgact tctcgtgcca gacgaggaga  11340
tgtggtattg agtggaacca accctgctct tctactgatg acgtttccct tgctaaggta  11400
tgccctcggt ttcaagtggg tgctgctggt gcatgatgtg tttcccgaga acttggtgcc  11460
ggcgggcgtt ctgaagaaag atagtattgc ctaccggctt ctacgtcgtc tcttttcttt  11520
catttactca tccgctgatc gtctagtcgt aatagggcgc gatatggaag ctcttatgaa  11580
agagaaggtg aatgacccgc gatctttggt ctttatttcg aattgggcct gtgagaaaga  11640
```

```
ggttttccca gtaccgagag aggatgctcc ttttatcaat attcctgaat ggaaaggtaa  11700
aagggttttc caattttttg gtaatgtcgg tcgattacaa ggtatagaaa acatactttc  11760
tgctattcag ttggttaaaa acgagaaggc ggcttttgct tttattggag atggtgcctt  11820
ggtcgacagt gtaaaaaaac acgcgctgga agatcagtgt gctcggttga ggtattttgg  11880
aaggctgcca ttagccgaaa agaattttgg tttggctgcc tgtgacgttg ccttagttac  11940
cttagaagaa ggaatgttcg ggcttggggt tcccagcaag gcatatttct ccatggcagc  12000
agacaaaccg attctagctg tcatggaaaa aggggctgaa atctcccgta taatagatga  12060
gaccggaatc ggttggaact gtccgccgaa tgatccggtt gctttggcaa gattgatcga  12120
tgagatttgt gaactcgact tgtctagttt aggcggagtc ccgcggagtg tccttcagca  12180
aaattattct gaatatattt cattggaaaa attcgctgcc tgtgttcgac cgcttctgtc  12240
tgagtcgaaa atatgatgaa ggtgctggta accggggcta gcggttttgt cgggagtgcg  12300
ctttgcaggt cgcttgctgc cgcccccttt caggttgtcg gacaagtacg atccctgtac  12360
aatcccgtta cgggggttga gtatgttcga gcggagctga aagagagcac taagcttgat  12420
gctgcgctgc ggggtgttga atgtgtagtt catctagctg gacgagccca tatctttgga  12480
aggcagcgtg attcactaga tatttttcgg aaggtgaatc gcgatgctac tctggcgctt  12540
gctcggcagg cgatcgaagc atctgtaaag cgtttcattt ttgttagttc tattggtgta  12600
aatggcgctt taaccaaaga aaagcccttc gatgagaact ccaagccggc tcctcatgca  12660
gaatatgcga tttcaaagtt tgaggctgaa gtagcgcttc gggagctttt caagcattcc  12720
tcaacagaac ttgttatcgt caggcctcca ctcgtttacg actggaaagc tcctggaaat  12780
ttctcgcgat tgttgaagct ggttgcttcg ggacttcctc ttccatttgg ttgcatagat  12840
aaccgacgaa gttttgtttc tctggataat ttagttgact ttctagcttg ctgtatgacg  12900
cacccttctg ctgccggcga actgtttttg gtatccgatg gtcaggagat ttctaccaag  12960
caactggtga ctgcgcttgc tgcgggaatg gggcgtcgcc ccatcatgtg gcctgttcct  13020
aggtttattc tgaggtttct taaattagta ggaaagggtg ggttatacac tcagttatgc  13080
tgctcactag aggtcgactc gtcgaaaggc aggcttttgc ttggttggga accccgcaag  13140
agcacccttt ccgcgttgga agatgttggt agaatatatg tcaaacgtac tgaatgatta  13200
tctgcaggcg ctttgctact agcatggcgt accacgcaga acaatcgaat agaaccctgt  13260
tgaaggggtg agagtatttt tggggataaa tttataaatg gaagaatggt atttgttact  13320
cgctgcagct ggggtttcgg gactgcttac aggcctcttg cgtcgttatg ccttagcgag  13380
gagcttactt gacaccccta actctcgaag ttcccatgtc gttcccactc cacgcggagg  13440
aggggtcgcc attgtagtta ctttttgtct catgctgcct atttgggctg tactgggaaa  13500
tatctcatgg gccgtgtcct gggctttact tctcgctggc ggcggggttg ccattattgg  13560
attcatggat gatcacggtc atatcgccgc acgctggcgt ctgctgggac attttagtgc  13620
agccttggtc tcattgtact tttgaatgg cataccacca tttcagattg ttggtgtcag  13680
ttgggacctg gggtggttcg gaggacttct ctttgctttc tatctcgtgt ggttgctgaa  13740
tctctataac ttcatggatg ggatcgatgg acttgctagc cttcaggcca tttttgtctg  13800
tgttggtggg gcattattat actggctgaa tggccaactg acgcaggctt tgctcccctt  13860
atcgctagct tttgccgttt ttggattctt gttctggaat tttccacccc caaaaatttt  13920
catgggagat gcgggtagtg gtcttctggg gattgtttta ggaattcttt ccattcatgc  13980
```

```
catgtggatg aatacgaatt ttttctgggc atggttggtc ctgttaggcg ttttcatcgt  14040
cgatgcgacc tataccctga ttcgtcgctt gctgagaggg gacaaggtgt atgaggctca  14100
tcgaagccat gcctatcaat acgcaagccg atactatgga aagcatgctc ctgttacgat  14160
tggcgtcacg gcattgaacg tcatctggct cctccctata gccttgttgg tcgggagtgg  14220
gtctctagag cctttgatgg gcatcgtcat agcctacgtc cctctcgttt ttctggcagt  14280
gaggttcaag gcgggtaagc tagagtcgtc cgctcaggcc taaaggagta ggggaatgct  14340
agatcgttta agagtaaagt tgttatccat gcctcgtcgc tggaaacgtt tgcttcaagt  14400
ggctacggat atccttctgg tatggctgtc tctgtggctc gcttttgtgg tccgtctagg  14460
cacagacgat atgatcgacg tgttcggcga gcatgcatgg cttttcatca ctgcgccggt  14520
catcgccatt ccactattca ttcgcttcgg catgtatcgc gcggtgatgc gctatctcgg  14580
taacgacgca ttgatcgcca tcgccaaggc ggtgaccatc tcggctctgg tgctgtcgct  14640
ggtggtgtac tggtatcgtg gcgcgccggc gccggtgccg cgttccctgg tgttcaacta  14700
ctggtggttg agcatgctgc tgatcggcgg cttgcgtctg gccatgcgcc agtatttcat  14760
gggcgactgg tactctgctg tgcagtcggt accatttctc aaccgccagg atggcctgcc  14820
cagggtggtt atctatgggg cgggggcggc cggcaaccag ttggttgcgg cgttgcgtct  14880
cggtcgggcg atgcgtccgg tggcgttcat cgatgacgac aagcagatcg ccaaccgggt  14940
cattgccggt ctgcgggtct ataccgccaa gcatatccgc cagatgatcg acgagacggg  15000
cgcgcaggag gttctcctgg cgattccttc cgccactcgg gcccggcgcc gagagattct  15060
cgagtccctg gagccgttcc cgctgcacgt gcgcagcatg cccggcttca tggacctggc  15120
cagcggccgg gtcaaggtgg atgacctgca ggaggtggac atcgctgacc tgctggggcg  15180
cgacagcgtc gcaccgcgca aggagctgct ggaacggtgc atccgcggtc aggtggtgat  15240
ggtgaccggg gcgggcggct ctatcggttc ggaactctgt cggcagatca tgagttgttc  15300
gcctagcgtg ctgatcctgt tcgaacacag cgaatacaac ctctatagca tccatcagga  15360
actggagcgt cggatcaagc gcgagtcgct ttcggtgaac ctgttgccga tcctcggttc  15420
ggtgcgcaat cccgagcgcc tggtggacgt gatgcgtacc tggaaggtca ataccgtcta  15480
ccatgcggcg gcctacaagc atgtgccgat cgtcgagcac aacatcgccg agggcgttct  15540
caacaacgtg ataggcacct tgcatgcggt gcaggccgcg gtgcaggtcg gcgtgcagaa  15600
cttcgtgctg atttccaccg acaaggcggt gcggccgacc aatgtgatgg gcagcaccaa  15660
gcgcctggcg gaaatggtcc ttcaggcgct cagcaacgaa tcggcgccgg tgctgttcgg  15720
cgaccggaag gacgtgcatc acgtcaacaa gacccgtttc accatggtcc gcttcggcaa  15780
cgtcctcggt tcgtccggtt cggtcattcc gctgttccgc gagcagatca agcgcggcgg  15840
cccggtgacg gtcacccacc cgagcatcac ccgttacttc atgaccattc ccgaggcggc  15900
gcagttggtc atccaggccg gttcgatggg gcagggcgga gatgtattcg tgctggacat  15960
ggggccgccg gtgaagatcc tggagctcgc cgagaagatg atccacctgt ccggcctgag  16020
cgtgcgttcc gagcgttcgc cccatggtga catcgccatc gagttcagtg gcctgcgtcc  16080
tggcgagaag ctctacgaag agctgctgat cggtgacaac gtgaatccca ccgaccatcc  16140
gatgatcatg cgggccaacg aggaacacct gagctgggag gccttcaagg tcgtgctgga  16200
gcagttgctg gccgccgtgg agaaggacga ctactcgcgg gttcgccagt tgctgcggga  16260
aaccgtcagc ggctatgcgc ctgacggtga aatcgtcgac tggatctatc gccagaggcg  16320
gcgagaaccc tgagtcatcg ttctccggaa aaggccgcct agcggccttt tttgttttct  16380
```

```
ccgtacgatg tttccggtgc cggaccagga agcgactgct ttgctggggc tgtcgatcca  16440
ggtgcgttcc acggcgataa ggtggtttcg tggatgggca acatgtcgcg aaggtaaagt  16500
cagccgcatt gttgaattca tcgaaaaacc ggatcagcca caaacgctgg aatcagacat  16560
catggccgtg ggccgttatg tgctttctgc cgatatttgg ccggaacttg aacgcactca  16620
gccaggtgca tggggacgta ttcagctgac tgatgccatt gccgaactgg cgaaaaaaca  16680
gtctgttgac gccatgctga tgactggtga cagctacgac tgtggtaaaa aaatgggtta  16740
tatgcaggcg tttgtgaagt atggactacg caacctgaaa gaaggagcga agttccgcaa  16800
aggtattgag aaattgctta gcgagtaagt ttaaaaaata gacgccctta tagggcgtaa  16860
taacaaataa cggtagtcaa cattcgacgc ggtgatgcag atatgcccgg aatgctgata  16920
ccgtttttttc attctaaaaa actcatcatt tcattgagtt aactacaaaa tttagcactg  16980
tttttataa tgtttcttct tgtttctggc atcaattggt aagataatta gtgtttgagt  17040
ttagaggctt tgcggcagag aagcggagct taacacgtct gtgagagtac gcagtgcact  17100
ggtagctgta aagccagtgg cggtagcgtg tttaaataaa tacattagta atactacata  17160
ttacatcatt gtaggctatt taagcgctac atgataagcg acagcgctag caatcaaatc  17220
ttttaaagtt acttctcagg aatagtaaaa ggaggacagc tatgttgaaa aaagagtatt  17280
taaaaaaccc ttatttagtt ttgtttgcga tgattatatt agcttatgtt tttagtgtat  17340
tttgcaggtt ttattgggtt tggtgggcaa gtgagtttaa tgagtatttt ttcaataatc  17400
agttaatgat catttcaaat gatggctatg cttttgctga gggcgcaaga gatatgatag  17460
caggttttca tcagcctaat gatttgagtt attatggatc ttctttatcc gcgcttactt  17520
attggcttta taaaatcaca cctttttctt ttgaaagtat cattttatat atgagtactt  17580
ttttatcttc tttggtggtg attcctacta ttttgctagc taacgaatac aaacgtcctt  17640
taatgggctt tgtagctgct cttttagcaa gtatagcaaa cagttattat aatcgcacta  17700
tgagtgggta ttatgatacg gatatgctgg taattgtttt gcctatgttt attttatttt  17760
ttatggtaag aatgatttta aaaaaagact ttttttcatt gattgccttg ccgttattta  17820
taggaattta tctttggtgg tatccttcaa gttatacttt aaatgtagct ttaattggac  17880
ttttttaat ttatacactt atttttcata gaaaagaaaa gattttttat atagctgtga  17940
ttttgtcttc tcttactctt tcaaatatag catggtttta tcaaagtgcc attatagtaa  18000
tactttttgc tttattcgcc ttagagcaaa aacgcttaaa ttttatgatt ataggaattt  18060
taggtagtgc aactttgata tttttgattt taagtggtgg ggttgatcct atactttatc  18120
agcttaaatt ttatattttt agaagtgatg aaagtgcgaa tttaacgcag ggctttatgt  18180
atttaatgt caatcaaacc atacaagaag ttgaaaatgt agatcttagc gaatttatgc  18240
gaagaattag tggtagtgaa attgtttttt tgttttcttt gtttggtttt gtatggcttt  18300
tgagaaaaca taaaagtatg attatggctt tacctatatt ggtgcttggg tttttagcct  18360
taaaaggggg gcttagattt accatttatt ctgtacctgt aatggcctta ggatttggtt  18420
ttttattgag cgagtttaag gctataatgg ttaaaaaata tagccaatta acttcaaatg  18480
tttgtattgt ttttgcaact attttgactt tagctccagt atttatccat atttacaact  18540
ataaagcgcc aacagttttt tctcaaaatg aagcatcatt attaaatcaa ttaaaaaata  18600
tagccaatag agaagattat gtggtaactt ggtgggatta tggttatcct gtgcgttatt  18660
atagcgatgt gaaaacttta gtagatggtg gaaagcattt aggtaaggat aattttttcc  18720
```

```
cttcttttgc tttaagcaaa gatgaacaag ctgcagctaa tatggcaaga cttagtgtag  18780
aatatacaga aaaaagcttt tatgctccgc aaaatgatat tttaaaaaca gacattttgc  18840
aagccatgat gaaagattat aatcaaagca atgtggattt gtttctagct tcattatcaa  18900
aacctgattt taaaatcgat acgccaaaaa ctcgtgatat ttatctttat atgcccgcta  18960
gaatgtcttt gatttttttct acggtggcta gtttttcttt tattaattta gatacaggag  19020
ttttggataa accttttacc tttagcacag cttatccact tgatgttaaa aatggagaaa  19080
tttatcttag caacggagtg gttttaagcg atgattttag aagttttaaa ataggtgata  19140
atgtggtttc tgtaaatagt atcgtagaga ttaattctat taaacaaggt gaatacaaaa  19200
tcactccaat tgatgataag gctcagtttt atattttttta tttaaaggat agtgctattc  19260
cttacgcaca atttatttta atggataaaa ccatgtttaa tagtgcttat gtgcaaatgt  19320
ttttttttagg aaattatgat aagaatttat ttgacttggt gattaattct agagatgcta  19380
aggtttttaa acttaaaatt tacccatacg atgttccaga ttacgcttaa acatgtgaat  19440
tc                                                                 19442
```

<210> SEQ ID NO 18
<211> LENGTH: 19616
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 18

```
gaattccctg aggcaattct tctttgatga cggctgatgg tgaggttgac ctggtgaagc     60
tggtcaagga gctttgggtt aacaaggttc tgattcttct gactactctt cttgcattaa    120
tcgggtcttt tacctatgcg tatctgagta agcctgtata tgaatatagg gttgcagtag    180
tgcctcctgc tcttgggtct atcgaaggtt tcaatgttgg tagaagggag aatggcctag    240
atgcatatac tgttagaagt atctatgcga tcttttcgcg caatctgctt tcggatgaga    300
ataaaaaaga gttcttctat aagatatacc ttccccaggt gggtgaggga gcggaaagcg    360
aagatgagca ggaggagttt tataagaagt tctccaaaga ggtaaagatt gatcctgcta    420
acaagccaga tgcagaccgt tatacggtaa ttgtggaggg cacgaagcga gaggttcttg    480
ctacatgggc acaagctttc gtgcgtttgg ctgcggatcg ggccgtgcat gaggttattg    540
atagtgcagg tagagatttc caggtaagaa atgctgcaat gcagagccgc ataaccgtgc    600
tgcagaatat ggcgaagggc cgccgtgatg atagaattgc acgtttgaag gaggcattgc    660
tgattgcgga gtcgctcaag atagatggcc cgccattaat agaaggggcg tccgagcaac    720
aactctcctc gatcatggat ggtgacttga tgtacatgcg aggagctaag gcgctgcgcg    780
ctgaaatcaa caatcttgag tcgcgtagtg tagatgctcc attcattcct gagttgagaa    840
ctctccaaga gaaactatct tggaactcca gtttgtctgt ggattctgat gcggtggctg    900
tctacaagga agacgaggga ctctcttttt caaatcaacc cattaagccg aagaagattc    960
ttatagttac tataggtact ttggcaggat tgataattgg aattctactc gcagtgctcg   1020
ctggttttat aaggaagctt cgtagcgatg gctctcttcg ctaagttttg atctaaaccc   1080
tgatgccact tactggcatc agggcttact tgttgtagtt gttgaattgt attagggggt   1140
atcgagtaga atgtcaataa ggcggggcgt tttctactcc ggtatatcca tgggcagcaa   1200
ctatcttttg cctcttgctg cgattccttt tctcacgaga acattgtcaa gcgaagcgtt   1260
```

-continued

```
tggccaattg gtgattgccc aggccgtggc tgtcattcta tgtcaactgg tagactttgg   1320
atttattctg gcaggatcaa gaaaggctgc cattatcgat aacaaagttg aactgtctag   1380
tttcttttct gttgtacaga gtgctagatt cttattgttg ctgctttcac ttttagtgct   1440
ggccattttg gctgtatctt ctattttacc aatccccttg cttgtattgg ttgcggctgc   1500
tcttccggca gtagttggaa attatcttca agcagtatgg ttctttcagg gaagagcgct   1560
gtttggatgg ttggcgctta ccaatttttt gtctaaggta ttttatttcc tattggtcgt   1620
ttttttgtc acgaaggatt ctgaccttgt gctggcttcg ttggggtttg gtttttccta   1680
tgtcataggt ggaagtgctc tctgttgtat tttattttct atgggaatac ggtggcgccc   1740
ggttctcgag aaagacagaa ttctcgatat attgcgtgac ggtgctcgat cttttctttc   1800
tctggctttt cttagcttgc acatgcaagt gctcgttgcg gcggttggtg ttgttggtgg   1860
agcctccgcg gccggagtgc tttctactgc ggataaattc cttcgcggga tcgcggctgc   1920
tacttcaccc atagctagcg ctctatttcc gacttttagc aggatgtatg cgagtgccga   1980
cccggcagtc ggcagtttaa gaaggaaagc gctaggtctg atgttactaa tagctattcc   2040
tagttgttta tttcttttct tattttctga atacatttca tatctcctat tcccggaaca   2100
gtccagaggt ctaactgttg taataagaat gttttcgata gtgccagtgt ttgcttgtat   2160
tggtgttctg tatggagggt tgactcttgt tccttctggg tatgatggtg tatatttgcg   2220
agcaattttt tttgcggaat tgggcggggt attaacattt atcctcttgg cgctttgggg   2280
ggatgagctt tttggagcgt ggacgctggt cgttacagag gtctctttgg ggatgggaat   2340
gtttttcctg gccacggtta agttgagaga gaaaaggga ctttgatctt aaggcgatcg   2400
ctaggaggac agctatgcgt attgcgattc tgggcgcgac caacattaaa catatgagcc   2460
tgctgagcca ttatctgaac catattgatc tgaacattaa cgaagtggat attatttata   2520
ccgataaata tgatattgaa gaacatattc agggcatcaa caactactac aaatacaaag   2580
tggatatcaa agaagattgg accttcatca agaaagcgat tgcgtattat cgttttcgtc   2640
cgtatgcgat gaaaattctg aaagaaaacc gttatgattt tgtgattgtg tggggcagct   2700
acaccggcca tctgttcaaa agctttctgg aaaaacatta caaaaacaaa ttcatcctga   2760
acatccgtga ttacttttc gaaaacaaca aactgattaa atatcgtatg aagaaaatcg   2820
tggatgcgag ccgtgtgacc accctgagca gcgaaggctt tctgaaattc ctgccgaaaa   2880
gcgaaaaata ccgtatcatc tacagctaca acatgagcat catccgtgaa agcaacgtga   2940
ccgatggctt taaaaaacgt tggccgatta acattggctt tattggcaac gtgcgtttta   3000
acgaaattaa ccagaaactg attaaagaac tggcgaacga tagccgtttt catatgcagt   3060
attttggcac cggcagcgaa aaactggaag tgtttgcgcg tgaaaacttt attaacaaca   3120
ttacctttag cggcggcttt gatctgaaag aaaccccgaa atatctgaac gaaattgata   3180
ttctgaacaa cctgtttggc aaccagaaca ttgcgctgga taccgcgctg agcattcgta   3240
tgtattatgc gctgtttctg aacaaaccga ttattaccac cgatgatacc tttaccgcga   3300
ccgaagcgaa caaatttggc ctgggcttta gcattaaccc ggaaaacctg aaaggcattg   3360
gcgatgaact gatggattgg tataacaacc tggatgtgat ggatattaac cataaacgtg   3420
aagcgtatcg taacgatgtg attgaaaaca acaaacagtt ttatcaggaa attggccgta   3480
tttttaacga agaacagaaa ctgattagcg aagaagatct gtaacgttta aacaggagga   3540
cagctatgaa caaaatttat aacgtgacca gctatgtgat tgcgattctg atgtttccgt   3600
gcctgatgct gggcgataaa ccgctgctgt ttctggcgcc gattagctat ggcgtgggca   3660
```

```
aactgttcat cagcttcagc aacaacccga acttcaaatt cagcaaaatc gtgtacgatg   3720
tgctgggctt tctgcgtctg gtgtttattc cggcgatgat tgtgtttttc caggatagca   3780
ccattgataa cctgccgctg ggccaggcgt attttaacca ggcggtgatt tatatgagcg   3840
tggaatttat tattggcagc ctgtttattc tgattctgag caaactgttc aagcatgaag   3900
ttgtgagccg taacagcttt accctgagcg gcagcagcat ttattatatt gtgtttggcc   3960
tggtgatttg cggcattttt gtggcgtttc cggaagtgcg taaaaacatt agctttctga   4020
ttattaaaac cgatgcgatg ggccgtggca ccgaagcgac cagcggcctg aacgtgctgt   4080
ttgtgatgct gtttcagctg gcgctggcgc tgctgtttct gatcatcgcg tacgcgagct   4140
acaaaaaata caaagaaaac ccgaaaatca tctacgtggt gctgccgctg gcgattggca   4200
ttctgaacat tagcctgatt gtgggcgaac gtcgtagcta tcagctgtat accatggtgg   4260
cggtgctgac cgttgtgagc atcctgttta gcaaacataa acgtcgtatc aacatcatca   4320
tcatcagcgt gggcatcttc gtgctggcgc tgatgaccct gtataaagaa ctgtatgtgt   4380
ttaactatag cagctatagc gaagcgctga acagcaccag cgtgagcaac ctgaaaattg   4440
tggataccct gcagagctat ttttatggcc cgagcaacat tgcggcgagc attgattatc   4500
tgaactatta taacggcagc tttaaacagt atctgtttga taacacccgt gcggtgtttg   4560
gctttaactt tttcctggat aaaaaacagc tgattaccag ccagctgttt aaccagctga   4620
tttatggcag caaacagctg accggccatc tgattagcag cgcgggctat ggcattattt   4680
attttggccc gctgtttttc tacctgaacc tgattgcgaa catctttttc gcgtttctga   4740
gcgaatacat catccgtaaa agccatagcc tggaagtgat cttcatcggc acctacatct   4800
acatgcgtct gattaccagc atttttagcc atccgacccc gctgattacc ctgattagca   4860
tgattctggt ggtgtatgtg attgcgatca tcccgggcat catcatcaag aaattcacca   4920
aaaaagtggg catcgaagat tacaaagatg atgatgataa ataacgttta aacaggagga   4980
cagctatgat tgtgaaaacc tttatgaaaa gcaaaatttt tcgtctgatg aacaccccgc   5040
tgctgctgtt ttataaaaaa gaatatctga ccggctatta ttttgaaaac aaagtggcgg   5100
gctggctgtg ggcgtggaaa gcggtgccat tcaagctgct gggcattaac accagcctgc   5160
cgtttccggc ggatattacc gtgcgtatgc ataacccgaa caacattgtg tttgataaaa   5220
acgatattca tatttttcag agcccgggca cctattttaa caactttagc gcggtgattt   5280
atattggccg tggcgtgtat attgcgccga acgtgggcat tattaccgcg aaccataaca   5340
ttaaaaacct gaaaagccat gcgccgggcg aagatgtgaa aattggcaac tatagctgga   5400
ttggcatgaa cagcgtgatt ctgccgggcg tggaactggg cgaacatacc attgtgggcg   5460
cgggcagcgt ggtgaccaaa agctttccgg aaggcaacgt ggtgattggc ggcaacccgg   5520
cgaaaattat taagaaaatc agctatccgt atgatgtgcc ggattatgcg taattaatta   5580
accaggtgca cgaagaaaat tatgagatta aataaattta ttggcgattc gtttttaatg   5640
attttaagca gtggcatcgc tcaagtcata ttaatcatca ctaccccaat tattacaaga   5700
ctatattcac ctacagaatt tggtgagttt acaatttttt caaatatcgc aatgatttta   5760
ataccaataa taaatgcaag atacgatttg ttgattgtga ataccaaaaa tgaccgtagt   5820
gctaatatac tttcacaaat cagttttttg atatcattgc ttattttatt aatactgata   5880
ccaatatttg cgattagtgc atgtttatac ccaaacttta tattagattt tattttcatt   5940
attattatgt tgtttttggt aagtttaaca aacattttta caaattatct aaataaggaa   6000
```

```
agaaagtata aagtgttaag tttgattaat gtgtttagag ctggatcaat ggctttactt   6060
caaatcattt tcggactttt agcattagga agtttaggat taattattgg tttttcatta   6120
tcctatatcg caggcattac actaggatat aaaacgttta aaaagcactt taatattgtg   6180
agagataaag aagaaactaa agcattattt ttagaaaata aaaatcagtt agtttattca   6240
acaccatcaa tattattaaa tagtttgtct ttctcggttg ttgtgttctt tataggtatt   6300
ttgtatacca atacagaagt gggtatttat ggtatggcca taagagtact aggcatacca   6360
gtgacaatta tttcattagg gttatcaaaa atatttatgc aacaagccaa tgactattat   6420
attgaacatg gtaacttccg aaatttatta cttaaattta gttccatact ggttatagtt   6480
tctataattc tttatgtgcc actttatttg ttcagtgaag aattagtcaa tatattatta   6540
ggacatagct gggttgacgc aattacagtt ataaaaattg ttatcccatt atttgttata   6600
aggctgattg tatcaacggt atcactttct gtgattgtat tacaaaaaca acagttagaa   6660
ttaatactac aagcgttatt tttaataggt actactgcaa catttgttat atcaaaaatg   6720
cttaatttaa ctttttttaaa ctttgtatct attaatacaa ttgttttaat cgtatcgtac   6780
atgatatttt tcatagcact ctattatttt gctaaaaata aacagttcaa aaattctagt   6840
tatccgtatg atgtgccgga ttatgcgtaa gtgcaccata tgaatatcct ccttagttcc   6900
tattccgaag ttcctattct ctagaaagta taggaacttc ggcgcgccta cctgtgacgg   6960
aagatcactt cgcagaataa ataaatcctg gtgtccctgt tgataccggg aagccctggg   7020
ccaacttttg gcgaaaatga gacgttgatc ggcacgtaag aggttccaac tttcaccata   7080
atgaaataag atcactaccg ggcgtatttt ttgagttgtc gagattttca ggagctaagg   7140
aagctaaaat ggagaaaaaa atcactggat ataccaccgt tgatatatcc caatggcatc   7200
gtaaagaaca ttttgaggca tttcagtcag ttgctcaatg tacctataac cagaccgttc   7260
agctggatat tacggccttt ttaaagaccg taaagaaaaa taagcacaag ttttatccgg   7320
cctttattca cattcttgcc cgcctgatga atgctcatcc ggaattacgt atggcaatga   7380
aagacggtga gctggtgata tgggatagtg ttcacccttg ttacaccgtt ttccatgagc   7440
aaactgaaac gttttcatcg ctctggagtg aataccacga cgatttccgg cagtttctac   7500
acatatattc gcaagatgtg gcgtgttacg gtgaaaacct ggcctatttc cctaaagggt   7560
ttattgagaa tatgtttttc gtctcagcca atccctgggt gagtttcacc agttttgatt   7620
taaacgtggc caatatggac aacttcttcg cccccgtttt caccatgggc aaatattata   7680
cgcaaggcga caaggtgctg atgccgctgg cgattcaggt tcatcatgcc gtttgtgatg   7740
gcttccatgt cggcagatgc ttaatgaata caacagtact gcgatgagtg gcagggcggg   7800
gcgtaaggcg cgccatttaa atgaagttcc tattccgaag ttcctattct ctagaaagta   7860
taggaacttc gaagcagctc cagcctacac gtaaagaggt ggtgtatgga taagaactct   7920
gttctgttaa ttaccggtgg aactggttcc tttggaaatg ccgttttgaa gcgttttctg   7980
gatacagata ttggtgaaat acgtgtattc agtcgggatg agaagaagca agatgatatg   8040
cgtaagtgct atgctcaccc caagttgagg ttttatattg gagatgtccg cgactatcaa   8100
agcactctga atgctactcg cggtgtggac tacattttcc atgcggctgc attgaaacag   8160
gttccctctt gtgagttcta cccgatggag gctgtgaaga ccaatgtcat cggaacggaa   8220
aatgtcctcg aatctgctat ccagaatggc gtcaaaaaag tcgtttgtct gagtacggat   8280
aaggcagttt acccaatcaa tgccatgggt atttcaaagg ccatgatgga aaaggtcatg   8340
gtcgccaagt ctcgaaacct ggaacgcact cctaccgtaa tttgtggcac ccgttatggt   8400
```

```
aacgtcatgg cttcaagggg ctcggtcatt cctctcttta tcgagcaaat gcgatcaggc   8460
cagcctctca caatcactga tccaaacatg acacgtttca tgatgacgct tacggatgcc   8520
gtagaccttg tgctttatgc tttcgagcat ggtaccaatg gagatctttt tgtacagaaa   8580
gcaccggctg caaccatcga ggtgctggct catgcgctta ctcaattgct tggcaagaat   8640
ggttatccta tcaatgtaat aggtacgcgt catggagaga agctttatga ggcgcttctt   8700
agtcgagagg aaatggcctg tgctgaagac atgggtgact attatcgtat ccccccagat   8760
ttgcgtgatc tgaactatag taagtttgtg gagcaaggcg aggaaaaaat tactcataca   8820
gaggactata attctcataa taccaaacgt ctggatatcg aaggaatgaa aaagctgttg   8880
ctgaagttgg atttcattcg tgctattcag cgtggcgaga gtgccagtcc agaggaataa   8940
acgatgaaag ttcttgtaac tggcgcgaat ggatttgttg gaaggaatct gtgcgctcat   9000
cttgcagagc ggggtggtat cgaggtggtg ccattcaccc gcgagagtag tgttggtaat   9060
ttgcctgagc taattcgttc cgtcgatttt atttttcatc ttgccggggt caatcgtccg   9120
gaaaaaccag aagagtttaa gatcgggaat tccgaactca cgtatgctct gtgtgaggcg   9180
gtaaggtcca atggacgagc cataccactt ctttatactt catccattca ggctgaggtg   9240
gataatgagt acggtttaag caagcgagcc gcagaagagc atctccaagt gctaggtgag   9300
gatattggtt gtcctgtcta catatttcgc cttcctaatg tattcggtaa atggtcgcgt   9360
ccgaattata attcagcggt tgcgactttt tgtcataata ttattcgaga tattccgatt   9420
caaattaaca attcctcggc agagatcact cttgtataca tagatgatgt ggttcgcacc   9480
ttcatgaaag tcatggatgg gaagctatcc aatgcagttt cactacaggt cgagccccag   9540
tatcagattt ctgttggtga gctcgcagaa caattgtatg agtttcgtaa tagtcgaaag   9600
tcactgacta ccgcaagggt tggctcggga ttgacgcgcg ccttgtactc gacttatcta   9660
agtttcttgc cagaagatag ttttagttac gacgtgccaa tgcattcgga tccgcgtggc   9720
acattcgtcg agatgctgaa gaccgcggac tctggccagt tctcgttttt tacggctcat   9780
ccaggtgtta ccaggggcgg gcattaccat cactcgaaaa ccgaaaagtt tctggttatc   9840
aaagggatgg cacgtttcaa gtttagaaac atcctgaccg gggcatttta cgaaatttgc   9900
actaatggtg aaaaggcaga aattgtcgaa acagtacctg gatggactca tgacattact   9960
aatgtcggaa ctgacgatat ggtagtcatg ttgtgggcta acgaagtatt tgatcgggaa  10020
aatccggata cctacgcttg ttcagtaggc gaaggtgcgt aaggtatagt gagataacaa  10080
tgcagaagct aaaagtcgtt acggttgttg gaactcgtcc tgagattatt cgcttgtcta  10140
gggtcatggc gaagcttgat cagtactgcg atcatgtact tgtccatact ggacagaatt  10200
atgattacga acttaatgaa atattttttc aggacctcgg tataagaaag ccggattatt  10260
ttctaaacgc cgccgggtct tccggggctg aaacgatagg gaatgtaata atcgcagtcg  10320
atcgtgttct gggcgaaata gatcccgatg cgctgctcgt gctgggtgat accaatagtt  10380
gtatggcggt actgcctgca aaacggcgta agataccgac ctttcatatg gaagcaggca  10440
atcgctgttt cgatatgcgt gtgcctgaag agataaatcg gcgcattgtc gatcatacag  10500
ctgatgtaaa tttgacctat agtacaattg cgcgtgatta tctcttgcgt gaaggacttt  10560
ctccagacat ggttatcaag actggtagcc ctatgttcga agttctcgag cactatcgtg  10620
acgggatcga gtcctccgat attcttgaaa ggctcgggtt gaaaacagag cggttctttg  10680
tcgtgagtgc gcaccgagag gaaaacatag attcggataa gaatttcttg aagttggttt  10740
```

```
ctatgctcaa cgctgtggca gaaaagtact cgctgcccgt catcgtatca actcacccta  10800
gaacaaaaaa gagaattgag gcgacggagg caaagtttca cgagggtatt aaactgctga  10860
aacccctcgg ctttaaggat tacaataaac tgcaaattac agccaaggca gttatttctg  10920
acagtgggac catcagtgag gagtcttcaa tactgaattt tcccgctttg aatattcgtg  10980
aggctcatga acgcccagaa ggcatggaag aggctgtggt gatgatggtc ggactggatt  11040
cggatcgagt actacaagca ctcgaggtgt tggagggaca gaggcgcgac gcagagcgca  11100
tgttacgctt ggtcgctgac tatagcatgc ccaacgtttc tgaaaagatt gttcgcatag  11160
ttcatagcta tcgggactat gtcatgcgaa ctgtctggaa aaaatattaa cttgaggcgt  11220
ggagttgatg gcaaggatat ttgtggtttc tgagtatgtc ggtgccaatc agaactccac  11280
gggatactat tgggagaaga taataggaaa gatgcagcgg gagtttggtg ggctaaccgt  11340
aattttcccg ctgaccgcag gtgaaacccc gcctgtggtt tcaccttccg ttgagcaaga  11400
atgctttaag tttccgagga gcaataagaa taggctcctt tctagaggat tggcgcagat  11460
ttttcaggcg tttctgttct cagtaaaatt gacttctcgt gccagacgag gagatgtggt  11520
attgagtgga accaaccctg ctcttctact gatgacgttt cccttgctaa ggtatgccct  11580
cggtttcaag tgggtgctgc tggtgcatga tgtgtttccc gagaacttgg tgccggcggg  11640
cgttctgaag aaagatagta ttgcctaccg gcttctacgt cgtctctttt ctttcattta  11700
ctcatccgct gatcgtctag tcgtaatagg gcgcgatatg gaagctctta tgaaagagaa  11760
ggtgaatgac ccgcgatctt tggtctttat ttcgaattgg gcctgtgaga aagaggtttt  11820
cccagtaccg agagaggatg ctccttttat caatattcct gaatggaaag gtaaaagggt  11880
tttccaattt tttggtaatg tcggtcgatt acaaggtata gaaaacatac tttctgctat  11940
tcagttggtt aaaaacgaga aggcggcttt tgcttttatt ggagatggtg ccttggtcga  12000
cagtgtaaaa aaacacgcgc tggaagatca gtgtgctcgg ttgaggtatt ttggaaggct  12060
gccattagcc gaaaagaatt ttggtttggc tgcctgtgac gttgccttag ttaccttaga  12120
agaaggaatg ttcgggcttg ggggttcccag caaggcatat ttctccatgg cagcagacaa  12180
accgattcta gctgtcatgg aaaaagggcc tgaaatctcc cgtataatag atgagaccgg  12240
aatcggttgg aactgtccgc cgaatgatcc ggttgctttg gcaagattga tcgatgagat  12300
ttgtgaactc gacttgtcta gtttaggcgg agtcccgcgg agtgtccttc agcaaaatta  12360
ttctgaatat atttcattgg aaaaattcgc tgcctgtgtt cgaccgcttc tgtctgagtc  12420
gaaaatatga tgaaggtgct ggtaaccggg gctagcggtt ttgtcgggag tgcgctttgc  12480
aggtcgcttg ctgccgcccc ctttcaggtt gtcggacaag tacgatccct gtacaatccc  12540
gttacggggg ttgagtatgt tcgagcggag ctgaaagaga gcactaagct tgatgctgcg  12600
ctgcggggtg ttgaatgtgt agttcatcta gctggacgag cccatatctt tggaaggcag  12660
cgtgattcac tagatatttt tcggaaggtg aatcgcgatg ctactctggc gcttgctcgg  12720
caggcgatcg aagcatctgt aaagcgtttc atttttgtta gttctattgg tgtaaatggc  12780
gctttaacca aagaaaagcc cttcgatgag aactccaagc cggctcctca tgcagaatat  12840
gcgatttcaa agtttgaggc tgaagtagcg cttcgggagc ttttcaagca ttcctcaaca  12900
gaacttgtta tcgtcaggcc tccactcgtt tacgactgga aagctcctgg aaatttctcg  12960
cgattgttga agctggttgc ttcgggactt cctcttccat ttggttgcat agataaccga  13020
cgaagttttg tttctctgga taatttagtt gactttctag cttgctgtat gacgcaccct  13080
tctgctgccg gcgaactgtt tttggtatcc gatggtcagg agatttctac caagcaactg  13140
```

```
gtgactgcgc ttgctgcggg aatggggcgt cgccccatca tgtggcctgt tcctaggttt  13200
attctgaggt ttcttaaatt agtaggaaag ggtgggttat acactcagtt atgctgctca  13260
ctagaggtcg actcgtcgaa aggcaggctt ttgcttggtt gggaaccccg caagagcacc  13320
ctttccgcgt tggaagatgt tggtagaata tatgtcaaac gtactgaatg attatctgca  13380
ggcgctttgc tactagcatg gcgtaccacg cagaacaatc gaatagaacc ctgttgaagg  13440
ggtgagagta tttttgggga taaatttata aatggaagaa tggtatttgt tactcgctgc  13500
agctggggtt tcgggactgc ttacaggcct cttgcgtcgt tatgccttag cgaggagctt  13560
acttgacacc cctaactctc gaagttccca tgtcgttccc actccacgcg gaggaggggt  13620
cgccattgta gttacttttt gtctcatgct gcctatttgg gctgtactgg gaaatatctc  13680
atgggccgtg tcctgggctt tacttctcgc tggcggcggg gttgccatta ttggattcat  13740
ggatgatcac ggtcatatcg ccgcacgctg gcgtctgctg ggacatttta gtgcagcctt  13800
ggtctcattg tactttttga atggcatacc accatttcag attgttggtg tcagttggga  13860
cctggggtgg ttcggaggac ttctctttgc tttctatctc gtgtggttgc tgaatctcta  13920
taacttcatg gatgggatcg atggacttgc tagccttcag gccattttttg tctgtgttgg  13980
tggggcatta ttatactggc tgaatggcca actgacgcag gctttgctcc ccttatcgct  14040
agcttttgcc gtttttggat tcttgttctg gaattttcca cccccaaaaa ttttcatggg  14100
agatgcgggt agtggtcttc tggggattgt tttaggaatt ctttccattc atgccatgtg  14160
gatgaatacg aatttttttct gggcatggtt ggtcctgtta ggcgttttca tcgtcgatgc  14220
gacctatacc ctgattcgtc gcttgctgag aggggacaag gtgtatgagg ctcatcgaag  14280
ccatgcctat caatacgcaa gccgatacta tggaaagcat gctcctgtta cgattggcgt  14340
cacggcattg aacgtcatct ggctcctccc tatagccttg ttggtcggga gtgggtctct  14400
agagcctttg atgggcatcg tcatagccta cgtccctctc gtttttctgg cagtgaggtt  14460
caaggcgggt aagctagagt cgtccgctca ggcctaaagg agtaggggaa tgctagatcg  14520
tttaagagta aagttgttat ccatgcctcg tcgctggaaa cgtttgcttc aagtggctac  14580
ggatatcctt ctggtatggc tgtctctgtg gctcgctttt gtggtccgtc taggcacaga  14640
cgatatgatc gacgtgttcg gcgagcatgc atggcttttc atcactgcgc cggtcatcgc  14700
cattccacta ttcattcgct tcggcatgta tcgcgcggtg atgcgctatc tcggtaacga  14760
cgcattgatc gccatcgcca aggcggtgac catctcggct ctggtgctgt cgctggtggt  14820
gtactggtat cgtggcgcgc cggcgccggt gccgcgttcc ctggtgttca actactggtg  14880
gttgagcatg ctgctgatcg gcggcttgcg tctggccatg cgccagtatt tcatgggcga  14940
ctggtactct gctgtgcagt cggtaccatt tctcaaccgc caggatggcc tgcccagggt  15000
ggttatctat ggggcggggg cggccggcaa ccagttggtt gcggcgttgc gtctcggtcg  15060
ggcgatgcgt ccggtggcgt tcatcgatga cgacaagcag atcgccaacc gggtcattgc  15120
cggtctgcgg gtctataccg ccaagcatat ccgccagatg atcgacgaga cgggcgcgca  15180
ggaggttctc ctggcgattc cttccgccac tcgggcccgg cgccgagaga ttctcgagtc  15240
cctggagccg ttcccgctgc acgtgcgcag catgcccggc ttcatggacc tggccagcgg  15300
ccgggtcaag gtggatgacc tgcaggaggt ggacatcgct gacctgctgg ggcgcgacag  15360
cgtcgcaccg cgcaaggagc tgctggaacg gtgcatccgc ggtcaggtgg tgatggtgac  15420
cggggcgggc ggctctatcg gttcggaact ctgtcggcag atcatgagtt gttcgcctag  15480
```

```
cgtgctgatc ctgttcgaac acagcgaata caacctctat agcatccatc aggaactgga  15540
gcgtcggatc aagcgcgagt cgctttcggt gaacctgttg ccgatcctcg gttcggtgcg  15600
caatcccgag cgcctggtgg acgtgatgcg tacctggaag gtcaataccg tctaccatgc  15660
ggcggcctac aagcatgtgc cgatcgtcga gcacaacatc gccgagggcg ttctcaacaa  15720
cgtgataggc accttgcatg cggtgcaggc cgcggtgcag gtcggcgtgc agaacttcgt  15780
gctgatttcc accgacaagg cggtgcggcc gaccaatgtg atgggcagca ccaagcgcct  15840
ggcggaaatg gtccttcagg cgctcagcaa cgaatcggcg ccggtgctgt tcggcgaccg  15900
gaaggacgtg catcacgtca acaagacccg tttcaccatg gtccgcttcg gcaacgtcct  15960
cggttcgtcc ggttcggtca ttccgctgtt ccgcgagcag atcaagcgcg gcggcccggt  16020
gacggtcacc cacccgagca tcacccgtta cttcatgacc attcccgagg cggcgcagtt  16080
ggtcatccag gccggttcga tggggcaggg cggagatgta ttcgtgctgg acatggggcc  16140
gccggtgaag atcctggagc tcgccgagaa gatgatccac ctgtccggcc tgagcgtgcg  16200
ttccgagcgt tcgccccatg gtgacatcgc catcgagttc agtggcctgc gtcctggcga  16260
gaagctctac gaagagctgc tgatcggtga caacgtgaat cccaccgacc atccgatgat  16320
catgcgggcc aacgaggaac acctgagctg ggaggccttc aaggtcgtgc tggagcagtt  16380
gctggccgcc gtggagaagg acgactactc gcgggttcgc cagttgctgc gggaaaccgt  16440
cagcggctat gcgcctgacg gtgaaatcgt cgactggatc tatcgccaga ggcggcgaga  16500
accctgagtc atcgttctcc ggaaaaggcc gcctagcggc ctttttttgtt ttctccgtac  16560
gatgtttccg gtgccggacc aggaagcgac tgctttgctg gggctgtcga tccaggtgcg  16620
ttccacggcg ataaggtggt ttcgtggatg ggcaacatgt cgcgaaggta aagtcagccg  16680
cattgttgaa ttcatcgaaa aaccggatca gccacaaacg ctggaatcag acatcatggc  16740
cgtgggccgt tatgtgcttt ctgccgatat ttggccggaa cttgaacgca ctcagccagg  16800
tgcatgggga cgtattcagc tgactgatgc cattgccgaa ctggcgaaaa aacagtctgt  16860
tgacgccatg ctgatgactg gtgacagcta cgactgtggt aaaaaaatgg gttatatgca  16920
ggcgtttgtg aagtatggac tacgcaacct gaaagaagga gcgaagttcc gcaaaggtat  16980
tgagaaattg cttagcgagt aagtttaaaa aatagacgcc cttatagggc gtaataacaa  17040
ataacggtag tcaacattcg acgcggtgat gcagatatgc ccggaatgct gataccgttt  17100
tttcattcta aaaaactcat catttcattg agttaactac aaaatttagc actgtttttt  17160
ataatgtttc ttcttgtttc tggcatcaat tggtaagata attagtgttt gagtttagag  17220
gctttgcggc agagaagcgg agcttaacac gtctgtgaga gtacgcagtg cactggtagc  17280
tgtaaagcca gtggcggtag cgtgtttaaa taaatacatt agtaatacta catattacat  17340
cattgtaggc tatttaagcg ctacatgata agcgacagcg ctagcaatca aatcttttaa  17400
agttacttct caggaatagt aaaaggagga cagctatgtt gaaaaaagag tatttaaaaa  17460
acccttattt agttttgttt gcgatgatta tattagctta tgtttttagt gtattttgca  17520
ggttttattg ggtttggtgg gcaagtgagt ttaatgagta ttttttcaat aatcagttaa  17580
tgatcatttc aaatgatggc tatgcttttg ctgagggcgc aagagatatg atagcaggtt  17640
ttcatcagcc taatgatttg agttattatg gatcttcttt atccgcgctt acttattggc  17700
tttataaaat cacacctttt tcttttgaaa gtatcatttt atatatgagt acttttttat  17760
cttctttggt ggtgattcct actattttgc tagctaacga atacaaacgt cctttaatgg  17820
gctttgtagc tgctctttta gcaagtatag caaacagtta ttataatcgc actatgagtg  17880
```

```
ggtattatga tacggatatg ctggtaattg ttttgcctat gtttatttta ttttttatgg  17940

taagaatgat tttaaaaaaa gacttttttt cattgattgc cttgccgtta tttataggaa  18000

tttatctttg gtggtatcct tcaagttata ctttaaatgt agctttaatt ggactttttt  18060

taatttatac acttattttt catagaaaag aaaagatttt ttatatagct gtgattttgt  18120

cttctcttac tctttcaaat atagcatggt tttatcaaag tgccattata gtaatacttt  18180

ttgctttatt cgccttagag caaaaacgct taaattttat gattatagga attttaggta  18240

gtgcaacttt gatatttttg attttaagtg gtggggttga tcctatactt tatcagctta  18300

aattttatat ttttagaagt gatgaaagtg cgaatttaac gcagggcttt atgtatttta  18360

atgtcaatca aaccatacaa gaagttgaaa atgtagatct tagcgaattt atgcgaagaa  18420

ttagtggtag tgaaattgtt tttttgtttt ctttgtttgg ttttgtatgg cttttgagaa  18480

aacataaaag tatgattatg gctttaccta tattggtgct tgggttttta gccttaaaag  18540

gggggcttag atttaccatt tattctgtac ctgtaatggc cttaggattt ggttttttat  18600

tgagcgagtt taaggctata atggttaaaa aatatagcca attaacttca aatgtttgta  18660

ttgtttttgc aactattttg actttagctc cagtatttat ccatatttac aactataaag  18720

cgccaacagt tttttctcaa aatgaagcat cattattaaa tcaattaaaa aatatagcca  18780

atagagaaga ttatgtggta acttggtggg attatggtta tcctgtgcgt tattatagcg  18840

atgtgaaaac tttagtagat ggtggaaagc atttaggtaa ggataatttt ttcccttctt  18900

ttgctttaag caaagatgaa caagctgcag ctaatatggc aagacttagt gtagaatata  18960

cagaaaaaag cttttatgct ccgcaaaatg atattttaaa aacagacatt ttgcaagcca  19020

tgatgaaaga ttataatcaa agcaatgtgg atttgtttct agcttcatta tcaaaacctg  19080

attttaaaat cgatacgcca aaaactcgtg atatttatct ttatatgccc gctagaatgt  19140

ctttgatttt ttctacggtg gctagttttt cttttattaa tttagataca ggagttttgg  19200

ataaaccttt tacctttagc acagcttatc cacttgatgt taaaaatgga gaaatttatc  19260

ttagcaacgg agtggtttta agcgatgatt ttagaagttt taaaataggt gataatgtgg  19320

tttctgtaaa tagtatcgta gagattaatt ctattaaaca aggtgaatac aaaatcactc  19380

caattgatga taaggctcag ttttatattt tttatttaaa ggatagtgct attccttacg  19440

cacaatttat tttaatggat aaaaccatgt ttaatagtgc ttatgtgcaa atgttttttt  19500

taggaaatta tgataagaat ttatttgact tggtgattaa ttctagagat gctaaggttt  19560

ttaaacttaa aatttaccca tacgatgttc cagattacgc ttaaacatgt gaattc      19616
```

<210> SEQ ID NO 19
<211> LENGTH: 20597
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

```
gaattccctg aggcaattct tctttgatga cggctgatgg tgaggttgac ctggtgaagc     60

tggtcaagga gctttgggtt aacaaggttc tgattcttct gactactctt cttgcattaa    120

tcgggtcttt tacctatgcg tatctgagta agcctgtata tgaatatagg gttgcagtag    180

tgcctcctgc tcttgggtct atcgaaggtt tcaatgttgg tagaagggag aatggcctag    240

atgcatatac tgttagaagt atctatgcga tcttttcgcg caatctgctt tcggatgaga    300
```

```
ataaaaaaga gttcttctat aagatatacc ttccccaggt gggtgaggga gcggaaagcg    360
aagatgagca ggaggagttt tataagaagt tctccaaaga ggtaaagatt gatcctgcta    420
acaagccaga tgcagaccgt tatacggtaa ttgtggaggg cacgaagcga gaggttcttg    480
ctacatgggc acaagctttc gtgcgtttgg ctgcggatcg ggccgtgcat gaggttattg    540
atagtgcagg tagagatttc caggtaagaa atgctgcaat gcagagccgc ataaccgtgc    600
tgcagaatat ggcgaagggc cgccgtgatg atagaattgc acgtttgaag gaggcattgc    660
tgattgcgga gtcgctcaag atagatggcc cgccattaat agaaggggcg tccgagcaac    720
aactctcctc gatcatggat ggtgacttga tgtacatgcg aggagctaag gcgctgcgcg    780
ctgaaatcaa caatcttgag tcgcgtagtg tagatgctcc attcattcct gagttgagaa    840
ctctccaaga gaaactatct tggaactcca gtttgtctgt ggattctgat gcggtggctg    900
tctacaagga agacgaggga ctctcttttt caaatcaacc cattaagccg aagaagattc    960
ttatagttac tataggtact ttggcaggat tgataattgg aattctactc gcagtgctcg   1020
ctggttttat aaggaagctt cgtagcgatg gctctcttcg ctaagttttg atctaaaccc   1080
tgatgccact tactggcatc agggcttact tgttgtagtt gttgaattgt attagggggt   1140
atcgagtaga atgtcaataa ggcggggcgt tttctactcc ggtatatcca tgggcagcaa   1200
ctatcttttg cctcttgctg cgattccttt tctcacgaga acattgtcaa gcgaagcgtt   1260
tggccaattg gtgattgccc aggccgtggc tgtcattcta tgtcaactgg tagactttgg   1320
atttattctg gcaggatcaa gaaaggctgc cattatcgat aacaaagttg aactgtctag   1380
tttcttttct gttgtacaga gtgctagatt cttattgttg ctgctttcac ttttagtgct   1440
ggccattttg gctgtatctt ctattttacc aatccccttg cttgtattgg ttgcggctgc   1500
tcttccggca gtagttggaa attatcttca agcagtatgg ttctttcagg gaagagcgct   1560
gtttggatgg ttggcgctta ccaatttttt gtctaaggta ttttatttcc tattggtcgt   1620
tttttttgtc acgaaggatt ctgaccttgt gctggcttcg ttggggtttg gtttttccta   1680
tgtcataggt ggaagtgctc tctgttgtat tttattttct atgggaatac ggtggcgccc   1740
ggttctcgag aaagacagaa ttctcgatat attgcgtgac ggtgctcgat cttttctttc   1800
tctggctttt cttagcttgc acatgcaagt gctcgttgcg gcggttggtg ttgttggtgg   1860
agcctccgcg gccggagtgc tttctactgc ggataaattc cttcgcggga tcgcggctgc   1920
tacttcaccc atagctagcg ctctatttcc gacttttagc aggatgtatg cgagtgccga   1980
cccggcagtc ggcagtttaa gaaggaaagc gctaggtctg atgttactaa tagctattcc   2040
tagttgttta tttcttttct tattttctga atacatttca tatctcctat tcccggaaca   2100
gtccagaggt ctaactgttg taataagaat gttttcgata gtgccagtgt ttgcttgtat   2160
tggtgttctg tatggagggt tgactcttgt tccttctggg tatgatggtg tatatttgcg   2220
agcaattttt tttgcggaat tgggcggggt attaacattt atcctcttgg cgctttgggg   2280
ggatgagctt tttggagcgt ggacgctggt cgttacagag gtctctttgg ggatgggaat   2340
gtttttcctg gccacggtta agttgagaga gaaaagggga ctttgatctt aagatgagag   2400
tagaaaataa taatgtttct gggcaaaacc atgacccgga acagattgat ttgattgatt   2460
tactagtgca gttgtggcgt ggcaagatga caatcatcat ttccgtcatt gtggctattg   2520
ccctagctat tggatatttg gcagtagcga aggagaaatg gacgtcaaca gcaattatca   2580
ctcagcccga tgtggggcaa attgctggct ataacaatgc catgaatgtt atctatggtc   2640
```

-continued

```
aggctgcacc gaaagtatcg gatttgcagg agacgttaat tggtcgcttc agttctgcct   2700
tctctgcatt agcagaaacg ctggataatc aggaagaacc agaaaaactt accatcgaac   2760
cttctgttaa gaaccagcaa ttaccattga ctgtttctta tgttgggcaa actgcagagg   2820
gcgcacaaat gaagttggcc caatacattc agcaagttga cgataaagtg aatcaagagt   2880
tagaaaagga tctcaaggac aacattgctc tgggacggaa aaacttgcag gactctttaa   2940
gaacgcagga agtggttgcg caggagcaga aagatctgcg tatccgtcag attcaggaag   3000
cgttgcagta tgcgaatcag gcgcaggtga caaaaccgca gattcaacag actggcgaag   3060
atatcacaca agatacgttg ttccttttgg ggagcgaagc gctggagtcg atgattaagc   3120
atgaggcgac ccgtccgttg gtgttctcac caaactacta tcagactcgt caaaacctgc   3180
ttgatatcga aagcttaaag gttgatgatc ttgatattca tgcttaccgc tatgtaatga   3240
aaccgacgtt acctattcgt cgtgatagcc cgaaaaaggc aattaccttg attctggcgg   3300
tgctgctggg tggcatggtt ggcgcgggga ttgtgctggg gcgtaatgct ctacgcaatt   3360
acaacgcgaa gtaagcgatc gctaggagga cagctatgcg tattgcgatt ctgggcgcga   3420
ccaacattaa acatatgagc ctgctgagcc attatctgaa ccatattgat ctgaacatta   3480
acgaagtgga tattatttat accgataaat atgatattga agaacatatt cagggcatca   3540
acaactacta caaatacaaa gtggatatca aagaagattg gaccttcatc aagaaagcga   3600
ttgcgtatta tcgttttcgt ccgtatgcga tgaaaattct gaaagaaaac cgttatgatt   3660
ttgtgattgt gtggggcagc tacaccggcc atctgttcaa aagctttctg gaaaaacatt   3720
acaaaaacaa attcatcctg aacatccgtg attacttttt cgaaaacaac aaactgatta   3780
aatatcgtat gaagaaaatc gtggatgcga gccgtgtgac caccctgagc agcgaaggct   3840
ttctgaaatt cctgccgaaa agcgaaaaat accgtatcat ctacagctac aacatgagca   3900
tcatccgtga aagcaacgtg accgatggct ttaaaaaacg ttggccgatt aacattggct   3960
ttattggcaa cgtgcgtttt aacgaaatta accagaaact gattaaagaa ctggcgaacg   4020
atagccgttt tcatatgcag tattttggca ccggcagcga aaaactggaa gtgtttgcgc   4080
gtgaaaactt tattaacaac attaccttta gcggcggctt tgatctgaaa gaaaccccga   4140
aatatctgaa cgaaattgat attctgaaca acctgtttgg caaccagaac attgcgctgg   4200
ataccgcgct gagcattcgt atgtattatg cgctgtttct gaacaaaccg attattacca   4260
ccgatgatac ctttaccgcg accgaagcga acaaatttgg cctgggcttt agcattaacc   4320
cggaaaacct gaaaggcatt ggcgatgaac tgatggattg gtataacaac ctggatgtga   4380
tggatattaa ccataaacgt gaagcgtatc gtaacgatgt gattgaaaac aacaaacagt   4440
tttatcagga aattggccgt atttttaacg aagaacagaa actgattagc gaagaagatc   4500
tgtaacgttt aaacaggagg acagctatga acaaaattta taacgtgacc agctatgtga   4560
ttgcgattct gatgtttccg tgcctgatgc tgggcgataa accgctgctg tttctggcgc   4620
cgattagcta tggcgtgggc aaactgttca tcagcttcag caacaacccg aacttcaaat   4680
tcagcaaaat cgtgtacgat gtgctgggct ttctgcgtct ggtgtttatt ccggcgatga   4740
ttgtgttttt ccaggatagc accattgata acctgccgct gggccaggcg tattttaacc   4800
aggcggtgat ttatatgagc gtggaattta ttattggcag cctgtttatt ctgattctga   4860
gcaaactgtt caagcatgaa gttgtgagcc gtaacagctt taccctgagc ggcagcagca   4920
tttattatat tgtgtttggc ctggtgattt gcggcatttt tgtggcgttt ccggaagtgc   4980
gtaaaaacat tagctttctg attattaaaa ccgatgcgat gggccgtggc accgaagcga   5040
```

```
ccagcggcct gaacgtgctg tttgtgatgc tgtttcagct ggcgctggcg ctgctgtttc   5100
tgatcatcgc gtacgcgagc tacaaaaaat acaaagaaaa cccgaaaatc atctacgtgg   5160
tgctgccgct ggcgattggc attctgaaca ttagcctgat tgtgggcgaa cgtcgtagct   5220
atcagctgta taccatggtg gcggtgctga ccgttgtgag catcctgttt agcaaacata   5280
aacgtcgtat caacatcatc atcatcagcg tgggcatctt cgtgctggcg ctgatgaccc   5340
tgtataaaga actgtatgtg tttaactata gcagctatag cgaagcgctg aacagcacca   5400
gcgtgagcaa cctgaaaatt gtggataccc tgcagagcta tttttatggc ccgagcaaca   5460
ttgcggcgag cattgattat ctgaactatt ataacggcag ctttaaacag tatctgtttg   5520
ataacacccg tgcggtgttt ggctttaact ttttcctgga taaaaaacag ctgattacca   5580
gccagctgtt taaccagctg atttatggca gcaaacagct gaccggccat ctgattagca   5640
gcgcgggcta tggcattatt tattttggcc cgctgttttt ctacctgaac ctgattgcga   5700
acatcttttt cgcgtttctg agcgaataca tcatccgtaa aagccatagc ctggaagtga   5760
tcttcatcgg cacctacatc tacatgcgtc tgattaccag catttttagc catccgaccc   5820
cgctgattac cctgattagc atgattctgg tggtgtatgt gattgcgatc atcccgggca   5880
tcatcatcaa gaaattcacc aaaaaagtgg gcatcgaaga ttacaaagat gatgatgata   5940
aataacgttt aaacaggagg acagctatga ttgtgaaaac ctttatgaaa agcaaaattt   6000
ttcgtctgat gaacaccccg ctgctgctgt tttataaaaa agaatatctg accggctatt   6060
attttgaaaa caaagtggcg ggctggctgt gggcgtggaa agcggtgcca ttcaagctgc   6120
tgggcattaa caccagcctg ccgtttccgg cggatattac cgtgcgtatg cataacccga   6180
acaacattgt gtttgataaa aacgatattc atatttttca gagcccgggc acctatttta   6240
acaactttag cgcggtgatt tatattggcc gtggcgtgta tattgcgccg aacgtgggca   6300
ttattaccgc gaaccataac attaaaaacc tgaaaagcca tgcgccgggc gaagatgtga   6360
aaattggcaa ctatagctgg attggcatga acagcgtgat tctgccgggc gtggaactgg   6420
gcgaacatac cattgtgggc gcgggcagcg tggtgaccaa aagctttccg gaaggcaacg   6480
tggtgattgg cggcaacccg gcgaaaatta ttaagaaaat cagctatccg tatgatgtgc   6540
cggattatgc gtaattaatt aaccaggtgc acgaagaaaa ttatgagatt aaataaattt   6600
attggcgatt cgtttttaat gattttaagc agtggcatcg ctcaagtcat attaatcatc   6660
actaccccaa ttattacaag actatattca cctacagaat ttggtgagtt tacaattttt   6720
tcaaatatcg caatgatttt aataccaata ataaatgcaa gatacgattt gttgattgtg   6780
aataccaaaa atgaccgtag tgctaatata ctttcacaaa tcagtttttt gatatcattg   6840
cttattttat taatactgat accaatattt gcgattagtg catgtttata cccaaacttt   6900
atattagatt ttattttcat tattattatg ttgtttttgg taagtttaac aaacattttt   6960
acaaattatc taaataagga aagaaagtat aaagtgttaa gtttgattaa tgtgtttaga   7020
gctggatcaa tggctttact tcaaatcatt ttcggacttt tagcattagg aagtttagga   7080
ttaattattg gtttttcatt atcctatatc gcaggcatta cactaggata taaaacgttt   7140
aaaaagcact ttaatattgt gagagataaa gaagaaacta aagcattatt tttagaaaat   7200
aaaaatcagt tagtttattc aacaccatca atattattaa atagtttgtc tttctcggtt   7260
gttgtgttct ttataggtat tttgtatacc aatacagaag tgggtattta tggtatggcc   7320
ataagagtac taggcatacc agtgacaatt atttcattag ggttatcaaa aatatttatg   7380
```

-continued

```
caacaagcca atgactatta tattgaacat ggtaacttcc gaaatttatt acttaaattt   7440
agttccatac tggttatagt ttctataatt ctttatgtgc cactttattt gttcagtgaa   7500
gaattagtca atatattatt aggacatagc tgggttgacg caattacagt tataaaaatt   7560
gttatcccat tatttgttat aaggctgatt gtatcaacgg tatcactttc tgtgattgta   7620
ttacaaaaac aacagttaga attaatacta caagcgttat ttttaatagg tactactgca   7680
acatttgtta tatcaaaaat gcttaattta actttttttaa actttgtatc tattaataca   7740
attgttttaa tcgtatcgta catgatattt ttcatagcac tctattattt tgctaaaaat   7800
aaacagttca aaaattctag ttatccgtat gatgtgccgg attatgcgta agtgcaccat   7860
atgaatatcc tccttagttc ctattccgaa gttcctattc tctagaaagt ataggaactt   7920
cggcgcgcct acctgtgacg gaagatcact tcgcagaata aataaatcct ggtgtccctg   7980
ttgataccgg gaagccctgg gccaactttt ggcgaaaatg agacgttgat cggcacgtaa   8040
gaggttccaa ctttcaccat aatgaaataa gatcactacc gggcgtattt tttgagttgt   8100
cgagattttc aggagctaag gaagctaaaa tggagaaaaa aatcactgga tataccaccg   8160
ttgatatatc ccaatggcat cgtaaagaac attttgaggc atttcagtca gttgctcaat   8220
gtacctataa ccagaccgtt cagctggata ttacggcctt tttaaagacc gtaaagaaaa   8280
ataagcacaa gttttatccg gcctttattc acattcttgc ccgcctgatg aatgctcatc   8340
cggaattacg tatggcaatg aaagacggtg agctggtgat atgggatagt gttcaccctt   8400
gttacaccgt tttccatgag caaactgaaa cgttttcatc gctctggagt gaataccacg   8460
acgatttccg gcagtttcta cacatatatt cgcaagatgt ggcgtgttac ggtgaaaacc   8520
tggcctattt ccctaaaggg tttattgaga atatgttttt cgtctcagcc aatccctggg   8580
tgagtttcac cagttttgat ttaaacgtgg ccaatatgga caacttcttc gcccccgttt   8640
tcaccatggg caaatattat acgcaaggcg acaaggtgct gatgccgctg gcgattcagg   8700
ttcatcatgc cgtttgtgat ggcttccatg tcggcagatg cttaatgaat acaacagtac   8760
tgcgatgagt ggcagggcgg ggcgtaaggc gcgccattta aatgaagttc ctattccgaa   8820
gttcctattc tctagaaagt ataggaactt cgaagcagct ccagcctaca cgtaaagagg   8880
tggtgtatgg ataagaactc tgttctgtta attaccggtg gaactggttc ctttggaaat   8940
gccgttttga agcgttttct ggatacagat attggtgaaa tacgtgtatt cagtcgggat   9000
gagaagaagc aagatgatat gcgtaagtgc tatgctcacc ccaagttgag gttttatatt   9060
ggagatgtcc gcgactatca aagcactctg aatgctactc gcggtgtgga ctacattttc   9120
catgcggctg cattgaaaca ggttccctct tgtgagttct acccgatgga ggctgtgaag   9180
accaatgtca tcggaacgga aaatgtcctc gaatctgcta tccagaatgg cgtcaaaaaa   9240
gtcgtttgtc tgagtacgga taaggcagtt tacccaatca atgccatggg tatttcaaag   9300
gccatgatgg aaaaggtcat ggtcgccaag tctcgaaacc tggaacgcac tcctaccgta   9360
atttgtggca cccgttatgg taacgtcatg gcttcaaggg gctcggtcat tcctctcttt   9420
atcgagcaaa tgcgatcagg ccagcctctc acaatcactg atccaaacat gacacgtttc   9480
atgatgacgc ttacggatgc cgtagacctt gtgctttatg ctttcgagca tggtaccaat   9540
ggagatcttt ttgtacagaa agcaccggct gcaaccatcg aggtgctggc tcatgcgctt   9600
actcaattgc ttggcaagaa tggttatcct atcaatgtaa taggtacgcg tcatggagag   9660
aagctttatg aggcgcttct tagtcgagag gaaatggcct gtgctgaaga catgggtgac   9720
tattatcgta tccccccaga tttgcgtgat ctgaactata gtaagtttgt ggagcaaggc   9780
```

```
gaggaaaaaa ttactcatac agaggactat aattctcata ataccaaacg tctggatatc   9840
gaaggaatga aaaagctgtt gctgaagttg gatttcattc gtgctattca gcgtggcgag   9900
agtgccagtc cagaggaata aacgatgaaa gttcttgtaa ctggcgcgaa tggatttgtt   9960
ggaaggaatc tgtgcgctca tcttgcagag cggggtggta tcgaggtggt gccattcacc  10020
cgcgagagta gtgttggtaa tttgcctgag ctaattcgtt ccgtcgattt tatttttcat  10080
cttgccgggg tcaatcgtcc ggaaaaacca gaagagttta agatcgggaa ttccgaactc  10140
acgtatgctc tgtgtgaggc ggtaaggtcc aatggacgag ccataccact tctttatact  10200
tcatccattc aggctgaggt ggataatgag tacggtttaa gcaagcgagc cgcagaagag  10260
catctccaag tgctaggtga ggatattggt tgtcctgtct acatatttcg ccttcctaat  10320
gtattcggta aatggtcgcg tccgaattat aattcagcgg ttgcgacttt ttgtcataat  10380
attattcgag atattccgat tcaaattaac aattcctcgg cagagatcac tcttgtatac  10440
atagatgatg tggttcgcac cttcatgaaa gtcatggatg ggaagctatc caatgcagtt  10500
tcactacagg tcgagcccca gtatcagatt tctgttggtg agctcgcaga acaattgtat  10560
gagtttcgta atagtcgaaa gtcactgact accgcaaggg ttggctcggg attgacgcgc  10620
gccttgtact cgacttatct aagtttcttg ccagaagata gttttagtta cgacgtgcca  10680
atgcattcgg atccgcgtgg cacattcgtc gagatgctga agaccgcgga ctctggccag  10740
ttctcgtttt ttacggctca tccaggtgtt accaggggcg ggcattacca tcactcgaaa  10800
accgaaaagt ttctggttat caaagggatg gcacgtttca agtttagaaa catcctgacc  10860
ggggcatttt acgaaatttg cactaatggt gaaaaggcag aaattgtcga aacagtacct  10920
ggatggactc atgacattac taatgtcgga actgacgata tggtagtcat gttgtgggct  10980
aacgaagtat ttgatcggga aaatccggat acctacgctt gttcagtagg cgaaggtgcg  11040
taaggtatag tgagataaca atgcagaagc taaaagtcgt tacggttgtt ggaactcgtc  11100
ctgagattat tcgcttgtct agggtcatgg cgaagcttga tcagtactgc gatcatgtac  11160
ttgtccatac tggacagaat tatgattacg aacttaatga aatatttttt caggacctcg  11220
gtataagaaa gccggattat tttctaaacg ccgccgggtc ttccggggct gaaacgatag  11280
ggaatgtaat aatcgcagtc gatcgtgttc tgggcgaaat agatcccgat gcgctgctcg  11340
tgctgggtga taccaatagt tgtatggcgg tactgcctgc aaaacggcgt aagataccga  11400
cctttcatat ggaagcaggc aatcgctgtt tcgatatgcg tgtgcctgaa gagataaatc  11460
ggcgcattgt cgatcataca gctgatgtaa atttgaccta tagtacaatt gcgcgtgatt  11520
atctcttgcg tgaaggactt tctccagaca tggttatcaa gactggtagc cctatgttcg  11580
aagttctcga gcactatcgt gacgggatcg agtcctccga tattcttgaa aggctcgggt  11640
tgaaaacaga gcggttcttt gtcgtgagtg cgcaccgaga ggaaaacata gattcggata  11700
agaatttctt gaagttggtt tctatgctca acgctgtggc agaaaagtac tcgctgcccg  11760
tcatcgtatc aactcaccct agaacaaaaa agagaattga ggcgacggag gcaaagtttc  11820
acgagggtat taaactgctg aaacccctcg gctttaagga ttacaataaa ctgcaaatta  11880
cagccaaggc agttatttct gacagtggga ccatcagtga ggagtcttca atactgaatt  11940
ttcccgcttt gaatattcgt gaggctcatg aacgcccaga aggcatggaa gaggctgtgg  12000
tgatgatggt cggactggat tcggatcgag tactacaagc actcgaggtg ttggagggac  12060
agaggcgcga cgcagagcgc atgttacgct tggtcgctga ctatagcatg cccaacgttt  12120
```

```
ctgaaaagat tgttcgcata gttcatagct atcgggacta tgtcatgcga actgtctgga  12180
aaaaatatta acttgaggcg tggagttgat ggcaaggata tttgtggttt ctgagtatgt  12240
cggtgccaat cagaactcca cgggatacta ttgggagaag ataataggaa agatgcagcg  12300
ggagtttggt gggctaaccg taattttccc gctgaccgca ggtgaaaccc cgcctgtggt  12360
ttcaccttcc gttgagcaag aatgctttaa gtttccgagg agcaataaga ataggctcct  12420
ttctagagga ttggcgcaga tttttcaggc gtttctgttc tcagtaaaat tgacttctcg  12480
tgccagacga ggagatgtgg tattgagtgg aaccaaccct gctcttctac tgatgacgtt  12540
tcccttgcta aggtatgccc tcggtttcaa gtgggtgctg ctggtgcatg atgtgtttcc  12600
cgagaacttg gtgccggcgg gcgttctgaa gaaagatagt attgcctacc ggcttctacg  12660
tcgtctcttt tctttcattt actcatccgc tgatcgtcta gtcgtaatag ggcgcgatat  12720
ggaagctctt atgaaagaga aggtgaatga cccgcgatct ttggtcttta tttcgaattg  12780
ggcctgtgag aaagaggttt tcccagtacc gagagaggat gctcctttta tcaatattcc  12840
tgaatggaaa ggtaaaaggg ttttccaatt ttttggtaat gtcggtcgat tacaaggtat  12900
agaaaacata ctttctgcta ttcagttggt taaaaacgag aaggcggctt ttgcttttat  12960
tggagatggt gccttggtcg acagtgtaaa aaaacacgcg ctggaagatc agtgtgctcg  13020
gttgaggtat tttggaaggc tgccattagc cgaaaagaat tttggtttgg ctgcctgtga  13080
cgttgcctta gttaccttag aagaaggaat gttcgggctt ggggttccca gcaaggcata  13140
tttctccatg gcagcagaca aaccgattct agctgtcatg gaaaaagggg ctgaaatctc  13200
ccgtataata gatgagaccg gaatcggttg gaactgtccg ccgaatgatc cggttgcttt  13260
ggcaagattg atcgatgaga tttgtgaact cgacttgtct agtttaggcg gagtcccgcg  13320
gagtgtcctt cagcaaaatt attctgaata tatttcattg gaaaaattcg ctgcctgtgt  13380
tcgaccgctt ctgtctgagt cgaaaatatg atgaaggtgc tggtaaccgg ggctagcggt  13440
tttgtcggga gtgcgctttg caggtcgctt gctgccgccc cctttcaggt tgtcggacaa  13500
gtacgatccc tgtacaatcc cgttacgggg gttgagtatg ttcgagcgga gctgaaagag  13560
agcactaagc ttgatgctgc gctgcggggt gttgaatgtg tagttcatct agctggacga  13620
gcccatatct ttggaaggca gcgtgattca ctagatattt ttcggaaggt gaatcgcgat  13680
gctactctgg cgcttgctcg gcaggcgatc gaagcatctg taaagcgttt catttttgtt  13740
agttctattg gtgtaaatgg cgctttaacc aaagaaaagc ccttcgatga gaactccaag  13800
ccggctcctc atgcagaata tgcgatttca aagtttgagg ctgaagtagc gcttcgggag  13860
cttttcaagc attcctcaac agaacttgtt atcgtcaggc ctccactcgt ttacgactgg  13920
aaagctcctg gaaatttctc gcgattgttg aagctggttg cttcgggact tcctcttcca  13980
tttggttgca tagataaccg acgaagtttt gtttctctgg ataatttagt tgactttcta  14040
gcttgctgta tgacgcaccc ttctgctgcc ggcgaactgt tttggtatcc cgatggtcag  14100
gagatttcta ccaagcaact ggtgactgcg cttgctgcgg gaatggggcg tcgccccatc  14160
atgtggcctg ttcctaggtt tattctgagg tttcttaaat tagtaggaaa gggtgggtta  14220
tacactcagt tatgctgctc actagaggtc gactcgtcga aaggcaggct tttgcttggt  14280
tgggaacccc gcaagagcac cctttccgcg ttggaagatg ttggtagaat atatgtcaaa  14340
cgtactgaat gattatctgc aggcgctttg ctactagcat ggcgtaccac gcagaacaat  14400
cgaatagaac cctgttgaag ggtgagagt atttttgggg ataaatttat aaatggaaga  14460
atggtatttg ttactcgctg cagctggggt ttcgggactg cttacaggcc tcttgcgtcg  14520
```

```
ttatgcctta gcgaggagct tacttgacac ccctaactct cgaagttccc atgtcgttcc  14580
cactccacgc ggaggagggg tcgccattgt agttactttt tgtctcatgc tgcctatttg  14640
ggctgtactg ggaaatatct catgggccgt gtcctgggct ttacttctcg ctggcggcgg  14700
ggttgccatt attggattca tggatgatca cggtcatatc gccgcacgct ggcgtctgct  14760
gggacatttt agtgcagcct tggtctcatt gtactttttg aatggcatac caccatttca  14820
gattgttggt gtcagttggg acctggggtg gttcggagga cttctctttg ctttctatct  14880
cgtgtggttg ctgaatctct ataacttcat ggatgggatc gatggacttg ctagccttca  14940
ggccattttt gtctgtgttg gtggggcatt attatactgg ctgaatggcc aactgacgca  15000
ggctttgctc cccttatcgc tagcttttgc cgtttttgga ttcttgttct ggaattttcc  15060
acccccaaaa attttcatgg gagatgcggg tagtggtctt ctggggattg ttttaggaat  15120
tctttccatt catgccatgt ggatgaatac gaatttttc tgggcatggt tggtcctgtt  15180
aggcgttttc atcgtcgatg cgacctatac cctgattcgt cgcttgctga gaggggacaa  15240
ggtgtatgag gctcatcgaa gccatgccta tcaatacgca agccgatact atggaaagca  15300
tgctcctgtt acgattggcg tcacggcatt gaacgtcatc tggctcctcc ctatagcctt  15360
gttggtcggg agtgggtctc tagagccttt gatgggcatc gtcatagcct acgtccctct  15420
cgtttttctg gcagtgaggt tcaaggcggg taagctagag tcgtccgctc aggcctaaag  15480
gagtagggga atgctagatc gtttaagagt aaagttgtta tccatgcctc gtcgctggaa  15540
acgtttgctt caagtggcta cggatatcct tctggtatgg ctgtctctgt ggctcgcttt  15600
tgtggtccgt ctaggcacag acgatatgat cgacgtgttc ggcgagcatg catggctttt  15660
catcactgcg ccggtcatcg ccattccact attcattcgc ttcggcatgt atcgcgcggt  15720
gatgcgctat ctcggtaacg acgcattgat cgccatcgcc aaggcggtga ccatctcggc  15780
tctggtgctg tcgctggtgg tgtactggta tcgtggcgcg ccggcgccgg tgccgcgttc  15840
cctggtgttc aactactggt ggttgagcat gctgctgatc ggcggcttgc gtctggccat  15900
gcgccagtat ttcatgggcg actggtactc tgctgtgcag tcggtaccat ttctcaaccg  15960
ccaggatggc ctgcccaggg tggttatcta tggggcgggg gcggccggca accagttggt  16020
tgcggcgttg cgtctcggtc gggcgatgcg tccggtggcg ttcatcgatg acgacaagca  16080
gatcgccaac cgggtcattg ccggtctgcg ggtctatacc gccaagcata tccgccagat  16140
gatcgacgag acgggcgcgc aggaggttct cctggcgatt ccttccgcca ctcgggcccg  16200
gcgccgagag attctcgagt ccctggagcc gttcccgctg cacgtgcgca gcatgcccgg  16260
cttcatggac ctggccagcg gccgggtcaa ggtggatgac ctgcaggagg tggacatcgc  16320
tgacctgctg gggcgcgaca gcgtcgcacc gcgcaaggag ctgctggaac ggtgcatccg  16380
cggtcaggtg gtgatggtga ccggggcggg cggctctatc ggttcggaac tctgtcggca  16440
gatcatgagt tgttcgccta gcgtgctgat cctgttcgaa cacagcgaat acaacctcta  16500
tagcatccat caggaactgg agcgtcggat caagcgcgag tcgctttcgg tgaacctgtt  16560
gccgatcctc ggttcggtgc gcaatcccga gcgcctggtg gacgtgatgc gtacctggaa  16620
ggtcaatacc gtctaccatg cggcggccta caagcatgtg ccgatcgtcg agcacaacat  16680
cgccgagggc gttctcaaca acgtgatagg caccttgcat gcggtgcagg ccgcggtgca  16740
ggtcggcgtg cagaacttcg tgctgatttc caccgacaag gcggtgcggc cgaccaatgt  16800
gatgggcagc accaagcgcc tggcggaaat ggtccttcag gcgctcagca acgaatcggc  16860
```

```
gccggtgctg ttcggcgacc ggaaggacgt gcatcacgtc aacaagaccc gtttcaccat  16920
ggtccgcttc ggcaacgtcc tcggttcgtc cggttcggtc attccgctgt tccgcgagca  16980
gatcaagcgc ggcggcccgg tgacggtcac ccacccgagc atcacccgtt acttcatgac  17040
cattcccgag gcggcgcagt tggtcatcca ggccggttcg atggggcagg gcggagatgt  17100
attcgtgctg gacatggggc cgccggtgaa gatcctggag ctcgccgaga agatgatcca  17160
cctgtccggc ctgagcgtgc gttccgagcg ttcgccccat ggtgacatcg ccatcgagtt  17220
cagtggcctg cgtcctggcg agaagctcta cgaagagctg ctgatcggtg acaacgtgaa  17280
tcccaccgac catccgatga tcatgcgggc caacgaggaa cacctgagct gggaggcctt  17340
caaggtcgtg ctggagcagt tgctggccgc cgtggagaag gacgactact cgcgggttcg  17400
ccagttgctg cgggaaaccg tcagcggcta tgcgcctgac ggtgaaatcg tcgactggat  17460
ctatcgccag aggcggcgag aaccctgagt catcgttctc cggaaaaggc cgcctagcgg  17520
cctttttgt tttctccgta cgatgtttcc ggtgccggac caggaagcga ctgctttgct  17580
ggggctgtcg atccaggtgc gttccacggc gataaggtgg tttcgtggat gggcaacatg  17640
tcgcgaaggt aaagtcagcc gcattgttga attcatcgaa aaaccggatc agccacaaac  17700
gctggaatca gacatcatgg ccgtgggccg ttatgtgctt tctgccgata tttggccgga  17760
acttgaacgc actcagccag gtgcatgggg acgtattcag ctgactgatg ccattgccga  17820
actggcgaaa aaacagtctg ttgacgccat gctgatgact ggtgacagct acgactgtgg  17880
taaaaaaatg ggttatatgc aggcgtttgt gaagtatgga ctacgcaacc tgaaagaagg  17940
agcgaagttc cgcaaaggta ttgagaaatt gcttagcgag taagtttaaa aaatagacgc  18000
ccttataggg cgtaataaca aataacggta gtcaacattc gacgcggtga tgcagatatg  18060
cccggaatgc tgataccgtt ttttcattct aaaaaactca tcatttcatt gagttaacta  18120
caaaatttag cactgttttt tataatgttt cttcttgttt ctggcatcaa ttggtaagat  18180
aattagtgtt tgagtttaga ggctttgcgg cagagaagcg gagcttaaca cgtctgtgag  18240
agtacgcagt gcactggtag ctgtaaagcc agtggcggta gcgtgtttaa ataaatacat  18300
tagtaatact acatattaca tcattgtagg ctatttaagc gctacatgat aagcgacagc  18360
gctagcaatc aaatctttta aagttacttc tcaggaatag taaaaggagg acagctatgt  18420
tgaaaaaaga gtatttaaaa aacccttatt tagttttgtt tgcgatgatt atattagctt  18480
atgtttttag tgtattttgc aggttttatt gggtttggtg ggcaagtgag tttaatgagt  18540
attttttcaa taatcagtta atgatcattt caaatgatgg ctatgctttt gctgagggcg  18600
caagagatat gatagcaggt tttcatcagc ctaatgattt gagttattat ggatcttctt  18660
tatccgcgct tacttattgg ctttataaaa tcacaccttt ttcttttgaa agtatcattt  18720
tatatatgag tactttttta tcttctttgg tggtgattcc tactattttg ctagctaacg  18780
aatacaaacg tcctttaatg ggctttgtag ctgctctttt agcaagtata gcaaacagtt  18840
attataatcg cactatgagt gggtattatg atacggatat gctggtaatt gttttgccta  18900
tgtttatttt atttttatg gtaagaatga ttttaaaaaa agactttttt tcattgattg  18960
ccttgccgtt atttatagga atttatcttt ggtggtatcc ttcaagttat actttaaatg  19020
tagctttaat tggacttttt ttaatttata cacttatttt tcatagaaaa gaaaagattt  19080
tttatatagc tgtgattttg tcttctctta ctctttcaaa tatagcatgg ttttatcaaa  19140
gtgccattat agtaatactt tttgctttat tcgccttaga gcaaaaacgc ttaaatttta  19200
tgattatagg aattttaggt agtgcaactt tgatattttt gattttaagt ggtggggttg  19260
```

```
atcctatact ttatcagctt aaattttata tttttagaag tgatgaaagt gcgaatttaa  19320

cgcagggctt tatgtatttt aatgtcaatc aaaccataca agaagttgaa aatgtagatc  19380

ttagcgaatt tatgcgaaga attagtggta gtgaaattgt ttttttgttt tctttgtttg  19440

gttttgtatg gcttttgaga aaacataaaa gtatgattat ggctttacct atattggtgc  19500

ttgggttttt agccttaaaa ggggggctta gatttaccat ttattctgta cctgtaatgg  19560

ccttaggatt tggtttttta ttgagcgagt ttaaggctat aatggttaaa aaatatagcc  19620

aattaacttc aaatgtttgt attgttttttg caactatttt gactttagct ccagtattta  19680

tccatattta caactataaa gcgccaacag tttttttctca aaatgaagca tcattattaa  19740

atcaattaaa aaatatagcc aatagagaag attatgtggt aacttggtgg gattatggtt  19800

atcctgtgcg ttattatagc gatgtgaaaa ctttagtaga tggtggaaag catttaggta  19860

aggataattt tttcccttct tttgctttaa gcaaagatga acaagctgca gctaatatgg  19920

caagacttag tgtagaatat acagaaaaaa gcttttatgc tccgcaaaat gatattttaa  19980

aaacagacat tttgcaagcc atgatgaaag attataatca aagcaatgtg gatttgtttc  20040

tagcttcatt atcaaaacct gattttaaaa tcgatacgcc aaaaactcgt gatatttatc  20100

tttatatgcc cgctagaatg tctttgattt tttctacggt ggctagtttt tcttttatta  20160

atttagatac aggagttttg gataaacctt ttacctttag cacagcttat ccacttgatg  20220

ttaaaaatgg agaaatttat cttagcaacg gagtggtttt aagcgatgat tttagaagtt  20280

ttaaaatagg tgataatgtg gtttctgtaa atagtatcgt agagattaat tctattaaac  20340

aaggtgaata caaaatcact ccaattgatg ataaggctca gttttatatt ttttatttaa  20400

aggatagtgc tattccttac gcacaattta ttttaatgga taaaaccatg tttaatagtg  20460

cttatgtgca aatgtttttt ttaggaaatt atgataagaa tttatttgac ttggtgatta  20520

attctagaga tgctaaggtt tttaaactta aaatttaccc atacgatgtt ccagattacg  20580

cttaaacatg tgaattc                                                 20597
```

```
<210> SEQ ID NO 20
<211> LENGTH: 8815
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

agtcgacctg caggatgaga gtagaaaata ataatgtttc tgggcaaaac catgacccgg     60

aacagattga tttgattgat ttactagtgc agttgtggcg tggcaagatg acaatcatca    120

tttccgtcat tgtggctatt gccctagcta ttggatattt ggcagtagcg aaggagaaat    180

ggacgtcaac agcaattatc actcagcccg atgtggggca aattgctggc tataacaatg    240

ccatgaatgt tatctatggt caggctgcac cgaaagtatc ggatttgcag gagacgttaa    300

ttggtcgctt cagttctgcc ttctctgcat tagcagaaac gctggataat caggaagaac    360

cagaaaaact taccatcgaa ccttctgtta agaaccagca attaccattg actgtttctt    420

atgttgggca aactgcagag ggcgcacaaa tgaagttggc ccaatacatt cagcaagttg    480

acgataaagt gaatcaagag ttagaaaagg atctcaagga caacattgct ctgggacgga    540

aaaacttgca ggactcttta agaacgcagg aagtggttgc gcaggagcag aaagatctgc    600

gtatccgtca gattcaggaa gcgttgcagt atgcgaatca ggcgcaggtg acaaaaccgc    660
```

```
agattcaaca gactggcgaa gatatcacac aagatacgtt gttccttttg gggagcgaag    720
cgctggagtc gatgattaag catgaggcga cccgtccgtt ggtgttctca ccaaactact    780
atcagactcg tcaaaacctg cttgatatcg aaagcttaaa ggttgatgat cttgatattc    840
atgcttaccg ctatgtaatg aaaccgacgt tacctattcg tcgtgatagc ccgaaaaagg    900
caattacctt gattctggcg gtgctgctgg gtggcatggt tggcgcgggg attgtgctgg    960
ggcgtaatgc tctacgcaat tacaacgcga agtaacctgc aggcatgcaa gcttctgttt   1020
tggcggatga gagaagaaat tcgtcgcccg ccataaactg ccaggcatca aattaagcag   1080
aaggccatcc tgacggatgg cctttttgcg tttctacaaa ctcttcctgt ctagcaggtg   1140
gcacttttcg gggaaatgtg cgcggaaccc ctatttgttt atttttctaa atacattcaa   1200
atatgtatcc gctcatgcta gaaatatttt atctgattaa taagatgatc ttcttgagat   1260
cgttttggtc tgcgcgtaat ctcttgctct gaaaacgaaa aaaccgcctt gcagggcggt   1320
ttttcgaagg ttctctgagc taccaactct ttgaaccgag gtaactggct tggaggagcg   1380
cagtcaccaa aacttgtcct ttcagtttag ccttaaccgg cgcatgactt caagactaac   1440
tcctctaaat caattaccag tggctgctgc cagtggtgct tttgcatgtc tttccgggtt   1500
ggactcaaga cgatagttac cggataaggc gcagcggtcg gactgaacgg ggggttcgtg   1560
catacagtcc agcttggagc gaactgccta cccggaactg agtgtcaggc gtggaatgag   1620
acaaacgcgg ccataacagc ggaatgacac cggtaaaccg aaaggcagga acaggagagc   1680
gcacgaggga gccgccaggg gaaacgcctg gtatctttat agtcctgtcg ggtttcgcca   1740
ccactgattt gagcgtcaga tttcgtgatg cttgtcaggg gggcggagcc tatggaaaaa   1800
cggctttgcc gcggccctct cacttccctg ttaagtatct tcctggcatc ttccaggaaa   1860
tctccgcccc gttcgtaagc catttccgct cgccgcagtc gaacgaccga gcgtagcgag   1920
tcagtgagcg aggaagcgga atatatcctg tatcacatat tctgctgacg caccggtgca   1980
gcctttttc tcctgccaca tgaagcactt cactgacacc ctcatcagtg ccaacatagt   2040
aagccagtat acactccgct agcgctgatg tccggcggtg cttttgccgt tacgcaccac   2100
cccgtcagta gctgaacagg agggacagct gatagaaaca gaagccactg gagcacctca   2160
aaaacaccat catacactaa atcagtaagt tggcagcatc acccgacgca ctttgcgccg   2220
aataaagtgt aggctggagc tgcttcgaag ttcctatact ttctagagaa taggaacttc   2280
ggaataggaa cttcaagatc ccctcacgct gccgcaagca ctcagggcgc aagggctgct   2340
aaaggaagcg gaacacgtag aaagccagtc cgcagaaacg gtgctgaccc cggatgaatg   2400
tcagctactg ggctatctgg acaagggaaa acgcaagcgc aaagagaaag caggtagctt   2460
gcagtgggct tacatggcga tagctagact gggcggtttt atggacagca agcgaaccgg   2520
aattgccagc tggggcgccc tctggtaagg ttgggaagcc ctgcaaagta aactggatgg   2580
ctttcttgcc gccaaggatc tgatggcgca ggggatcaag atctgatcaa gagacaggat   2640
gaggatcgtt tcgcatgatt gaacaagatg gattgcacgc aggttctccg gccgcttggg   2700
tggagaggct attcggctat gactgggcac aacagacaat cggctgctct gatgccgccg   2760
tgttccggct gtcagcgcag gggcgcccgg ttctttttgt caagaccgac ctgtccggtg   2820
ccctgaatga actgcaggac gaggcagcgc ggctatcgtg gctggccacg acgggcgttc   2880
cttgcgcagc tgtgctcgac gttgtcactg aagcgggaag ggactggctg ctattgggcg   2940
aagtgccggg gcaggatctc ctgtcatctc accttgctcc tgccgagaaa gtatccatca   3000
```

```
tggctgatgc aatgcggcgg ctgcatacgc ttgatccggc tacctgccca ttcgaccacc   3060
aagcgaaaca tcgcatcgag cgagcacgta ctcggatgga agccggtctt gtcgatcagg   3120
atgatctgga cgaagagcat caggggctcg cgccagccga actgttcgcc aggctcaagg   3180
cgcgcatgcc cgacggcgag gatctcgtcg tgacccatgg cgatgcctgc ttgccgaata   3240
tcatggtgga aaatggccgc ttttctggat tcatcgactg tggccggctg ggtgtggcgg   3300
accgctatca ggacatagcg ttggctaccc gtgatattgc tgaagagctt ggcggcgaat   3360
gggctgaccg cttcctcgtg ctttacggta tcgccgctcc cgattcgcag cgcatcgcct   3420
tctatcgcct tcttgacgag ttcttctgag cgggactctg gggttcgaaa tgaccgacca   3480
agcgacgccc aacctgccat cacgagattt cgattccacc gccgccttct atgaaaggtt   3540
gggcttcgga atcgttttcc gggacgccgg ctggatgatc ctccagcgcg gggatctcat   3600
gctggagttc ttcgcccacc ccagcttcaa aagcgctctg aagttcctat actttctaga   3660
gaataggaac ttcggaatag gaactaagga ggatattcat atggtttttt taaggcagtt   3720
attggtgccc ttaaacgcct ggtgctacgc ctgaataagt gataataagc ggatgaatgg   3780
cagaaattcg aaagcaaatt cgacccggtc gtcggttcag ggcagggtcg ttaaatagcc   3840
gcttatgtct attgctggtt taccggttta ttgactaccg gaagcagtgt gaccgtgtgc   3900
ttctcaaatg cctgaggcca gtttgctcag gctctccccg tggaggtaat aattgacgat   3960
atgatcattt attctgcctc ccagagcctg ataaaaacgg ttagcgcttc gttaatacag   4020
atgtaggtgt tccacagggt agccagcagc atcctgcgat gcagatccgg aacataatgg   4080
tgcagggcgc ttgtttcggc gtgggtatgg tggcaggccc cgtggccggg ggactgttgg   4140
gcgctgccgg cacctgtcct acgagttgca tgataaagaa gacagtcata agtgcggcga   4200
cgatagtcat gccccgcgcc caccggaagg agctaccgga cagcggtgcg gactgttgta   4260
actcagaata agaaatgagg ccgctcatgg cgttgactct cagtcatagt atcgtggtat   4320
caccggttgg ttccactctc tgttgcgggc aacttcagca gcacgtaggg gacttccgcg   4380
tttccagact ttacgaaaca cggaaaccga agaccattca tgttgttgct caggtcgcag   4440
acgttttgca gcagcagtcg cttcacgttc gctcgcgtat cggtgattca ttctgctaac   4500
cagtaaggca accccgccag cctagccggg tcctcaacga caggagcacg atcatgcgca   4560
cccgtggcca ggacccaacg ctgcccgaga tgcgccgcgt gcggctgctg gagatggcgg   4620
acgcgatgga tatgttctgc caagggttgg tttgcgcatt cacagttctc cgcaagaatt   4680
gattggctcc aattcttgga gtggtgaatc cgttagcgag gtgccgccgg cttccattca   4740
ggtcgaggtg gcccggctcc atgcaccgcg acgcaacgcg gggaggcaga caaggtatag   4800
ggcggcgcct acaatccatg ccaacccgtt ccatgtgctc gccgaggcgg cataaatcgc   4860
cgtgacgatc agcggtccag tgatcgaagt taggctggta agagccgcga gcgatccttg   4920
aagctgtccc tgatggtcgt catctacctg cctggacagc atggcctgca acgcgggcat   4980
cccgatgccg ccggaagcga gaagaatcat aatggggaag gccatccagc ctcgcgtcgc   5040
gaacgccagc aagacgtagc ccagcgcgtc ggccaattcg cgctaactta cattaattgc   5100
gttgcgctca ctgcccgctt tccagtcggg aaacctgtcg tgccagctgc attaatgaat   5160
cggccaacgc gcggggagag gcggtttgcg tattgggcgc cagggtggtt tttcttttca   5220
ccagtgagac gggcaacagc tgattgccct tcaccgcctg gccctgagag agttgcagca   5280
agcggtccac gctggtttgc cccagcaggc gaaaatcctg tttgatggtg gttgacggcg   5340
ggatataaca tgagctgtct tcggtatcgt cgtatcccac taccgagata tccgcaccaa   5400
```

```
cgcgcagccc ggactcggta atggcgcgca ttgcgcccag cgccatctga tcgttggcaa   5460
ccagcatcgc agtgggaacg atgccctcat tcagcatttg catggtttgt tgaaaaccgg   5520
acatggcact ccagtcgcct tcccgttccg ctatcggctg aatttgattg cgagtgagat   5580
atttatgcca gccagccaga cgcagacgcg ccgagacaga acttaatggg cccgctaaca   5640
gcgcgatttg ctggtgaccc aatgcgacca gatgctccac gcccagtcgc gtaccgtctt   5700
catgggagaa aataatactg ttgatgggtg tctggtcaga gacatcaaga aataacgccg   5760
gaacattagt gcaggcagct tccacagcaa tggcatcctg gtcatccagc ggatagttaa   5820
tgatcagccc actgacgcgt tgcgcgagaa gattgtgcac cgccgcttta caggcttcga   5880
cgccgcttcg ttctaccatc gacaccacca cgctggcacc cagttgatcg gcgcgagatt   5940
taatcgccgc gacaatttgc gacggcgcgt gcagggccag actggaggtg gcaacgccaa   6000
tcagcaacga ctgtttgccc gccagttgtt gtgccacgcg gttgggaatg taattcagct   6060
ccgccatcgc cgcttccact ttttcccgcg ttttcgcaga aacgtggctg gcctggttca   6120
ccacgcggga aacggtctga taagagacac cggcatactc tgcgacatcg tataacgtta   6180
ctggtttcac attcaccacc ctgaattgac tctcttccgg gcgctatcat gccataccgc   6240
gaaaggtttt gcaccattcg atggtgtcaa cgtaaatgca tgccgcttcg ccttcgcgcg   6300
cgaattggcc gccatgccgg cgataatggc ctgcttctcg ccgaaacgtt tggtggcggg   6360
accagtgacg aaggcttgag cgagggcgtg caagattccg aataccgcaa gcgacaggcc   6420
gatcatcgtc gcgctccagc gaaagcggtc ctcgccgaaa atgacccaga gcgctgccgg   6480
cacctgtcct acgagttgca tgataaagaa gacagtcata agtgcggcga cgatagtcat   6540
gccccgcgcc caccggaagg agctgactgg gttgaaggct ctcaagggca tcggcggagc   6600
ttatcgactg cacggtgcac caatgcttct ggcgtcaggc agccatcgga agctgtggta   6660
tggctgtgca ggtcgtaaat cactgcataa ttcgtgtcgc tcaaggcgca ctcccgttct   6720
ggataatgtt ttttgcgccg acatcataac ggttctggca aatattctga aatgagctgt   6780
tgacaattaa tcatcggctc gtataatgtg tggaattgtg agcggataac aatttcacac   6840
aggaaacaga attcgagctc atgaaaaaga tttggctggc cctggcagga ctggttctgg   6900
ccttttcagc aagtgcagct gaagaagcct ttgatctgtg gaatgagtgt gcaaaagcat   6960
gtgtactgga tctgaaagat ggtgtgagat ccagcagaat gtcagtggat ccagccattg   7020
cagatacaaa tggccagggt gtactgcatt actctatggt tctggaaggt ggtaatgatg   7080
ccctgaaact ggccattgat aatgcactgt ctatcaccag tgatggtctg acaatcagac   7140
tggagggagg ggtggaaccc aataagcctg tcagatacag ctatacaaga caagccagag   7200
gttcttggag cctgaactgg ctggtgccta ttgggcatga aaaaccatct aacattaaag   7260
tttttattca tgaactgaat gcaggcaatc agctgtctca tatgagccca atttatacca   7320
ttgaaatggg ggatgaactg ctggctaaac tggccagaga tgctacattc tttgtcagag   7380
cccatgaatc aaatgagatg cagcctaccc tggccattag ccatgctggt gtgagtgttg   7440
tcatggcaca aactcagccc aggagagaga aaaggtggtc tgagtggacc agtggcaaag   7500
tgctgtgcct gctggatcct ctggatggtg tttataacta tctggcccaa cagaggtgta   7560
acctggatga tacctgggaa ggtaaaatct atagagtgct ggcaggtaat ccagcaaaac   7620
atgacctgga tatcaaggat aataacaata gcacccctac tgtaatcagc catagactgc   7680
atttcccaga gggaggttca ctggctgccc tgactgctca tcaggcctgt catctgccac   7740
```

```
tggaaacttt caccagacac aggcagccaa gaggctggga acagctggaa caatgtggct   7800
atccagttca gaggctggtt gccctgtacc tggcagcaag actgagctgg aatcaggtag   7860
atcaggttat tagaaatgca ctggccagcc cagggagtgg gggtgacctg ggtgaggcaa   7920
ttagagaaca gcctgagcag gccagactgg ccctgactct ggcagcagct gaaagtgaaa   7980
gatttgtgag acaggggaca ggcaatgatg aagcaggtgc agctaatgca gatgttgttt   8040
cactgacttg tcctgttgct aaagatcaga acaggaccaa aggtgaatgt gctggaccag   8100
ctgattcagg agatgcactg ctggagagga actatccaac tggtgcagaa ttcctgggag   8160
atggtggtga tgtttctttt agcaccagag gcacacagaa ctggactgtg gaaagactgc   8220
tgcaggcaca tagacagctg gaagaaagag gctatgtatt tgttggctac catggtactt   8280
tcctggaagc agcacagtcc attgtctttg gaggggttag agccagaagc caggatctgg   8340
atgctatttg gagaggtttt tatattgctg gggatccagc cctggcctat ggatatgcac   8400
aagatcagga acctgatgcc agaggcagaa tcagaaatgg tgccctgctg agggtttatg   8460
ttcctaggtc tagcctgcca ggattttata gaacctctct gaccctggca gcccctgaag   8520
cagcaggtga ggtggagaga ctgattggtc atcctctgcc actgagactg gatgccatta   8580
cagggccaga agaagaaggt ggcagagtga caattctggg ttggcccctg gcagagagga   8640
cagtagttat tccttcagca atccctacag atccaaggaa tgtgggtggg gacctggatc   8700
catcctcaat tccagataag gaacaggcaa tttcagccct gcctgattat gctagtcagc   8760
caggtaaacc acctagagaa gatctgaaac accaccacca ccaccactga tctag        8815
```

<210> SEQ ID NO 21
<211> LENGTH: 993
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21

```
gaattcatga gagtagaaaa taataatgtt tctgggcaaa accatgaccc ggaacagatt     60
gatttgattg atttactagt gcagttgtgg cgtggcaaga tgacaatcat catttccgtc    120
attgtggcta ttgccctagc tattggatat ttggcagtag cgaaggagaa atggacgtca    180
acagcaatta tcactcagcc cgatgtgggg caaattgctg gctataacaa tgccatgaat    240
gttatctatg gtcaggctgc accgaaagta tcggatttgc aggagacgtt aattggtcgc    300
ttcagttctg ccttctctgc attagcagaa acgctggata atcaggaaga accagaaaaa    360
cttaccatcg aaccttctgt taagaaccag caattaccat tgactgtttc ttatgttggg    420
caaactgcag agggcgcaca aatgaagttg gcccaataca ttcagcaagt tgacgataaa    480
gtgaatcaag agttagaaaa ggatctcaag gacaacattg ctctgggacg gaaaaacttg    540
caggactctt taagaacgca ggaagtggtt gcgcaggagc agaaagatct gcgtatccgt    600
cagattcagg aagcgttgca gtatgcgaat caggcgcagg tgacaaaacc gcagattcaa    660
cagactggcg aagatatcac acaagatacg ttgttccttt tggggagcga agcgctggag    720
tcgatgatta agcatgaggc gacccgtccg ttggtgttct caccaaacta ctatcagact    780
cgtcaaaacc tgcttgatat cgaaagctta aaggttgatg atcttgatat tcatgcttac    840
cgctatgtaa tgaaaccgac gttacctatt cgtcgtgata gcccgaaaaa ggcaattacc    900
ttgattctgg cggtgctgct gggtggcatg gttggcgcgg ggattgtgct ggggcgtaat    960
```

gctctacgca attacaacgc gaagtaagtc gac 993

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Asp Asn Asn Asn Ser Thr Pro Thr Val Ile Ser His Arg
1 5 10

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Asp Gln Asn Arg
1

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic consensus sequence
<220> FEATURE:
<221> NAME/KEY: MOD_RES
<222> LOCATION: (1)..(1)
<223> OTHER INFORMATION: Asp or Glu
<220> FEATURE:
<221> NAME/KEY: MOD_RES
<222> LOCATION: (2)..(2)
<223> OTHER INFORMATION: Any amino acid except Pro
<220> FEATURE:
<221> NAME/KEY: MOD_RES
<222> LOCATION: (4)..(4)
<223> OTHER INFORMATION: Any amino acid except Pro
<220> FEATURE:
<221> NAME/KEY: MOD_RES
<222> LOCATION: (5)..(5)
<223> OTHER INFORMATION: Ser or Thr
<220> FEATURE:
<223> OTHER INFORMATION: See specification as filed for detailed description of substitutions and preferred embodiments

<400> SEQUENCE: 24

Xaa Xaa Asn Xaa Xaa
1 5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Asp Asn Asn Asn Ser
1 5

<210> SEQ ID NO 26

<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Asp Gln Asn Arg Thr
1 5

<210> SEQ ID NO 27
<211> LENGTH: 2160
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27
gaattcatgt tgaaaaaaga gtatttaaaa aacccttatt tagttttgtt tgcgatgatt 60
atattagctt atgtttttag tgtattttgc aggttttatt gggtttggtg ggcaagtgag 120
tttaatgagt attttttcaa taatcagtta atgatcattt caaatgatgg ctatgctttt 180
gctgagggcg caagagatat gatagcaggt tttcatcagc ctaatgattt gagttattat 240
ggatcttctt tatccgcgct tacttattgg ctttataaaa tcacaccttt ttcttttgaa 300
agtatcattt tatatatgag tactttttta tcttctttgg tggtgattcc tactattttg 360
ctagctaacg aatacaaacg tcctttaatg ggctttgtag ctgctctttt agcaagtata 420
gcaaacagtt attataatcg cactatgagt gggtattatg atacggatat gctggtaatt 480
gttttgccta tgtttatttt atttttatg gtaagaatga ttttaaaaaa agactttttt 540
tcattgattg ccttgccgtt atttatagga atttatcttt ggtggtatcc ttcaagttat 600
actttaaatg tagctttaat tggacttttt ttaatttata cacttatttt tcatagaaaa 660
gaaaagattt tttatatagc tgtgattttg tcttctctta ctctttcaaa tatagcatgg 720
ttttatcaaa gtgccattat agtaatactt tttgctttat tcgccttaga gcaaaaacgc 780
ttaaatttta tgattatagg aattttaggt agtgcaactt tgatattttt gattttaagt 840
ggtggggttg atcctatact ttatcagctt aaattttata tttttagaag tgatgaaagt 900
gcgaatttaa cgcagggctt tatgtatttt aatgtcaatc aaaccataca agaagttgaa 960
aatgtagatc ttagcgaatt tatgcgaaga attagtggta gtgaaattgt ttttttgttt 1020
tctttgtttg gttttgtatg gcttttgaga aaacataaaa gtatgattat ggctttacct 1080
atattggtgc ttgggttttt agccttaaaa ggggggctta gatttaccat ttattctgta 1140
cctgtaatgg ccttaggatt tggtttttta ttgagcgagt ttaaggctat aatggttaaa 1200
aaatatagcc aattaacttc aaatgtttgt attgtttttg caactatttt gactttagct 1260
ccagtattta tccatattta caactataaa gcgccaacag tttttctca aaatgaagca 1320 tcattattaa atcaattaaa aaatatagcc aatagagaag attatgtggt aacttgggcg 1380
gcttatggtt atcctgtgcg ttattatagc gatgtgaaaa ctttagtaga tggtggaaag 1440
catttaggta aggataattt tttcccttct tttgctttaa gcaaagatga acaagctgca 1500

-continued

```
gctaatatgg caagacttag tgtagaatat acagaaaaaa gcttttatgc tccgcaaaat   1560

gatattttaa aaacagacat tttgcaagcc atgatgaaag attataatca aagcaatgtg   1620

gatttgtttc tagcttcatt atcaaaacct gattttaaaa tcgatacgcc aaaaactcgt   1680

gatatttatc tttatatgcc cgctagaatg tctttgattt tttctacggt ggctagtttt   1740

tcttttatta atttagatac aggagttttg gataaacctt ttacctttag cacagcttat   1800

ccacttgatg ttaaaaatgg agaaatttat cttagcaacg gagtggtttt aagcgatgat   1860

tttagaagtt ttaaaatagg tgataatgtg gtttctgtaa atagtatcgt agagattaat   1920

tctattaaac aaggtgaata caaaatcact ccaattgatg ataaggctca gttttatatt   1980

ttttatttaa aggatagtgc tattccttac gcacaattta ttttaatgga taaaaccatg   2040

tttaatagtg cttatgtgca aatgtttttt ttaggaaatt atgataagaa tttatttgac   2100

ttggtgatta attctagaga tgctaaggtt tttaaactta aaatttaccc atacgatgtt   2160
```

CAPSULAR GRAM-POSITIVE BACTERIA BIOCONJUGATE VACCINES

CROSS-REFERENCE TO RELATED APPLICATIONS

This application is a divisional of U.S. patent application Ser. No. 13/100,603, filed May 4, 2011, now U.S. Pat. No. 8,871,491 which claims the benefit under 35 U.S.C. §119(e) of U.S. Provisional Patent Application No. 61/332,170, filed May 6, 2010, each of which are herein incorporated by reference in their entirety.

STATEMENT AS TO FEDERALLY SPONSORED RESEARCH

Aspects of this invention were made with government support under grant 1R01AI088754-2, subgrant 105699, awarded by the National Institutes of Health. The government has certain rights in these aspects of the invention.

SEQUENCE LISTING

The instant application contains a Sequence Listing which has been submitted in ASCII format via EFS-Web and is herein incorporated by reference in its entirety. Said ASCII copy, created on May 2, 2011, is named 031229US.txt and is 206,590 bytes in size.

BACKGROUND OF THE INVENTION

Vaccines have been one of the great public health inventions of modern medicine and have saved millions of lives. Immunizations have been proven to be an ideal means to prevent and control infections. Each year vaccines prevent up to 3 million deaths and 750,000 children are saved from disability. (Global Alliance for Vaccines and Immunization—Press Releases (Mar. 11, 2006) at www.gavialliance.org/media_centre/press_releases/2006_03_09_en_pr_queenrania_delhi.php). In 1999 the CDC declared immunizations the number one public health achievement of the 20$^{th}$ century (Ten great public health achievements-United States, 1900-1999. MMWR Morb Mortal Wkly Rep 48:241-3 (Apr. 2, 1999)). Some bacteria like those causing tetanus or diphtheria produce a toxin that is largely responsible for the disease. This toxin can be used in a detoxified form as vaccine. However, for most bacteria there is no single toxin that can be used to develop a vaccine.

Among the most successful vaccines are surface polysaccharides of bacterial pathogens like *Haemophilus influenzae, Neisseria meningitidis*, and *Streptococcus pneumoniae* conjugated to carrier proteins. These bacteria are surrounded by a capsule, which promotes microbial virulence and resistance to phagocytic killing, as well as preventing them from desiccation.

Bacterial polysaccharides can elicit a long-lasting immune response in humans if they are coupled to a protein carrier that contains T-cell epitopes. This concept was elaborated 80 years ago (Avery, O. T., and W. F. Goebel. 1929. Chemo-immunological studies on conjugated carbohydrate-proteins. II Immunological specificity of synthetic sugar-proteins. J. Exp. Med. 50:521-533), and proven later for the polysaccharide of *Haemophilus influenza* type B (HIB) coupled to the protein carrier diphtheria toxin (Anderson, P. 1983. Antibody responses to *Haemophilus influenzae* type b and diphtheria toxin induced by conjugates of oligosaccharides of the type b capsule with the nontoxic protein CRM197. Infect Immun 39:233-8; Schneerson, R., O. Barrera, A. Sutton, and J. B. Robbins. 1980. Preparation, characterization, and immunogenicity of *Haemophilus influenzae* type b polysaccharide-protein conjugates. J Exp Med 152:361-76). This glycoconjugate was also the first conjugated vaccine to be licensed in the USA in 1987 and introduced into the US infant immunization schedule shortly thereafter. Besides HIB, conjugated vaccines were successfully used against the encapsulated human pathogens *N. meningitidis* and *S. pneumoniae*. Routine use of these vaccines has resulted in decreased nasopharyngeal colonization, as well as infection. Currently approximately ~25% of the global vaccine market comprises conjugated vaccines.

Gram-positive bacteria have a cell membrane that is surrounded by capsular polysaccharides. *Staphylococcus* is one such Gram-positive bacterium.

*Staphylococcus aureus* causes infection. *S. aureus* is an opportunistic bacterial pathogen responsible for a diverse spectrum of human diseases. Although *S. aureus* may colonize mucosal surfaces of normal humans, it is also a major cause of wound infections and has the invasive potential to induce severe infections, including osteomyelitis, endocarditis, and bacteremia with metastatic complications (Lowy, F. D. 1998. *Staphylococcus aureus* infections. New Engl J Med 339:520-32). *S. aureus* is one of the most common agents implicated in ventilator-associated pneumonia, and it is an important and emerging cause of community-acquired pneumonia, affecting previously healthy adults and children lacking predisposing risk factors (Kollef, M. H., A. Shorr, Y. P. Tabak, V. Gupta, L. Z. Liu, and R. S. Johannes. 2005. Epidemiology and outcomes of health-care-associated pneumonia: results from a large US database of culture-positive pneumonia. Chest 128:3854-62; Shorr, A. F. 2007. Epidemiology and economic impact of meticillin-resistant *Staphylococcus aureus*: review and analysis of the literature. Pharmacoeconomics 25:751-68).

*S. aureus* is the second most common cause of nosocomial bacteremia, and methicillin-resistant *S. aureus* (MRSA) strains account for more than 50% of all infections in intensive care units in the U.S. *S. aureus* infections within the hospital and in the community are increasing. MRSA strains were isolated from 2% of staphylococcal infections in 1974 and from 63% of staphylococcal infections in 2004. Many of the nosocomial MRSA strains are multi-drug resistant, and even methicillin-sensitive strains can be deadly. A recent report using population-based, active case finding revealed that 94,360 invasive MRSA infections occurred in the U.S. in 2005, and that the majority of these (58%) occurred outside of the hospital (Klevens, R. M., M. A. Morrison, J. Nadle, S. Petit, K. Gershman, S. Ray, L. H. Harrison, R. Lynfield, G. Dumyati, J. M. Townes, A. S. Craig, E. R. Zell, G. E. Fosheim, L. K. McDougal, R. B. Carey, and S. K. Fridkin. 2007. Invasive methicillin-resistant *Staphylococcus aureus* infections in the United States. JAMA 298:1763-71). In this analysis, more Americans died from MRSA (>18,000 deaths) in 2005 than from AIDS.

*S. aureus* USA100, also known as the New York/Japan clone, is an MRSA strain that represents the predominant U.S. hospital-acquired MRSA strain (McDougal, L. K., C. D. Steward, G. E. Killgore, J. M. Chaitram, S. K. McAllister, and F. C. Tenover. 2003. Pulsed-field gel electrophoresis typing of oxacillin-resistant *Staphylococcus aureus* isolates from the United States: establishing a national database. J Clin Microbiol 41:5113-20).

Epidemiologic analyses indicate that *S. aureus* causes approximately 2 million clinical infections each year in the U.S. alone (Fridkin, S. K., J. C. Hageman, M. Morrison, L.

T. Sanza, K. Como-Sabetti, J. A. Jernigan, K. Harriman, L. H. Harrison, R. Lynfield, and M. M. Farley. 2005. Methicillin-resistant *Staphylococcus aureus* disease in three communities. N Engl J Med 352:1436-44; King, M. D., B. J. Humphrey, Y. F. Wang, E. V. Kourbatova, S. M. Ray, and H. M. Blumberg. 2006. Emergence of community-acquired methicillin-resistant *Staphylococcus aureus* USA 300 clone as the predominant cause of skin and soft-tissue infections. Ann Intern Med 144:309-17; Klevens, R. M., M. A. Morrison, J. Nadle, S. Petit, K. Gershman, S. Ray, L. H. Harrison, R. Lynfield, G. Dumyati, J. M. Townes, A. S. Craig, E. R. Zell, G. E. Fosheim, L. K. McDougal, R. B. Carey, S. K. Fridkin, and M. I. for the Active Bacterial Core surveillance. 2007. Invasive methicillin-resistant *Staphylococcus aureus* infections in the United States. JAMA 298: 1763-1771). Not only are *S. aureus* infections increasing in number, but the resistance of *S. aureus* to antibiotics is also on the increase. MRSA accounts for 40%-60% of nosocomial *S. aureus* infections in the U.S., and many of these strains are multi-drug resistant. Notorious as a major source of nosocomial infections, *S. aureus* has recently taken on a new role in causing an escalating number of community-acquired infections in non-hospitalized persons without predisposing risk factors. Virulent community-associated MRSA (CA-MRSA) strains are becoming more prevalent across the U.S. and Europe, and their dissemination has been observed globally (Baggett, H. C., T. W. Hennessy, K. Rudolph, D. Bruden, A. Reasonover, A. Parkinson, R. Sparks, R. M. Donlan, P. Martinez, K. Mongkolrattanothai, and J. C. Butler. 2004. Community-onset methicillin-resistant *Staphylococcus aureus* associated with antibiotic use and the cytotoxin Panton-Valentine leukocidin during a furunculosis outbreak in rural Alaska. J Infect Dis 189:1565-73; Gilbert, M., J. MacDonald, D. Gregson, J. Siushansian, K. Zhang, S. Elsayed, K. Laupland, T. Louie, K. Hope, M. Mulvey, J. Gillespie, D. Nielsen, V. Wheeler, M. Louie, A. Honish, G. Keays, and J. Conly. 2006. Outbreak in Alberta of community-acquired (USA300) methicillin-resistant *Staphylococcus aureus* in people with a history of drug use, homelessness or incarceration. Canad Med Assoc J 175:149-54; Kazakova, S. V., J. C. Hageman, M. Matava, A. Srinivasan, L. Phelan, B. Garfinkel, T. Boo, S. McAllister, J. Anderson, B. Jensen, D. Dodson, D. Lonsway, L. K. McDougal, M. Arduino, V. J. Fraser, G. Killgore, F. C. Tenover, S. Cody, and D. B. Jernigan. 2005. A clone of methicillin-resistant *Staphylococcus aureus* among professional football players. N Engl J Med 352:468-75).

Not only has *S. aureus* resistance to methicillin become more common, but numerous isolates with reduced susceptibility to vancomycin have been reported. Seven clinical isolates of *S. aureus* that carry vanA and are fully resistant to vancomycin have been isolated in the U.S. These isolates are also methicillin resistant (Chang, S., D. M. Sievert, J. C. Hageman, M. L. Boulton, F. C. Tenover, F. P. Downes, S. Shah, J. T. Rudrik, G. R. Pupp, W. J. Brown, D. Cardo, and S. K. Fridkin. 2003. Infection with vancomycin-resistant *Staphylococcus aureus* containing the vanA resistance gene. New Engl J Med 348:1342-7). Because *S. aureus* cannot always be controlled by antibiotics and MRSA isolates are becoming increasingly prevalent in the community, additional control strategies, such as a vaccine, are sorely needed.

*S. aureus* capsular polysaccharides are involved in infection. Many virulence factors contribute to the pathogenesis of staphylococcal infections, including surface-associated adhesions, secreted exoproteins and toxins, and immune evasion factors (Foster, T. J. 2005. Immune evasion by staphylococci. Nature Reviews Microbiology 3:948-58). Like many invasive bacterial pathogens, *S. aureus* produces a capsular polysaccharide (CP) (FIG. 4) that enhances its resistance to clearance by host innate immune defenses. Most clinical isolates of *S. aureus* are encapsulated, and serotype 5 and 8 strains predominate (Arbeit, R. D., W. W. Karakawa, W. F. Vann, and J. B. Robbins. 1984. Predominance of two newly described capsular polysaccharide types among clinical isolates of *Staphylococcus aureus*. Diagn Microbiol Infect Dis 2:85-91). The type 5 (CP5) and type 8 (CP8) capsular polysaccharides have similar trisaccharide repeating units comprised of N-acetyl mannosaminuronic acid (ManNAcA), N-acetyl L-fucosamine (L-FucNAc), and N-acetyl D-fucosamine (D-FucNAc) (Jones, C. 2005. Revised structures for the capsular polysaccharides from *Staphylococcus aureus* types 5 and 8, components of novel glycoconjugate vaccines. Carbohydr Res 340:1097-106). CP5 and CP8 are serologically distinct, and this can be attributed to differences in the linkages between the sugars and in the sites of O-acetylation (FIG. 4).

Previous studies have correlated *S. aureus* capsule production with resistance to in vitro phagocytic uptake and killing (Fattom, A., R. Schneerson, S. C. Szu, W. F. Vann, J. Shiloach, W. W. Karakawa, and J. B. Robbins. 1990. Synthesis and immunologic properties in mice of vaccines composed of *Staphylococcus aureus* type 5 and type 8 capsular polysaccharides conjugated to *Pseudomonas aeruginosa* exotoxin A. Infect Immun 58:2367-74; Thakker, M., J.-S. Park, V. Carey, and J. C. Lee. 1998. *Staphylococcus aureus* serotype 5 capsular polysaccharide is antiphagocytic and enhances bacterial virulence in a murine bacteremia model. Infect Immun 66:5183-5189; Watts, A., D. Ke, Q. Wang, A. Pillay, A. Nicholson-Weller, and J. C. Lee. 2005. *Staphylococcus aureus* strains that express serotype 5 or serotype 8 capsular polysaccharides differ in virulence. Infect Immun 73:3502-11). Human neutrophils phagocytose capsule-negative mutants in the presence of nonimmune serum with complement activity, whereas encapsulated isolates require both capsule-specific antibodies and complement for optimal opsonophagocytic killing (Bhasin, N., A. Albus, F. Michon, P. J. Livolsi, J.-S. Park, and J. C. Lee. 1998. Identification of a gene essential for O-acetylation of the *Staphylococcus aureus* type 5 capsular polysaccharide. Mol Microbiol 27:9-21; Thakker, M., J.-S. Park, V. Carey, and J. C. Lee. 1998. *Staphylococcus aureus* serotype 5 capsular polysaccharide is antiphagocytic and enhances bacterial virulence in a murine bacteremia model. Infect Immun 66:5183-5189; Watts, A., D. Ke, Q. Wang, A. Pillay, A. Nicholson-Weller, and J. C. Lee. 2005. *Staphylococcus aureus* strains that express serotype 5 or serotype 8 capsular polysaccharides differ in virulence. Infect Immun 73:3502-11). Nilsson et al. (Nilsson, I.-M., J. C. Lee, T. Bremell, C. Ryden, and A. Tarkowski. 1997. The role of staphylococcal polysaccharide microcapsule expression in septicemia and septic arthritis. Infect Immun 65:4216-4221) reported that peritoneal macrophages from mice phagocytosed significantly greater numbers of a CP5-negative mutant compared to the parental strain Reynolds. Once phagocytosed, the CP5-positive strain survived intracellularly to a greater extent than the mutant strain. Cunnion et al. (Cunnion, K. M., J. C. Lee, and M. M. Frank. 2001. Capsule production and growth phase influence binding of complement to *Staphylococcus aureus*. Infect Immun 69:6796-6803) compared opsonization of isogenic *S. aureus* strains and demonstrated that the CP5-positive strain bound 42% less serum complement (C') than the acapsular mutant.

*S. aureus* vaccine development conventionally has involved the capsule as a target. Vaccine design for protection against staphylococcal disease is complicated by the protean manifestations and clinical complexity of *S. aureus* infections in humans. Many *S. aureus* vaccine candidates have been investigated in animal models of infection, but it has been reported that only two immunization regimens have completed phase III clinical trials (Schaffer, A. C., and J. C. Lee. 2008. Vaccination and passive immunisation against *Staphylococcus aureus*. Int J Antimicrob Agents 32 Suppl 1:S71-8). The first vaccine is based on the two capsular polysaccharides (CPs) (FIG. 4) that are most prevalent among clinical strains of *S. aureus*. Fattom et al. (Fattom, A. R. Schneerson, S. C. Szu, W. F. Vann, J. Shiloach, W. W. Karakawa and J. B. Robbins. 1990. Synthesis and immunologic properties in mice of vaccines composed of *Staphylococcus aureus* type and type 8 capsular polysaccharides conjugated to *Pseudomonas aeruginosa* exotoxin. Infect Immun 58: 2367-74) conjugated the serotype 5 (CP5) and serotype 8 (CP8) polysaccharides to nontoxic recombinant *P. aeruginosa* exoprotein A (rEPA). The conjugate vaccines were immunogenic in mice and humans, and they induced opsonic antibodies that showed efficacy in protecting rodents from lethality and from nonlethal staphylococcal infection (Fattom, A. R. Schneerson, S. C. Szu, W. F. Vann, J. Shiloach, W. W. Karakawa and J. B. Robbins. 1990. Synthesis and immunologic properties in mice of vaccines composed of *Staphylococcus aureus* type 5 and type 8 capsular polysaccharides conjugated to *Pseudomonas aeruginosa* exotoxin. Infect Immun 58: 2367-74; Fattom, A., R. Schneerson, D. C. Watson, W. W. Karakawa, D. Fitzgerald, I. Pastan, X. Li, J. Shiloach, D. A. Bryla, and J. B. Robbins. 1993. Laboratory and clinical evaluation of conjugate vaccines composed of *S. aureus* type 5 and type 8 capsular polysaccharides bound to *Pseudomonas aeruginosa* recombinant exoprotein A. Infect Immun 61:1023-32; Fattom, A. I., J. Sarwar, A. Ortiz, and R. Naso. 1996. A *Staphylococcus aureus* capsular polysaccharide (CP) vaccine and CP-specific antibodies protect mice against bacterial challenge. Infect Immun 64:1659-65; Lee, J. C., J. S. Park, S. E. Shepherd, V. Carey, and A. Fattom. 1997. Protective efficacy of antibodies to the *Staphylococcus aureus* type 5 capsular polysaccharide in a modified model of endocarditis in rats. Infect Immun 65:4146-51). Passive immunization studies have indicated that both CP5- and CP8-specific antibodies significantly reduce infection in a murine model of *S. aureus* mastitis (Tuchscherr, L. P., F. R. Buzzola, L. P. Alvarez, J. C. Lee, and D. O, Sordelli. 2008. Antibodies to capsular polysaccharide and clumping factor A prevent mastitis and the emergence of unencapsulated and small-colony variants of *Staphylococcus aureus* in mice. Infect Immun 76:5738-44). The combined CP5- and CP8-conjugate vaccine was shown to be safe in humans and elicited antibodies that showed opsonophagocytic activity.

*S. aureus* vaccine development has also involved surface proteins as a target. The second *S. aureus* clinical vaccine trial was based on the protective efficacy of antibodies to staphylococcal adhesions in preventing staphylococcal infections. *S. aureus* clumping factor A is a cell wall-anchored protein that is surface expressed, mediates staphylococcal adherence to fibrinogen (Foster, T. J., and M. Hook. 1998. Surface protein adhesins of *Staphylococcus aureus*. Trends Microbiol 6:484-8), and promotes the attachment of *S. aureus* to biomaterial surfaces (Vaudaux, P. E., P. Francois, R. A. Proctor, D. McDevitt, T. J. Foster, R. M. Albrecht, D. P. Lew, H. Wabers, and S. L. Cooper. 1995. Use of adhesion-defective mutants of *Staphylococcus aureus* to define the role of specific plasma proteins in promoting bacterial adhesion to canine arteriovenous shunts. Infection & Immunity 63:585-90), blood clots, and damaged endothelial surfaces (Moreillon, P., J. M. Entenza, P. Francioli, D. McDevitt, T. J. Foster, P. Francois, and P. Vaudaux. 1995. Role of *Staphylococcus aureus* coagulase and clumping factor in pathogenesis of experimental endocarditis. Infection & Immunity 63:4738-43). The fibrinogen-binding domain of ClfA is located within region A of the full-length protein (McDevitt, D., P. Francois, P. Vaudaux, and T. J. Foster. 1995. Identification of the ligand-binding domain of the surface-located fibrinogen receptor (clumping factor) of *Staphylococcus aureus*. Molecular Microbiology 16:895-907). ClfA plays an important role in *S. aureus* binding to platelets, an interaction that is critical in animal models of catheter-induced staphylococcal endocarditis (Sullam, P. M., A. S. Bayer, W. M. Foss, and A. L. Cheung. 1996. Diminished platelet binding in vitro by *Staphylococcus aureus* is associated with reduced virulence in a rabbit model of infective endocarditis. Infection & Immunity 64:4915-21).

Nanra et al. reported that antibodies to ClfA induced opsonophagocytic killing of *S. aureus* in vitro (Nanra, J. S., Y. Timofeyeva, S. M. Buitrago, B. R. Sellman, D. A. Dilts, P. Fink, L. Nunez, M. Hagen, Y. V. Matsuka, T. Mininni, D. Zhu, V. Pavliak, B. A. Green, K. U. Jansen, and A. S. Anderson. 2009. Heterogeneous in vivo expression of clumping factor A and capsular polysaccharide by *Staphylococcus aureus*: Implications for vaccine design. Vaccine 27:3276-80). Furthermore, mice immunized with a recombinant form of the binding region A of ClfA showed reductions in arthritis and lethality induced by *S. aureus* (Josefsson, E., O. Hartford, L. O'Brien, J. M. Patti, and T. Foster. 2001. Protection against experimental *Staphylococcus aureus* arthritis by vaccination with clumping factor A, a novel virulence determinant. Journal of Infectious Diseases 184:1572-80). Passive immunization experiments were performed in rabbits given a human polyclonal immunoglobulin preparation that contained elevated levels of antibodies specific for ClfA (Vernachio, J., A. S. Bayer, T. Le, Y. L. Chai, B. Prater, A. Schneider, B. Ames, P. Syribeys, J. Robbins, J. M. Patti, J. Vernachio, A. S. Bayer, T. Le, Y.-L. Chai, B. Prater, A. Schneider, B. Ames, P. Syribeys, J. Robbins, and J. M. Patti. 2003. Anti-clumping factor A immunoglobulin reduces the duration of methicillin-resistant *Staphylococcus aureus* bacteremia in an experimental model of infective endocarditis. Antimicrobial Agents & Chemotherapy 47:3400-6). The combination therapy resulted in better bacterial clearance from the blood of rabbits with catheter-induced *S. aureus* endocarditis than did vancomycin treatment alone. In addition, passive transfer of ClfA-specific antibodies significantly reduced infection in a murine model of *S. aureus* mastitis (Tuchscherr, L. P., F. R. Buzzola, L. P. Alvarez, J. C. Lee, and D. O. Sordelli. 2008. Antibodies to capsular polysaccharide and clumping factor A prevent mastitis and the emergence of unencapsulated and small-colony variants of *Staphylococcus aureus* in mice. Infect Immun 76: 5738-44).

A phase III clinical trial was reportedly designed to protect against late-onset sepsis in 2000 low birth weight, premature neonates. The infants received up to four administrations of Veronate, a human immunoglobulin preparation pooled from donors with elevated antibody titers against ClfA and SdrG. Despite the promising results from a similar phase II clinical trial, this prophylactic therapy resulted in no reduction in the frequency of staphylococcal infections in the neonates (DeJonge, M., D. Burchfield, B. Bloom, M. Duenas, W. Walker, M. Polak, E. Jung, D. Millard, R.

Schelonka, F. Eyal, A. Morris, B. Kapik, D. Roberson, K. Kesler, J. Patti, and S. Hetherington. 2007. Clinical trial of safety and efficacy of INH-A21 for the prevention of nosocomial staphylococcal bloodstream infection in premature infants. J Pediatr 151:260-5).

It has been shown that protein glycosylation occurs, but rarely does so naturally, in prokaryotic organisms. On the other hand, N-linked protein glycosylation is an essential and conserved process occurring in the endoplasmic reticulum of eukaryotic organisms. It is important for protein folding, oligomerization, stability, quality control, sorting and transport of secretory and membrane proteins (Helenius, A., and Aebi, M. (2004). Roles of N-linked glycans in the endoplasmic reticulum. Annu. Rev. Biochem. 73, 1019-1049). Protein glycosylation has a profoundly favorable influence on the antigenicity, the stability and the half-life of a protein. In addition, glycosylation can assist the purification of proteins by chromatography, e.g. affinity chromatography with lectin ligands bound to a solid phase interacting with glycosylated moieties of the protein. It is therefore established practice to produce many glycosylated proteins recombinantly in eukaryotic cells to provide biologically and pharmaceutically useful glycosylation patterns.

Conjugate vaccines have been successfully used to protect against bacterial infections. The conjugation of an antigenic polysaccharide to a protein carrier is required for protective memory response, as polysaccharides are T-cell independent antigens. Polysaccharides have been conjugated to protein carriers by different chemical methods, using activation reactive groups in the polysaccharide as well as the protein carrier. (Qian, F., Y. Wu, O. Muratova, H. Zhou, G. Dobrescu, P. Duggan, L. Lynn, G. Song, Y. Zhang, K. Reiter, N. MacDonald, D. L. Narum, C. A. Long, L. H. Miller, A. Saul, and G. E. Mullen. 2007. Conjugating recombinant proteins to *Pseudomonas aeruginosa* ExoProtein A: a strategy for enhancing immunogenicity of malaria vaccine candidates. Vaccine 25:3923-3933; Pawlowski, A., G. Kallenius, and S. B. Svenson. 2000. Preparation of pneumococcal capsular polysaccharide-protein conjugates vaccines utilizing new fragmentation and conjugation technologies. Vaccine 18:1873-1885; Robbins, J. B., J. Kubler-Kielb, E. Vinogradov, C. Mocca, V. Pozsgay, J. Shiloach, and R. Schneerson. 2009. Synthesis, characterization, and immunogenicity in mice of *Shigella sonnei* O-specific oligosaccharide-core-protein conjugates. Proc Natl Acad Sci USA 106:7974-7978).

Conjugate vaccines can be administered to children to protect them against bacterial infections and can provide a long lasting immune response to adults. Constructs of the invention have been found to generate an IgG response in animals. It is believed that the polysaccharide (i.e. sugar residue) triggers a short-term immune response that is sugar-specific. Indeed, the human immune system generates a strong response to specific polysaccharide surface structures of bacteria, such as O-antigens and capsular polysaccharides. However, as the immune response to polysaccharides is IgM dependent, the immune system develops no memory. The protein carrier that carries the polysaccharide, however, triggers an IgG response that is T-cell dependent and that provides long lasting protection since the immune system develops memory. For this reason, in developing a vaccine, it is advantageous to develop it as a protein carrier—polysaccharide conjugate.

Prokaryotic organisms rarely produce glycosylated proteins. However, it has been demonstrated that a bacterium, the food-borne pathogen *Campylobacter jejuni*, can glycosylate its proteins (Szymanski, et al. (1999). Evidence for a system of general protein glycosylation in *Campylobacter jejuni*. Mol. Microbiol. 32, 1022-1030). The machinery required for glycosylation is encoded by 12 genes that are clustered in the pgl locus. Disruption of glycosylation affects invasion and pathogenesis of *C. jejuni* but is not lethal as in most eukaryotic organisms (Burda P. and M. Aebi, (1999). The dolichol pathway of N-linked glycosylation. Biochim Biophys Acta 1426(2):239-57). It has been shown that the pgl locus is responsible for N-linked protein glycosylation in *Campylobacter* and that it is possible to reconstitute the N-glycosylation of *C. jejuni* proteins by recombinantly expressing the pgl locus and acceptor glycoprotein in *E. coli* at the same time (Wacker, M., D. Linton, P. G. Hitchen, M. Nita-Lazar, S. M. Haslam, S. J. North, M. Panico, H. R. Morris, A. Dell, B. W. Wren, and M. Aebi. 2002. N-linked glycosylation in *C. jejuni* and its functional transfer into *E. coli*. Science 298:1790-3).

The N-linked protein glycosylation biosynthetic pathway of *Campylobacter* has significant similarities to the polysaccharide biosynthesis pathway in bacteria (Bugg, T. D., and P. E. Brandish. 1994. From peptidoglycan to glycoproteins: common features of lipid-linked oligosaccharide biosynthesis. FEMS Microbiol Lett 119:255-62). Based on the knowledge that antigenic polysaccharides of bacteria and the oligosaccharides of *Campylobacter* are both synthesized on the carrier lipid, undecaprenyl pyrophosphate (UndPP), the two pathways were combined in *E. coli* (Feldman, M. F., M. Wacker, M. Hernandez, P. G. Hitchen, C. L. Marolda, M. Kowarik, H. R. Morris, A. Dell, M. A. Valvano, and M. Aebi. 2005. Engineering N-linked protein glycosylation with diverse O antigen lipopolysaccharide structures in *Escherichia coli*. Proc Natl Acad Sci USA 102:3016-21). It was demonstrated that PglB does not have a strict specificity for the lipid-linked sugar substrate. The antigenic polysaccharides assembled on UndPP are captured by PglB in the periplasm and transferred to a protein carrier (Feldman, M. F., M. Wacker, M. Hernandez, P. G. Hitchen, C. L. Marolda, M. Kowarik, H. R. Morris, A. Dell, M. A. Valvano, and M. Aebi. 2005. Engineering N-linked protein glycosylation with diverse O antigen lipopolysaccharide structures in *Escherichia coli*. Proc Natl Acad Sci USA 102:3016-21; Wacker, M., M. F. Feldman, N. Callewaert, M. Kowarik, B. R. Clarke, N. L. Pohl, M. Hernandez, E. D. Vines, M. A. Valvano, C. Whitfield, and M. Aebi. 2006. Substrate specificity of bacterial oligosaccharyltransferase (OTase) suggests a common transfer mechanism for the bacterial and eukaryotic systems. Proc Natl Acad Sci USA 103:7088-93). It was shown that *Campylobacter* PglB transfers a diverse array of UndPP linked oligosaccharides if they contain an N-acetylated hexosamine at the reducing terminus (Wacker et al. (2006)), allowing conjugation of an antigenic polysaccharide to a protein of choice through an N-glycosidic linkage. While this may provide a theoretical basis for production of conjugated vaccines in vivo, many difficult challenges need to be overcome in order to realize this theoretical possibility.

Based on this previous discovery that *C. jejuni* contains a general N-linked protein glycosylation system, *E. coli* had been modified to include the N-linked protein glycosylation machinery of *C. jejuni*. In this way, glycosylated forms of proteins native to *C. jejuni* in an *E. coli* host were produced. It had been further shown that this process could be used to produce glycosylated proteins from different origins in modified *E. coli* host for use as vaccine products. Production by *E. coli* is advantageous because large cultures of such modified *E. coli* hosts can be produced which produce large quantities of useful vaccine.

Using this process to produce a glycosylated protein in a modified *E. coli* host for use as a vaccine product for *S. aureus* encounters problems that have been perceived to be insurmountable. First, *E. coli* is a Gram-negative bacterium and its saccharide biosynthesis pathways differ greatly from those of a Gram-positive bacterium, such as *S. aureus*, after the polymerization step. In addition, it would have been infeasible to genetically engineer *E. coli* to produce the *S. aureus* capsular polysaccharide directly consistent with previous technologies. For example, *S. aureus* is a Gram positive organism and its capsule synthesis is associated with cell envelope structure and construction of the cellular hull. The capsule producing biosynthetic machinery is specifically designed to arrange the capsular polysaccharide (PS) on the outside of the cell and its cell wall. It would have been extremely difficult, for at least the reason that it would be highly resource-intensive, to produce this capsule in a modified *E. coli* organism, because the cell envelope of *E. coli* is constructed in a fundamentally different way. The biosynthetic machinery for capsule assembly from PS precursor would be non-functional due to the different environment. Whereas the *S. aureus* capsule must transit a single membrane, in *E. coli* there is an additional membrane which needs to be crossed to reach the final location of an authentic capsule. Furthermore, as the *S. aureus* capsule is very large, it was believed to be infeasible to make a large capsule like the *S. aureus* capsule between the two membranes of *E. coli*.

The principle that enzymes from different organisms can work together has been shown before (e.g. Rubires, X., F. Saigi, N. Pique, N. Climent, S. Merino, S. Alberti, J. M. Tomas and M. Regue. 1997. A gene (wbbL) from *Serratia marcescens* N28b (O4) complements the rfb-50 mutation of *Escherichia coli* K-12 derivatives. J. Bacteriol 179(23): 7581-6). However, it is believed that no modified LPS polysaccharide from a Gram-positive organism has previously been produced in a Gram-negative organism.

BRIEF SUMMARY OF THE INVENTION

We have now surprisingly discovered a novel *S. aureus* bioconjugate vaccine. This novel *S. aureus* vaccine is based on the novel and unexpected discovery that an oligo- or polysaccharide of a prokaryote having one Gram strain can glycosylate a protein in a host prokaroyte having a different Gram strain. Further novel and unexpected features of the invention include without limitation the embodiments set forth below.

More generally, the present invention is directed to a bioconjugate vaccine, such as a Gram-positive vaccine, comprising a protein carrier comprising an inserted nucleic acid consensus sequence; at least one oligo- or polysaccharide from a bacterium such as a Gram-positive bacterium linked to the consensus sequence, and, optionally, an adjuvant. Further, the invention is directed to a Gram-positive bacteria vaccine, such as an *S. aureus* vaccine, or other bacteria vaccine, made by a glycosylation system using a modified LPS biosynthetic pathway, which comprises the production of a modified capsular polysaccharide or LPS.

The instant invention is additionally directed to a recombinant N-glycosylated protein comprising a protein comprising at least one inserted consensus sequence D/E-X-N-Z-S/T, wherein X and Z may be any natural amino acid except proline; and at least one oligo- or polysaccharide from a bacterium such as a Gram-positive bacterium linked to said consensus sequence.

The present is furthermore directed to a combination of a modified capsular polysaccharide of *S. aureus* with a protein antigen from the same organism by N-glycosidic linkage.

The invention is further directed to host prokaryotic organisms comprising a nucleotide sequence encoding one or more glycosyltransferase of a first prokaryotic species, such as a Gram-positive species; one or more glycosyltransferases of a different prokaryotic species, such as a Gram-negative species; a nucleotide sequence encoding a protein; and a nucleotide sequence encoding an OTase. The invention is additionally directed to an engineered host prokaryotic organism comprising an introduced nucleotide sequence encoding glycosyltransferases native only to a Gram-positive prokaryotic organism; a nucleotide sequence encoding a protein; and a nucleotide sequence encoding an OTase.

The invention is furthermore directed to methods of producing a bioconjugate vaccine in a host prokaryotic organism comprising nucleic acids encoding one or more glycosyltransferases of a first prokaryotic species, such as a Gram-positive species, for example, *S. aureus*; one or more glycosyltransferases of a second prokaryotic species, a protein; and an OTase. In addition, the present invention is directed to the production of bioconjugate vaccines by producing in Gram-negative bacteria modified capsular polysaccharides, which can be transferred to lipid A core by WaaL and/or linked to a carrier of choice by the OTase.

The invention is further directed to methods of producing glycosylated proteins in a host prokaryotic organism comprising nucleotide sequence encoding glycosyltransferases native to a first prokaryotic organism and also encoding glycosyltransferases native to a second prokaryotic organism that is different from the first prokaryotic organism. The present invention is additionally directed to the production of proteins N-glycosylated with capsular polysaccharides of Gram-positive bacteria, which are synthesized by a combination of different glycosyltransferases from different organisms. The invention is furthermore directed to the production of glycosylated proteins in a host prokaryotic organism comprising an introduced nucleotide sequence encoding glycosyltransferases native only to a Gram-positive prokaryotic organism.

The instant invention is moreover directed to plasmids, such as, plasmids comprising one or more of SEQ. ID NO: 2, SEQ ID NO: 3 and SEQ ID NO: 4. The invention also includes plasmids comprising one or more of SEQ. ID NO: 6; SEQ. ID NO: 7; SEQ. ID NO: 8 and SEQ. ID NO: 16. The invention also relates to plasmids comprising one or more of SEQ. ID NO: 10; SEQ. ID NO: 11; and SEQ. ID NO: 12. Moreover, the invention is directed to plasmids comprising one or more of SEQ. ID NO: 13; SEQ. ID NO: 15; SEQ. ID NO: 15; SEQ. ID NO: 17; SEQ ID NO: 18; SEQ. ID NO: 19; SEQ. ID NO: 20; SEQ. ID NO: 21 and SEQ. ID NO: 27.

The invention is additionally directed to transformed bacterial cells, such as, for example, bacterial cells transformed with a plasmid comprising one or more of SEQ. ID NO. 2; SEQ. ID NO: 3; SEQ. ID NO: 4; SEQ. ID NO: 17; SEQ. ID NO: 18; SEQ. ID NO: 19 and SEQ. ID NO: 20; SEQ. ID NO: 21; and SEQ. ID NO: 27. The instant invention is further directed to a bacterial cell transformed with a plasmid comprising one or more of SEQ. ID NO: 5; SEQ. ID NO: 8; SEQ. ID NO: 9; SEQ. ID NO: 10; SEQ. ID NO: 11; SEQ. ID NO: 12; SEQ. ID NO: 13; SEQ. ID NO: 14; SEQ. ID NO: 15 and SEQ. ID NO: 16.

The instant invention is further directed to a method of inducing an immune response against an infection caused by Gram-positive and other bacteria in a mammal. In one embodiment, the method comprises administering to said mammal an effective amount of a pharmaceutical composition comprising: protein comprising at least one inserted consensus sequence D/E-X-N-Z-S/T, wherein X and Z may be any natural amino acid except proline; and one or more oligo- or polysaccharides, the one or more oligo- or polysaccharides being the same or different as another of the one or more oligo- or polysaccharides, from a Gram-positive bacterium linked to said consensus sequence.

In another aspect, the invention features a method of identifying a target polysaccharide for use in glycosylating a protein with said target polysaccharide, in whole or in part. Said glycosylated protein comprising the target polysaccharide can be used, for example, in vaccine compositions. In one embodiment, the method of identifying a target polysaccharide includes: identifying a Gram-positive bacterium, such as *S. aureus*, as a target; identifying a first repeating unit of a polysaccharide produced by said Gram-positive bacterium comprising at least three monomers; identifying a polysaccharide produced by a bacterium of a Gram-negative species comprising a second repeating unit comprising two of the same monomers as said first repeating unit.

The present invention is also directed to a method for modifying a bacterium of a first bacterial species such as a Gram-negative species. In one embodiment, the method includes: identifying a first repeating unit of a polysaccharide of a Gram-positive species, such as *S. aureus*, comprising three monomers; identifying a polysaccharide produced by a bacterium of a second Gram-negative species comprising another repeating unit comprising two of the same monomers of the first repeating unit; inserting into said bacterium of a first Gram-negative species one or more nucleotide sequences encoding glycosyltransferases that assemble a trisaccharide comprising: a) said second repeating unit; and b) a monomer of said first repeating unit not present in said second repeating unit; inserting a nucleotide sequence encoding a protein; and inserting a nucleotide sequence encoding an OTase.

BRIEF DESCRIPTION OF THE DRAWINGS

FIG. 11G and FIG. 11G-1 present the results of HPLC analysis of the full CP5 glycan repertoire present on UndPP in *E. coli* cells in an embodiment of the present invention.

FIG. 17A depicts the results of passive immunization using anti CP5-EPA antibodies, according to an embodiment of the present invention, in mice challenged i.p. with ~$3.6.10^7$ CFU of *S. aureus* strain Reynolds.

FIG. 17B depicts the results of passive immunization using anti CP5-EPA antibodies, according to an embodiment of invention, in mice injected with 2 mg CP5-EPA IgG.

FIG. 17C depicts the results of passive immunization using anti CP5-EPA antibodies, according to an embodiment of the invention, in mice injected with 300 μg CP5-EPA IgG

DETAILED DESCRIPTION OF THE INVENTION

Figure 1:
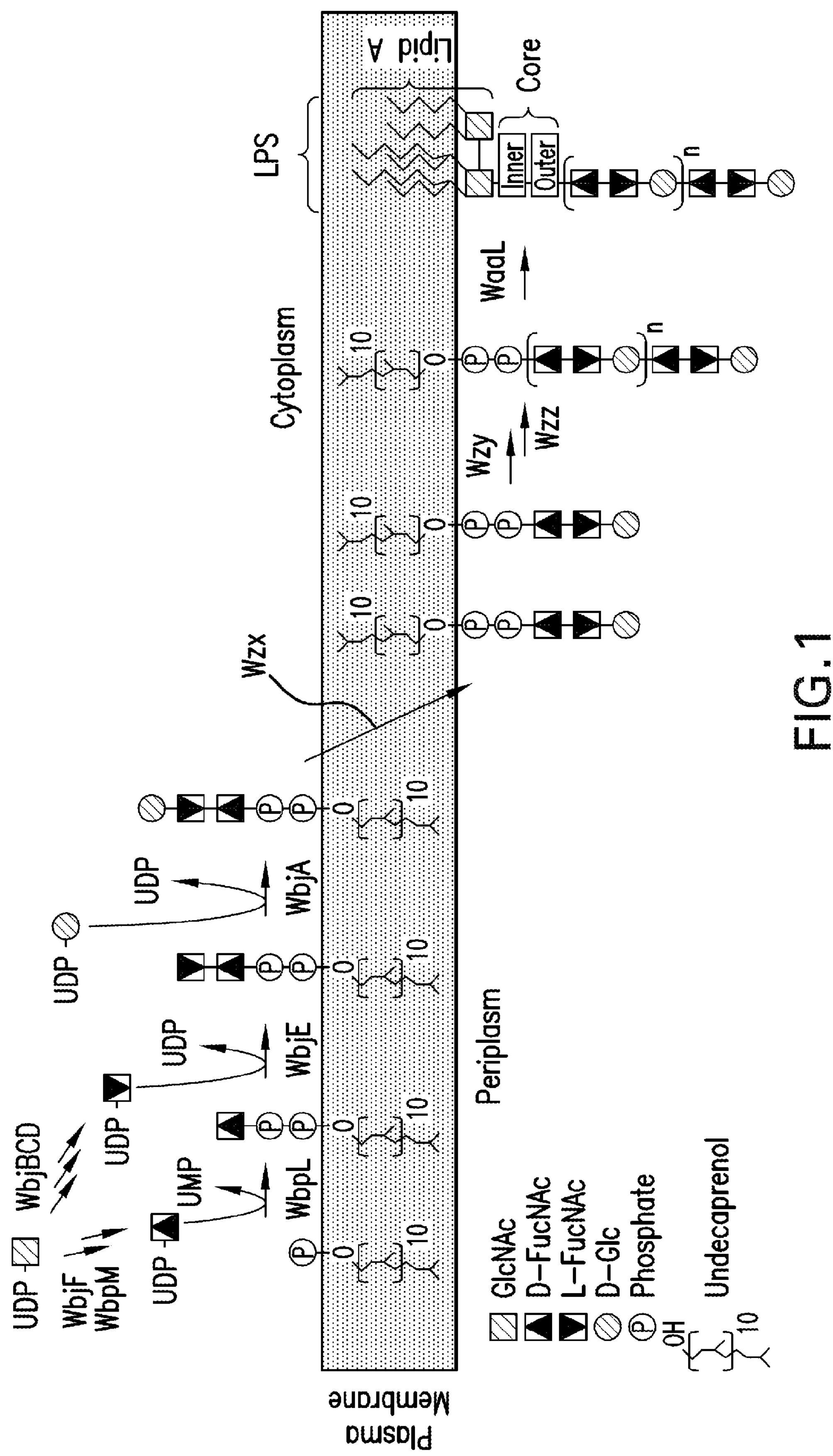
FIG. 1 depicts a pathway for the wzx/wzy-dependent O-antigen biosynthesis, exemplified by the *P. aeruginosa* O11 O-antigen biosynthesis. Protein names putatively responsible for the presented reactions are indicated above or below the arrows, including uridine diphosphate (UDP) and uridine monophosphate (UMP).

According to an embodiment of the present invention, an LPS polysaccharide from a Gram-positive organism has now been shown to be produced in a Gram-negative organism. We believe that this is a novel result that represents an important and significant departure from the prior art.

Nucleic acids within the scope of the invention are exemplified by the nucleic acids of the invention contained in the Sequence Listing. Any nucleic acid encoding an immunogenic component, or portion thereof, which is capable of expression in a host cell, can be used in the present invention. The following sequence descriptions are provided to facilitate understanding of certain terms used throughout the application and are not to be construed as limiting embodiments of the invention.

SEQ ID NO: 1 depicts pLAFR1 (Gene Bank Accession AY532632.1) containing the O11 O-antigen sequence from *P. aeruginosa* PAO103 in the EcoRI site, complementary strand (partially from Gen Bank Accession AF236052).

SEQ ID NO: 2 depicts pLAFR1 containing the CP5 chimeric cluster, corresponding to the pLAFR1-O11 with the cap5HIJ genes replacing wbjA-wzy by homologous recombination. The inserted sequence also contains a cat cassette for selection of homologous recombined clones.

SEQ ID NO: 3 depicts pLAFR1 containing the CP5 chimeric cluster with the cap5K flippase gene, corresponding to the pLAFR1-O11 with the cap5HIJ genes replacing wbjA-wzy by homologous recombination and the cap5K cloned between cap5J and the cat cassette.

SEQ ID NO: 4 depicts pLAFR1 containing the CP8 chimeric cluster including a flippase gene, corresponding to the pLAFR1-O11 with the cap8 KHIJ genes replacing wbjA-wzy. The inserted sequence also contains a cat cassette for selection of homologous recombined clones.

SEQ ID NO: 5 depicts an expression plasmid for Hla H35L production. The ORF encoding Hla H35L is cloned into NdeI/SacI in pEC415.

SEQ ID NO. 6 depicts the expression plasmid for Hla-H35L site 202 production. The ORF encodes an N-terminal DsbA signal peptide from *E. coli*, a glycosite around amino acid position 202, and a C-terminal HIS-tag. This construct is cloned into NheI/SalI on pEC415.

SEQ ID NO: 7 depicts the expression plasmid for Hla-H35L site 238 production. The ORF encodes an N-terminal DsbA signal peptide from *E. coli*, a glycosite around amino acid position 238, and a C-terminal HIS-tag. The above mentioned construct is cloned into NheI/SalI on pEC415.

SEQ ID NO: 8 depicts the expression plasmid for Hla-H35L site 272 production. The ORF encodes an N-terminal DsbA signal peptide from *E. coli*, a glycosite around amino acid position 272, and a C-terminal HIS-tag. The above mentioned construct is cloned into NheI/SalI on pEC415.

SEQ ID NO: 9 depicts an expression plasmid for ClfA production. The gene was chemically synthesized and cloned into the NdeI/SacI in pEC415 expression vector.

SEQ ID NO: 10 depicts the expression plasmid for ClfA site 290 production. The ORF encodes an N-terminal DsbA signal peptide from *E. coli*, a glycosite around amino acid position 290, and a C-terminal HIS-tag. The above mentioned construct is cloned into NheI/SalI on pEC415.

SEQ ID NO: 11 depicts the expression plasmid for ClfA site 327 production. The ORF encodes an N-terminal DsbA signal peptide from *E. coli*, a glycosite around amino acid position 327, and a C-terminal HIS-tag. The above mentioned construct is cloned into NheI/SalI on pEC415.

SEQ ID NO: 12 depicts the expression plasmid for ClfA site 532 production The ORF encodes an N-terminal DsbA signal peptide from *E. coli*, a glycosite around amino acid position 532, and a C-terminal HIS-tag. The above mentioned construct is cloned into NheI/SalI on pEC415.

SEQ ID NO: 13 depicts the amino acid sequence of recombinant, genetically detoxified EPA with a signal sequence and two glycosylation sites at positions 260 and 402.

SEQ ID NO: 14 depicts the amino acid sequence of recombinant, genetically detoxified EPA without signal sequence and two glycosylation sites at positions 241 and 383.

SEQ ID NO: 15 depicts the ORF encoding AcrA cloned via NheI/SalI into pEC415.

SEQ ID NO: 16 depicts the expression plasmid for Hla-H35L site 130 production. The ORF encodes an N-terminal DsbA signal peptide from *E. coli*, a glycosite around amino acid position 130, and a C-terminal HIS-tag. The above mentioned construct is cloned NheI/SalI into pEC415.

SEQ ID NO: 17 depicts CP5 producing gene cluster with cap5K flippase followed by a pglB expression cassette consisting of the intergene DNA sequence between galF and wbqA of *E. coli* serotype O121 and the pglB ORF. The insert is cloned in the EcoRI site of pLAFR1.

SEQ ID NO: 18 depicts CP8 producing gene cluster with cap8K flippase followed by a pglB expression cassette consisting of the intergene DNA sequence between galF and wbqA of *E. coli* serotype O121 and the pglB ORF. The insert is cloned in the EcoRI site of pLAFR1.

SEQ ID NO: 19 depicts CP8 producing gene cluster with cap8K flippase followed by a pglB expression cassette consisting of the intergene DNA sequence between galF and wbqA of *E. coli* serotype O121 and the pglB ORF, in addition this sequence has the gene for wzz of the *E. coli* serovar O7 cloned into SfaAI/BspTI, i.e. between wzx of *Pseudomonas aeruginosa O*11 and cap8H. The insert is cloned in the EcoRI site of pLAFR1.

SEQ ID NO: 20 depicts an expression plasmid for EPA and wzz. The backbone is pACT3 in which the resistance cassette was replaced (kanamycin for chloranphenicol)

SEQ ID NO: 21 depicts wzz of *E. coli* serotype O7 cloned in pext21 Eco/Sal.

SEQ ID NO: 22 depicts a peptide sequence set forth in the Examples.

SEQ ID NO: 23 depicts a peptide sequence set forth in the Examples.

SEQ ID NO: 24 depicts a protein consensus sequence, D/E-X-N-Z-S/T, wherein X and Z may be any natural amino acid except proline.

SEQ ID NO: 25 depicts a glycosylation site.

SEQ ID NO: 26 depicts a glycosylation site.

SEQ ID NO: 27 depicts an expression plasmid containing the pglB ORF cloned in EcoRI/BamHI sites.

Descriptions of terms and abbreviations appear below as used in the specification and consistent with the usages known to one of ordinary skill in the art. The descriptions are provided to facilitate understanding of such terms and abbreviations and are not to be construed as limiting embodiments of the invention.

AcrA refers to a glycoprotein from *C. jejuni*.

Active immunization refers to the induction of immunity (antibodies) after exposure to an antigen.

APCs refers to antigen presenting cells.

Amp refers to ampicillin.

Bacteremia refers to the presence of viable bacteria in the circulating blood.

C' refers to complement.

CapA is an enzyme proposed to be a chain length determinant in *S. aureus CP*5.

CapB is an enzyme proposed to be a regulator of polysaccharide chain length in *S. aureus* CP5.

CapC is an enzyme proposed to encode a transporter protein in *S. aureus CP*5.

CapD an enzyme having 4,6 dehydratase activity and converts the precursor UDPGlcNAc to UDP-2-acetamido-2,6 dideoxy-D-xylo-4-hexylose in *S. aureus* CP5.

CapE is a 4,6-dehydratase 3,5-epimerase catalyzing the epimerization of UDP-D-GlcNAc to UDP-2-acetamido-2,6-dideoxy-D-lyxo-4-hexylose in *S. aureus* CP5.

CapF is a reductase, catalyzes the reduction form UDP-2-acetamido-2,6-dideoxy-D-lyxo-4-hexylose to UDP-L-6dTalNAc in *S. aureus* CP5.

CapG is a 2-Epimerase, catalyzes the epimerization form UDP-L-6dTalNAc to UDP-LFucNAc in *S. aureus* CP5.

CapH in *S. aureus* CP5 is an O-acetyltransferase.

CapH in CP8 is a transferase similar to CapI from *S. aureus* CP5.

CapI in *S. aureus* CP5 is a glycosyltransferase which catalyzes the transfer of UDP-ManNAcA into carrier lipid-D-FucNAc-L-FucNAc producing carrier lipid-D-FucNAc-L-FucNAc-ManNAcA.

CapI in CP8 is a polymerase which is similar to CapJ in *S. aureus* CP5.

CapJ in *S. aureus* CP5 is a polymerase.

CapJ in CP8 is an O-acetyltransferase similar to CapH in *S. aureus* CP5.

CapK in *S. aureus* CP5 is a flippase.

CapK in *S. aureus* CP8 is a flippase similar to the CapK in CP5.

CapL is a transferase which catalyzes the transfer of UDP-L-FucNAc onto D-FucNAc-carrier lipid producing carrier lipid-D-FucNAc-L-FucNAc in *S. aureus* CP5.

CapM is a transferase which catalyzes the transfer of UDP-D-FucNAc on to carrier lipid producing carrier lipid-D-FucNAc in *S. aureus* CP5.

CapN is a 4-reductase which catalyzes the reduction from UDP-2-acetamido-2,6-dideoxy-D-xylo-4-hexylose to UDP-D-FucNAc in *S. aureus* CP5.

CapO is a dehydrogenase which catalyzes the conversion of UDP-D-ManNAc into UDP-ManNAcA in *S. aureus* CP5.

CapP is a 2-epimerase which catalyzes the epimerization of UDP-D-GlcNAc to UDP-D-ManNAc in *S. aureus* CP5.

CFU refers to Colony formation unit.

ClfA refers to *S. aureus* clumping factor A, a cell wall-anchored protein.

Conjugate vaccine refers to a vaccine created by covalently attaching a polysaccharide antigen to a carrier protein. Conjugate vaccine elicits antibacterial immune responses and immunological memory. In infants and elderly people a protective immune response against polysaccharide antigens can be induced if these antigens are conjugated with proteins that induce a T-cell dependent response.

Consensus sequence refers to a sequence of amino acids, -D/E-X-N-Z-S/T- wherein X and Z may be any natural amino acid except Proline, within which the site of carbohydrate attachment to N-linked glycoproteins is found.

Capsular polysaccharide, in its naturally occurring form, refers to a thick, mucous-like layer of polysaccharide, is water soluble and commonly acidic. Naturally-occurring capsular polysaccharides consist of regularly repeating units of one to several monosaccharides/monomers.

CP5 refers to *Staphylococcus aureus* type 5 capsular polysaccharide or serotype 5 capsular polysaccharide.

CP8 refers to *Staphylococcus aureus* type 8 capsular polysaccharide or serotype 8 capsular polysaccharide.

D-FucNAc refers to N-acetyl D-fucosamine.

ECA refers to enterobacterial common antigen.

ELISA refers to Enzyme-linked immunosorbent assay, a biochemical technique used mainly in immunology to detect the presence of an antibody or an antigen in a sample.

EPA or EPAr refers to nontoxic recombinant *P. aeruginosa* exoprotein A.

Glycoconjugate vaccine refers to a vaccine comprising a protein carrier linked to an antigenic or immunogenic oligosaccharide.

Glycosyltransferase refers to enzymes that act as a catalyst for the transfer of a monosaccharide unit from an activated nucleotide sugar to a glycosyl acceptor molecule.

Gram-positive strain refers to a bacterial strain that stains purple with Gram staining (a valuable diagnostic tool). Gram-positive bacteria have a thick mesh-like cell wall made of peptidoglycan (approximately 50-90% of cell wall).

Gram-negative strain refers to a bacterial strain which has a thinner layer (approximately 10% of cell wall) which stains pink. Gram-negative bacteria also have an additional outer membrane that contains lipids, and is separated from the cell wall by the periplasmic space.

Hla (alpha toxin) refers to alpha hemolysin, which is a secreted pore-forming toxin and an essential virulence factor antigen of *S. aureus.*

Hla H35L refers to a mutant form of Hla nontoxic alpha-toxin mutant from *S. aureus*.

Histidine tag, or polyhistidine-tag, is an amino acid motif in proteins that consists of at least five histidine (His) residues, often at the N- or C-terminus of the protein, and used to purify in a simple and fast manner by specifically binding to a nickel affinity column.

IV refers to intravenously.

kDa refers to kilo Daltons, is an atomic mass unit.

L-FucNAc refers to N-acetyl L-fucosamine.

LPS refers to lipopolysaccharide. Lipopolysaccharides (LPS), also known as lipoglycans, are large molecules consisting of a lipid and a polysaccharide joined by a covalent bond; they are found in the outer membrane of Gram-negative bacteria, act as endotoxins and elicit strong immune responses in animals.

ManNAcA refers to N-acetyl mannosaminuronic acid.

Methicillin-resistant *S. aureus* strains (MRSA) refers to methicillin-resistant *S. aureus* strain associated with longer hospital stay and more infections in intensive care units which leads to more antibiotic administration.

N-glycans or N-linked oligosaccharides refers to mono-, oligo- or polysaccharides of variable compositions that are linked to an $\epsilon$-amide nitrogen of an asparagine residue in a protein via an N-glycosidic linkage.

N-linked protein glycosylation refers to a process or pathway to covalently link “glycans” (mono-, oligo- or polysaccharides) to a nitrogen of asparagine (N) side-chain on a target protein.

O-antigens or O-polysaccharides refers to a repetitive glycan polymer contained within an LPS. The O antigen is attached to the core oligosaccharide, and comprises the outermost domain of the LPS molecule.

Oligosaccharides or Polysaccharides refers to homo- or heteropolymer formed by covalently bound carbohydrates (monosaccharides), and includes but is not limited to repeating units (monosaccharides, disaccharides, trisaccharides, etc.) linked together by glycosidic bonds.

Opsonophagocytic activity refers to phagocytosis of a pathogen in the presence of complement and specific antibodies. The in vitro opsonophagocytic activities (OPAs) of serum antibodies are believed to represent the functional activities of the antibodies in vivo and thus to correlate with protective immunity.

OTase or OST refers to oligosaccharyl transferase, which catalyzes a mechanistically unique and selective transfer of an oligo- or polysaccharide (glycosylation) to the asparagine (N) residue at the consensus sequence of nascent or folded proteins.

Passive immunization is the transfer of active humoral immunity in the form of already made antibodies, from one individual to another.

Periplasmic space refers to the space between the inner cytoplasmic membrane and external outer membrane of Gram-negative bacteria.

PMNs refers to polymorphonuclear neutrophils, which are the most abundant white blood cells in the peripheral blood of humans, and many (though not all) mammals.

Protein carrier refers to a protein that comprises the consensus sequence into which the oligo- or polysaccharide is attached.

RU refers to a repeating unit comprising specific polysaccharides synthesized by assembling individual monosaccharides into an oligo- or polysaccharide.

Signal sequence refers to a short (e.g., approximately 3-60 amino acids long) peptide at the N-terminal end of the protein that directs the protein to different locations.

UDP-D-ManNAc is UDP-N-acetyl-D-mannosamine.

UDP-D-ManNAcA is UDP-N-acetyl-D-mannosaminuronic acid.

UDP-D-QuiNAc is UDP-N-acetyl-D-quinovosamine.

UDP-L-FucNAc is UDP-N-acetyl-L-fucosamine.

UDP-L-6dTalNAc is UDPN-acetyl-L-pneumosamine.

Und refers to undecaprenyl or undecaprenol lipid composed by eleven prenol units.

UndP refers to undecaprenyl phosphate, which is a universal lipid carrier (derived from Und) of glycan biosynthetic intermediates for carbohydrate polymers that are exported to the bacterial cell envelope.

UndPP refers to undecaprenyl pyrophosphate, which is a phosphorylated version of UndP.

wbjA is a glucosyltransferase in *P. aeruginosa O*11.

wbjB is a putative epimerase similar to enzymes required to the capsule biosynthesis of CP5 and CP8 in *S. aureus.* wbjC is a putative epimerase in *P. aeruginosa O*11.

wbjD is a putative epimerase in *P. aeruginosa O*11.

wbjE is a putative epimerase in *P. aeruginosa O*11.

wbjF is a glycosyltransferase in *P. aeruginosa O*11.

wbpL is a glycosyltransferase that participates in LPS biosynthesis in *P. aeruginosa O*11.

wbpM is a glycosyltransferase that participates in LPS biosynthesis in *P. aeruginosa O*11.

Embodiments of the invention are at least partially based on the discovery that *C. jejuni* contains a general N-linked protein glycosylation system, an unusual feature for prokaryotic organisms. Various proteins of *C. jejuni* have been shown to be modified by a heptasaccharide. This heptasaccharide is assembled on UndPP, the carrier lipid, at the cytoplasmic side of the inner membrane by the stepwise addition of nucleotide activated monosaccharides catalyzed by specific glycosyltransferases. The lipid-linked oligosaccharide is then flipped into (i.e., it diffuses transversely) the periplasmic space by a flippase, e.g., PglK. In the final step of N-linked protein glycosylation, the OTase (e.g., PglB) catalyzes the transfer of the oligosaccharide from the carrier lipid to Asn residues within the consensus sequence Asp/Glu-Xaa-Asn-Zaa-Ser/Thr (i.e., D/E-X-N-Z-S/T), where the Xaa and Zaa can be any amino acid except Pro. We had successfully transferred the glycosylation cluster for the heptasaccharide into *E. coli* and were able to produce N-linked glycoproteins of *Campylobacter.*

A novel and inventive method to modify a Gram-negative host bacterium, such as *E. coli*, has been developed to produce glycosylated proteins for use as vaccine products against a Gram-positive bacterium such as *S. aureus*. The development of this method required overcoming significant and in many respects unexpected problems, and departing substantially from conventional wisdom and the prior art.

In this novel and inventive method, another Gram-negative bacterium was identified that produces a polysaccharide that has structural similarity to the polysaccharide of interest of the target organism, for example *S. aureus*. For purposes of this invention, structural similarity manifests itself as repeating units in the polysaccharide of the target (e.g., *S. aureus*) that are partially identical to repeating units in the polysaccharide of the identified, other Gram-negative bacterium. Because this latter bacterium is Gram-negative, as is the host, for example, *E. coli* organism, we initially hypothesized (and later verified by experiment as discussed below) that use of its biosynthesis pathways in a modified *E. coli* organism would allow the biosynthesis of the constructed RU antigen and its flipping from the cytoplasm into the periplasm of the modified *E. coli* organism. Further, we hypothesized (and later verified by experiment as discussed below) that the size of the polysaccharide produced through this biosynthesis pathway would be much smaller than the polysaccharide produced by the biosynthesis pathway of Gram positive *S. aureus.*

As a result, and as discussed below, the novel and innovative method we developed solved the aforementioned difficult problems.

Furthermore, it was surprisingly found that aspects of the LPS pathway in a Gram-negative organism could be used to produce polysaccharides that contain some of the same repeating units as capsular polysaccharides native to Gram-positive bacteria, such as, for example, *S. aureus*, as detailed below.

Therefore, in making the polysaccharide section of the glycosylated protein vaccine for *S. aureus*, one surprising solution is to construct the polysaccharide section at least partially based on a polysaccharide native to a Gram-negative bacterium like *E. coli*. We further discovered that, in doing so, it is apparently important to find a bacterium which produces a polysaccharide that is as similar as possible to the polysaccharide of interest produced by *S. aureus. P. aeruginosa* is such a bacterium.

FIG. 1 provides a step-by-step depiction of an embodiment of the preparation of nucleotide-activated monosaccharides in the cytoplasm either by enzymes provided in the O-antigen cluster or by house keeping enzymes of the Gram-negative host cell, as would be apparent to one of skill in the art in light of this specification. The steps of the process proceed from left to right in the depiction of FIG. 1. In the embodiment depicted in FIG. 1, a glycosylphosphate transferase (WbpL) adds D-FucNAc phosphate to UndP, forming UndPP-FucNAc. Specific glycosyltransferases then elongate the UndPP-D-FucNAc molecule further by adding monosaccharides forming the repeating unit (RU) oligosaccharide (WbjE, WbjA). The RU is then flipped into the periplasmic space by the Wzx protein. The Wzy enzyme polymerizes periplasmic RUs to form the O-antigen polysaccharide. Polymer length is controlled by the Wzz protein. Many bacterial oligo- and polysaccharides are assembled on UndPP and then transferred to other molecules. In other words, UndPP is a general building platform for sugars in bacteria. In *E. coli* and, it is believed, most other Gram negative bacteria, the O-antigen is transferred from UndPP to Lipid A core by the *E. coli* enzyme WaaL to form lipopolysaccharide (LPS).

Figure 2:
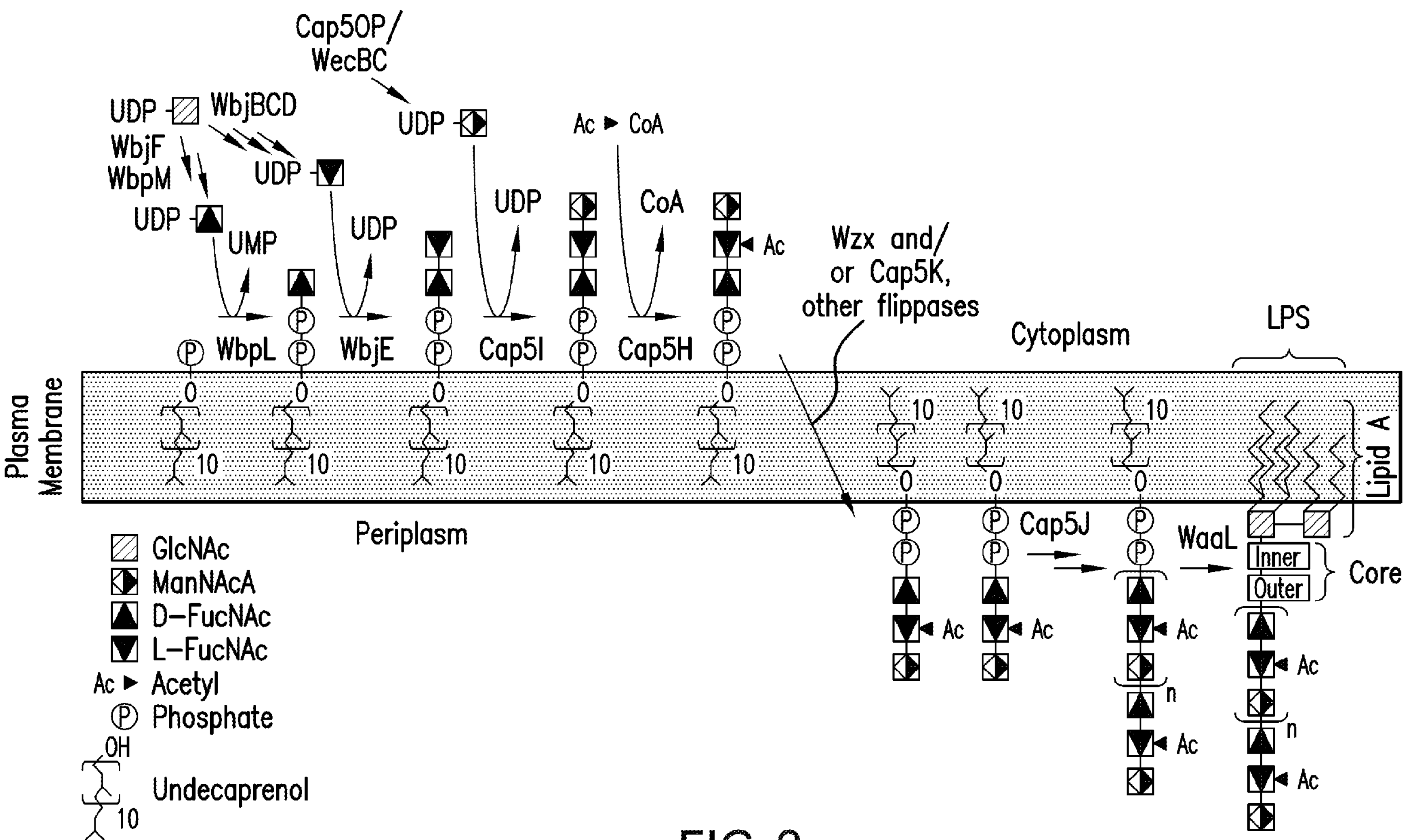
FIG. 2 depicts a proposed pathway for the engineered *S. aureus* capsular polysaccharide serotype 5 (CP5) biosynthesis in *E. coli*. The enzymes provided by the O-antigen cluster of *P. aeruginosa* O11 are indicated as in FIG. 1. Enzymes from *S. aureus* CP5 are indicated as Cap5 (compare to FIG. 6). WecB and WecC are *E. coli* enzymes required for the production of UDP-ManNAcA. Other depicted proteins and enzymes include uridine diphosphate (UDP), uridine monophosphate (UMP), and coenzyme A (CoA).

FIG. 2 depicts an embodiment of preparation of nucleotide-activated monosaccharides in the cytoplasm by enzymes provided in the O-antigen cluster of *P. aeruginosa* O11, by house keeping enzymes of the Gram-negative host cell, and by *S. aureus* and/or *E. coli* enzymes known to be required for UDP-ManNAcA biosynthesis (Cap5OP and/or WecBC), as would be apparent to one of skill in the art in light of this specification. In the depiction of FIG. 2, the steps of the process proceed from left to right. As in O11 biosynthesis, WbpL and WbjE synthesize the core disaccharide. Then, the *S. aureus* glycosyltransferase Cap5I adds D-ManNAcA. Cap5H adds an acetyl group to the second FucNAc residue. Acetylation may be the final step of RU synthesis as shown in FIG. 2. Flipping is possible by one or all of the Wzx proteins in the system, which are recombinantly expressed Wzx of *P. aeruginosa* or Cap5K, or endogenously expressed Wzx-like enzymes e.g. of the ECA cluster encoded in the *E. coli* chromosome. Polymerization is an exclusive activity of the Cap5J polymerase forming the CP5 polysaccharide on UndPP. As other UndPP linked polysaccharides, the CP5 sugar is transferred to Lipid A core by the *E. coli* enzyme WaaL to form recombinant LPS (LPS capsule).

Figure 3:
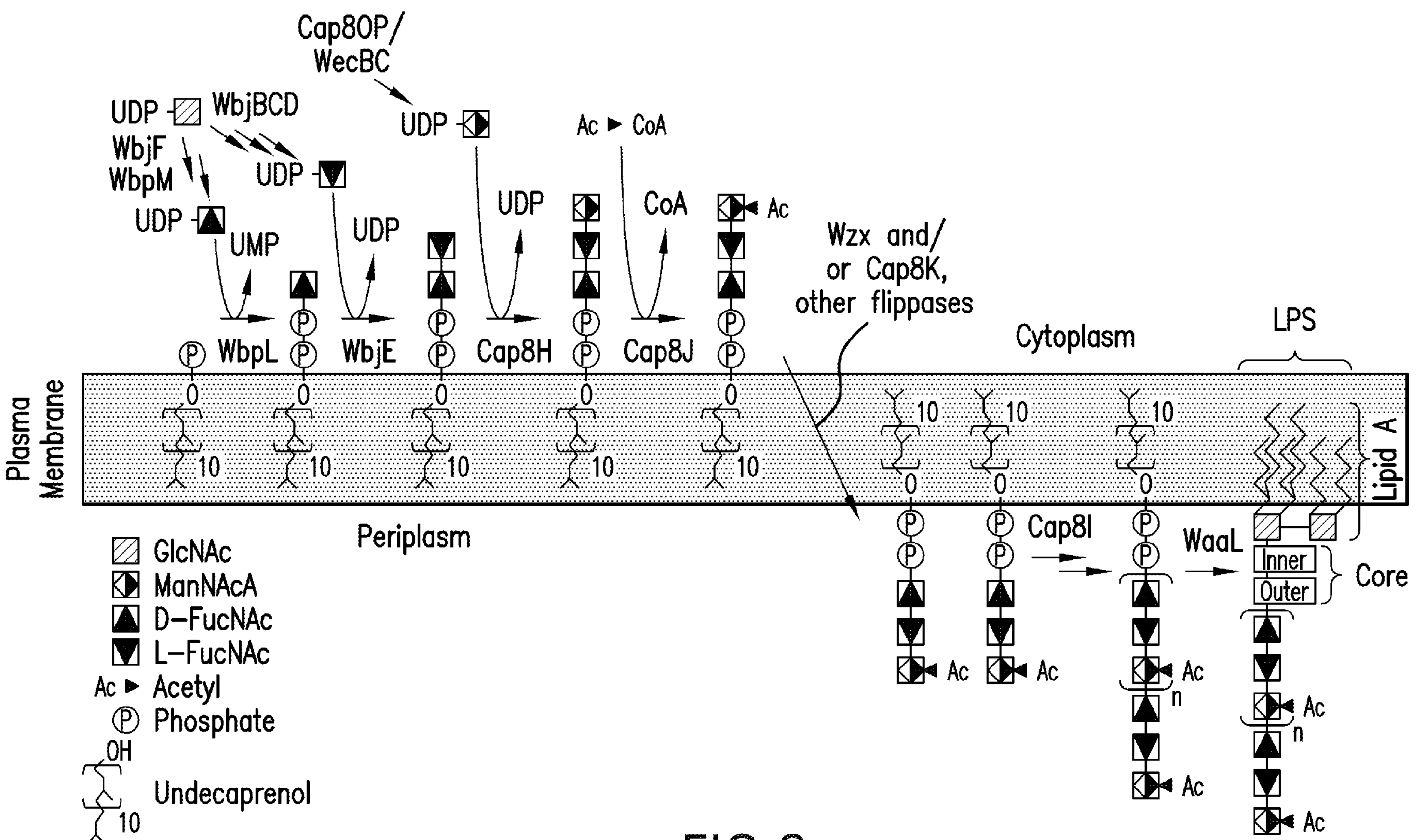
FIG. 3 depicts a proposed pathway for the engineered *S. aureus* capsular polysaccharide serotype 8 (CP8) biosynthesis. Gene names are indicated by arrows (compare to FIGS. 1, 2, and 6). UDP, UMP: uridine diphosphate, uridine monophosphate. CoA: coenzyme A.

FIG. 3 depicts the preparation of nucleotide-activated monosaccharides in the cytoplasm by enzymes provided in the O-antigen cluster of *P. aeruginosa O*11, by house keeping enzymes of the Gram-negative host cell, and by *S. aureus* and/or *E. coli* enzymes known to be required for UDP-ManNAcA biosynthesis (Cap8OP and/or WecBC), as would be apparent to one of ordinary skill in the art in light of this specification. In the depiction of FIG. 3, the steps of the process proceed from left to right. As in O11 biosynthesis, WbpL and WbjE synthesize the core disaccharide. Then, the *S. aureus* glycosyltransferase Cap8H adds D-ManNAcA. Cap8J adds an acetyl group to the second FucNAc residue. It is not known if acetylation occurs on the activated sugar or the lipid bound RU. Flipping is possible by one or all of the Wzx proteins in the system, which are recombinantly expressed Wzx of *P. aeruginosa* or Cap8K, or endogenously expressed Wzx-like enzymes e.g. of the ECA cluster encoded in the *E. coli* chromosome. Polymerization is an exclusive activity of the Cap8I polymerase forming CP8 polysaccharide on UndPP. The CP8 sugar is then transferred to Lipid A core in *E. coli* by the enzyme WaaL.

Figure 4:
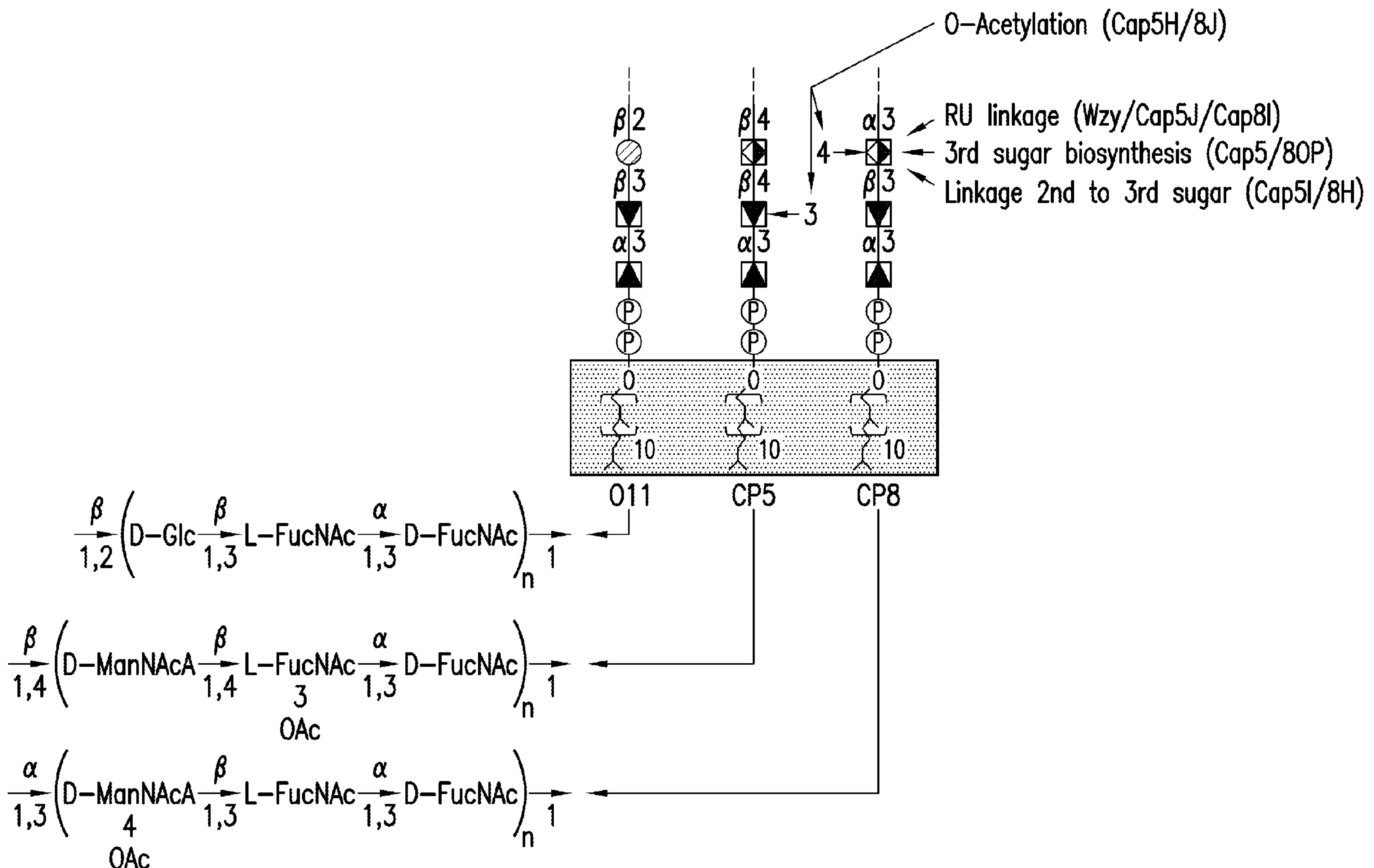
FIG. 4 depicts the structural overlap of capsular *S. aureus* and *P. aeruginosa* O-antigen Repeating Unit (RU) Structures.

FIG. 4 illustrates the different structures of the O11, CP5 and CP8 polysaccharides. It is shown in FIG. 4 that the RUs share the identical stem structure consisting of the UndPP and the disaccharide α-D-FucNAc-(1,3)-L-FucNAc. The *S. aureus* RUs are partially decorated with a single O-acetyl group, either on the middle L-FucNAc or on the ManNAcA residue, which is characteristic for the *S. aureus* RUs. The connectivity of the second and third sugar in the *S. aureus* RUs is different between them, as well as the connectivity between the polymerized RUs. On the right, the sugar structures are shown in a different representation. The number by the back arrows (CP5 and CP8) indicates the position of the carbon modified with an O-acetyl group. An alternative representation of the RU structures is shown on the bottom left. As shown in FIG. 4, there is great overlap between the RU in the O11 antigen that is part of a polysaccharide native to *P. aeruginosa* and those of the CP5 and CP8 capsules of the respective strains of *Staphylococcus*. In particular, as show in FIG. 4, the L-FucNAc→D-FucNAc portion in the RU it is identical in both.

In another aspect, the invention features a method of identifying a target polysaccharide for use in glycosylating a protein with said target polysaccharide, in whole or in part. Said glycosylated protein comprising the target polysaccharide can be used, for example, in vaccine compositions. The method of identifying a target polysaccharide includes: identifying a Gram-positive bacterium, such as *S. aureus*, as a target; identifying a first repeating unit of a polysaccharide produced by said Gram-positive bacterium comprising at least three monomers; identifying a polysaccharide produced by a bacterium of a Gram-negative species comprising a second repeating unit comprising at least two of the same monomers as said first repeating monomer unit.

Accordingly, in one embodiment of the invention, a method of modifying a bacterium of a first Gram-negative species includes: identifying a Gram-positive bacterium, such as *S. aureus*, as a target; identifying a first repeating unit of a polysaccharide produced by said Gram-positive bacterium comprising at least three monomers; identifying a polysaccharide produced by a bacterium of a second Gram-negative species comprising a second repeating unit comprising at least two of the same monomers as said first repeating unit; inserting into said bacterium of a first Gram-negative species one or more nucleotide sequences encoding glycosyltransferases that assemble a trisaccharide containing: a) said second repeating unit; and b) a monomer of said first repeating unit not present in said second repeating unit; inserting a nucleotide sequence encoding a protein, such as a protein comprising at least one inserted consensus sequence D/E-X-N-Z-S/T, wherein X and Z may be any natural amino acid except proline; and inserting a nucleotide sequence encoding an OTase.

In an embodiment of the invention, the method further comprises inserting into a host Gram-negative bacterium one or more nucleotide sequences encoding glycosyltransferases that assemble a trisaccharide containing a monomer of a first repeating unit not present in a second repeating unit and that assemble the second repeating unit. An additional embodiment of the invention involves inserting one or more glycosyltransferases from a Gram-negative bacterium that assemble at least one monomer unit from a first repeating unit and one or more glycosyltransferases from a Gram-positive bacterium, such as *S. aureus*, that assemble at least two monomers from a second repeating unit. The method additionally comprises inserting into inserting into a Gram-negative host bacterium a nucleotide sequence encoding a protein and a nucleotide sequence encoding an OTase.

In at least one embodiment of the invention, a host *E. coli* strain is generated carrying the corresponding nucleic acids encoding the required enzymes from the CP5 and CP8 strains of *S. aureus*, which will build up, flip and polymerize the constructed repeating units. In an embodiment, the specific glycosyltransferases needed correspond to those forming the L-FucNAc→D-FucNAc RU that are native to *P. aeruginosa*, and to glycosyltransferases corresponding to the ones adding the D-ManNAcA monosaccharide to the complete the RU that are native to each of the CP5 and CP8 strains of *S. aureus*. Such an embodiment may further include using a plasmid to inject the nucleic acids into the host cell. An additional embodiment involves using, in one plasmid, nucleic acids encoding for the glycosyltransferases corresponding to L-FucNAc→D-FucNAc, and, in a different plasmid, nucleic acids encoding for the glycosyltransferases corresponding to D-ManNAcA. One benefit of such embodiments, surprising in light of the prior art, is that the modified LPS biosynthesis pathway of *P. aeruginosa* that is now responsible for producing the constructed RU polymer of the *S. aureus* capsule results in a structure that is much smaller than the capsule of *S. aureus*.

The instant invention is additionally directed to a recombinant N-glycosylated protein comprising at least one inserted consensus sequence D/E-X-N-Z-S/T, wherein X and Z may be any natural amino acid except proline; and at least one oligo- or polysaccharide from a Gram-positive bacterium linked to said consensus sequence. In another embodiment, the recombinant N-glycosylated protein comprises two or more of said inserted consensus sequences. In yet an additional embodiment, the recombinant N-glycosylated protein comprises two or more of said *S. aureus* oligo- or polysaccharides. In a still further embodiment, the recombinant N-glycosylated protein comprises two or more of said inserted consensus sequences and oligo- or polysaccharides from different *S. aureus* strains, for example, from *S. aureus* capsular polysaccharide 5 strain and capsular polysaccharide 8 strain.

The present invention is furthermore directed to a combination of a modified capsular polysaccharide of *S. aureus* with a protein antigen from the same organism by N-glycosidic linkage.

Embodiments of the present invention include a protein that is glycosylated in nature. Such naturally glycosylated proteins (e.g., *C. jejuni* proteins) contain natural consensus sequences but do not comprise any additional (i.e., introduced) optimized consensus sequences. Naturally glycosylated proteins include prokaryotic and eukaryotic proteins. Embodiments of the instant invention further include a recombinant N-glycosylated protein, comprising one or more of the following N-glycosylated partial amino acid sequence(s): D/E-X-N-Z-S/T, (optimized consensus sequence) wherein X and Z may be any natural amino acid except Pro, and wherein at least one of said N-glycosylated partial amino acid sequence(s) is introduced. The introduction of specific partial amino acid sequence(s) (optimized consensus sequence(s)) into proteins leads to proteins that are efficiently N-glycosylated by an OTase, such as, for example, an OTase from *Campylobacter* spp., such as, for example, an OTase from *C. jejuni*, at the positions of introduction.

The term "partial amino acid sequence(s)" as it is used in the context of the present invention will also be referred to as "optimized consensus sequence(s)" or "consensus sequence(s)". The optimized consensus sequence is N-glycosylated by an OTase, such as, for example, an OTase from *Campylobacter* spp., such as, for example, an OTase from *C. jejuni*.

In accordance with the internationally accepted one letter code for amino acids the abbreviations D, E, N, S and T denote aspartic acid, glutamic acid, asparagine, serine, and threonine, respectively.

The introduction of the optimized consensus sequence can be accomplished by the addition, deletion and/or substitution of one or more amino acids. The addition, deletion and/or substitution of one or more amino acids for the purpose of introducing the optimized consensus sequence can be accomplished by chemical synthetic strategies well known to those skilled in the art such as solid phase-assisted chemical peptide synthesis. Alternatively, and preferred for larger polypeptides, the proteins of the present invention can be prepared by standard recombinant techniques by adding nucleic acids encoding for one or more optimized consensus sequences into the nucleic acid sequence of a starting protein, which may be a protein that is naturally glycosylated or may be a protein that is not naturally glycosylated.

In a preferred embodiment, the proteins of the present invention may comprise one or more, preferably at least two or at least three, and more preferably at least five of said introduced N-glycosylated optimized amino acid sequences.

The presence of one or more N-glycosylated optimized amino acid sequence(s) in the proteins of the present invention can be of advantage for increasing their antigenicity, increasing their stability, affecting their biological activity, prolonging their biological half-life and/or simplifying their purification.

The optimized consensus sequence may include any amino acid except proline in position(s) X and Z. The term "any amino acids" is meant to encompass common and rare natural amino acids as well as synthetic amino acid derivatives and analogs that will still allow the optimized consensus sequence to be N-glycosylated by the OTase. Naturally occurring common and rare amino acids are preferred for X and Z. X and Z may be the same or different.

It is noted that X and Z may differ for each optimized consensus sequence in a protein according to the present invention.

The N-glycan bound to the optimized consensus sequence will be determined by the specific glycosyltransferases and their interaction when assembling the oligosaccharide on a lipid carrier for transfer by the OTase. Those skilled in the art can design the N-glycan by varying the type(s) and amount of the specific glycosyltransferases present in the desired host cell. (Raetz & Whitfield, Lipopolysaccharide Endotoxins, NIH-PA Author Manuscript 1-57, 19-25 (published in final edited form as: Annual Rev. Biochem., 71: 635-700 (2002)); Reeves et al., Bacterial Polysaccharide Synthesis and Gene Nomenclature, Trends in Microbio. 4(3): 495-503, 497-98 (December 1996); and Whitfield, C. and I. S. Roberts. 1999. Structure, assembly and regulation of expression of capsules in *Escherichia coli*. Mol Microbiol 31(5): 1307-19).

"Polysaccharides" as used herein include saccharides comprising at least two monosaccharides. Polysaccharides include oligosaccharides, trisaccharides, repeating units comprising one or more monosaccharides (or monomers), and other saccharides recognized as polysaccharides by one of ordinary skill in the art. N-glycans are defined herein as mono-, oligo- or polysaccharides of variable compositions that are linked to an ϵ-amide nitrogen of an asparagine residue in a protein via an N-glycosidic linkage.

Polysaccharides of embodiments of the invention include without limitation *S. aureus* polysaccharides such as CP5 and CP8. Embodiment of the invention further includes *S. aureus* polysaccharides that target a bacterium, such as a polysaccharide that targets a methicillin-resistant strain of *S. aureus*. Where it is mentioned herein that polysaccharides target a bacterial strain, such polysaccharides include polysaccharides that are from the bacterium against which an immune or antigenic response is desired and further include polysaccharides that are the same as, based on, derived from, native to or engineered from the bacterium against which an immune or antigenic response is desired.

There is no limitation on the origin of the recombinant protein of the invention. In one embodiment, said protein is derived from mammalian, bacterial, viral, fungal or plant proteins. In a further embodiment, the protein is derived from mammalian, most preferably human proteins. For preparing antigenic recombinant proteins according to the invention, preferably for use as active components in vaccines, it is preferred that the recombinant protein is derived from a bacterial, viral or fungal protein. Glycosylation of proteins of various origins is known to one of skill in the art. Kowarik et al. "Definition of the bacterial N-glycosylation site consensus sequence" EMBO J. (2006) 1-10.

In an example in an embodiment, genetically detoxified *P. aeruginosa* Exotoxin (EPA) is a suitable protein carrier. For producing a version of EPA that may be glycosylated, the nucleic acids encoding for EPA need to be modified by insertion of glycosylation sites as previously discussed.

Protein carriers intended for use in embodiments of the invention should preferably have certain immunological and pharmacological features. From an immunological perspective, preferably, a protein carrier should: (1) have T-cell epitopes; (2) be capable of delivering an antigen to antigen presenting cells (APCs) in the immune system; (3) be potent and durable; and (4) be capable of generating an antigen-specific systemic IgG response. From a pharmacological perspective, a protein carrier should preferably: (1) be non-toxic; and (2) be capable of delivering antigens efficiently across intact epithelial barriers. More preferably, in addition to these immunological and pharmacological features, a protein carrier considered for use in the production of a bacterial bioconjugate should: (1) be easily secreted into the periplasmic space; and (2) be capable of having antigen epitopes readily introduced as loops or linear sequences into it. Informed by this disclosure and knowledge of one of ordinary skill in the art, a practitioner of ordinary skill in the art may routinely consider and identify suitable protein carriers that may be used in particular embodiments of the invention.

In an embodiment of the invention, the *Campylobacter* protein AcrA is a protein carrier.

In a further embodiment of the invention, genetically detoxified *P. aeruginosa* Exotoxin (EPA) is a protein carrier in which the target organism for which a vaccine is desired is *S. aureus*. Unlike AcrA which contains natural glycosylation sites, EPA contains no such natural glycosylation sites and needs to be modified by insertion of glycosylation sites (e.g., insertion of nucleic acids encoding for the optimized consensus sequence as discussed earlier into the nucleic acid sequence encoding for EPA). In an additional embodiment, EPA is modified to introduce two glycosylation sites that will allow glycosylation with the *S. aureus* antigen. In a still further embodiment, two consensus sequences are introduced as discussed in Example 10 of WO 2009/104074.

The amino acid sequence of EPA, as modified in an embodiment of this invention to contain two glycosylation sites, is provided as SEQ ID NO: 13 (with signal sequence) and SEQ ID NO.: 14 (without signal sequence). The glycosylation sites in SEQ ID NO: 13 are DNNNS and DQNRT at positions 260DNNNS and 402DQNRT. The glycosylation sites in SEQ ID NO: 14 are DNNNS and DQNRT at positions 241DNNNS and 383DQNRT.

A carrier protein such as EPA is a protein on which N-glycosylation sites may be added in the production of a bacterial bioconjugate. N-glycosylation sites require introduction of the consensus sequences discussed previously, namely, insertion of D/E-X-N-Z-S/T sequons, wherein X and Z may be any natural amino acid except proline. We have found that such consensus sequences preferably are introduced in surface loops, by insertion rather than mutation and by the use of additionally inserted flanking residues and by mutation of flanking residues to optimize the operation of the N-glycosylation site.

Some well-characterized protein subunit antigens of *S. aureus* are the alpha hemolysin (alpha toxin, Hla), clumping factor alpha (ClfA), IsdB, and Panton-Valentine Leukocidin (PVL).

Hla is a secreted pore-forming toxin and an essential virulence factor of MRSA in a mouse model of *S. aureus* pneumonia. The level of Hla expression by independent *S. aureus* strains directly correlates with their virulence. Active immunization with a mutant form of Hla (Hla H35L, SEQ ID NO: 5), which cannot form pores (Menzies, B. E., and D. S. Kernodle. 1996. Passive immunization with antiserum to a nontoxic alpha-toxin mutant from *Staphylococcus aureus* is protective in a murine model. Infect Immun 64:1839-41; Jursch, R., A. Hildebrand, G. Hobom, J. Tranum-Jensen, R. Ward, M. Kehoe and S. Bhakdi. 1994. Histidine residues near the N terminus of staphylococcal alpha-toxin as reporters of regions that are critical for oligomerization and pore formation. Infect Immun 62(6): 2249-56), was shown to generate antigen-specific immunoglobulin G responses and to afford protection against staphylococcal pneumonia. Transfer of Hla-specific antibodies protects naive animals against *S. aureus* challenge and prevents the injury of human lung epithelial cells during infection (Bubeck Wardenburg, J., A. M. Palazzolo-Ballance, M. Otto, O, Schneewind, and F. R. DeLeo. 2008. Panton-Valentine leukocidin is not a virulence determinant in murine models of community-associated methicillin-resistant *Staphylococcus aureus* disease. J Infect Dis 198:1166-70). To be used as a vaccine, the H35L mutation in Hla is required to eliminate toxicity of the protein (Menzies, B. E., and D. S. Kernodle. 1994. Site-directed mutagenesis of the alpha-toxin gene of *Staphylococcus aureus*: role of histidines in toxin activity in vitro and in a murine model. Infect Immun 62:1843-7). ClfA contains a protease resistant domain which is used for immunization. Passive immunization of mice with anti-ClfA and anti CP5 antibodies effectively sterilized mammary glands in mammary gland infection model (Tuchscherr, L. P., F. R. Buzzola, L. P. Alvarez, J. C. Lee, and D. O. Sordelli. 2008. Antibodies to capsular polysaccharide and clumping factor A prevent mastitis and the emergence of unencapsulated and small-colony variants of *Staphylococcus aureus* in mice. Infect Immun 76: 5738-44).

A further embodiment of the invention includes glycosylation of proteins native to *S. aureus*, for example, Hla and ClfA. In additional example embodiments of the invention, the protein carrier used may be selected to be the Hla protein, for example Hla H35L (for example, SEQ ID NO: 6, SEQ ID NO: 7, SEQ ID NO: 8 or SEQ ID NO: 16). In another additional example embodiment of the invention, the protein carrier is the ClfA protein (for example, SEQ ID NO: 10, SEQ ID NO: 11 or SEQ ID NO: 12).

The invention is further directed to recombinant host prokaryotic organisms comprising: a nucleotide sequence encoding one or more glycosyltransferase of a first prokaryotic species, such as a Gram-positive species; one or more glycosyltransferases of a different prokaryotic species, such as a Gram-negative species; a nucleotide sequence encoding a protein; and a nucleotide sequence encoding an OTase. The invention is additionally directed to a recombinant host prokaryotic organism comprising an introduced nucleotide sequence encoding glycosyltransferases native only to a Gram-positive prokaryotic organism; a nucleotide sequence encoding a protein; and a nucleotide sequence encoding an OTase. The invention is also directed to a recombinant or engineered host prokaryotic organism comprising: a nucleotide sequence encoding a glycosyltransferase native to a first prokaryotic species, which is, for example, different from the host prokaryotic organism; a nucleotide sequence encoding a glycosyltransferase native to a second prokaryotic species different from the species of said first prokaryotic organism and, for example, different from said host. The engineered prokaryotic organism can also, for example, comprise a first prokaryotic species that is a Gram-positive species. The engineered prokaryotic organism can also, for example, comprise a second prokaryotic species that is a Gram-negative species. The invention further includes a recombinant or engineered Gram-negative host prokaryotic organism comprising: a nucleotide sequence encoding a glycosyltransferase native to a Gram-negative prokaryotic species that is, for example, different from said host prokaryotic organism; a nucleotide sequence encoding a glycosyltransferase native to *S. aureus*; a nucleotide sequence encoding a protein; and a nucleotide sequence encoding an OTase. The invention further includes a recombinant or engineered *E. coli* host comprising: a nucleotide sequence encoding a glycosyltransferase native to *P. aeruginosa*; a nucleotide sequence encoding one or more glycosyltransferases native to *S. aureus* CP5 strain and/or to *S. aureus* CP8 strain; a nucleotide sequence encoding a *P. aeruginosa* EPA, *S. aureus* alpha hemolysin, or *S. aureus* clumping factor A protein carrier; and a nucleotide sequence encoding an OTase, for example, and OTase native to *C. jejuni*.

In addition to using the biosynthesis pathway of the other Gram-negative organism in the modified host *E. coli* organism, in a further embodiment, also included within the host *E. coli* organism are nucleic acids encoding for (i) glycosyltransferases for construction the structure of the repeating units of the polysaccharide of the other Gram-negative organism (that are identical to the repeating units of the polysaccharide of interest of the target Gram-positive *S. aureus* organism), and (ii) glycosyltransferases for construction of the units of the polysaccharide of interest of the target Gram-positive *S. aureus* organism that are not found in the relevant polysaccharide of the other Gram-negative organism, and (iii) enzymes for flipping and polymerization of the constructed RU of interest of the target Gram-positive *S. aureus* organism to form a *S. aureus* capsule like polysaccharide. In particular, in this embodiment, the nucleic acids encoding for (i) originated with the other Gram-negative bacterium, whereas the nucleic acids encoding for (ii) and (iii) originated with the target Gram-positive *S. aureus* organism.

Another aspect of the invention is directed to: an engineered host prokaryotic organism comprising: i) a nucleotide sequence encoding glycosyltransferases native to a Gram-positive prokaryotic species; ii) a nucleotide sequence encoding a protein; and iii) a nucleotide sequence encoding an OTase, wherein the sequences encoding transporter genes of said Gram-positive prokaryotic species are deleted. Such an embodiment involves an introduced nucleic acid construct that encodes only Gram-positive glycosyltransferases.

Regarding the other nucleic acids that would be inserted into the host in one or more other embodiments, nucleic acids encoding a protein, such as AcrA, Hla, ClfA or EPA (SEQ ID NO: 15, SEQ ID NO: 6, SEQ ID NO: 7, SEQ ID NO: 8, SEQ ID NO: 16; SEQ ID NO: 10, SEQ ID NO: 11, SEQ ID NO: 12; SEQ ID NO: 13, SEQ ID NO: 14), and the oligosaccharyltransferase of *C. jejuni* (SEQ ID NO: 27), which are part of the glycosylation machinery of that organism, are injected into the host in addition to the nucleic acids encoding for glycosyltransferases from each of *P. aeruginosa* and *S. aureus*. As a result, the modified *E. coli* organism can glycosylate the AcrA protein with the polysaccharide produced in that organism by action of the glycosyltransferases from *S. aureus* and the other Gram-negative bacterium.

One embodiment of the invention involves an engineered host prokaryotic organism comprising: i) a nucleotide sequence encoding a glycosyltransferase native to a first prokaryotic species different from the host prokaryotic organism; ii) a nucleotide sequence encoding a glycosyltransferase native to a second prokaryotic species, for example, a Gram-positive prokaryotic species, different from the host prokaryotic organism; iii) a nucleotide sequence encoding a protein; and iv) a nucleotide sequence encoding an OTase. In embodiments of the invention, the first prokaryotic species is a Gram-negative species, for example, *P. aeruginosa*.

In the context of the present invention, host cells refer to any host cell, e.g., an eukaryotic or prokaryotic host cell. In other embodiments the host cell is a prokaryotic host cell, e.g. *Escherichia* ssp., *Campylobacter* ssp., *Salmonella* ssp., *Shigella* ssp., *Helicobacter* ssp., *Pseudomonas* ssp. or *Bacillus* ssp. In still further embodiments, the host cell is *Escherichia coli, Campylobacter jejuni, Salmonella typhimurium*, etc.

The invention is furthermore directed to methods of producing a bioconjugate vaccine comprising introducing into a host prokaryotic organism nucleic acids encoding one or more glycosyltransferases of *S. aureus*; one or more glycosyltransferases of a second prokaryotic species, a protein; and an OTase. In addition, the present invention is directed to the production of bioconjugate vaccines by producing in Gram-negative bacteria modified capsular polysaccharides on undecaprenol (Und), and linking these polysaccharide antigens to a protein carrier of choice.

The invention is further directed to methods of producing glycosylated proteins in a host prokaryotic organism comprising nucleotide sequence encoding glycosyltransferases native to a first prokaryotic organism and also encoding glycosyltransferases native to a second prokaryotic organism that is different from the first prokaryotic organism. The present invention is additionally directed to the production of proteins N-glycosylated with capsular polysaccharides of Gram-positive bacteria, which are synthesized by a combination of different glycosyltransferases from different organisms. The invention is furthermore directed to the production of glycosylated proteins in a host prokaryotic organism comprising an introduced nucleotide sequence encoding glycosyltransferases native only to a Gram-positive prokaryotic organism.

As in known in the art, the biosynthesis of different polysaccharides is conserved in bacterial cells. The polysaccharides are assembled on carrier lipids from common precursors (activated sugar nucleotides) at the cytoplasmic membrane by different glycosyltransferases with defined specificity. (Whitfield, C., and I. S. Roberts. 1999. Structure, assembly and regulation of expression of capsules in *Escherichia coli*. Mol Microbiol 31: 1307-19). The biosynthetic pathway for polysaccharide production of O-antigen in Gram-negative and for capsular polysaccharide Type I in Gram-positive is conserved. The process uses the same lipid carrier, i.e., UndP, for polysaccharide assembly. It starts with the addition of a monosaccharide-1-phosphate to the carrier lipid UndP at the cytoplasmic side of the membrane. The antigen is built up by sequential addition of monosaccharides from activated sugar nucleotides by different glycosyltransferases. The lipid-linked oligosaccharide or RU is then flipped through the membrane by the flippase. RUs are polymerized by the enzyme Wzy in the periplasmic space, forming the so-called O-antigen in Gram negative bacteria or capsular polysaccharide in Gram-positive bacteria. Gram negative bacteria use the Wzz enzyme to regulate the length of the polymer, which is then transferred to lipid A core forming LPS. LPS is further translocated to the outer membrane exposing the O-antigen to the outside (as depicted, for example, in FIG. 1). Gram-positive bacteria, in contrast, form the capsule from this lipid-bound precursor by further transport using a different and specialized enzymatic machinery. The biosynthetic pathways of these polysaccharides enable the production of bioconjugates in vivo by capturing the polysaccharides in the periplasm onto a protein carrier.

The process of polysaccharide construction differs for capsular polysaccharides in that the capsular polysaccharide is released from the carrier lipid after polymerization and exported to the surface. In Gram-positive bacteria like *S. aureus* that do not contain a periplasmic compartment, the polymerization of the antigen takes place at the outer side of the membrane. In addition, length regulation in *S. aureus* is included in the machinery of three enzymes responsible for capsule assembly. In this assembly, the polysaccharide is released from the carrier lipid and exported to the surface by an enzymatic process.

The genetic elements found in the gene cluster required for functional capsule expression in *S. aureus* resemble the genetic machinery found in wzy dependent O-antigen synthesis clusters. (Dean, C. R., C. V. Franklund, J. D. Retief, M. J. Coyne, Jr., K. Hatano, D. J. Evans, G. B. Pier, and J. B. Goldberg. 1999. Characterization of the serogroup O11 O-antigen locus of *Pseudomonas aeruginosa* PA103. J Bacteriol 181:4275-4284).

Despite these differences between polysaccharide construction in Gram-positive and Gram-negative bacteria, it was surprisingly discovered and verified that aspects of the LPS pathway in a Gram-negative organism could be used to produce polysaccharides that contain some of the same repeating units as capsular polysaccharides native to Gram-positive bacteria, such as, for example, *S. aureus*. As such polysaccharides are produced by LPS pathway mechanisms in the Gram-negative host, the structure of such polysaccharides is the same as in LPS polysaccharide precursors. Such polysaccharides produced in Gram-negative systems of the instant invention can be characterized, therefore, as "modified capsular polysaccharides" or "LPS capsules" for purposes of this application. Furthermore, this newly synthesized expression system and biosynthetic pathway, which combines the LPS and capsular biosynthetic pathways, may be characterized as being a "modified LPS biosynthetic pathway" for purposes of this application.

In one embodiment of the present invention, a modified polysaccharide produced by a modified LPS biosynthetic pathway comprises:

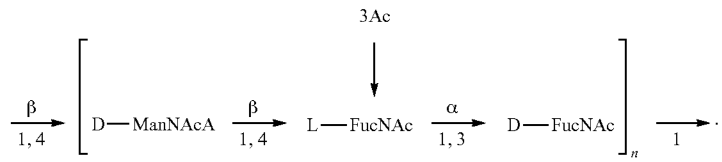

In a further embodiment of the present invention, a modified polysaccharide produced by a modified LPS biosynthetic pathway comprises:

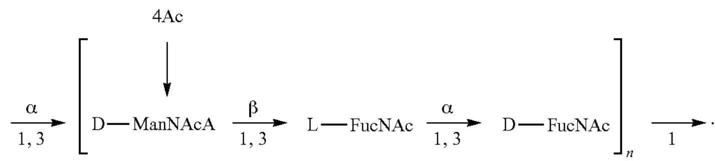

Using the technology of the invention, bacterial bioconjugates can be produced that are immunogenic. Genetic modifications can be made allowing in vivo conjugation of bacterial polysaccharides in desired proteins and at desired positions.

Another aspect of the invention involves production of LPS-capsules or modified LPSs conjugated to a protein carrier using the modified LPS biosynthetic pathway as discussed above.

Figure 6:
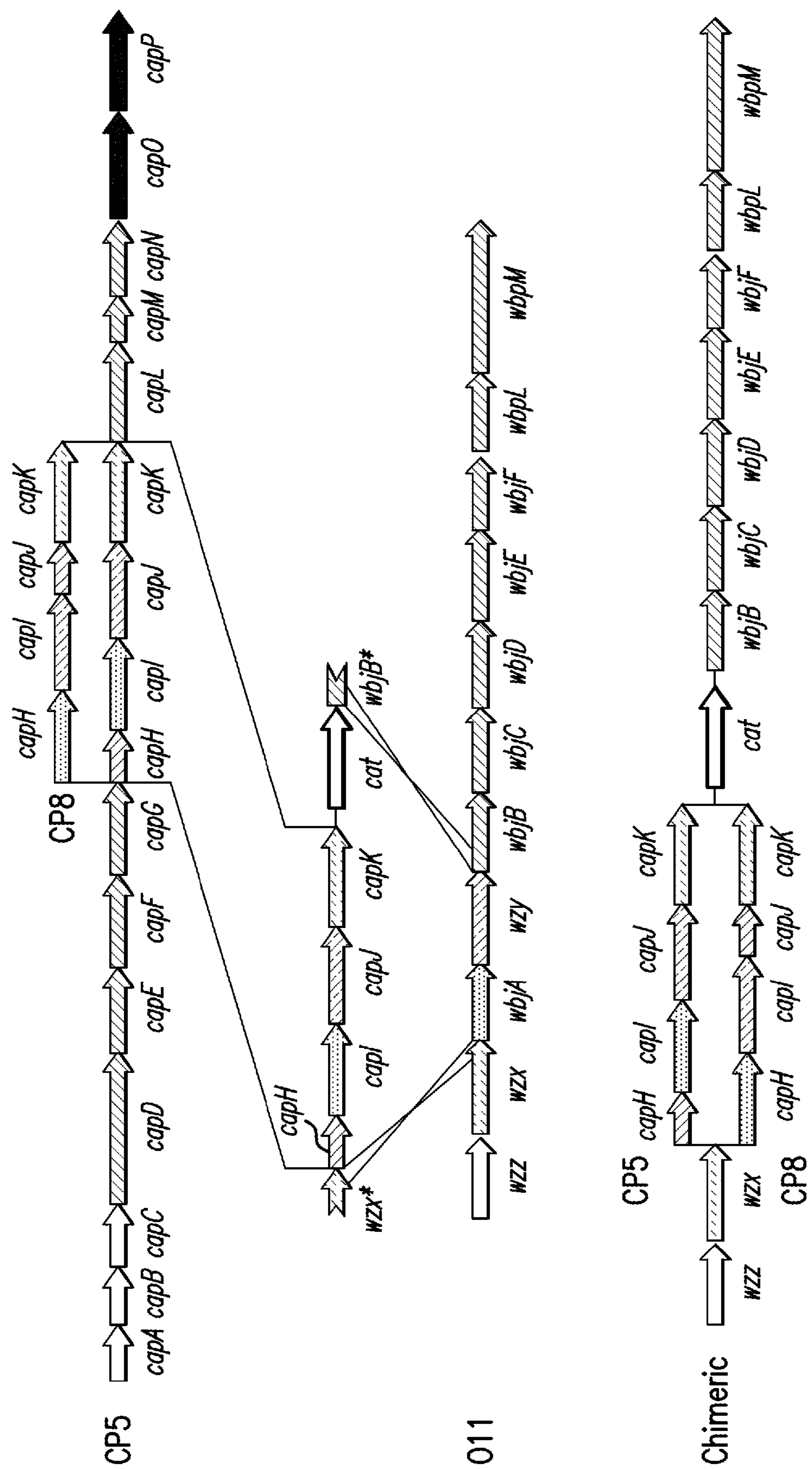
FIG. 6 depicts a strategy in an embodiment of the invention for the construction of the chimeric O11/CP5 and O11/CP8 gene clusters.

A further embodiment of the invention includes a nucleotide sequence construct that encodes the Cap5 and Cap8 complete polysaccharide biosynthesis cluster, wherein the deleted transporter genes are capA, capB and capC of *S. aureus* (see FIG. 6).

An additional embodiment of the invention includes integrating the CP5/O11 chimeric cluster (SEQ ID NO. 2, SEQ ID NO. 3 or SEQ ID NO. 17) or the CP8/O11 chimeric cluster (SEQ ID NO. 4, SEQ ID NO. 18 or SEQ ID NO. 19) into the genome of a host cell. A further embodiment of the invention involves integrating into the genome of a host cell: (a) the CP5/O11 chimeric cluster (SEQ ID NO. 2, SEQ ID NO. 3 or SEQ ID NO. 17) or CP8/O11 chimeric cluster (SEQ ID NO. 4 SEQ ID NO. 18 or SEQ ID NO. 19); (b) nucleic acids encoding the OTase; and (c) nucleic acids encoding a protein with or without an introduced consensus sequence.

Another embodiment of the instant invention is directed to plasmids, such as, for example, plasmids comprising one or more of SEQ. ID NO: 2; SEQ. ID NO: 3; SEQ ID NO: 4; SEQ. ID NO: 17; SEQ. ID NO: 18 and SEQ. ID NO: 19. The invention also includes plasmids comprising one or more of SEQ. ID NO: 13; SEQ. ID NO: 14 and SEQ. ID NO: 15. The invention also relates to plasmids comprising one or more of SEQ ID NO: 16; SEQ. ID NO: 6; SEQ. ID NO: 7 and SEQ. ID NO: 8. The invention also relates to plasmids comprising one or more of SEQ ID NO: 10; SEQ. ID NO: 11 and SEQ. ID NO: 12. Moreover, the invention is directed to plasmids comprising one or more of SEQ. ID NO: 20; SEQ. ID NO: 21 and SEQ. ID NO: 27.

Embodiments of the instant invention furthermore are directed to transformed bacterial cells, such as, for example, including a bacterial cell transformed with a plasmid comprising one or more of SEQ. ID NO. 2; SEQ. ID NO. 3; SEQ. ID NO: 4; SEQ. ID NO: 17; SEQ. ID NO: 18; SEQ. ID NO: 19; SEQ. ID NO: 20; SEQ. ID NO: 21 and SEQ. ID NO: 27. Further included in the invention is a bacterial cell transformed with a plasmid comprising one or more of SEQ. ID NO: 19 and SEQ ID NO: 20. Additionally included is a bacterial cell transformed with a plasmid comprising one or more of SEQ ID NO: 13, SEQ ID NO: 19 and SEQ ID NO: 21. The instant invention is further directed to a bacterial cell transformed with a plasmid comprising one or more of SEQ. ID NO: 16, SEQ ID NO: 6; SEQ ID NO: 7; SEQ ID NO: 8; SEQ ID NO: 10; SEQ ID NO: 11 and SEQ ID NO: 12. The invention is additionally directed to transformed bacterial cells, such as, for example, including a bacterial cell transformed with a plasmid comprising one or more of SEQ. ID NO. 3; SEQ. ID NO: 4; SEQ. ID NO: 17; SEQ. ID NO: 18; and SEQ. ID NO: 19, and wherein said bacterial cell expresses a glycosyltransferase native to *P. aeruginosa* and a glycosyltransferase native to *S. aureus* CP5 and/or CP8. Further included in the invention is a bacterial cell transformed with a plasmid comprising one or more of SEQ. ID NO: 17; SEQ ID NO: 18 and SEQ. ID NO: 19 wherein said bacterial cell expresses a glycosyltransferase native to *P. aeruginosa*, a glycosyltransferase native to *S. aureus* CP5 and/or CP8 and PglB. Still further included in the instant invention is (a) a bacterial cell transformed with a plasmid comprising SEQ. ID NO. 19, wherein said bacterial cell expresses a glycosyltransferase native to *P. aeruginosa*, a glycosyltransferase native to *S. aureus* CP8, Wzz of *E. coli* serovar O7 and PglB; (b) a bacterial cell transformed with a plasmid comprising one or more of SEQ. ID NO. 19 and SEQ. ID NO. 20, wherein said bacterial cell expresses a glycosyltransferase native to *P. aeruginosa*, a glycosyltransferase native to *S. aureus* CP8, Wzz (length regulator), EPA and PglB; and (c) a bacterial cell comprising one or more of SEQ. ID NO. 16; SEQ. ID NO: 6; SEQ. ID NO: 7; SEQ. ID NO: 8; SEQ. ID NO. 13; SEQ. ID NO: 14; SEQ. ID NO: 15; SEQ. ID NO: 10; SEQ. ID NO: 11 and SEQ. ID NO: 12.

Embodiments of the instant invention are additionally directed to a method of inducing an immune response against an infection caused by Gram-positive and other bacteria in a mammal, such as, for example, in a human. In one embodiment, the method comprises administering to said mammal an effective amount of a pharmaceutical composition comprising: protein comprising at least one inserted consensus sequence D/E-X-N-Z-S/T, wherein X and Z may be any natural amino acid except proline; and one or more oligo- or polysaccharides, the one or more oligo- or polysaccharides being the same or different as another of the one or more oligo- or polysaccharides, from a Gram-positive bacterium linked to said consensus sequence. A further embodiment of the present invention includes a method of inducing an immune response against an infection caused by *S. aureus* in a mammal, comprising administering to said mammal an effective amount of a pharmaceutical composition comprising: an inserted consensus sequence D/E-X-N-Z-S/T, wherein X and Z may be any natural amino acid except proline; at least one *S. aureus* oligo- or polysaccharide, such as CP5 polysaccharide; and a pharmaceutically acceptable adjuvant. Another embodiment of the invention is directed to inducing an immune response against an infection caused by *S. aureus* in a mammal, comprising administering to said mammal an effective amount of a pharmaceutical composition comprising: a protein comprising an inserted consensus sequence D/E-X-N-Z-S/T, wherein X and Z may be any natural amino acid except proline; at least one *S. aureus* CP8 polysaccharide; and a pharmaceutically acceptable adjuvant. A still further embodiment is directed to inducing an immune response against an infection caused by *S. aureus* in a mammal, comprising administering an effective amount of a pharmaceutical composition comprising a protein with two or more consensus sequences and oligo- or polysaccharides from different Gram-positive bacterial strains. A still further embodiment is directed to inducing an immune response against an infection caused by *S. aureus* in a mammal, comprising administering an effective amount of a pharmaceutical composition comprising a protein with two or more consensus sequences and polysaccharides comprising *S. aureus* CP5 and *S. aureus* CP8.

In instances in this specification where specific nucleotide or amino acid sequences are noted, it will be understood that the present invention encompasses homologous sequences that still embody the same functionality as the noted sequences. In an embodiment of the invention, such sequences are at least 85% homologous. In another embodiment, such sequences are at least 90% homologous. In still further embodiments, such sequences are at least 95% homologous. The determination of percent identity between two nucleotide or amino acid sequences is known to one of skill in the art.

Nucleic acid sequences described herein, such as those described in the sequence listings accompanying this specification, are examples only, and it will be apparent to one of skill in the art that these sequences can be combined in different ways. Additional embodiments of the invention include variants of nucleic acids. A variant of a nucleic acid (e.g., a codon-optimized nucleic acid) can be substantially identical, that is, at least 70% identical, for example, 75%, 80%, 85%, 90%, 91%, 92%, 93%, 94%, 95%, 96%, 97%, 98%, 99% or 99.5% identical, to SEQ ID NO:1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26 and/or SEQ ID NO: 27. Nucleic acid variants of a sequence that contains SEQ ID NO: 1, SEQ ID NO: 2, SEQ ID NO. 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, and/or SEQ ID NO: 27. Include nucleic acids with a substitution, variation, modification, replacement, deletion, and/or addition of one or more nucleotides (e.g., 2, 3, 4, 5, 6, 8, 10, 12, 15, 20, 25, 30, 35, 40, 50, 60, 70, 80, 90, 100, 150, 200, 250, 300, 350, 400, 450, 500 or more nucleotides) from a sequence that contains SEQ ID NO:1, SEQ ID NO: 2, SEQ ID NO: 3, SEQ ID. NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26 and/or SEQ ID NO: 27, or parts thereof.

Such variants include nucleic acids that encode prokaryotic glycosyltransferases and that i) are expressed in a host cell such as *E. coli* and ii) are substantially identical to SEQ ID NO: 2, SEQ ID NO: 3, SEQ ID NO: 4, SEQ ID NO: 17, SEQ ID NO: 18 and/or SEQ ID NO: 19 and/or parts thereof.

Nucleic acids described herein include recombinant DNA and synthetic (e.g., chemically synthesized) DNA. Nucleic acids can be double-stranded or single-stranded. In the case of single-stranded nucleic acids, the nucleic acid can be a sense strand or antisense strand. Nucleic acids can be synthesized using oligonucleotide analogs or derivatives, as known to one of skill in the art in light of this specification.

Plasmids that include a nucleic acid described herein can be transformed into host cells for expression. Techniques for transformation are known to those of skill in the art in light of this specification.

An additional embodiment of the invention involves producing Gram-positive bioconjugate vaccines containing LPS-capsules or modified LPSs conjugated to a protein carrier.

A further embodiment of the invention involves a novel bioconjugate vaccine. A further embodiment of the invention involves a novel approach for producing such bioconjugate vaccines that uses recombinant bacterial cells that directly produce immunogenic or antigenic bioconjugates. In one embodiment, bioconjugate vaccines can be used to treat or prevent bacterial diseases, such as diarrhea, nosocomial infections and meningitis. In further embodiments, bioconjugate vaccines may have therapeutic and/or prophylactic potential for cancer or other diseases.

In another embodiment of the present invention synthesized complexes of polysaccharides (i.e., sugar residues) and proteins (i.e., protein carriers) can be used as conjugate vaccines to protect against infections such as *S. aureus* infections. In one embodiment, a bioconjugate vaccine, such as a Gram-positive vaccine, comprises a protein carrier comprising an inserted nucleic acid consensus sequence; at least one oligo- or polysaccharide from a Gram-positive bacterium linked to the consensus sequence, and, optionally, an adjuvant. The present invention is further directed in another embodiment to a Gram-positive bioconjugate vaccine, such as a *S. aureus* vaccine, comprising a protein carrier comprising an inserted nucleic acid consensus sequence; at least one oligo- or polysaccharide from a Gram-positive bacterium, such as capsular polysaccharide or LPS capsule, linked to the consensus sequence, and, optionally, an adjuvant. In another embodiment of the invention, the *S. aureus* bioconjugate vaccine comprises two or more of these inserted consensus sequences. In a further embodiment, the *S. aureus* bioconjugate vaccine comprises two or more of *S. aureus* oligo- or polysaccharides. A still further embodiment comprises two or more of said inserted consensus sequences and oligo- or polysaccharides from different *S. aureus* strains, for example, from *S. aureus* capsular polysaccharide 5 strain (CP5) and capsular polysaccharide 8 strain (CP8).

An additional embodiment of the present invention involves an *S. aureus* vaccine made by a glycosylation system using a modified LPS pathway, which comprises the production of a modified capsular polysaccharide or LPS-capsule. A further additional embodiment involves an *S. aureus* vaccine made by a glycosylation system using a modified LPS pathway, which comprises the production of a modified capsular polysaccharide from introduced nucleic acids that do not encode glycosyltransferases of a Gram-negative prokaryotic species.

A further embodiment involves an *S. aureus* vaccine produced by a glycosylation system comprising nucleic acids encoding: i) one or more glycosyltransferases responsible for producing the L-FucNAc→D-FucNAc of the RU of the O11 antigen native to *P. aeruginosa*; ii) one or more glycosyltransferases responsible for producing the D-ManNAcA containing RU native to either the CP5 or CP8 strains of *S. aureus*; iii) one or more enzymes responsible for flipping and polymerization of the CP5 or CP8 constructed RUs, iv) a recombinant protein containing introduced consensus sequences; and v) oligosaccharyltransferase from *C. jejuni*. In this embodiment, the host organism may be a Gram-negative bacterium, for example, *E. coli*.

An additional embodiment of the invention involves an *S. aureus* vaccine produced by a glycosylation system comprising nucleic acids encoding: i) glycosyltransferases responsible for producing the L-FucNAc→D-FucNAc of the RU of the O11 antigen native to *P. aeruginosa*; ii) a glycosyltransferase responsible for producing the D-ManNAcA containing RU native to either the CP5 or CP8 strains of *S. aureus*; iii) AcrA protein of *C. jejuni*; and iv) oligosaccharyltransferase from *C. jejuni*. In this embodiment, the host organism may be a Gram-negative bacterium, for example, *E. coli*.

The vaccines of the instant invention have therapeutic and prophylactic utilities. It will be appreciated that the vaccine of the invention may be useful in the fields of human medicine and veterinary medicine. Thus, the subject to be immunized may be a human or other animal, for example, farm animals including cows, sheep, pigs, horses, goats and poultry (e.g., chickens, turkeys, ducks and geese) and companion animals such as dogs and cats.

In another aspect, the invention is directed to a method of generating vaccines for immunizing a mammal against a bacterium such as a Gram-positive bacterium. The method includes: immunizing a subject with a bioconjugate, such as a bioconjugate comprising a Gram-positive polysaccharide, e.g., an *S. aureus* polysaccharide, and a pharmaceutically acceptable carrier.

This invention also features vaccine compositions for protection against infection by a gram-positive bacterium such as *S. aureus* or for treatment of gram-positive infection such as *S. aureus* infection. In one embodiment, the vaccine compositions comprise one or more immunogenic components such as a polysaccharide, or a fragment or portion thereof, from *S. aureus*. In a further embodiment, the vaccine compositions comprise one or more immunogenic components such as a protein, or a fragment or portion thereof, from a Gram-negative or Gram-positive bacterium.

One aspect of the invention provides a vaccine composition for protection against infection by *S. aureus* which contains at least one immunogenic component or fragment of an *S. aureus* polysaccharide and a pharmaceutically acceptable carrier. Such immunogenic components or fragments can include, for example, an *S. aureus* polysaccharide of at least about two monomers in length or at least about three monomers in length. In a further aspect of the invention, an *S. aureus* RU comprises said monomers. Such repeating units can include, for example, an *S. aureus* RU of at least 1 (one) in length.

Immunogenic components or fragments of the invention can be obtained, for example, by screening polysaccharides or polypeptides produced recombinantly or through chemical synthesis, or, for example, by screening the bioconjugate comprising a polysaccharide and a protein. Screening immunogenic components or fragments of the invention can be performed using one or more of several different assays. For example, screening assays include ELISA and other assays known to one of ordinary skill in the art.

In one embodiment, immunogenic components or fragments are identified by the ability of the polysaccharide and/or protein to stimulate IgG antibodies against Gram-positive bacteria, such as *S. aureus* CP5 or CP8 polysaccharides, as determined by, for example, the immune response obtained in mice (FIG. 15A) and in rabbit (FIG. 15B) measuring specific anti CP5 antibodies (quantified by ELISA) against the glycoconjugate vaccine candidate CP5-EPA and other means known to a person of ordinary skill in the art.

In one embodiment, immunogenic components or fragments are identified by the ability of the polysaccharide and/or protein to stimulate opsonic activity, such as opsonophagocytic killing, as determined by, for example by the *S. aureus* killing ("in vitro" activity) with rabbit anti CP5-EPA antibodies (obtained in Example 7 below, see FIG. 15B) and other means known to a person of ordinary skill in the art.

In yet a further embodiment, immunogenic components or fragments are identified by the ability of the polysaccharide and/or protein to stimulate humoral and/or cell-mediated immunity against Gram-positive bacteria, such as *S. aureus*, as determined by, for example, by protection against bacterial infection ("challenge") using active immunization in mice (FIG. 18) with CP5-EPA and other means known to a person of ordinary skill in the art.

In an embodiment of the instant invention, a vaccine composition of the invention can be based on a glycoprotein comprising an immunogenic component or fragment of an *S. aureus* polysaccharide of the invention and optionally further comprising a pharmaceutically acceptable carrier or adjuvant. In further embodiments of the instant invention, a vaccine composition can be based on a glycoprotein comprising an immunogenic component or fragment of an *S. aureus* protein of the invention and optionally further comprising a pharmaceutically acceptable carrier or adjuvant. In yet a further aspect of the invention, a vaccine composition can be based on a glycoprotein comprising a immunogenic component or fragment of a *P. aeruginosa* protein of the invention and optionally further comprising a pharmaceutically acceptable carrier and/or adjuvant.

It is well-known to those of ordinary skill in the art how to modify a vaccine for administration to one mammal type, for example, mice, for administration to another mammal type, for example, humans. For example, one of skill would readily know that deletion of the histidine tag from the protein carrier of a glycoprotein used in a vaccine composition in mice would render the glycoprotein suitable for administration in a vaccine composition in humans. For example, deletion of the HISTIDINE tag (HIS-tag) in protein carriers such as, e.g. EPA (SEQ ID NO: 13), ClfA (SEQ ID NO: 10, SEQ ID NO: 11, SEQ ID NO: 12), and Hla (SEQ ID NO: 6, SEQ ID NO: 7, SEQ ID NO: 8, SEQ ID NO: 16) would be recognized for its use in a glycoprotein for administration to a human.

It should be understood that amelioration of any of the symptoms of a Gram-positive, for example *S. aureus*, or other bacterial infection or disease is a desirable clinical goal, including a lessening of the dosage of medication used for the Gram-positive-caused infection or disease, for example an *S. aureus*-caused infection or disease, or other bacterial-caused infection or disease, or an increase in the production of antibodies in the serum or mucous of patients. It will be apparent to those skilled in the art that some of the vaccine compositions of the invention are useful for preventing a Gram-positive infection, for example an *S. aureus* infection, or other bacterial infection, some are useful for treating a Gram-positive infection, for example an *S. aureus* infection, or other bacterial infection, and some are useful for both preventing and treating such infections.

Embodiments of the present invention such as vaccines and other pharmaceutical agents optionally may be prepared using suitable and pharmaceutically acceptable carriers, excipients, diluents and/or adjuvants, as are well-known in the art and apparent in light of this specification. An excipient, diluent or adjuvant may be a solid, semi-solid or liquid material which may serve as a vehicle or medium for the active ingredient. In light of this specification, one of ordinary skill in the art in the field of preparing compositions can readily select the proper form and mode of administration depending upon the particular characteristics of the product selected, the disease or condition to be treated, the stage of the disease or condition, and other relevant circumstances (*Remington's Pharmaceutical Sciences*, Mack Publishing Co. (1990)). The proportion and nature of the pharmaceutically acceptable diluent, excipient or adjuvant are determined by the solubility and chemical properties of the pharmaceutically active compound selected the chosen route of administration and standard pharmaceutical practice.

Accordingly, in embodiments of the invention, vaccine compositions comprise immunogenic components or fragments, e.g., *S. aureus* polysaccharide or fragment thereof and/or *S. aureus* or *P. aeruginosa* protein or fragment thereof and optionally include a pharmaceutically acceptable carrier. The term "pharmaceutically acceptable carrier" refers to a carrier that is non-toxic. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the antibody. Such pharmaceutically acceptable carriers include, for example, liquid, semi-solid, or solid diluents that serve as pharmaceutical vehicles, excipients, or media. Any diluent known in the art may be used. Exemplary diluents include, but are not limited to, polyoxyethylene sorbitan monolaurate, magnesium stearate, methyl- and propylhydroxybenzoate, talc, alginates, starches, lactose, sucrose, dextrose, sorbitol, mannitol, gum acacia, calcium phosphate, mineral oil, cocoa butter, and oil of *theobroma*.

Further, in additional embodiments of the invention, the vaccine composition can optionally include an adjuvant or a combination of adjuvants, including, but not limited to particulate adjuvants such as aluminium salts (aluminium hydroxide, aluminium phosphate, aluminium hydroxyphosphate sulphate, etc.); emulsions such as oil in water (MF59, AS03); lipid and salt combinations such as AS04; water in oil (Montanide); ISCOMS, liposomes/virosomes; nano- and microparticles, etc.; non particulated such as peptides; saponins (QS21); MPL A; cytokins; DNA derivates; bacterial toxins; etc. A further embodiment includes adjuvants used in animals such as Freund's Complete Adjuvant and Freund's Incomplete Adjuvant, mycolate-based adjuvants (e.g., trehalose dimycolate), bacterial lipopolysaccharide (LPS), peptidoglycans (i.e., mureins, mucopeptides, or glycoproteins such as N-Opaca, muramyl dipeptide [MDP], or MDP analogs), proteoglycans, streptococcal preparations (e.g., OK432), DEAE-dextran, neutral oils (such as miglyol), vegetable oils (such as arachis oil), Pluronic, the Ribi adjuvant system or interleukins, particularly those that stimulate cell-mediated immunity. The adjuvant used will depend, in part, on the composition and type of the glycoconjugate vaccine. The amount of adjuvant to administer will depend on the type and size of mammal. Optimal dosages may be readily determined by routine methods.

A further aspect of the present invention relates to a pharmaceutical composition, comprising at least one glycoprotein according to the invention. The preparation of medicaments comprising glycoproteins is well-known in the art. The preparation scheme for the final pharmaceutical composition and the mode and details of its administration will depend on the protein, the host cell, the nucleic acid and/or the vector employed.

It will be apparent to those of skill in the art that the therapeutically effective amount of polysaccharide or glycoprotein of this invention will depend, inter alia, upon the administration schedule, the unit dose of antibody administered, whether the polysaccharide or glycoprotein is administered in combination with other therapeutic agents, the immune status and health of the patient, and the therapeutic activity of the particular polysaccharide or glycoprotein.

The vaccine compositions and/or pharmaceutical preparations of the invention may be adapted for oral, parenteral or topical use and may be administered to the patient in the form of tablets, capsules, suppositories, solution, suspensions or any other suitable means or dosage form. In further aspects of the invention, the vaccine compositions and/or pharmaceutical preparations may be introduced into the subject to be immunized by any known method including, e.g., by intravenous, intradermal, intramuscular, intramammary, intraperitoneal, or subcutaneous injection; or by oral, sublingual, nasal, anal, or vaginal, delivery. The pharmaceutically active compounds of the present invention, while effective themselves, can be formulated and administered in the form of their pharmaceutically acceptable salts, such as acid addition salts or base addition salts, for purposes of stability, convenience of crystallization, increased solubility, and the like. Vaccine compositions in an embodiment of the invention are administered parenterally, e.g., by injection, either subcutaneously or intramuscularly. Methods for intramuscular immunization are described by Wolff et al. (1990)

Science 247: 1465-1468 and by Sedegah et al. (1994) Immunology 91: 9866-9870. Other modes of administration include oral and transdermal.

Vaccines of the invention can be administered as a primary prophylactic agent in, e.g., adults or in children, as a secondary prevention, after successful eradication of Gram-positive bacteria such as *S. aureus* in an infected host, or as a therapeutic agent in the aim to induce an immune response in a host to prevent infection by a Gram-positive bacterium such as *S. aureus*. The vaccines of the invention are administered in amounts readily determined by persons of ordinary skill in the art. The treatment may consist of a single dose or a plurality of doses over a period of time. For example, in some embodiments, it is expected that a typical dosage for humans of a vaccine of the present invention is about 1 to 25 μg of the oligosaccharide antigen, which will be bound to (and does not include the mass of) the protein carrier, in further embodiments about 1 μg to about 10 μg of the polysaccharide antigen, and in still further embodiments about 2 μg of the polysaccharide antigen. In additional embodiments, the sugar/protein ratio in the glycoconjugate or the vaccine is about 1:5 to about 1:10. Optionally, a vaccine, such as a bioconjugate vaccine of the present invention, may include an adjuvant. Those skilled in the art will recognize that the optimal dose may be more or less depending upon the patient's body weight, disease, the route of administration, and other factors. Those skilled in the art will also recognize that appropriate dosage levels can be obtained based on results with known vaccines. The number of doses will depend upon the disease, the formulation, and efficacy data from clinical trials.

The vaccine compositions can be packaged in forms convenient for delivery. Delivery forms compatible with entry of the immunogenic component or fragment into the recipient mammal are preferred.

One embodiment of the invention is generally directed to recombinantly producing a vaccine for a Gram-positive organism in a Gram-negative organism by using a modified LPS biosynthetic pathway. This is accomplished by inserting into a host which comprises of nucleic acids encoding for an oligosaccharyltransferase and a protein and nucleic acids encoding for glycosyltransferases originating from at least two different organisms. This embodiment is directed to genetically engineering an organism based on a natural organism into which are inserted nucleic acids coding for (i) a protein; (ii) an oligosaccharyltransferase, and (iii) glycosyltransferases from at least two differing organisms.

In an example of such an embodiment, a glycosylated-protein product is produced for use as a vaccine for *Staphylococcus aureus*. The vaccine products of the invention are produced in a genetically modified *E. coli* host. *S. aureus* is a Gram-positive bacterium, and has a polysaccharide capsule. A vaccine product for this organism could be based on a glycosylated protein whose sugar section had a structure similar to this capsular polysaccharide.

In another aspect, the instant invention is directed to a novel bioengineering approach for producing immunogenic conjugate vaccines that provide advantages over classical chemical conjugation methods. In an embodiment, the approach involves in vivo production of glycoproteins in bacterial cells, for example, Gram-negative cells such as *E. coli*.

As known to a person of ordinary skill in the art, the production and purification of glycoconjugate can vary depending on the vaccine candidate and the combination of plasmids used. For example, which purification procedure to choose is known based upon the protein carrier, the sugar component of the glycoconjugate and the intended use of the purified vaccine candidate, for example, in animals or humans. For use in humans, for example, it is known that the HIS-tag, which would otherwise facilitate purification, would be removed.

All publications mentioned herein are incorporated by reference in their entirety. It is to be understood that the term "or," as used herein, denotes alternatives that may, where appropriate, be combined; that is, the term "or" includes each listed alternative separately as well as their combination. As used herein, unless the context clearly dictates otherwise, references to the singular, such as the singular forms "a," an," and "the," include the plural, and references to the plural include the singular.

The invention is further defined by reference to the following examples that further describe the compositions and methods of the present invention, as well as its utility. It will be apparent to those skilled in the art that modifications, both to compositions and methods, may be practiced which are within the scope of the invention.

EXAMPLES

Example 1

Synthesis of CP5 and CP8 Polysaccharide in *E. coli* Cells

A goal of an embodiment of the invention is to produce the CP5 and CP8 antigenic polysaccharides in *E. coli*. As discussed above, we exploited in an novel way, surprising in view of the prior art, the fact that the CP and O-antigen production pathways functionally overlap, a fact which is represented in the structure of the RU (See FIGS. 1-4). The capsular glycans of CP5 and CP8 are polymers consisting of similar trisaccharide RUs of 2-Acetamido-2-deoxy-D-mannuronic acid (D-ManNAcA) and two 2-Acetamido-2,6-dideoxy galactose residues with D- and L-configurations (D- and L-FucNAc). The ManNAcA residues are linked differently in the two serotypes; additionally, the linkage between RUs in the polymerized glycan is different. In addition, there is an immunodominant O-acetyl modification at different positions in the two antigens (Jones, C. 2005. Revised structures for the capsular polysaccharides from *Staphylococcus aureus* types 5 and 8, components of novel glycoconjugate vaccines. Carbohydr Res 340:1097-106). The O11 antigen of *P. aeruginosa* LPS is similar in its structure to CP5 and CP8, as the O11 antigen of *P. aeruginosa* LPS contains [-3)-α-L-FucNAc-(1,3)-β-D-FucNAc-(1,2)-β-D-Glc-(1-] (FIG. 4). (Knirel, Y. A., V. V. Dashunin, A. S. Shashkov, N. K. Kochetkov, B. A. Dmitriev and I. L. Hofman. 1988. Somatic antigens of *Shigella*: structure of the O-specific polysaccharide chain of the *Shigella dysenteriae* type 7 lipopolysaccharide. Carbohydr Res 179: 51-60). The trisaccharide-RUs differ only in that the D-ManNAcA of *S. aureus* is replaced by a glucose unit, there is no O-acetyl modification in *P. aeruginosa* O11 LPS, and the difference in the linkage type between the $2^{nd}$ and $3^{rd}$ monosaccharide in the RU (FIG. 4).

To generate a genetic system able to synthesize the CP5 and CP8 glycans on UndPP, using the method of Dean et al., (Dean, C. R., C. V. Franklund, J. D. Retief, M. J. Coyne, Jr., K. Hatano, D. J. Evans, G. B. Pier, and J. B. Goldberg. 1999. Characterization of the serogroup O11 O-antigen locus of *Pseudomonas aeruginosa* PA103. J Bacteriol 181:4275-4284), we modified the *P. aeruginosa O*11 O-antigen gene cluster from strain PA103. The genes encoding the biosynthetic machinery for synthesis of the stem structure consisting of UndPP-D-FucNAc-L-FuncNAc were complemented with the *S. aureus* enzymes required for the completion of the *S. aureus* glycan (FIG. 1-4), which was also a novel use of this process. Therefore, using the method of Dean et al., all the genetic elements from *P. aeruginosa* PA103 required for the UndPP-FucNAc-FucNAc biosynthesis were expressed. The gene encoding the glycosyltransferase adding the third sugar was deleted and replaced by the corresponding genes from the cap5 or 8 clusters form *S. aureus* Mu50 (CP5) and MW2 (CP8) with slight modifications.

The genes encoding the enzymes synthesizing the specific residues for the *S. aureus* capsular polysaccharide were integrated step by step into the O11 background according to the functions of the genes predicted by Sau et al. (Sau, S., N. Bhasin, E. R. Wann, J. C. Lee, T. J. Foster, and C. Y. Lee. 1997. The *S. aureus* allelic genetic loci for serotype 5 and 8 capsule expression contain the type-specific genes flanked by common genes. Microbiology 143: 2395-405.; O'Riordan, K. and J. C. Lee. 2004. *Staphylococcus aureus* capsular polysaccharides. Clin Microbiol Rev 17(1): 218-34). Such steps are explained below.

Figure 5A:
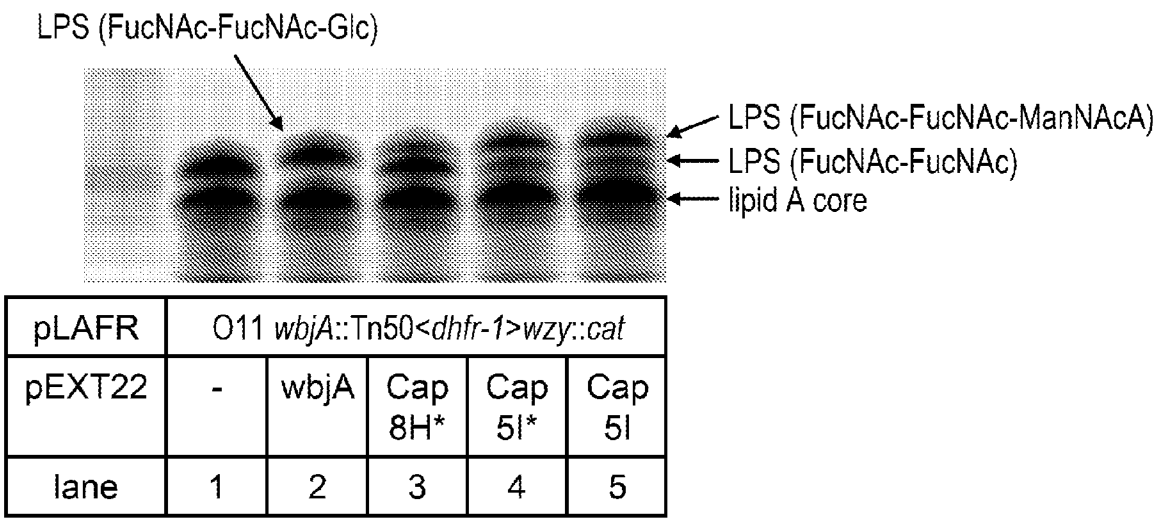
FIG. 5A depicts the SDS-PAGE analysis of the elongation of the incomplete O11 O-antigen RU (repeating unit) by *S. aureus* enzymes.

The cap5I/cap8H gene product was predicted to be the glycosyltransferase that adds the ManNAcA to UndPP-D-FucNAc-L-FuncNAc of the RU forming a linkage specific for each serotype (Sau, S., N. Bhasin, E. R. Wann, J. C. Lee, T. J. Foster, and C. Y. Lee. 1997. The *Staphylococcus aureus* allelic genetic loci for serotype 5 and 8 capsule expression contain the type-specific genes flanked by common genes. Microbiology 143: 2395-405.). To prove this, the activity of Cap5I and Cap8H was analyzed in *E. coli* in presence of a plasmid conferring production of the *P. aeruginosa O*11 O-antigen. Cells expressing the O11 cluster synthesize the O11 O-antigen first on UndPP, from where it is transferred to lipid A core by the *E. coli* enzyme WaaL, the O-antigen ligase, forming O11 specific lipopolysaccharide (LPS) (Goldberg, J. B., K. Hatano, G. S. Meluleni and G. B. Pier. 1992. Cloning and surface expression of *Pseudomonas aeruginosa* O antigen in *Escherichia coli*. Proc Natl Acad Sci USA 89(22): 10716-20). To synthesize this lipopolysaccharide, the O11 O-antigen cluster from *P. aeruginosa* PA103 was cloned into pLAFR1 (SEQ ID NO: 1). Then the wbjA gene encoding the glucosyltransferase, the enzyme adding the third sugar to the O11 RU, was deleted by transposon mutagenesis. The mutated cluster (O11 wbjA::Tn50<dhfr-1>) was further modified by homologous recombination to eliminate the polymerase activity of the wzy gene, forming O11 wbjA::Tn50<dhfr-1>wzy::cat, which denotes the mutated SEQ ID NO: 1, in which the genes for the glycosyltransferase wbjA and the wzy polymerase of the O11 gene cluster were inactivated. This modified cluster was expressed in W3110 ΔwecA cells, extracts were treated with proteinase K and analyzed by SDS PAGE and silver staining, according to the method disclosed in Tasi, et al. (Tsai, C. M., and C. E. Frasch. 1982. A sensitive silver stain for detecting lipopolysaccharides in polyacrylamide gels. Anal Biochem 119:115-9). The results are provided in FIG. 5A, showing silver staining of W3110 ΔwecA extracts expressing the mutated O11 cluster from pLAFR1 as described herein. The second line indicates the genes expressed from the inducible plasmid pEXT22. Asterisks indicate synthesized and codon optimized genes. Different relevant glycoforms are indicated with arrows.)

Analysis resulted in two major bands in the gels (FIG. 5A, lane 1). The signals correspond to the unmodified lipid A core (FIG. 5A, lower band) and LPS consisting of lipid A core and two FucNAc residues as expected in a truncated O11 RU. Upon expression of a wbjA wildtype copy from a separate, IPTG inducible plasmid, the upper band shifted to a slower electrophoretic mobility, indicating the addition of a glucose residue to the truncated O11 LPS (FIG. 5A, lane 2). When the predicted *S. aureus* glycosyltransferases Cap5I (lane 4) and Cap8H (FIG. 5A, lane 3) were expressed in trans instead of WbjA, a similar shift of the glycosylated lipid A core signal was observed, indicative of addition of a monosaccharide possibly even larger than glucose, most probably being ManNAcA. This data proves that *S. aureus* glycosyltransferases can elongate UndPP-D-FucNAc-L-FuncNAc glycolipid that has been synthesized by activity of *P. aeruginosa* enzymes.

In this way it was also confirmed that a prerequisite for *S. aureus* RU assembly in *E. coli* is the provision of UDP-ManNAcA, because the biosynthetic machinery is present in the *S. aureus* CP5/8 clusters but not in the O11 O-antigen cluster of *P. aeruginosa*. All other required nucleotide activated sugars are either provided by housekeeping functions of *E. coli* and the O11 O-antigen cluster of *P. aeruginosa*. *E. coli* is known to produce UDP-ManNAcA, the substrate for the ManNAcA glycosyltransferase, by expression of wecB and wecC. Those genes are constitutively expressed in the cluster responsible for enterobacterial common antigen (ECA) biosynthesis (Meier-Dieter, U., R. Starman, K. Barr, H. Mayer, and P. D. Rick. 1990. Biosynthesis of enterobacterial common antigen in *Escherichia coli*. J Biol Chem 265:13490-13497). The functional homolog for UDP-ManMAcA biosynthesis found in the CP cluster of *S. aureus* were found to complement the activities of wecBC as reported earlier (Kiser, K. B., N. Bhasin, L. Deng and J. C. Lee. 1999. *Staphylococcus aureus* cap5P encodes a UDP-N-acetylglucosamine 2-epimerase with functional redundancy. J. Bacteriol 181(16): 4818-24). This shows that the production of the CP antigens in *E. coli* relies on the functional expression of the wecBC genes in the host strain. Thus, to provide UDP-ManNAcA as substrate for Cap5I and Cap8H in a recombinant system, it was confirmed that WecB and WecC have to be expressed. In such a system, any prokaryotic strain expressing the enterobacterial common antigen like *E. coli* wildtype strain can be used, e.g. W3110 based cell types with or without a wecA deletion and with or without additional wzzE deletion.

Figure 5B:
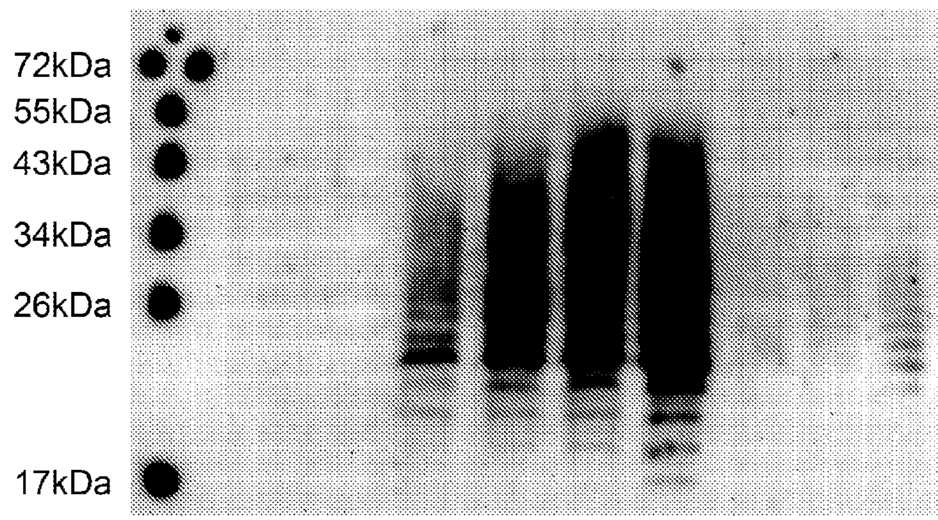
FIG. 5B depicts the immunodetection of the elongation of the incomplete O11 O-antigen RU by *S. aureus* enzymes.

Further elongation of the *S. aureus* capsular polysaccharide is thought to be required for maximal immunological activity of the glycan. The cap5J/cap8I genes encode the wzy homologs polymerizing the repeating units, and cap5K/cap8K encodes the flippase translocating the UndPP-bound trisaccharide from the cytoplasmic to the periplasmic side of the membrane. Cap5H/cap8J encodes the O-acetyltransferase modifying the L-FucNAc at position 3' or the ManNAcA at position 4' of the RU (Bhasin, N., A. Albus, et al. (1998). "Identification of a gene essential for O-acetylation of the *Staphylococcus aureus* type 5 capsular polysaccharide." Mol Microbiol 27(1): 9-21. The acetylation is an important determinant discriminating the immunological reactivity of the polysaccharide (Fattom, A. I., J. Sarwar, L. Basham, S. Ennifar, and R. Naso. 1998. Antigenic determinants of *S. aureus* type 5 and type 8 capsular polysaccharide vaccines. Infect Immun 66:4588-92). To show that the RUs could be elongated and acetylated, the *S. aureus* enzymes responsible for polymerization and O-acetylation were expressed from separate plasmids in presence of the mutated O11 cluster. Extracts from W3110 ΔwecA cells expressing the O11 wbjA::Tn50<dhfr-1>wzy::cat cluster and different genes of the CP5 cluster were treated with proteinase K and analyzed by SDS PAGE, electrotransfer followed by immunoblotting using an anti CP5 sugar (obtained from J. C. Lee at the Department of Medicine, Brigham and Women's Hospital, Harvard Medical School, Boston, Mass., USA). FIG. 5B shows the results of immunodetection of proteinase K treated *E. coli* extracts separated by SDS PAGE and electrotransfer using the anti CP5 antiserum. All extracts analyzed contained a *P. aeruginosa O*11 cluster with deletions of the wbjA and partially (indicated by an asterisk) the wzy genes expressed from the pLAFR plasmid as described herein, and two more plasmids (pEXT22, pACT3) expressing different Cap5 proteins (as indicated) that enable CP5 polymerization and O acetylation in these cells. Experimental details such as inducer concentrations and expression culture incubation temperatures are indicated.

In FIG. 5B, the results show ladder like signals typical for an O-antigen polymer in a higher molecular weight range. The different bands represent different numbers of linearly polymerized RUs on LPS or on UndPP, both of which are stable towards proteinase K digestion. Different intensities of the ladder like structure in presence or absence of the O-acetyltransferase were observed. Whereas strong signals were detected in the presence of cap5H (FIG. 5B, lanes 1-4), they were virtually absent in lanes without cap5H (FIG. 5B, lanes 5, 6). This means that O-acetylation either increases recognition by the specific antiserum, or that it enhances polymerization activity by either accelerating flipping or making polymerization as such more efficient or by inducing more RU production. The cap5H gene is functional when expressed from different backbone plasmids (FIG. 5B, lanes 1, 2 and 3, 4), although signal intensity is stronger when cap5H is expressed alone from a separate plasmid (compare FIG. 5B lane 1 to lane 3 and FIG. 5B, lane 2 to lane 4). It is surprising and remarkable that the less IPTG was used for induction of the *S. aureus* genes, the stronger the signals (compare FIG. 5B, lane 1 to 1 and 2 and FIG. 5B, lane 3 to lane 4).

Example 2

Synthesis of CP5 and CP8 Polymer on Lipid in *E. coli* Cells

As high expression of the cap5 specific genes lead to lower polymer formation, an alternative expression system for the recombinant glycans was constructed to address this problem. In detail, in a novel approach unexpected in light of the prior art, the *P. aeruginosa* glucosyltransferase (wbjA) and the polymerase (wzy) of O11 were replaced by the genes encoding the CP5/8-specific elements from the capsular gene cluster of *S. aureus* Mu50/MW2 (cap5/8HIJK and parts thereof) producing a single, chimeric gene cluster composed of *P. aeruginosa O*11 and *S. aureus* CP5 or CP8 genes (FIG. 6). The construct contained the specific genes of *S. aureus*. Each was tagged for expression detection and each contained an introduced ribosomal binding site, and was followed by a chloramphenicol resistance cassette (cat) for selection of recombined clones resulting in SEQ ID NO: 2, SEQ ID NO: 3, and SEQ ID NO: 4, according to the method of Datsenko, et al. (Datsenko, K. A., and B. L. Wanner. 2000. One-step inactivation of chromosomal genes in *Escherichia coli* K-12 using PCR products. Proc Natl Acad Sci USA 97:6640-5).

FIG. 6 depicts an embodiment of a strategy of the present invention for construction of chimeric O11/CP5 and O11/CP8 gene clusters of the present invention. The *S. aureus* CP5 and CP8 CP clusters (top) and the *P. aeruginosa* PA103 rfb cluster (O11, middle) are represented as published (Dean, C. R., C. V. Franklund, J. D. Retief, M. J. Coyne, Jr., K. Hatano, D. J. Evans, G. B. Pier, and J. B. Goldberg. 1999. Characterization of the serogroup O11 O-antigen locus of *Pseudomonas aeruginosa* PA103. J Bacteriol 181:4275-84; Sau, S., N. Bhasin, E. R. Wann, J. C. Lee, T. J. Foster and C. Y Lee. 1997. The *S. aureus* allelic genetic loci for serotype 5 and 8 capsule expression contain the type-specific genes flanked by common genes. Microbiology 143 (Pt 7): 2395-405). The homologous functions of the genes are described below. Complete forward diagonals indicate the genes responsible for synthesis of the D-FucNAc-L-FucNAc disaccharide on UndPP in the two organisms; dots indicate the glycosyltransferase genes adding the third monosaccharide to the RU. Wzx-like flippase genes are indicated by broken forward diagonals, the wzy-like RU polymerase genes are indicated by broken back diagonals. The CP5 cluster does not contain a Wzz length regulator (empty arrow), but a set of three genes composing the export machinery for capsular polysaccharide which includes the length regulator function in *S. aureus* (empty arrows). The O acetyl transferase gene, indicated by complete forward diagonals, is unique to the CP cluster. The genes required for UDP-ManNAcA biosynthesis in *S. aureus* are indicated in black. They are not required for production of the *P. aeruginosa* O-antigen. The genes responsible for the structural differences of the O11, CP5 and CP8 polysaccharides are clustered together in the beginning (O11: wbjA and wzy) or middle (CP5/8: cap5/8HIJK) of the respective gene clusters. The CP8 cluster is almost identical to the CP5 cluster considering length and DNA sequence, except for the middle part (cap5/8HIJK) conferring structural specificity. The chimeric cluster was constructed by replacing wbjA and wzy genes of a plasmid borne O11 cluster with the specificity part of the CP5 (or CP8) cluster (cap5/8HIJK) and a chloramphenicol acetyltransferase cassette represented by the empty arrow labeled cat (cat, for selection) by homologous recombination and classical clonings, resulting in SEQ ID NO: 2, SEQ ID NO: 3, and SEQ ID NO: 4. Asterisks at the broken arrows indicate incomplete gene sequences used for homologous recombination. The resulting two chimeric clusters are shown in the bottom panel, representing the DNA of SEQ ID NO: 3 and SEQ ID NO: 4.

To prove that the chimeric CP5 and CP8 of the present invention surprisingly assembles the correct RU on UndPP and assures that the repeating units are polymerized, proteinase K digestion of *E. coli* cells (W3310 ΔwecA) containing the full length chimeric clusters were separated by SDS-PAGE. Specifically, cells with a plasmid either containing or lacking the chimeric CP5 gene cluster (FIG. 7A) or the chimeric CP8 gene cluster (FIG. 7B) on the pLAFR plasmid were treated with Proteinase K, separated by SDS-PAGE and lipids were visualized by either silver staining (left panel in FIGS. 7A and 7B) or immunodetection with anti CP5 or CP8 antiserum after electrotransfer to nitrocellulose membranes (right panel in FIGS. 7A and B)). Constructs lacking (SEQ ID NO: 2) and containing (SEQ ID NO: 3) the flippase gene cap5K were tested. The former was found to be less active in CP5 LPS production.

Figures 7A, 7B:
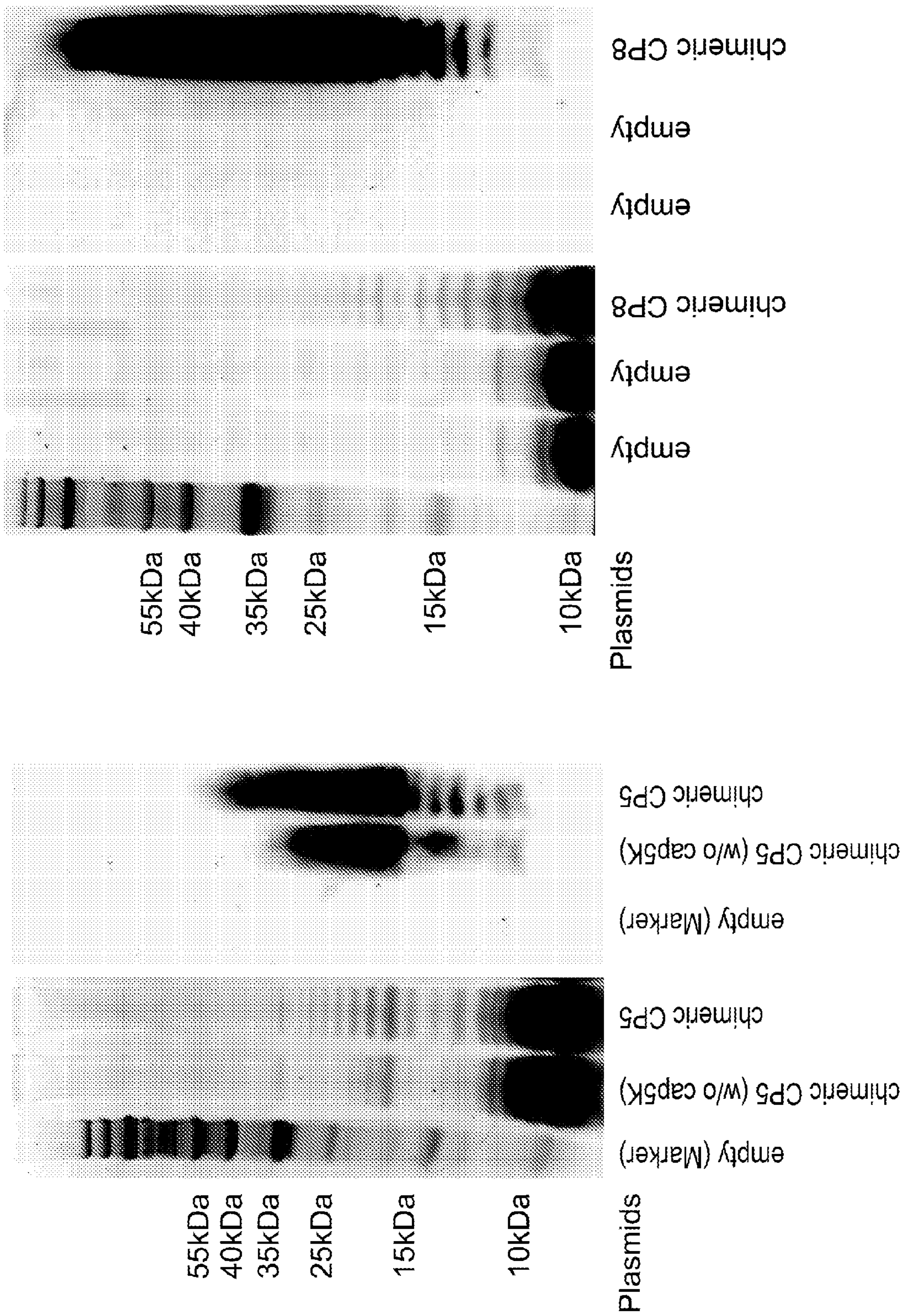
FIG. 7A depicts polymerized CP5 LPS of an embodiment of the invention detected in *E. coli* lipid extracts.
FIG. 7B depicts polymerized CP8 LPS of an embodiment of the invention detected in *E. coli* lipid extracts.

After electrotransfer and immunodetection with anti CP5 specific serum, extracts expressing the entire chimeric CP5 clusters show a ladder like signal similar to endogenous O-antigen structures from *E. coli* probed with their autologous serum (FIG. 7A, last two lanes on the right). This strongly suggests that the CP5 repeating units are polymerized, that there is a preferred polymer length, and that the CP5 antigen is transferred to lipid A core in these cells. The same extracts were visualized by silver staining after SDS PAGE (FIG. 7A, on the left side of the figure, the two lanes on the right labeled as: chimeric CP5 (w/o cap5K) and chimeric CP5 showing that indeed LPS is formed consisting of the lipid A core of *E. coli* decorated with the CP5 O-antigen-like structure. Intensity differences were obtained from extracts originating from cells that expressed the CP5 chimeric cluster with or without the cap5K flippase gene. Comparison of the two extracts shows that Cap5K expression considerably increases the polymer production (compare middle and right lanes in both panel of FIG. 7A).

As shown in FIG. 7B, the same results were observed with a CP8 chimeric cluster. Cells containing a plasmid either containing or lacking the chimeric CP8 gene cluster on the pLAFR plasmid were treated with Proteinase K, separated by SDS PAGE and lipids were either detected by silver staining (left panels) or immunodetection with anti CP8 antiserum after electrotransfer to nitrocellulose membranes (right panel). CP8 chimeric construct containing the flippase gene cap8K corresponds to SEQ ID NO: 4.

A further novel and surprising extension of the invention was developed by changing the plasmid backbones used for maintenance and expression of the chimeric cluster in *E. coli*. The resistance cassette in pLAFR1 containing the chimeric CP5 cluster was changed from Tet to Kan. Additionally the entire CP5 chimeric cluster containing the cap5K was subcloned into plasmid pDOC-C, according to the method of Lee et al. (Lee, D. J., L. E. Bingle, K. Heurlier, M. J. Pallen, C. W. Penn, S. J. Busby and J. L. Hobman. 2009. Gene doctoring: a method for recombineering in laboratory and pathogenic *Escherichia coli* strains. BMC Microbiol 9: 252) and pACYC177 (GeneBank accession #X06402).

Figure 8B:
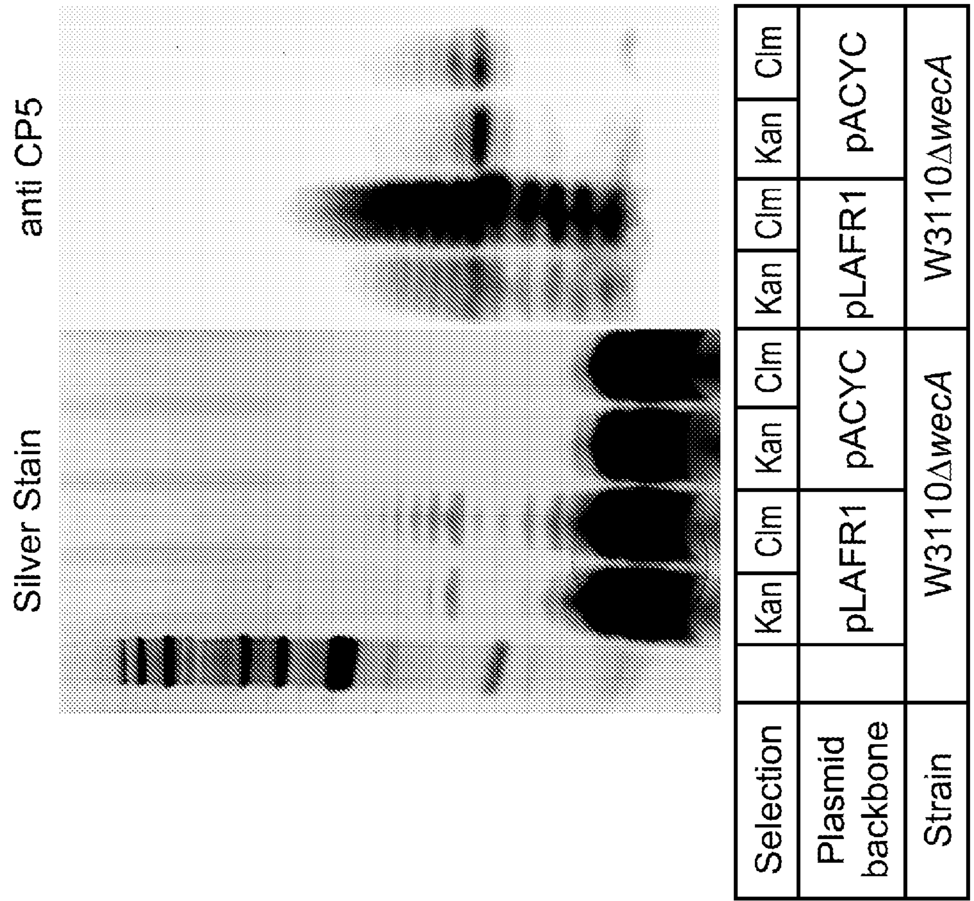
FIG. 8B depicts recombinant CP5 LPS production of an embodiment of the invention analyzed by SDS PAGE, stained by silver and immunodetection in dependence of antibiotic resistance gene on the pLAFR plasmid containing the chimeric cluster in W3110 ΔwecA cells.
Figure 8A:
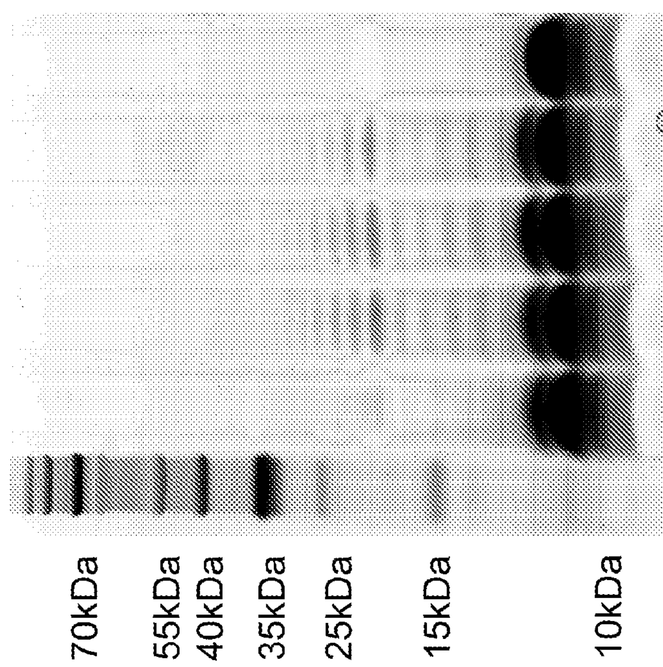
FIG. 8A depicts recombinant CP5 LPS production of an embodiment of the invention analyzed by SDS-PAGE and stained by silver in dependence of antibiotic resistance gene on the pLAFR plasmid containing the chimeric cluster in W3110 ΔwecA cells.

As shown in FIGS. 8A and 8B, all of these plasmids conferred CP5 polymer production as analyzed by SDS PAGE, electrotransfer and immunodetection with anti CP5 specific antiserum. In FIG. 8A, total cell extracts from cells containing different chimeric clusters were treated with Proteinase K and analyzed by SDS PAGE and silver staining. The plasmids contain different *S. aureus* specific genes and different resistance genes used for antibiotic selection are indicated: Tetracycline (Tet) and HIJ, SEQ ID NO: 2; Tet HIJK, SEQ ID NO: 3, Tet and no genes, empty plasmid control, numbers correspond to molecular weight markers. Lanes labeled Kanamycin (Kan) contains a variation of SEQ ID NO: 3 in which the tetracycline resistance cassette is replaced by a kanamycin resistance gene.

In FIG. 8B, the host strain was *E. coli* W3110 ΔwecA, as in FIG. 8A. The left lane in FIG. 8B corresponds to the molecular weight marker as in FIG. 8A. In FIG. 8B, total cell extracts from cells containing different chimeric clusters were treated with Proteinase K and analyzed by SDS PAGE and silver staining (left panel) and by anti CP5 immunoblotting after electrotransfer (right panel). The plasmids used contain the chimeric CP5 cluster indicated in SEQ ID NO: 3 either present in a modified pLAFR1 plasmid backbone containing a Kanamycin cassette instead of tetracycline (see FIG. 8A) or in pACYC containing a chloramphenicol resistance cassette.

Figure 9:
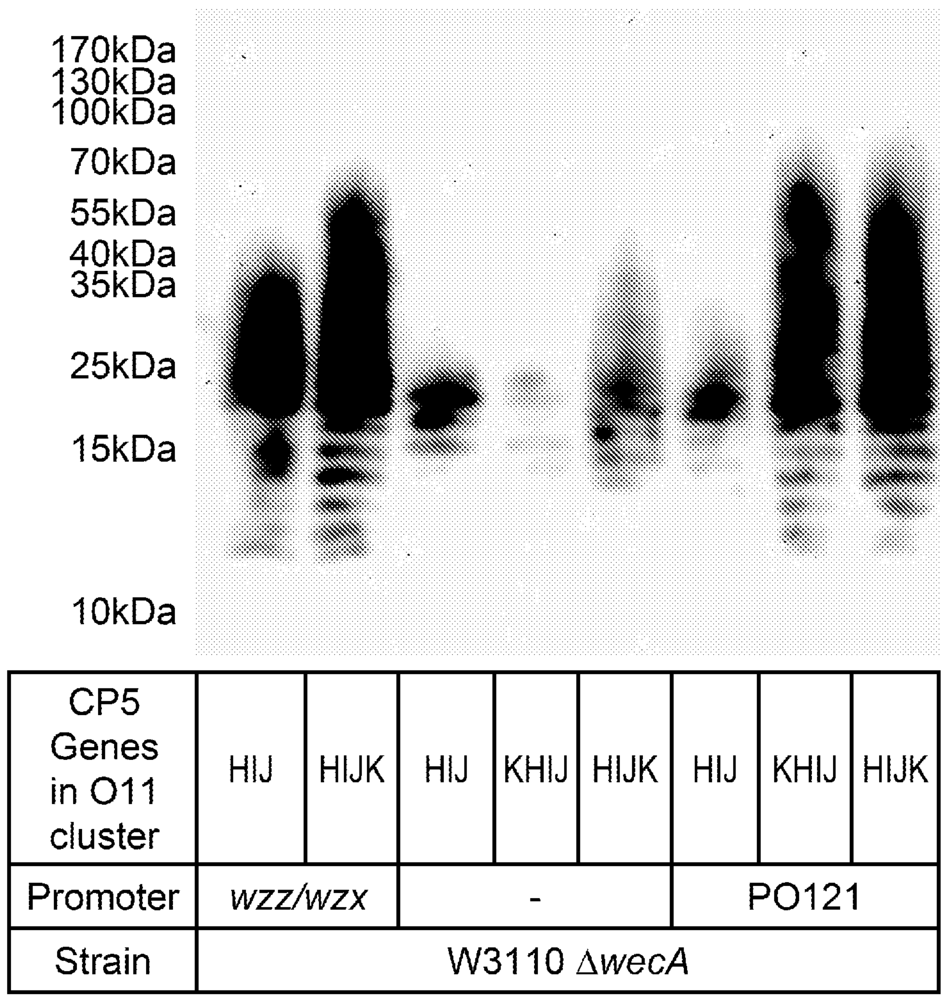
FIG. 9 depicts recombinant CP5 LPS production of an embodiment of the invention analyzed SDS PAGE and by immunodetection in dependence of promoter in front of the chimeric cluster in W3110 ΔwecA cells.

In addition different promoters were tested to express the chimeric O11-CP5 LPS. In these tests, the host strain was *E. coli* W3110 ΔwecA carrying the chimeric CP5 cluster. In this strain, the chimeric cluster replaced wecAwzzE genes. Total cell extracts from cells containing different chimeric clusters expressed from pLAFR1 were treated with Proteinase K and analyzed by SDS PAGE and anti CP5 immunoblotting after electrotransfer. The plasmids contained O11 clusters where wbjA and wzy were replaced by different *S. aureus* specificity genes (with a cat cassette) as indicated below the lanes in FIG. 9. In addition, the DNA in front of the cap5 specificity genes was changed and the effect on lipid glycosylation was analyzed. The effect of these different promoter regions was analyzed as depicted in FIG. 9. Wzz/wzx denotes the original genes (see FIG. 6) in front of the cap genes after the initial homologous recombination (FIG. 9 corresponding to the first two lanes). These two genes were removed (FIG. 9 corresponding to the three lanes in the middle) and replaced with the 0.6 kb region (PO121) (FIG. 9 corresponding to the three last lanes) in front of the *E. coli* O121 O-antigen cluster encoding a strong promoter sequence. Lanes denoted wzz/wzx and HIJ in FIG. 9 were derived from cells expressing SEQ ID NO: 2, lanes denoted wzz/wzx and HIJK derive from SEQ ID NO: 3. In FIG. 9, the molecular weight markers are indicated on the left of the gel frame.

As indicated FIG. 9, the results showed that a relevant promoter activity resides in the wzx gene (FIG. 9 first two lanes—wzz/wzx) and that it can be functionally replaced by a constitutive promoter from *E. coli*, e.g. the serovar O121 wb promoter (PO121 last three lanes in FIG. 9), without losing LPS production. Taken together, these results mean that the O11 and *S. aureus* elements for O11 O-antigen and CP5 capsular polymer production as described herein can be combined in many different *E. coli* expression systems resulting in production of recombinant *S. aureus* polysaccharide.

These results showed for the first time the production in *E. coli* of a capsular polysaccharide structure originating from a Gram-positive organism. This means that it was possible, contrary to prior art and conventional expectations, to combine the enzymes of the O11 cluster and the enzymes of *S. aureus* cap cluster to build up a chimeric polysaccharide, i.e. that the enzyme work together on the same structure in vivo.

Example 3

Molecular Structure Confirmation of the Recombinant Glycans

To confirm the activity of the chimeric CP5/O11 cluster in *E. coli* on a molecular level, a novel method allowing the analysis of UndPP linked sugars by using fluorescent labeling of the sugar at reducing end with 2-Aminobenzamide (2-AB) was developed. To enhance the analysis resolution, chimeric clusters were used containing deletions that increased the amount of unpolymerized RUs. Glycolipids from different *E. coli* cells expressing the chimeric cluster contained in the pLAFR1 plasmid and lacking the cap5K flippase (SEQ ID NO: 2) were analyzed as described below.

To extract UndPP-linked glycans, *E. coli* cells were washed with 0.9% NaCl and lyophilized. The dried cells were extracted once with 30 ml organic solvent (85 to 95% Methanol=M). The lyophilized cell pellet was further extracted twice with 5 ml Chloroform:Methanol:Water (C:M:W=10:10:3; v/v/v). The (M) extract was converted with chloroform and water to a final ratio of 3:48:47 (C:M:W). The 10:10:3 (C:M:W) extract was converted to a two-phase Bligh/Dyer (Bligh, E. G. and W. J. Dyer. 1959. A rapid method of total lipid extraction and purification. Can J Biochem Physiol 37(8): 911-7) system by addition of water, resulting in a final ratio of 10:10:9 (C:M:W). Phases were separated by centrifugation and the upper aqueous phase was kept for further processing.

To purify the extracted glycolipids, aqueous phase was subjected to a $tC_{18}$ Sep-PAK cartridge. The cartridge was conditioned with 10 ml methanol, followed by equilibration with 10 ml 3:48:47 (C:M:W). After loading of the sample, the cartridge was washed with 10 ml 3:48:47 (C:M:W) and eluted with 5 ml methanol and 5 ml 10:10:3 (C:M:W). The combined elutions were dried under $N_2$. The glycolipid samples were hydrolyzed by dissolving the dried samples in 2 ml n-propanol:2 M trifluoroacetic acid (1:1), heating to 50° C. for 15 min, and then evaporating to dryness under $N_2$ (Glover, K. J., E. Weerapana and B. Imperiali. 2005. In vitro assembly of the UndPP-linked heptasaccharide for prokaryotic N-linked glycosylation. Proc Natl Acad Sci USA 102 (40): 14255-9). The dried samples were labeled with 2-AB and the glycan cleanup was performed using the paper disk method as described (Bigge, J. C., T. P. Patel, J. A. Bruce, P. N. Goulding, S. M. Charles, R. B. Parekh. 1995. Nonselective and efficient fluorescent labeling of glycans using 2-amino benzamide and anthranilic acid. Anal Biochem 230(2): 229-38; Merry, A. H., D. C. Neville, L. Royle, B. Matthews, D. J. Harvey, R. A. Dwek and P. M. Rudd. 2002. Recovery of intact 2-aminobenzamide-labeled O-glycans released from glycoproteins by hydrazinolysis. Anal Biochem 304(1): 91-9). The 2-AB labeled glycans were separated by HPLC using a GlycoSep-N normal phase column according to Royle et al. but modified to a three solvent system (Royle, L., T. S. Mattu, E. Hart, J. I. Langridge, A. H. Merry, N. Murphy, D. J. Harvey, R. A. Dwek, P. M. Rudd. 2002. An analytical and structural database provides a strategy for sequencing O-glycans from microgram quantities of glycoproteins. Anal Biochem 304(1): 70-90). Solvent A was 10 mM ammonium formate pH 4.4 in 80% acetonitrile. Solvent B was 30 mM ammonium formate pH 4.4 in 40% acetonitrile. Solvent C was 0.5% formic acid. The column temperature was 30° C. and 2-AB labeled glycans were detected by fluorescence (excitation $\lambda ex=330$ nm, emission $\lambda em=420$ nm). Gradient conditions were a linear gradient of 100% A to 100% B over 160 min at a flow rate of 0.4 ml/min, followed by 2 min 100% B to 100% C, increasing the flow rate to 1 ml/min. The column was washed for 5 min with 100% C, returning to 100% A over 2 min and running for 15 min at 100% A at a flow rate of 1 ml/min, then returning the flow rate to 0.4 ml/min for 5 min. Samples were injected in water.

Dried fractions were resuspended in 5 ul 10% acetonitrile (ACN), 0.1% trifluoro acetic acid (TFA) and mixed 1:1 with matrix solution (40 mg/ml DHB in 50% ACN, 0.1% TFA) on the target plate. MS and MS/MS data were manually acquired in the positive ion mode on an Ultraflex-II MALDI-ToF/ToF mass spectrometer (Bruker Daltonik GmbH, Bremen, Germany). MS/MS were obtained using the LIFT method. A standard peptide mixture (Bruker Daltonik GmbH) was used for external calibration. Spectra were exported using the Flex Analysis software (Bruker Daltonik GmbH) and manually analyzed.

Figure 10A:
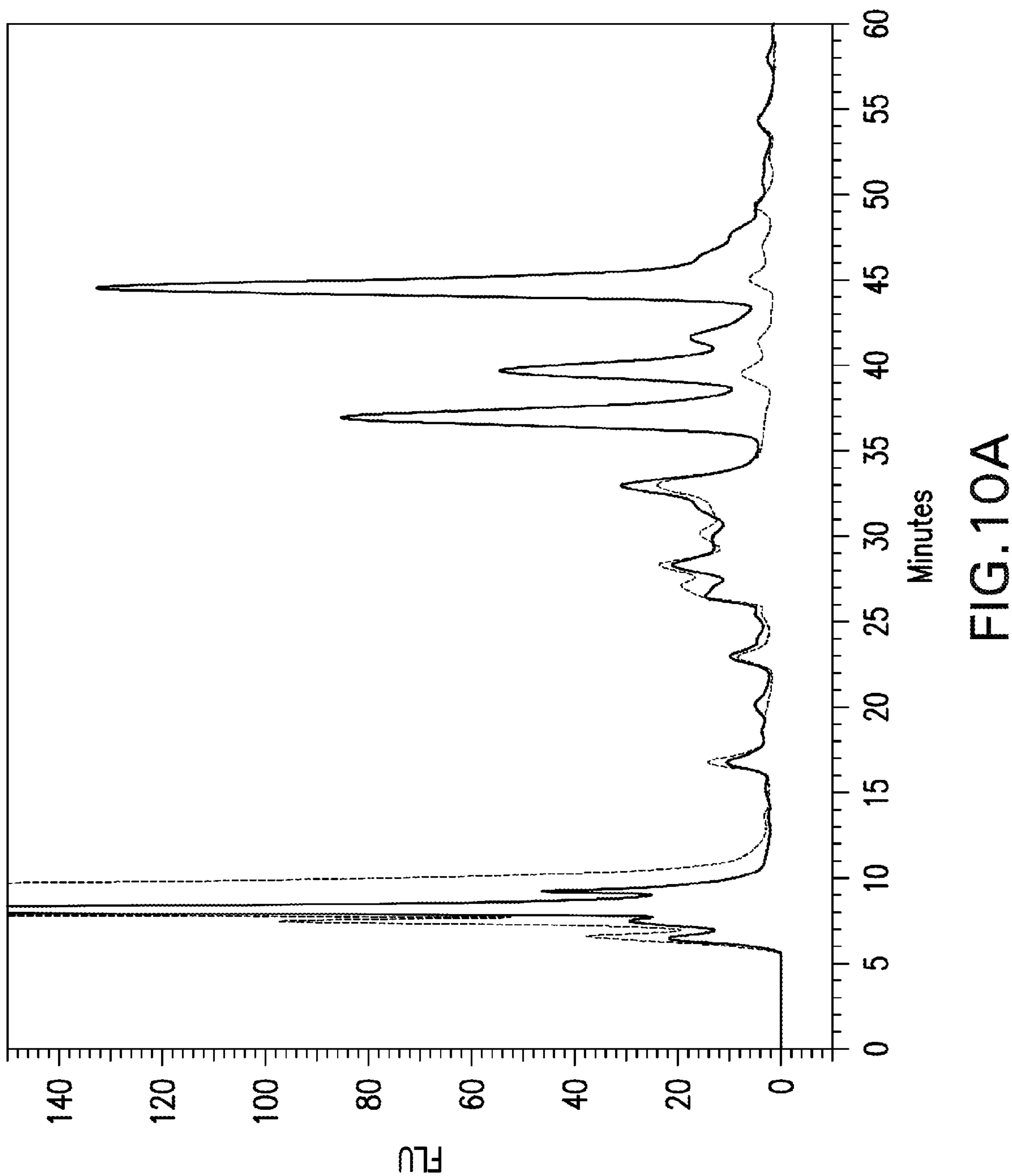
FIG. 10A shows the results of HPLC analysis of an embodiment of recombinant RU of CP5 of the present invention produced using the chimeric CP5 cluster (SEQ ID: 2).

Methanol extracts from *E. coli* W3110 ΔwecA (CP5) containing plasmids with (thick line) or without (thin, dashed line) the chimeric clusters were purified over tC18 cartridges and analyzed by normal phase HPLC. The fractions corresponding to the peaks shown in FIG. 10A found at 37', 40' and 45' elution were analyzed by MALDI-MS/MS. Samples eluting at 37 and 40 minutes were identified as recombinant CP5 RUs with and without the O-acetyl group attached, respectively. Sample eluting at 45 minutes was identified as non-acetylated *S. aureus* RU structure elongated by one deoxy-N-acetylhexosamine (as shown in FIG. 11E). In the CP5 chimeric cluster, cap5HIJ replaced the wbjA and wzy genes of the O11 cluster on pLAFR. The replacement contained the cat cassette in addition to the cap5HIJ genes (SEQ ID NO: 2).

Methanol extracts from *E. coli* W3110 ΔwecAwzzE containing plasmids with (thick line) or without (thin, dashed line) the chimeric cluster were purified over tC18 cartridges and analyzed by normal phase HPLC. FIG. 10B shows the results of HPLC analysis of recombinant RU of CP8 produced using a chimeric cluster (SEQ ID NO: 4 without polymerase). Peaks specific for cells expressing the recombinant sugar were identified at 23', 32', 38' and 45 of elution, collected and analyzed by MALDI-MS and MALDI-MS/MS. In the CP8 chimeric cluster, cap8HJK replaced the wbjA and wzy genes of the O11 cluster, i.e. a construct without the polymerase to accumulate single RU for analysis. The replacement contained the cat cassette in addition to the cap genes.

Figure 11A:
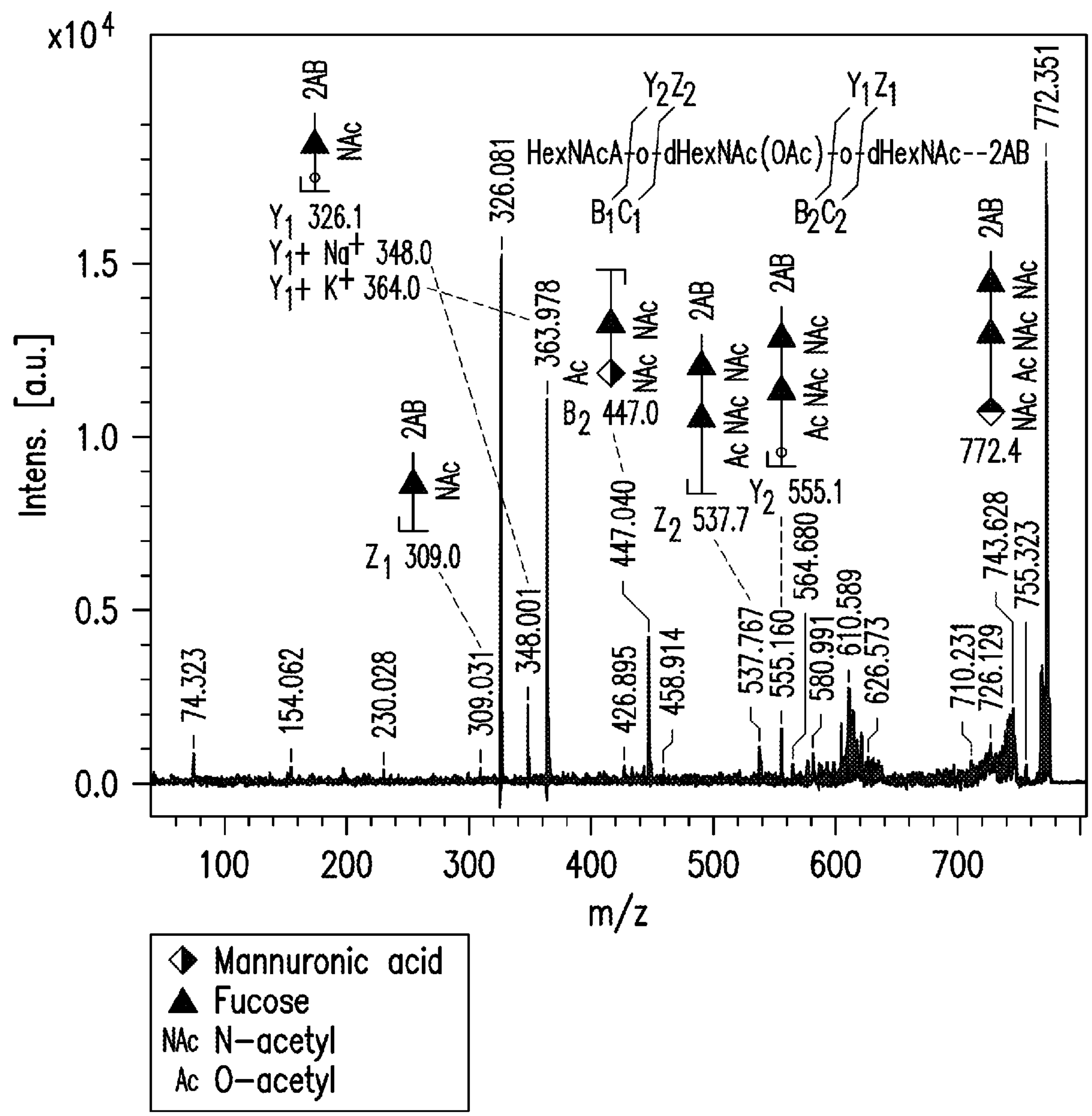
FIG. 11A shows the results of MALDI-MS/MS analysis of the specific peak generated by expression of an embodiment of the chimeric CP5 cluster of the present invention in *E. coli* eluting at 37 minutes seen in FIG. 10A.

FIG. 11A shows the results of MALDI-MS/MS analysis of the specific peak generated by expression of an embodiment of the chimeric CP5 cluster of the present invention in *E. coli* eluting at 37 minutes. The major mass m/z=772 ($[M+H]^+$) was selected and analyzed by MS/MS, which shows a fragmentation pattern consistent with the acetylated CP5 RU structure that was expected in light of the invention disclosed in this specification. The O-acetylated species are characterized by a specific loss of 42 plus the mass of the monosaccharide FucNAc (dHexNAc(OAc)) at the middle position of the RU. Fragment ions are indicated according to the nomenclature of the consortium for functional glycomics, CFG (www.functionalglycomics.org/static/consortium/Nomenclature.shtml). 2-AB, 2-aminobenzamide. The legend for the fragment ions is given in the inset of FIG. 11A.

Figure 11B:
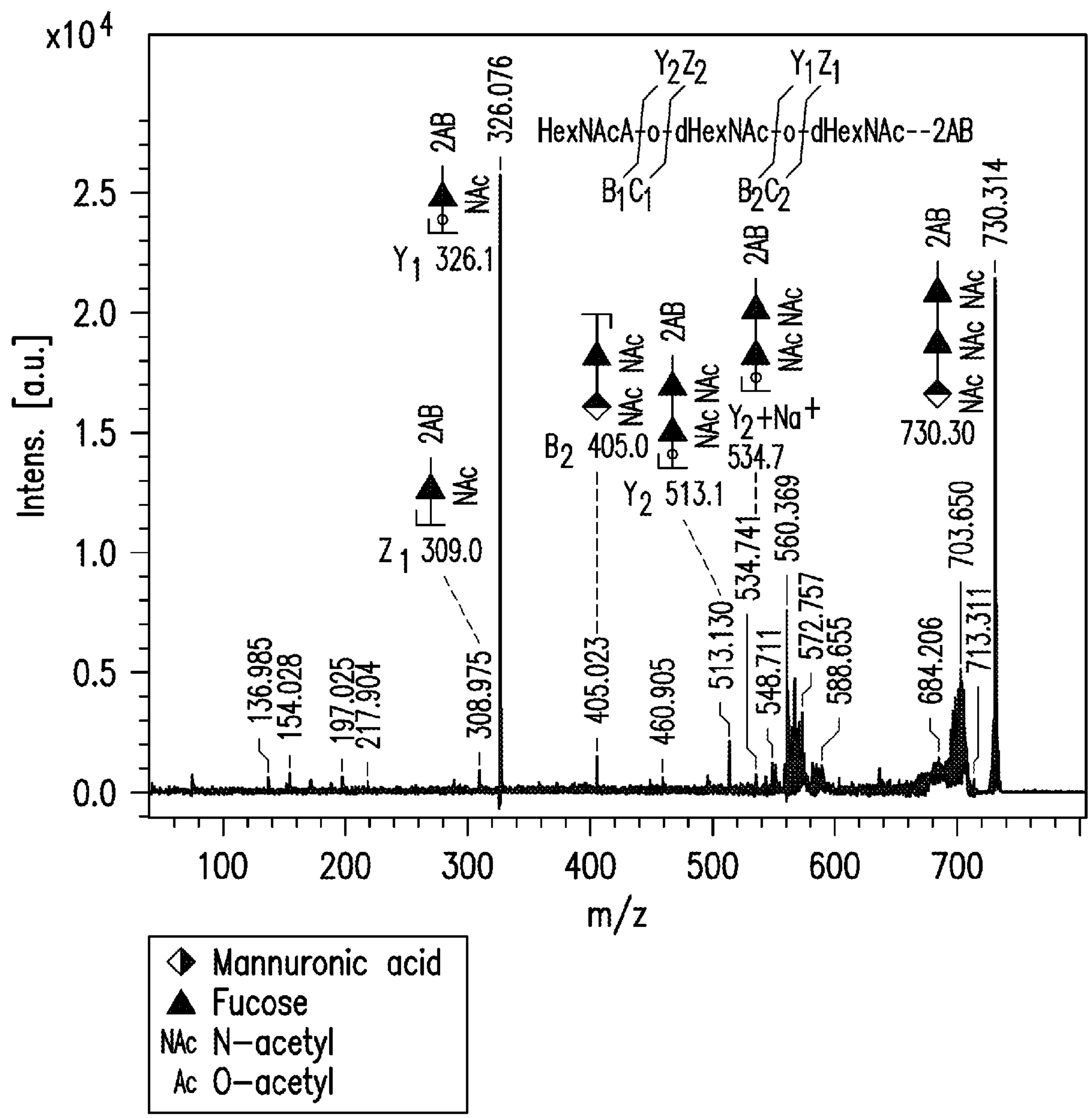
FIG. 11B shows the results of MALDI-MS/MS analysis of the specific peak generated by expression of an embodiment of the chimeric CP5 cluster of the present invention in *E. coli* eluting at 40 minutes seen in FIG. 10A.

FIG. 11B shows the results of MALDI-MS/MS analysis of the specific peak generated by expression of an embodiment of the chimeric CP5 cluster of the present invention in *E. coli* eluting at 40 minutes. The major mass of m/z=730 ($[M+H]^+$) was selected and analyzed by MS/MS, which shows fragmentation ion series consistent with the non-acetylated CP5 RU structure that was expected in light of the invention disclosed in this specification. 2-AB, 2-aminobenzamide. The legend for the fragment ions is given in the inset of FIG. 11B.

Figure 11C:
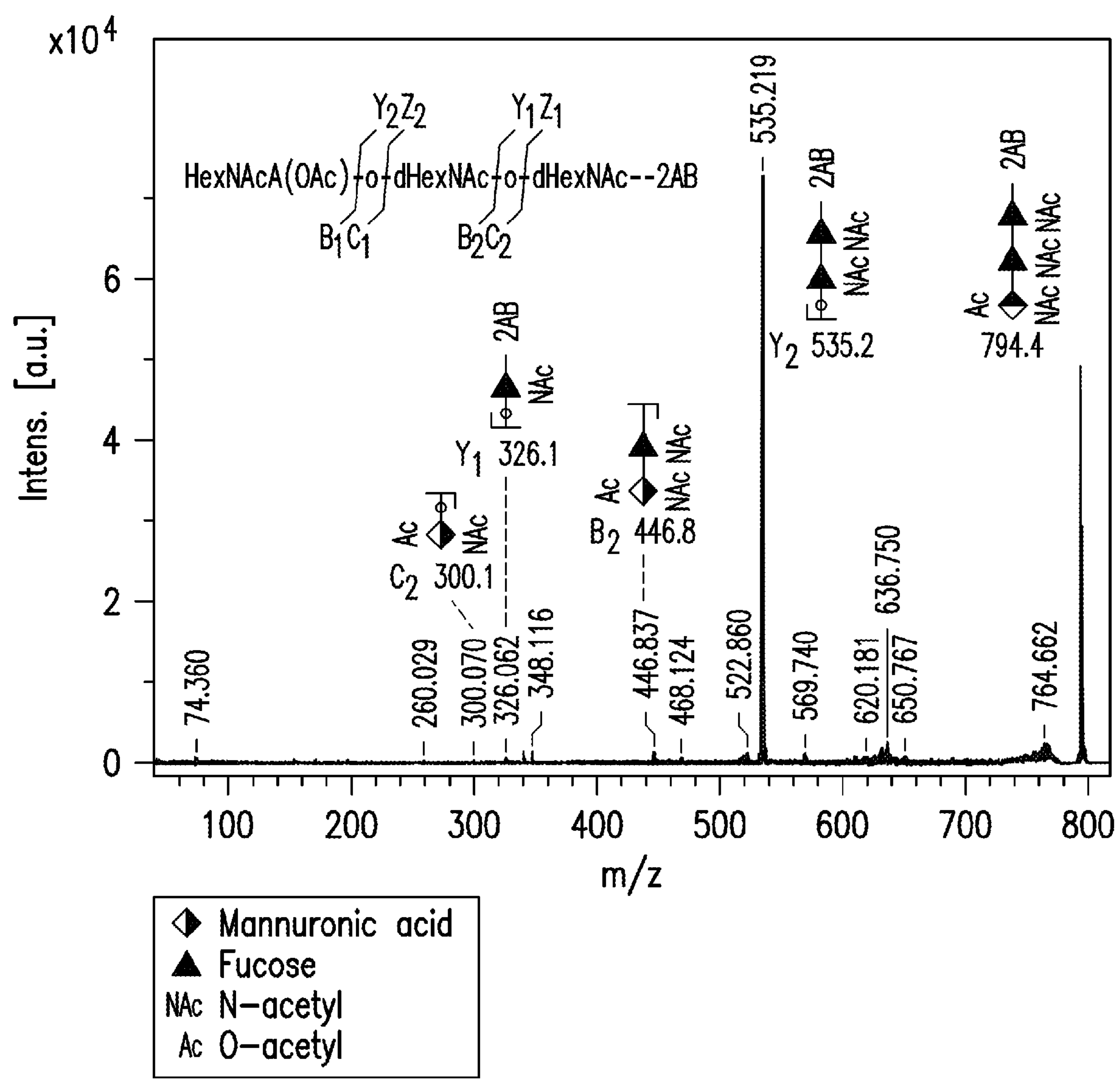
FIG. 11C shows the results of MALDI-MS/MS analysis of the specific peak generated by expression of an embodiment of the chimeric CP8 cluster of the present invention in *E. coli* eluting at 32 minutes seen in FIG. 10B.

FIG. 11C shows the results of MALDI-MS/MS analysis of the specific peak generated by expression of an embodiment of the chimeric CP8 cluster of the present invention in *E. coli* eluting at 32 minutes. A major mass of m/z=794 ($[M+Na]^+$) was selected and analyzed by MS/MS, which shows fragmentation ion series consistent with the acetylated CP8 RU structure that was expected in light of the invention disclosed by this specification. The O-acetylated species are characterized by a specific loss of 42 plus the mass of the monosaccharide ManNAcA (HexNAcA(OAc)) at the outermost position of the RU. Fragment ions are indicated according to the nomenclature of the CFG. 2-AB, 2-aminobenzamide. The legend for the fragment ions is given in the inset of FIG. 11C.

Figure 10B:
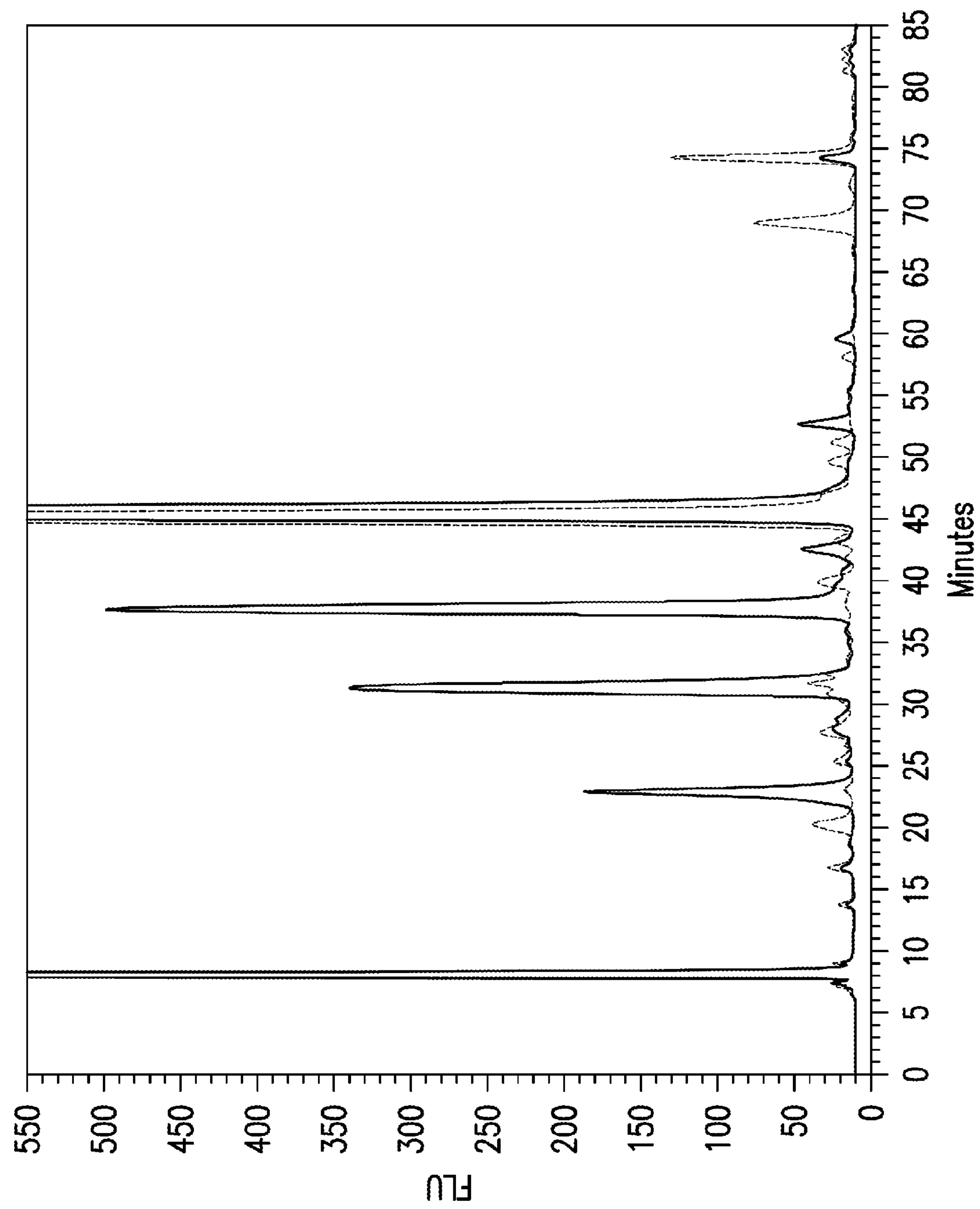
FIG. 10B shows the results of HPLC analysis of an embodiment of recombinant RU of CP8 of the present invention produced using a chimeric CP8 cluster lacking the cap8I polymerase.
Figure 11D:
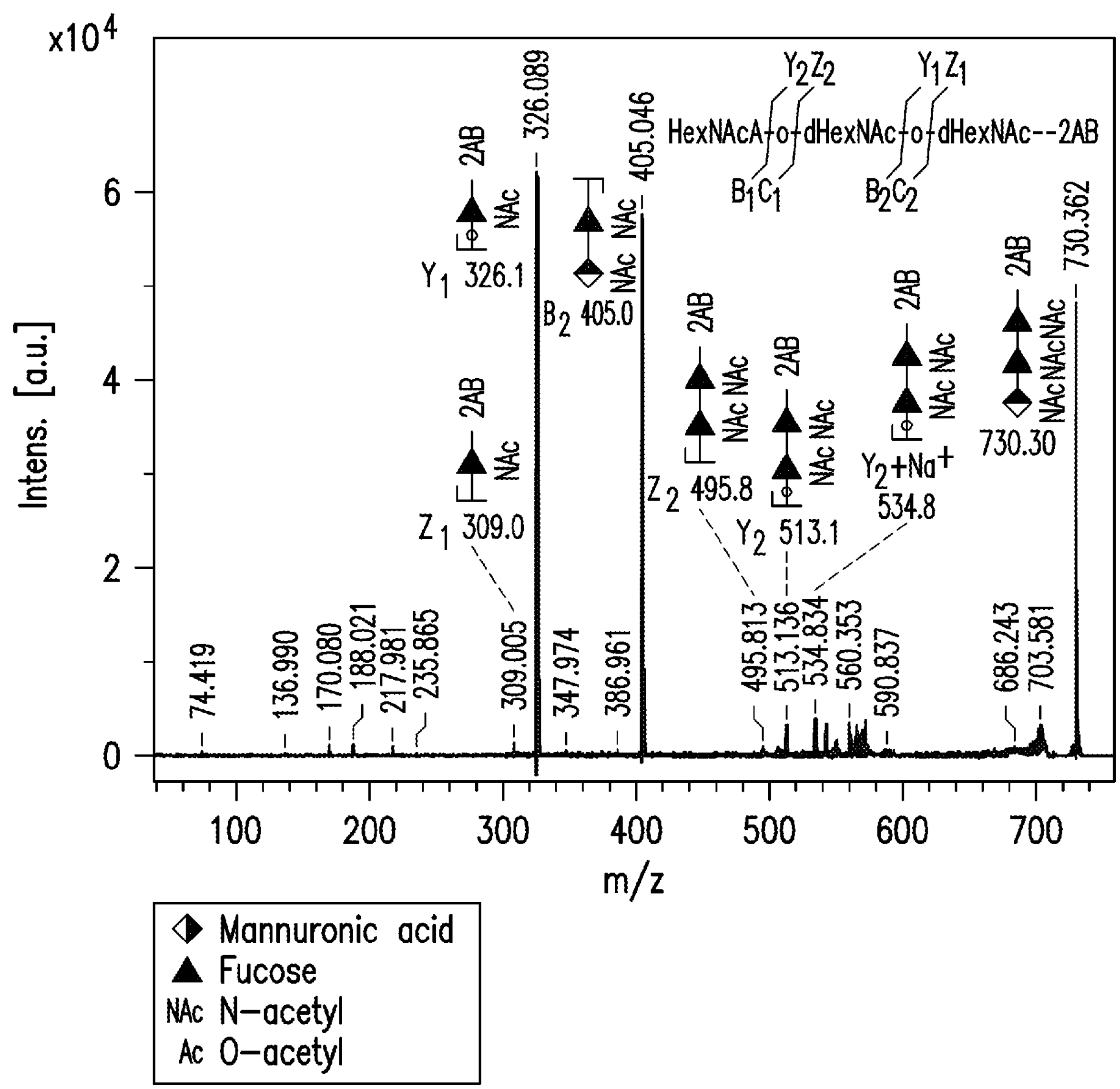
FIG. 11D shows the results of MALDI-MS/MS analysis of the specific peak generated by expression of an embodiment of the chimeric CP8 cluster of the present invention in *E. coli* eluting at 38 minutes seen in FIG. 10B.
Figure 11E:
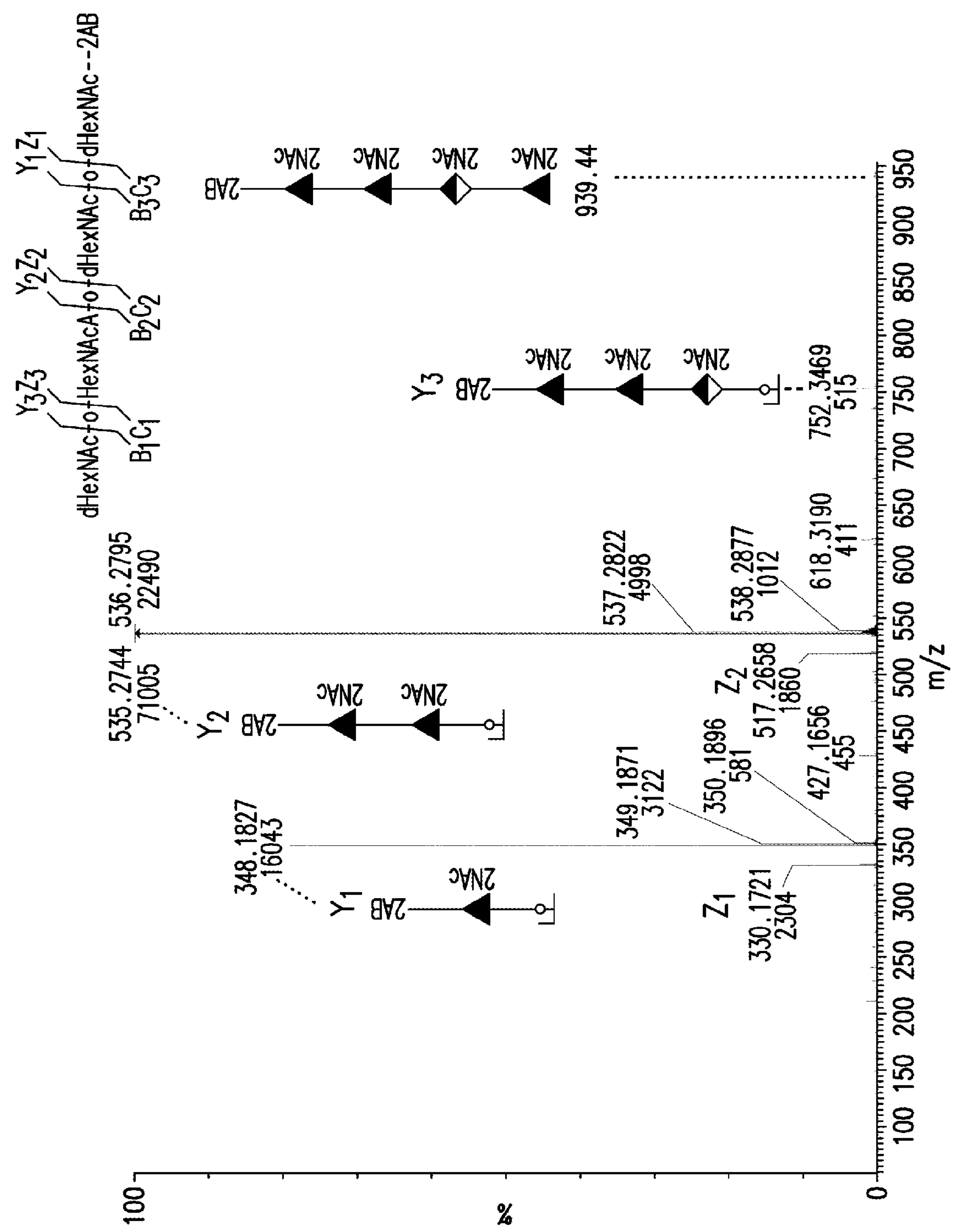
FIG. 11E shows the results of MALDI-MS/MS analysis of the specific peak generated by expression of an embodiment of the chimeric CP8 cluster of the present invention in *E. coli* eluting at 45 minutes seen in FIG. 10B.

FIG. 11D shows the results of MALDI-MS/MS analysis of the specific peak generated by expression of an embodiment of the chimeric CP8 cluster of the present invention in *E. coli* eluting at 38 minutes. The mass of m/z=730 ($[M+H]^+$) was selected and analyzed by MS/MS, which shows fragmentation ion series consistent with the non-acetylated CP8 RU structure that was also expected in light of the invention disclosed in this specification. Additional analysis showed that the later eluting peaks (shown in FIG. 10A at 40 min and FIG. 10B at 38 min) contain the non-O-acetylated trisaccharides of CP5 and 8 RUs. Fragment ions are indicated according to the nomenclature of the CFG. 2-AB, 2-aminobenzamide. The legend for the fragment ions is given in the inset of FIG. 11D.

MS results showed that the masses and fragmentation ion series are in agreement with the molecular structure of the CP5 RU oligosaccharide with the O acetylation of the middle FucNAc residue (i.e., the peak at 37' in FIG. 10A and in FIG. 11A) or without the O acetylation of the middle FucNAc residue (i.e., the peak 40' in FIG. 10A and in 11B). The signal at 45 minutes in FIG. 10A was identified as a tetrasaccharide, which is further analyzed below. The same analysis was repeated with the chimeric CP8 cluster that lacked the polymerase gene. In such extracts, signals consistent with the O-acetylated RU structure expected in light of the invention disclosed in this specification were found at 23' and 32' of elution, as shown FIGS. 10B and 11C. The presence of two different elution times for the same glycan sequence as identified by MALDI-MS/MS indicates an O-acetyl migration event taking place during sample preparation. Non-acetylated RUs were identified for CP5 and CP8 extracts at 40' and 38', as shown in FIGS. 11B and D, respectively. The CP5 and CP8 RU structures were present in different *E. coli* strains, including for example, W3110, W3310 ΔwecA, W3110 ΔwecAwzzE, and W3110 ΔwecAwzzE ΔwaaL.

Example 4

Improvement of the Repeating Unit Structure and its Analysis

The HPLC peak shown in FIG. 10B eluting at 45 minutes, derived from *E. coli* cells expressing the chimeric CP8 cluster (SEQ ID NO: 4) but lacking the wzy polymerase gene cap8I, was also analyzed by MALDI-MS/MS. The most intense ion in the full scan MS was m/z=939 ($[M+H]^+$) and sequence analysis was performed by MS/MS. The results of this MS/MS analysis are shown in FIG. 11E, and present a fragmentation ion series consistent with the non acetylated *S. aureus* capsular RU extended by a mass of a deoxy-N-acetylhexosamine at the non-reducing end, as expected in light of the invention disclosed in this specification. Fragment ions corresponding to the hypothetical structures are indicated according to the nomenclature of the CFG above the peaks. 2-AB, 2-aminobenzamide. The legend for the fragment ions is given in the inset of FIG. 11E.

The result shown in FIG. 11E suggested that an *E. coli* glycosyltransferase was able to modify the ManNAcA residue of the CP8 RU. Such an altered RU most probably would not be polymerized by cap8I. Analysis of the glycosyltransferase specificities in the *E. coli* host W3110 indicated that an enzyme from the ECA cluster may interfere with the recombinant sugar, specifically the wecF gene product, a putative 4-N-acetylfucosamine transferase. WecF naturally adds a 4-N-acetylfucosamine onto ManNAcA comprised in ECA, most likely the enzyme could also elongate CP8 and CP5 RU.

To solve this problem, another novel approach was developed. Specifically, genes of the ECA cluster located downstream of the wecC gene including wecF were deleted. This was accomplished using the method described by Datsenko et al. (Datsenko, K. A. and B. L. Wanner (2000). "One-step inactivation of chromosomal genes in *Escherichia coli* K-12 using PCR products." Proc Natl Acad Sci USA 97(12): 6640-6645). Different *E. coli* expression hosts were deleted in the waaL and rmlB-wecG gene regions and in some strains in wecA-wzzECA as well. Sep-PAK Purified extracts (Methanol and 10:10:3 extracts) from these mutated cells expressing the polymerase mutant CP8 chimeric cluster were analyzed by normal phase HPLC as described above.

Figure 11F:
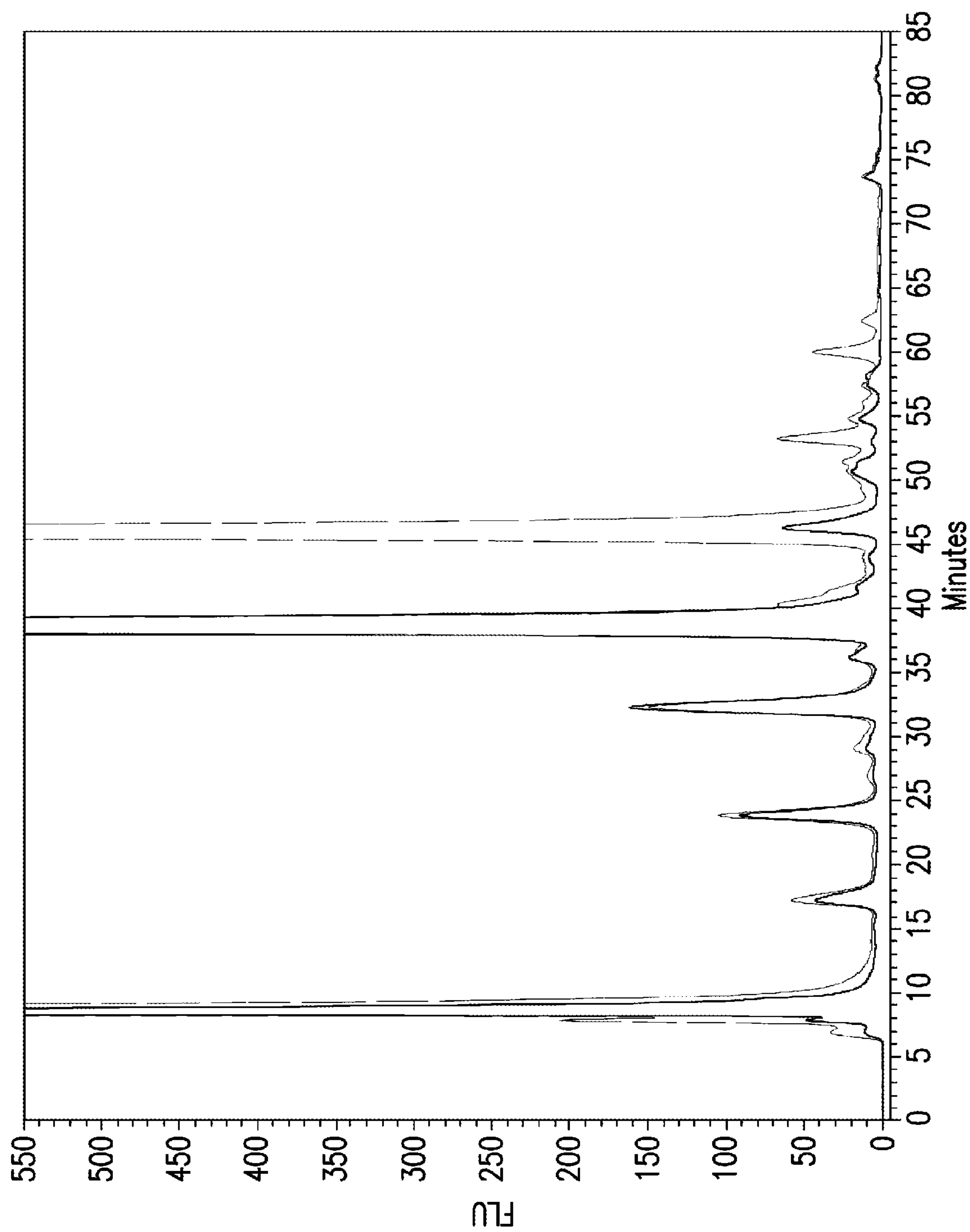
FIG. 11F shows the results of HPLC analysis of an embodiment of glycan structure optimization.

FIG. 11F presents the results of HPLC analyses of methanol extracts from *E. coli* W3110 ΔwaaL cells expressing the polymerase mutant of SEQ ID NO: 4 (thin, dashed line) compared to cells with an additional deletion of the ECA cluster genes rmlB-wecG (W3110 ΔwaaL ΔrmlB-wecG::cat) (thick line). Extracts were purified over tC18 cartridges and analyzed by normal phase HPLC. As shown in FIG. 11F, the major peak appearing at 45' in FIG. 10B was absent resulting in specific peaks for the acetylated and non acetylated CP8 RUs (FIG. 11F) indicating that one of the ECA glycosyltransferases—most probably wecF—is responsible for the aberrant elongation phenotype. Similar results were obtained when the CP5 chimeric cluster was tested in different strains. This implies that deleting *E. coli* borne glycosyltransferases and enzymes required for nucleotide activated sugar biosynthesis is a possible strategy for optimizing quality and quantity of recombinantly produced polysaccharides in *E. coli*. Target enzymes most likely would be encoded in the O-antigen cluster, the ECA cluster, and the colanic acid or capsule clusters.

Further evidence for the quality of the recombinant polysaccharide linked to UndPP was obtained from an optimized normal phase HPLC analysis of Sep-PAK purified, fluorescently labeled glycolipid extracts from chromosomally optimized expression hosts as described above. For optimal performance of the Sep-PAK columns for purification of charged CP5 and CP8 oligo- and polysaccharide-linked lipids, tert-butyl ammonium phosphate (TBAP) was added to the extracts before loading on the Sep-PAK cartridges. As reported by Trent, et al., the cation of this salt improves column binding of charged compounds by shielding negative charges with hydrophobic butyl chains (Trent, M. S., A. A. Ribeiro, et al. (2001). "Accumulation of a polyisoprene-linked amino sugar in polymyxin-resistant *Salmonella typhimurium* and *Escherichia coli*: structural characterization and transfer to lipid A in the periplasm." J Biol Chem 276(46): 43132-43144.). This optimized method was applied to the CP5 and CP8 samples obtained by methanol extraction from cells expressing CP5 or CP8 chimeric clusters containing a polymerase.

Figure 11G:
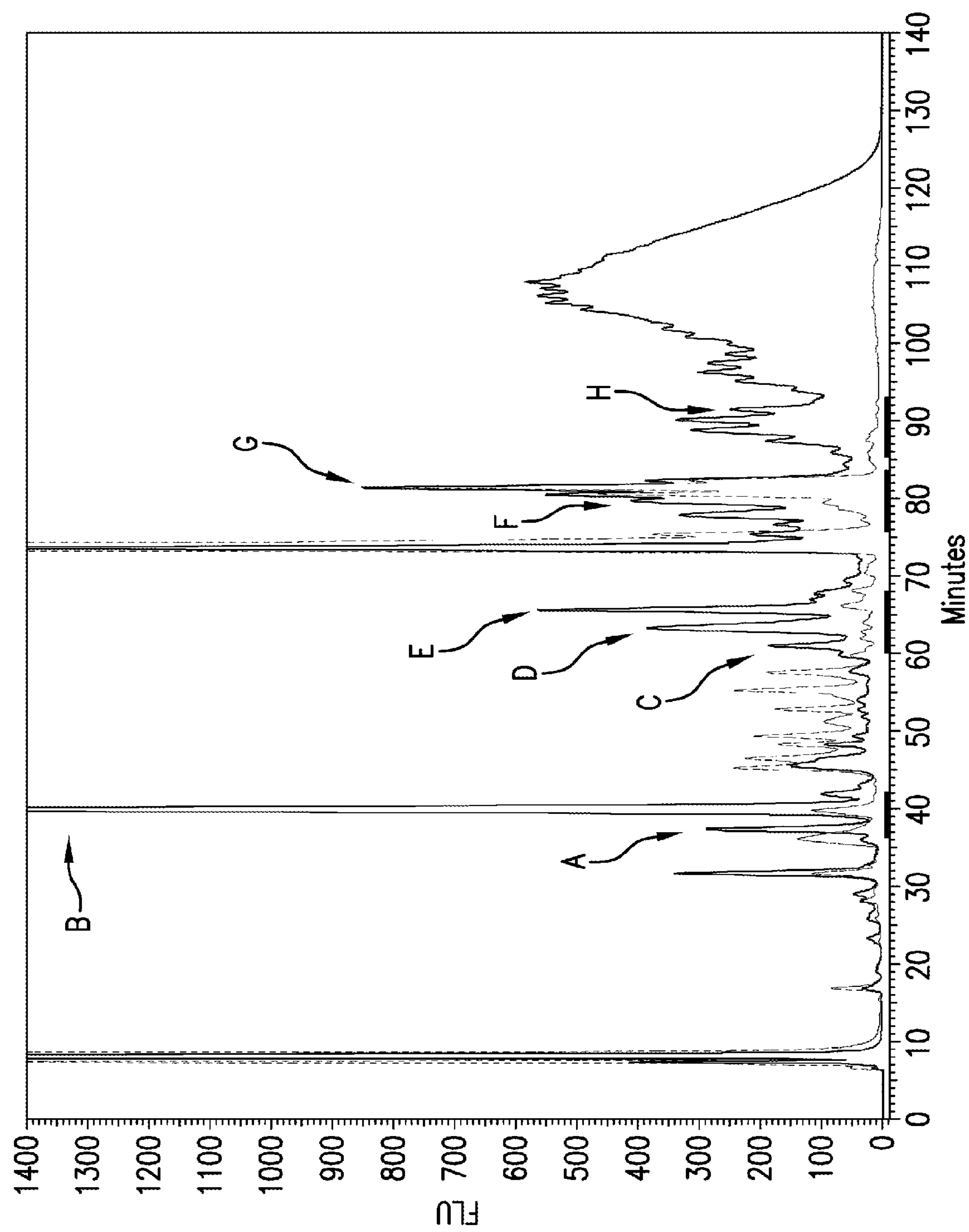
Figures 1, 11G:
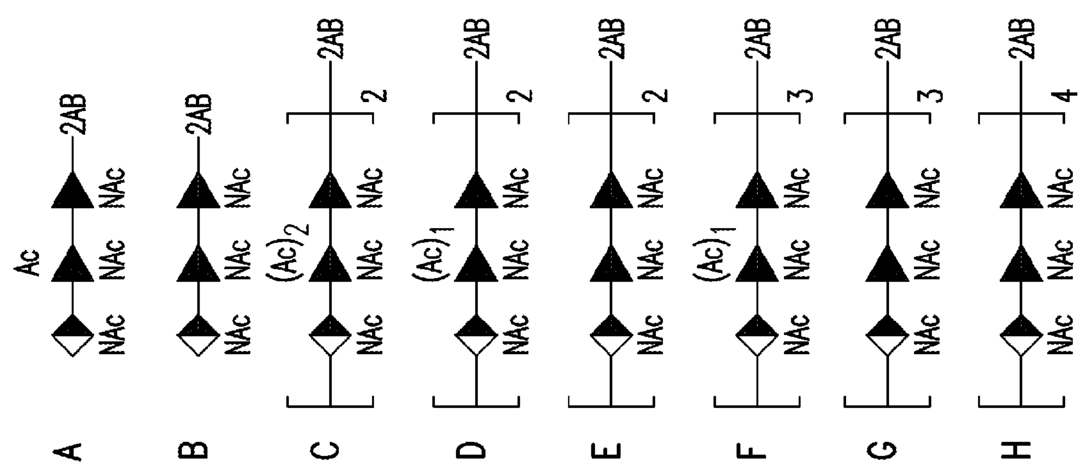

FIG. 11G provides the results of HPLC analysis showing the full CP5 glycan repertoire present on UndPP in *E. coli* cells. Methanol extracts from *E. coli* W3110 ΔwaaL ΔwecAwzzECA ΔrmlB-wecG::cat either expressing the chimeric CP5 cluster SEQ 3 (solid line) or an empty plasmid control (dashed line) were solid-phase extracted on Sep-PAK cartridges and treated with mild acid to hydrolyse sugars from UndPP. The resulting material was reacted with 2AB by reductive amination to label reducing ends of the glycans and analyzed by normal phase HPLC. Signals present in the solid line but not in the dashed line represent CP5 specific material. Capital letters indicate peaks containing polymers of the acetylated and/or non-acetylated CP5 RU as identified by MALDI-MS/MS of the collected fractions. The legend of FIG. 11G indicates the proposed molecular structures as deduced from MS/MS analysis. It should be noted that acetylated and non-acetylated RU polymers shown for MS/MS confirmed structures of the same polymerization degree group together in the chromatogram as indicated by thick bars. Capital letters show the following lengths: A and B: one RU; C, D and E: two RUs; F and G: three RUs; and H: four RUs. The broad peak between 95' and 125' in FIG. 11G most probably represents 5 or more polymerized RUs not resolved by the column.

Figure 11H:
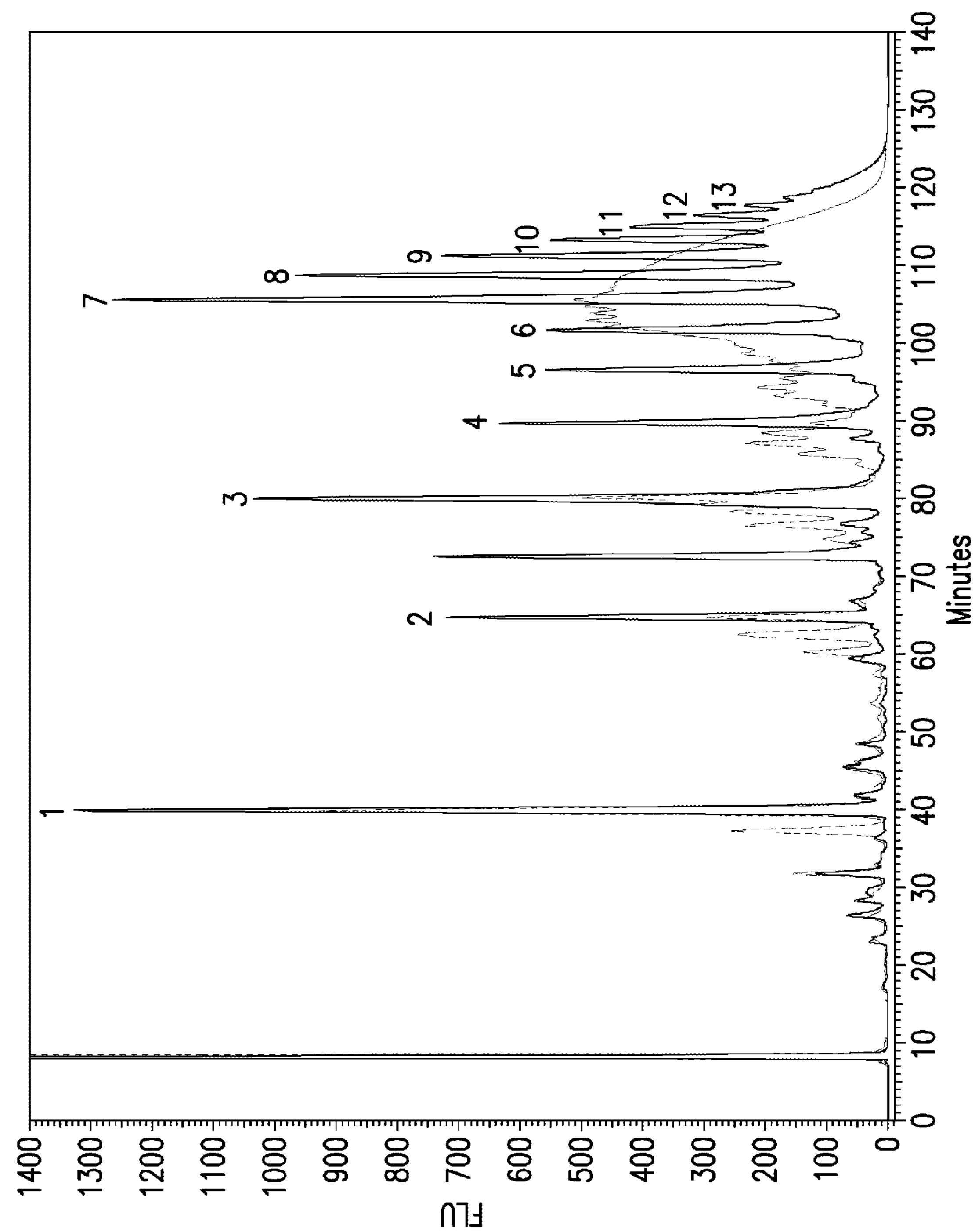
FIG. 11H presents the results of HPLC analysis of deacetylated CP5 glycans and RU homogeneity in an embodiment of the invention.

FIG. 11H presents further HPLC results, showing acetylated CP5 glycans and RU homogeneity. To prepare this HPLC analysis, 2AB labeled glycan samples of *E. coli* W3110 ΔwaaL ΔwecAwzzECA ΔrmlB-wecG::cat expressing the chimeric CP5 cluster SEQ ID NO.: 3 (prepared according to the procedures described above with reference to FIG. 11G) were treated with NaOH in aqueous solution and re-labeled. As showing in FIG. 11H, samples before (dashed) and after (solid line) alkali treatment were analyzed by HPLC. Numbers in FIG. 11H indicate the putative numbers of RUs in the corresponding peaks. It should be observed that, in FIG. 11H, the acetylated peaks shown in FIG. 11G unify in the signal from non-acetylated polymer, and that deacetylation resolved the RU units in the elution times after 95 minutes.

Figure 11I:
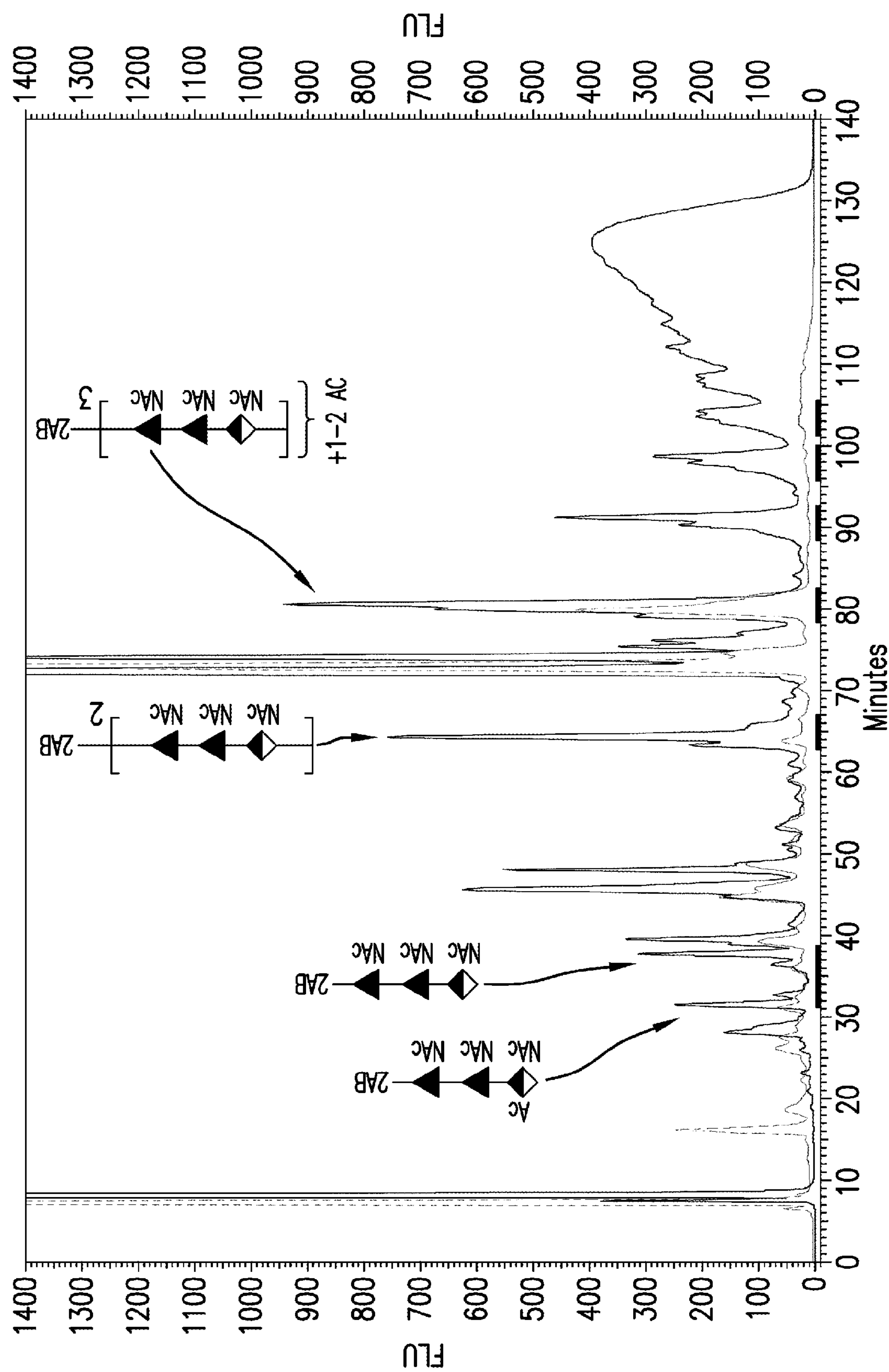
FIG. 11I provides the results of HPLC analysis of the CP8 glycan repertoire present on UndPP in *E. coli* cells in an embodiment of the present invention.

FIG. 11I provides the results of HPLC analysis showing the CP8 glycan repertoire present on UndPP in *E. coli* cells. Methanol extracts from *E. coli* W3110 ΔwaaL ΔwecAwzzECA ΔrmlB-wecG::cat either expressing the chimeric CP8 cluster SEQ ID NO.: 4 (solid line) or an empty plasmid control (dashed line) were solid-phase extracted on Sep-PAK cartridges and treated with mild acid to hydrolyse sugars from UndPP. The resulting material was reacted with 2AB by reductive amination to label reducing ends of the glycans and analyzed by normal phase HPLC. Signals present in the solid line but not in the dashed line represent CP8 specific material. Putative structures of acetylated and/or non-acetylated CP8 RU as identified by MALDI-MS/MS of the collected fractions are indicated. Note that as in the HPLC results with CP5 shown in FIG. 11G, acetylated and non acetylated CP8 RU polymers of the same polymerization degree group together in the chromatogram of FIG. 11H as indicated by thick bars. Material detected after 110' represents longer CP8 polymers.

Figure 11J:
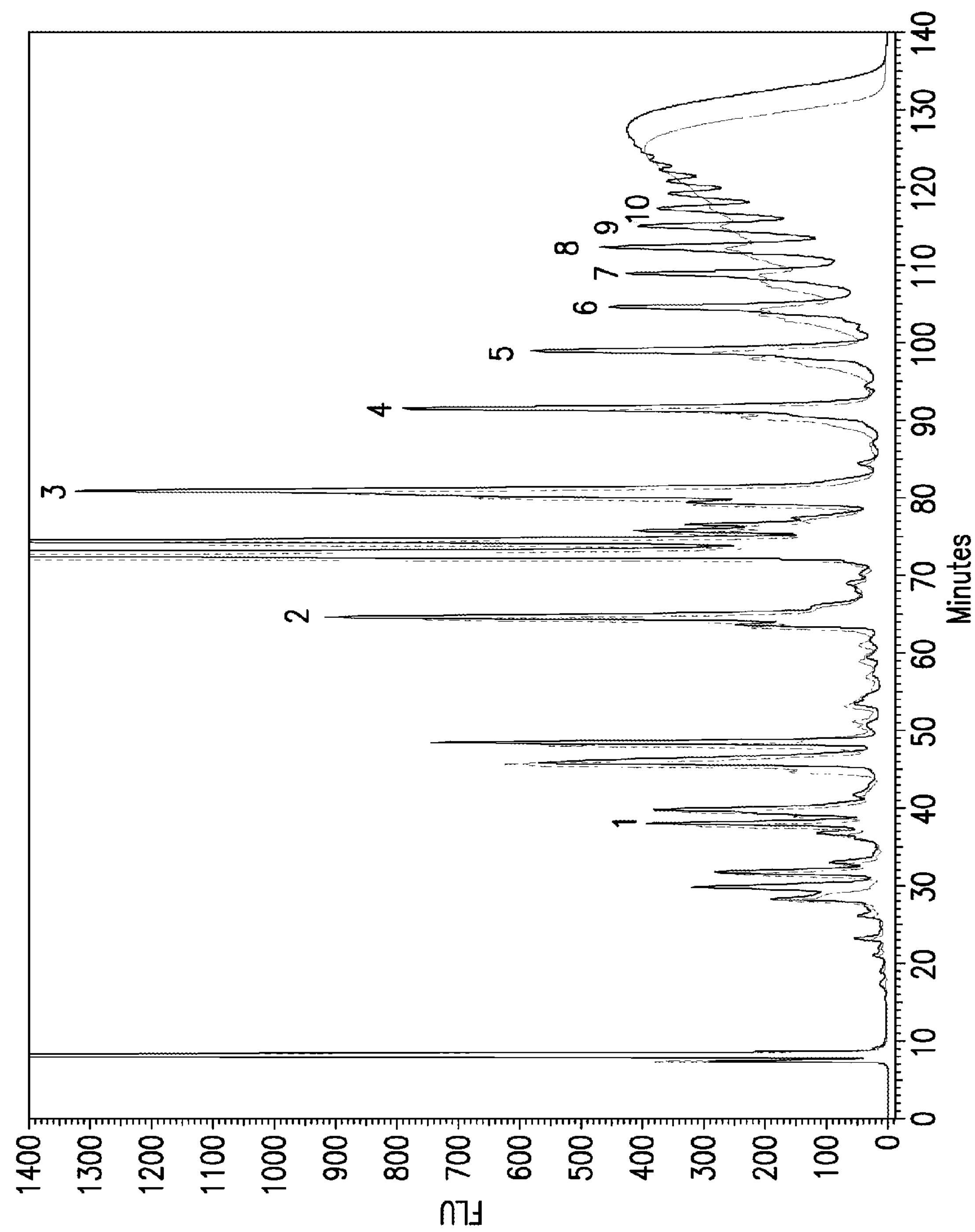
FIG. 11J shows HPLC results, in an embodiment of the present invention, of deacetylation of CP8 glycans and RU homogeneity.

FIG. 11J presents further HPLC results, showing deacetylation of CP8 glycans and RU homogeneity. 2AB labeled glycan samples from *E. coli* W3110 ΔwaaL ΔwecAwzzECA ΔrmlB-wecG::cat expressing the chimeric CP8 cluster SEQ ID NO.: 4 were treated with NaOH in aqueous solution and re-labeled. Samples before (dashed) and after (solid line) alkali treatment were analyzed by HPLC. Numbers indicate the putative numbers of RUs in the corresponding peaks. It should be noted that the acetylated peaks largely vanish and that signals of non-acetylated polymer increase, and that deacetylation resolved the RU units in the elution times after 110 minutes.

FIGS. 11H and 11J show HPLC results indicative of the characteristic ladder-like banding pattern of O-antigens when alkali treatment was performed on these CP5 and CP8 samples to remove the acetylation modifications from the oligo- and polysaccharides. The results show discrete sharp peaks with constantly decreasing elution time increments. This implies that such analyzed carbohydrate chains are linear polymers composed of identical RUs. This data shows that the recombinant CP5 and CP8 sugars produced in *E. coli* are regularly polymerized and partially acetylated. Non-acetylated CP5 and CP8 polymers elute similarly from the HPLC column as expected from their similarity in structure; however the normal phase chromatography also reveals differences: for example, CP5 polymerizes to a lesser extent than CP8, and acetylation is more frequent in CP5; in the RU lengths above 4, CP5 has a clear preference for making polymers of 7 RUs, whereas CP8 polymerizes to a broader degree; and as indicated by the HPLC and MS/MS results, CP5 is more efficient for glycan production than CP8.

In wzy dependent polymerization pathways, it has been reported by Marolda, et al., that a specific enzyme (wzz or cld for chain length determinant) is responsible for determining the average number of RU polymerization steps performed (Marolda, C. L., L. D. Tatar, et al. (2006). "Interplay of the Wzx translocase and the corresponding polymerase and chain length regulator proteins in the translocation and periplasmic assembly of lipopolysaccharide o antigen." J Bacteriol 188(14): 5124-5135.). Wzz enzymes cause a specific repeat number averages, e.g. short, long and very long sugar polymers and are known to transfer their length specificity to exogenous polysaccharide pathways. The lengths and amounts of the CP8 glycolipids were analyzed in the production strain resulting in longer and lower amount of this sugar. To increase the amount of molecules and thereby the sugar transfer efficiency for protein glycosylation, a downregulation of the CP8 sugar length was performed using a specific Wzz enzyme.

Figure 11K:
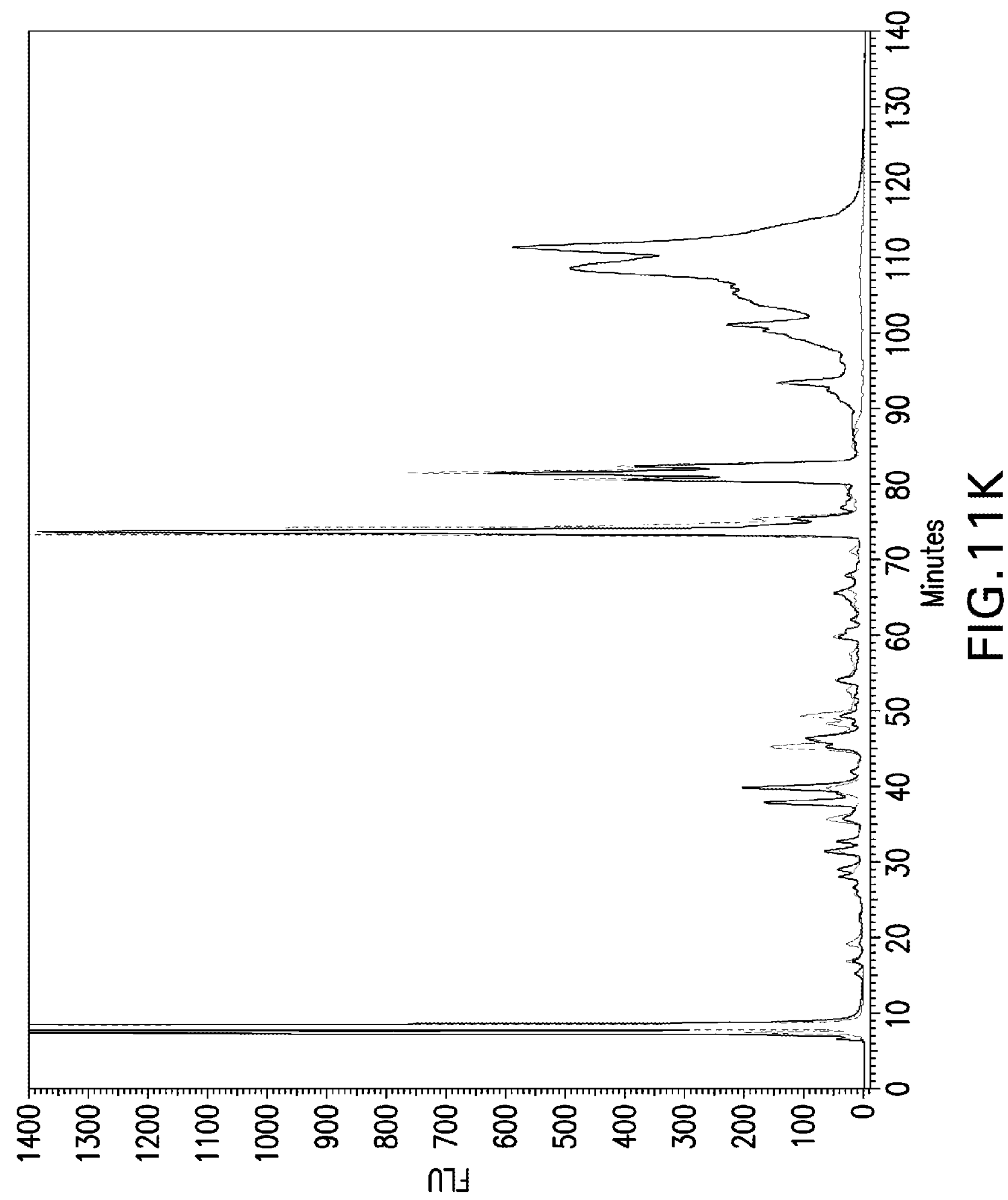
FIG. 11K presents HPLC results showing reduction in RU polymerization and increase in LLO induced by co-expression of wzzO7 with the CP8 chimeric cluster in an embodiment of the present invention.

To test the effect of a Wzz protein on the size and amounts of CP8 sugars on lipid, coexpression of Wzz from *E. coli* wzz O7 was performed from a separate plasmid (SEQ ID NO: 19). FIG. 11K presents the results of this test. Methanol extracts from *E. coli* W3110 ΔwaaL ΔwecAwzzECA ΔrmlB-wecG::cat either expressing the chimeric CP8 cluster SEQ ID NO: 4 and a plasmid borne, IPTG inducible copy of wzzO7 (SEQ ID NO: 21, solid line), or an empty plasmid control (dashed line) were solid phase extracted on Sep-PAK cartridges and treated with mild acid to hydrolyse sugars from UndPP. 2AB labeled glycans were analyzed by normal phase HPLC. Alkali treatment of the CP8 sample showed that more than 85% of the area between 95 and 115' represents 7 or 8 RU polymers of CP8, indicating a wide variety of acetylation. These results also indicate that the chimeric CP8 cluster induced: a) an intensification in repeat numbers of the most abundant glycan from 7 to 8, and b) a higher overall intensity of fluorescent signal as judged from the area under the chromatogram.

Alkali treatment confirmed the acetylation of the shortened glycan as in FIGS. 11I and 11J indicating that a recombinant polysaccharide's length can be regulated by a foreign Wzz enzyme. It is also possible to regulate the capsular sugar polymer length by an O-antigen derived Wzz enzyme. Furthermore, different promoters in front of the chimeric cluster when present on a plasmid cause different expression levels and different degrees of polymerization.

Example 5

Protein Glycosylation with the CP5 and CP8 Glycans and Product Characterization Different variants of the chimeric cluster were tested for bioconjugate production. The chimeric O11/CP5 gene clusters (SEQ ID NO: 2 and 3), which contain different variants of *S. aureus* specificity regions in the O11 O-antigen cluster in place of wbjA and wzy, were expressed in the host strain *E. coli* W3110 ΔwaaL ΔwecAwzzE::cat in the presence of PglB (SEQ ID NO: 27?) and EPA (SEQ ID NO: 13). W3110 ΔwaaL ΔwecAwzzE::cat host cells expressed EPA with two glycosylation sites (from SEQ ID NO: 13) and PglB (SEQ ID NO: 27) from separate plasmids in addition to the pLAFR1 plasmid with the O11 O-antigen cluster where the wbjA and wzy genes were replaced with different cap5 gene sets (and the cat cassette, SEQ ID NO: 2 and SEQ ID NO: 3).

The EPA protein is expressed containing: a) a N-terminal signal peptide sequence for export to the periplasm, b) two bacterial N-glycosylation consensus sequences engineered into the protein sequence (SEQ ID NO: 13) as set forth in Example 10 of WO 2009/104074, incorporated by reference herein in its entirety, and c) a hexa histag for purification. The cells were grown in 5 L Erlenmeyer flasks in LB medium. An overnight culture was diluted to $OD_{600nm}$=0.05. At $OD_{600nm}$ around 0.5, PglB expression was induced by addition of 1 mM IPTG and EPA expression was induced by addition of arabinose (0.2% final concentration). The cells were grown for 4 hours, induction was repeated and cells were grown for around additional 16 hours. Cells were pelleted by centrifugation; the cells were washed and suspended in 0.2 vol sucrose buffer, pelleted, and lysed by osmotic shock. The spheroplasts were pelleted by centrifugation, and the periplasmic proteins were loaded on a $Ni^{2+}$ affinity chromatography. EPA-CP5 bioconjugate without and with the *S. aureus* flippase gene cap5K (SEQ ID NO: 2 and 3) was eluted by 0.5M imidazole, and eluted peaks were pooled and analyzed by SDS PAGE and stained by Coomassie and silver (FIG. 12).

Figure 12:
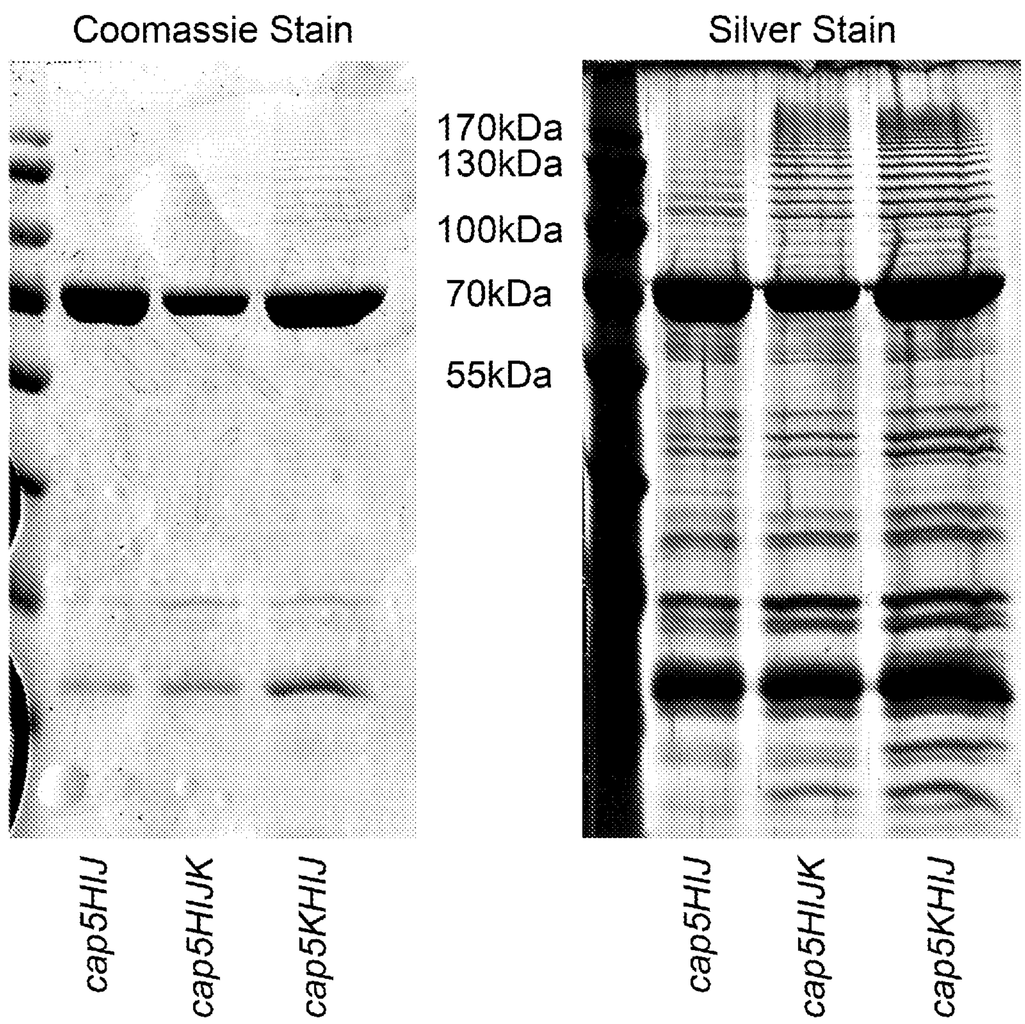
FIG. 12 shows the results of SDS-PAGE analysis of $Ni^{2+}$ affinity chromatography purified EPA-CP5 bioconjugate from cells in embodiments of the present invention without and with the *S. aureus* flippase gene cap5K (SEQ ID NO: 2 and 3).

FIG. 12 presents the SDS PAGE results. The left panel shows the coomassie stain, and the right panel shows the silver stain. The numbers in the middle indicate the sizes of the molecular weight marker. The letters below the lanes indicate the genes that were present in the chimeric cluster expressed in the strains used for bioconjugate production. The host strain was *E. coli* W3110 ΔwaaL ΔwecAwzzE::cat. The results show protein signal at 70 kDa (electrophoretic mobility) most likely corresponding to unglycosylated EPA, and a ladder of bands above (100-170 kDa). The ladder likely corresponds to EPA protein glycosylated with the CP5 recombinant *S. aureus* glycan. In addition, the results indicate that including the flippase gene in the system increases the glycoprotein yield (middle and right lanes).

In a separate analysis, CP5-EPA bioconjugate was produced in *E. coli* W3110 ΔwaaL ΔwecAwzzE::cat by co-expression of the chimeric CP5 gene cluster (SEQ ID NO: 3), PglB (SEQ ID NO: 27) from plasmid pEXT21 and EPA (containing two glycosylation sites, SEQ ID NO: 13) from separate plasmids. To obtain a more controlled process for bioconjugate production, the cells were grown in a 2-L bioreactor to an $OD_{600\ nm}$=30 at 37° C., and expression of PglB and EPA was induced by the addition of 1 mM IPTG and 0.2% arabinose. The cells were grown for 18 h at 37° C. under oxygen-limiting conditions. The cells were pelleted by centrifugation, washed and resuspended in 25% sucrose buffer at an $OD_{600\ nm}$=200, after 30 min. incubation at 4° C., the suspension was pelleted, and lysed by osmotic shock. The spheroplasts were pelleted by centrifugation, and the periplasmic proteins present in the supernatant were loaded on a $Ni^{2+}$ affinity chromatography. Glycosylated and unglycosylated EPA were eluted from the affinity column by 0.5 M imidazole and loaded on a SourceQ anionic exchange column. Glycosylated EPA was separated from unglycosylated EPA by applying a gradient of increasing concentration of NaCl.

Figures 13A, 13B:
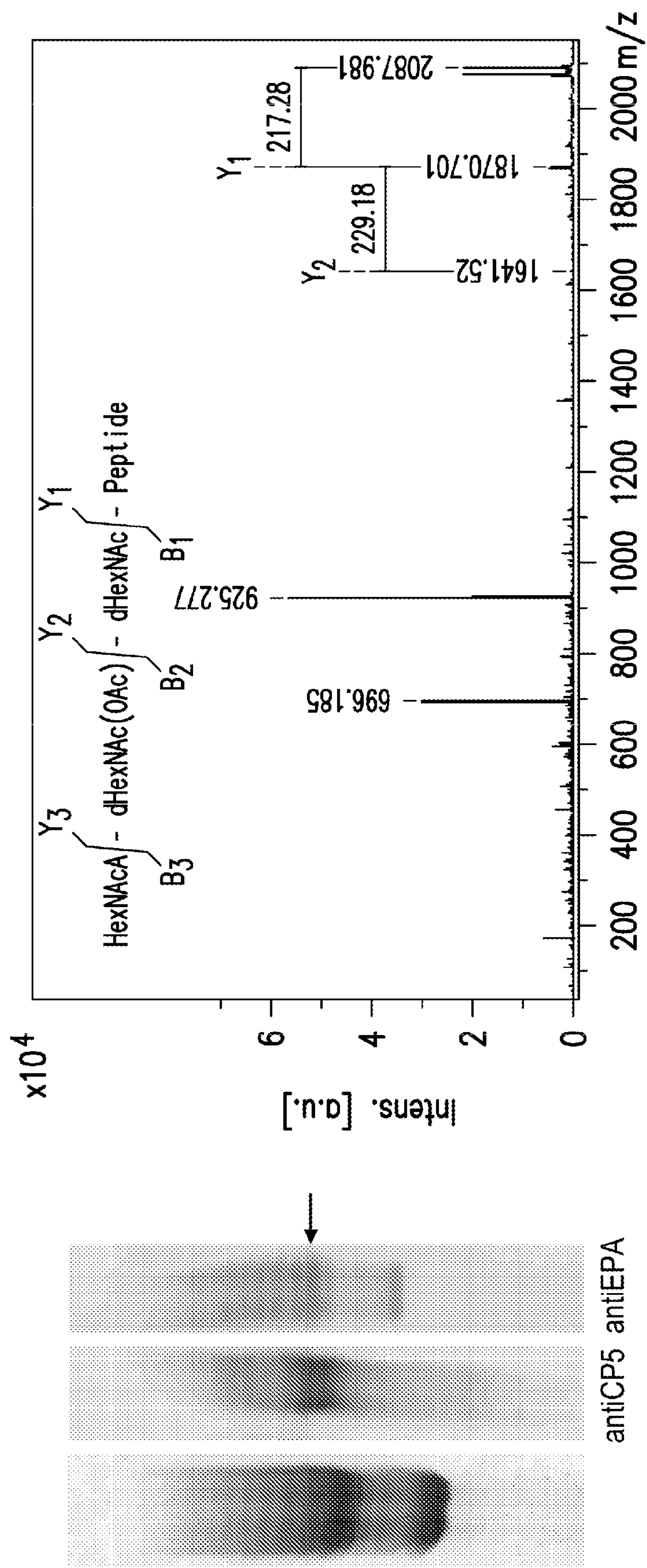
FIG. 13A presents analysis of CP5-EPA bioconjugate according to an embodiment of the present invention purified by $Ni^{2+}$ affinity chromatography and anionic exchange chromatography.
FIG. 13B depicts M/Z masses found for the glycosylation site in trypsinized peptide DNNNSTPTVISHR N-glycosidically linked to the O-acetylated RU mass (m/z=2088 ($[M+H]^+$)) according to an embodiment of the present invention. The inset illustrates the RU structure attached to the peptide.
Figure 13C:
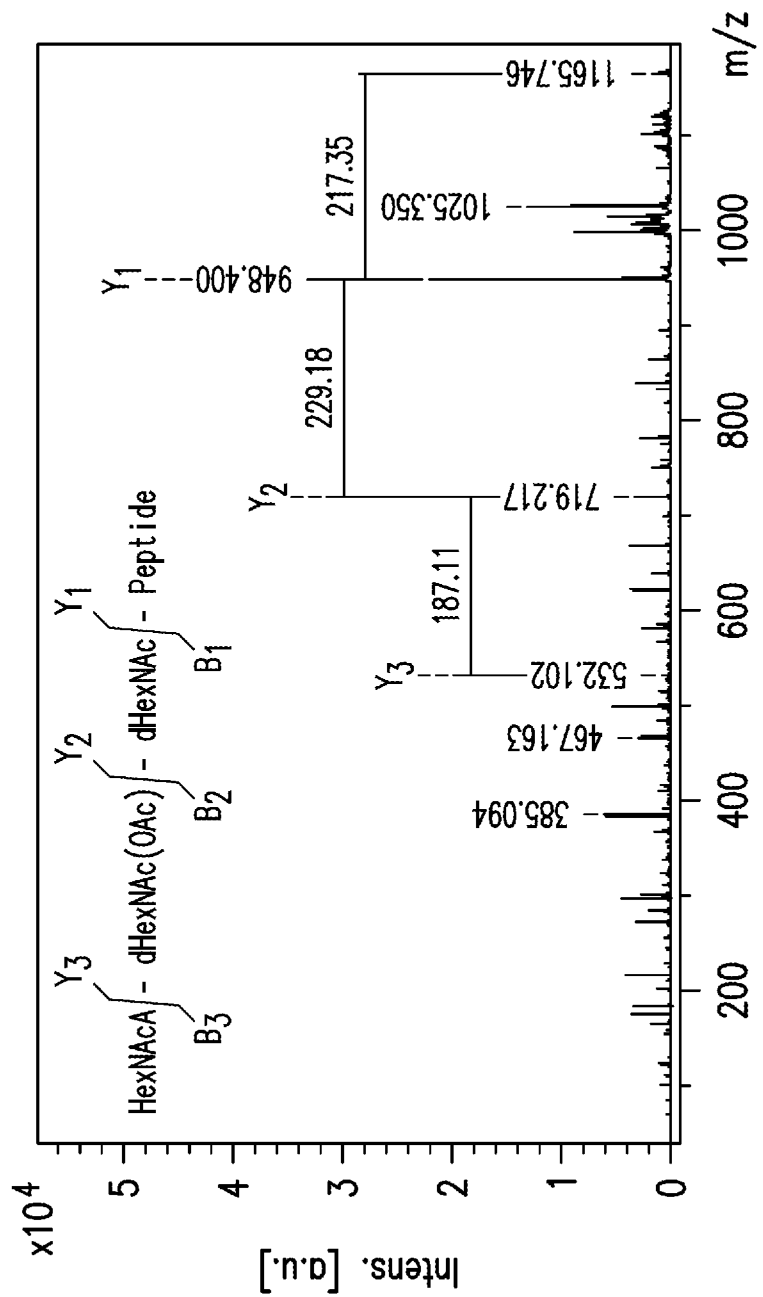
FIG. 13C depicts M/Z masses found for the glycosylation site in trypsinized peptide DQNR N-glycosidically linked to the O-acetylated RU mass (m/z=1165 ($[M+H]^+$)) according to an embodiment of the present invention. The inset illustrates the RU structure attached to the peptide.

As shown in FIG. 13A, the purified glycosylated EPA (CP5-EPA) was separated by SDS PAGE and stained by Coomassie (left lane) or transferred to nitrocellulose membranes and incubated with either anti CP5 antibodies (middle lane) or anti EPA antibodies (right lane). The purified bioconjugate was recognized by the EPA-specific antibodies (right lane), as well as the CP5-specific polyclonal antiserum (middle lane). The arrow indicates the position in the gel from where a piece was cut and used for trypsinization and analysis of glycopeptides by MALDI-MS/MS. FIG. 13B presents the MALDI-MS/MS of M/Z masses found for the glycosylation site in trypsinized peptide DNNNSTPTVISHR N-glycosidically linked to the O-acetylated RU mass (m/z=2088 ($[M+H]^+$)). MS/MS analysis of the m/z=2088 shows partial fragmentation of the sugar moiety as indicated. The inset illustrates the RU structure attached to the peptide derived from trypsinization of purified CP5-EPA from FIG. 13A. Sequential losses of ManNAcA (HexNAcA, 217 Da) and acetylated FucNAc (dHexNAc(OAc), 229 Da) support the expected glycan structure. FIG. 13C presents the MALDI-MS/MS of M/Z masses found for the glycosylation site in trypsinized peptide DQNR N-glycosidically linked to the O-acetylated RU mass (m/z=1165 ($[M+H]^+$)). MS/MS analysis of m/z=1165 shows the full Y-ion fragmentation ion series consistent with the CP5 RU structure. The inset illustrates the RU structure attached to the peptide derived from trypsinization of purified CP5-EPA from FIG. 13A. Sequential losses of ManNAcA (HexNAcA, 217 Da), acetylated FucNAc (dHexNAc (OAc), 229 Da), and FucNAc (dHexNAc, 187 Da) are shown, confirming the expected glycan structure on the peptide DQNR (m/z=532 Da ($[M+H^+]$)).

Figure 13D:
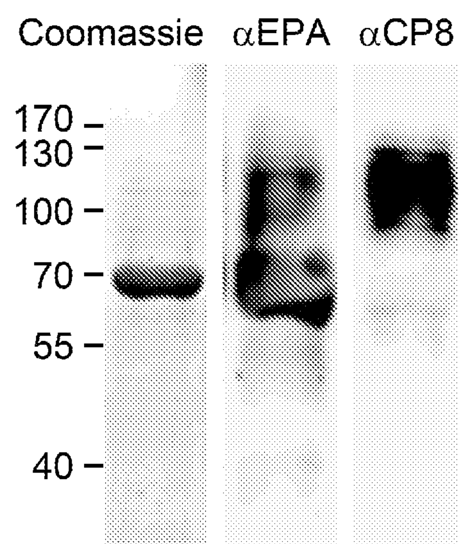
FIG. 13D depicts an analysis of $Ni^{2+}$ affinity chromatography and anionic exchange chromatography purified CP8-EPA bioconjugate according to an embodiment of the present invention.

In FIG. 13D the CP8 bioconjugate in *E. coli* was produced using the same strategy as production of the CP5 bioconjugate. CP8-EPA bioconjugate was produced in *E. coli* by co-expression of the chimeric CP8 gene cluster (SEQ ID NO: 4), PglB (within the pEXT21 plasmid (SEQ ID NO: 27)), and EPA containing two glycosylation sites (SEQ ID NO: 13). Cells were grown in a bioreactor with a starting volume of 7 L in semi-defined medium containing glycerol, peptone and yeast extract as C-sources. Cells were grown at 37° C. in batch or pulsed-batch mode to an $OD_{600\ nm}$ of 30, and expression of PglB and EPA was induced by the addition of 1 mM IPTG and 10% arabinose. After induction, cells were further cultivated in fed-batch mode for a period 15 hours under oxygen-limiting conditions. Cells were pelleted by centrifugation; the cells were washed and suspended in 0.2 vol sucrose buffer, pelleted, and lysed by osmotic shock. The spheroplasts were pelleted by centrifugation, and the periplasmic proteins were loaded on a $Ni^{2+}$ affinity chromatography. Glycosylated and unglycosylated EPA were eluted from the affinity column by 0.5 M imidazole and loaded on a SourceQ anionic exchange column. Glycosylated EPA was separated from unglycosylated EPA by applying a gradient of increasing concentration of NaCl.

As depicted in FIG. 13D, the purified protein was separated by SDS PAGE and stained by Coomassie (left lane) or transferred to nitrocellulose membranes and incubated with either anti CP8 antibodies (right lane) or anti EPA antibodies (middle lane).

Figure 13E:
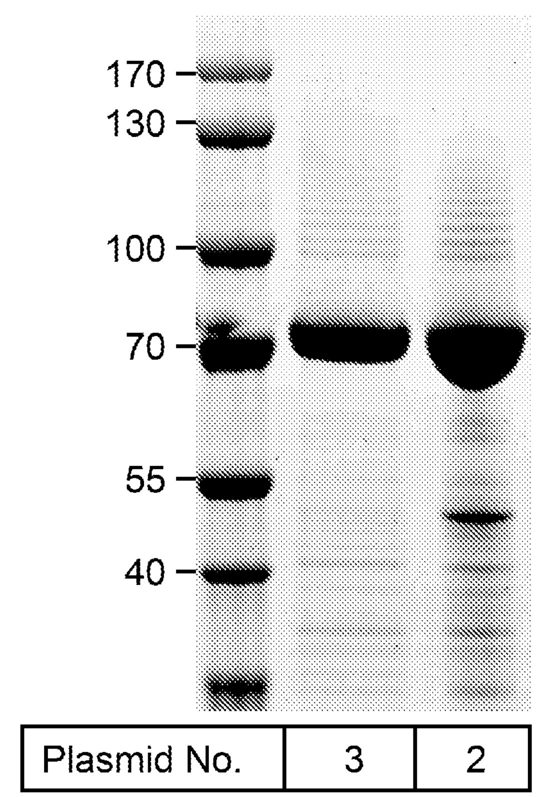
FIG. 13E depicts purified CP5-EPA bioconjugate from cells containing either 3 (left) or 2 plasmids (right lane) for glycoconjugate production according to an embodiment of the present invention.

Different strategies for further improving the glycosylation system were tested. In one strategy, to reduce the plasmid number in the production system to lower the burden of an additional antibiotic as well as maintaining an extra plasmid, the expression cassette for pglB was cloned into the plasmid containing the chimeric clusters for CP5 (SEQ ID NO: 17) and CP8 (SEQ ID NO: 18). The expression cassette is composed of the intergene region present between galF and wbqA of the *E. coli* O121 genome (for a promoter sequence), and the pglB sequence downstream of this. This expression cassette was cloned immediately downstream of the CP5 and CP8 chimeric clusters. We tested *E. coli* W3110 ΔwaaL ΔwecAwzzECA::cat containing the chimeric CP5 cluster (SEQ ID NO: 3) and pglB (SEQ ID NO: 27) on either separate plasmids or on the same plasmid (SEQ ID NO: 17). In addition, EPA (SEQ ID NO: 13) was expressed from a plasmid under the control of an arabinose inducible promoter. The cells were grown in 5 L Erlenmeyer flasks in LB medium at 37° C. An overnight culture was diluted to $OD_{600nm}$=0.05. At $OD_{600nm}$ around 0.5 PglB expression was induced by addition of 1 mM IPTG and EPA expression was induced by addition of arabinose (0.2% final concentration). The cells were grown for 4 hours, induction was repeated and cells were grown for around an additional 16 hours. The culture was pelleted by centrifugation; the cells were washed and suspended in 0.2 vol sucrose buffer, pelleted, and lysed by osmotic shock. The spheroplasts were pelleted by centrifugation, and the periplasmic proteins were loaded on a $Ni^{2+}$ affinity chromatography. EPA-CP5 was eluted by 0.5M imidazole, and eluted peaks were pooled and analyzed by SDS PAGE and by Coomassie. FIG. 13E depicts the SDS PAGE results. Cells containing either 3 (left) or 2 plasmids (right lane) for glycoconjugate production are shown. The results show that glycolipid and conjugate production for CP5-EPA was maintained.

Figure 13F:
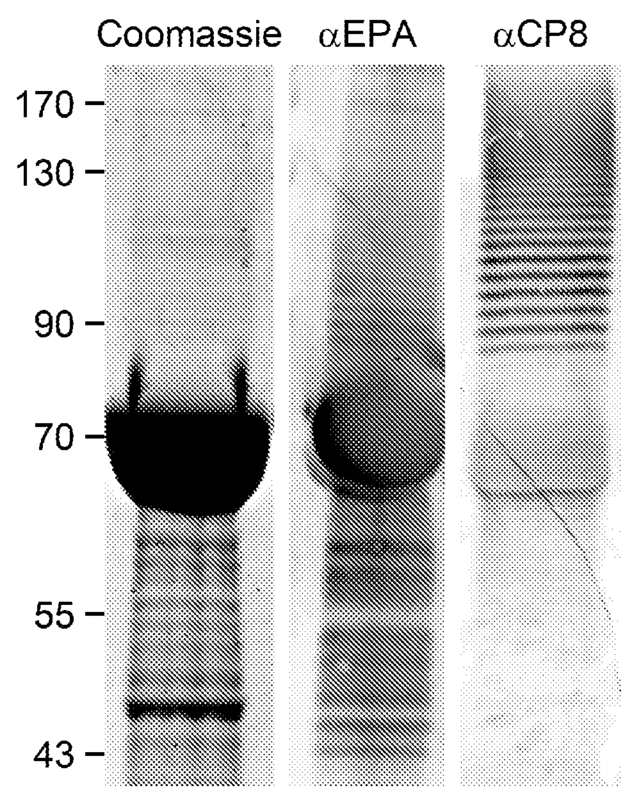
FIG. 13F depicts analysis of $Ni^{2+}$ affinity chromatography purified CP8-EPA bioconjugate according to an embodiment of the present invention.

A further optimization of the system was the integration of the wzz (polymer length regulator) protein sequence in the plasmids used for protein glycosylation. Exemplified by the system producing CP8-EPA, wzz was integrated into the plasmid borne chimeric CP8 cluster (SEQ ID NO: 19) and downstream of the epa gene within the expression plasmid for the carrier protein (SEQ ID NO: 20). CP8-EPA bioconjugate was produced in *E. coli* W3110 ΔwaaL ΔwecAwzzECA ΔrmlB-wecG::cat comprising 2 plasmids: one plasmid contained in addition to the chimeric CP8 gene cluster a copy of the wzz O7 gene and a DNA cassette for the constitutive expression of the pglB gene (SEQ ID NO: 19); the second plasmid contained first the gene for expression and secretion of the detoxified EPA protein containing two glycosylation sites, and second a wzzO7 copy under the control of the same promoter (SEQ ID NO: 20). The resulting strain, *E. coli* W3110 ΔwaaL ΔwecAwzzECA ΔrmlB-wecG::cat, containing the mentioned plasmids was grown in a bioreactor with a starting volume of 7 L in semi-defined medium containing glycerol, peptone and yeast extract as C-sources. Cells were grown in batch or pulsed-batch mode to an $OD_{600\ nm}$ of 30, and expression of PglB and EPA was induced. After induction, cells were further cultivated in fed-batch mode for a period 15 hours under oxygen-limiting conditions and collected by centrifugation. Cells were pelleted by centrifugation; the cells were washed and suspended in 0.2 vol sucrose buffer, pelleted, and lysed by osmotic shock. The spheroplasts were pelleted by centrifugation, and the periplasmic proteins were loaded on a $Ni^{2+}$ affinity chromatography. Glycosylated and unglycosylated EPA were eluted from the affinity column by 0.5 M imidazole. Formation of glycoconjugate CP8-EPA is shown in FIG. 13F by Coomassie and western blot using anti his and anti CP8 antisera. FIG. 13F shows the results of SDS PAGE separation of the purified protein and analysis by Coomassie staining (left lane) or transferred to nitrocellulose membranes and probed with either anti histag antibodies (middle lane) or anti CP8 antibodies (right lane).

Figure 14B:
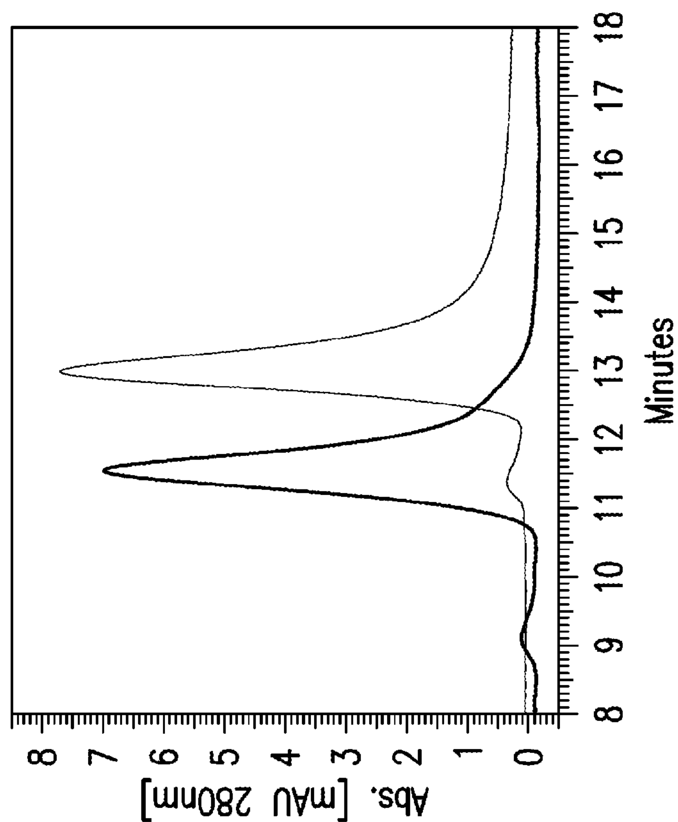
FIG. 14B shows characterization by size exclusion chromatography of CP5-EPA bioconjugate of an embodiment of the invention produced using the 3 plasmid system from FIG. 13A.
Figure 14A:
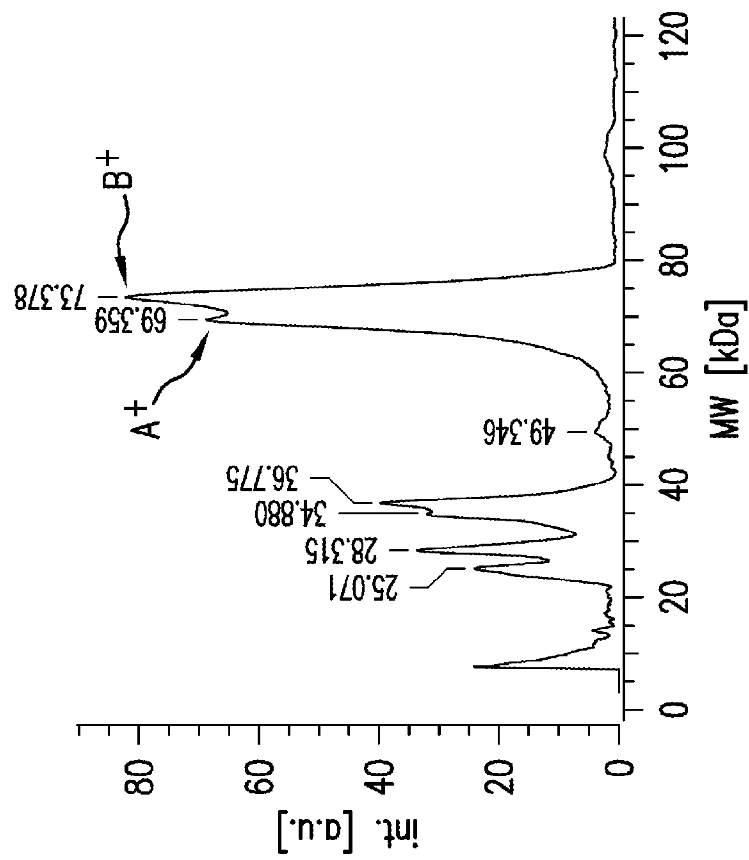
FIG. 14A presents High Mass MALDI analysis of a purified CP5-EPA bioconjugate of an embodiment of the invention produced using the 3 plasmid system from FIG. 13A.

Characterization of the CP5-EPA glycoconjugate was further refined by various analytical methods. CovalX (Schlieren, Switzerland) performed High Mass MALDI analysis of a purified CP5-EPA sample produced using the 3 plasmid system as used in the analyses depicted in FIG. 13A in W3110 ΔwaaL ΔwecAwzzECA::cat. FIG. 14A depicts the High Mass MALDI results. $A^+$ and $B^+$ point towards mass protein species ($[M+H]^+$) corresponding to unglycosylated EPA and glycosylated EPA, respectively. Oligomeric forms may be present at higher molecular weight and signals in the low MW area are contaminants or degradation products. The results presented in FIG. 14A show that the above protein preparation contained a largely monomeric protein population which is 4 kDa larger than the EPA protein alone, indicative of a medium sugar length of 5.2 repeating units. This is in agreement with the sugar length of 5-7 of the major glycoconjugate form in the preparation as analyzed by SDS-PAGE, Coomassie brilliant blue staining and counting the repeating units in the major conjugate form (see FIGS. 7, 8, and 13A).

CP5-EPA was further characterized by size exclusion chromatography (SEC-HPLC). We used the 3 plasmid system in W3110 ΔwaaL ΔwecAwzzECA::cat as used in the analyses depicted in FIG. 13A. The sample was purified by anionic exchange chromatography to remove unglycosylated EPA. Analysis was performed on a Supelco TSK G2000SWXL column. FIG. 14B shows the results of the SEC-HPLC analysis of the purified CP5-EPA sample. The UV trace measured at 280 nm is shown. The thick solid line derives from analyzing 3.25 μg purified CP5-EPA, the thin line was obtained from 5 μg purified, unglycosylated EPA. A major, homogenous peak at 11.5 minutes of elution is shown, whereas unglycosylated EPA eluted at 12.9 minutes (FIG. 14B). Calculation of the hydrodynamic radii of the two molecules resulted in a size of 42 kDa for unglycosylated EPA and 166 kDa for glycosylated EPA. This indicates that glycosylated EPA appears as an elongated, monomeric protein in solution as expected due to the linear structure of the glycan.

Our analyses therefore confirmed that the CP5-EPA bioconjugate consists of the EPA protein and the correct, O-acetylated glycan structure. Based on these results, it could also be predicted that the CP8-EPA bioconjugate consisted of the EPA protein and the correct, O-acetylated glycan structure.

Example 6

*S. aureus* Protein Glycosylation and Product Characterization

To prove the versatility of the "in vivo" glycosylation to generate glycoconjugate vaccine candidates several carrier proteins were used as substrate to be glycosylated with CP5. To further increase the immune response of the bioconjugate vaccine against *S. aureus*, the carrier protein EPA is exchanged by AcrA form *C. jejuni* and two proteins from *S. aureus*: Hla and ClfA. To be used as carrier proteins Hla and ClfA were modify by the insertion of the bacterial N-glycosylation sites. The process was performed as described in WO 2006/119987 generating four versions for Hla H35L: SEQ ID NO: 6, SEQ ID NO: 7, SEQ ID NO: 8, SEQ ID NO: 16 and three for ClfA: SEQ ID NO: 10, SEQ ID NO: 11, SEQ ID NO: 12.

Figure 14C:
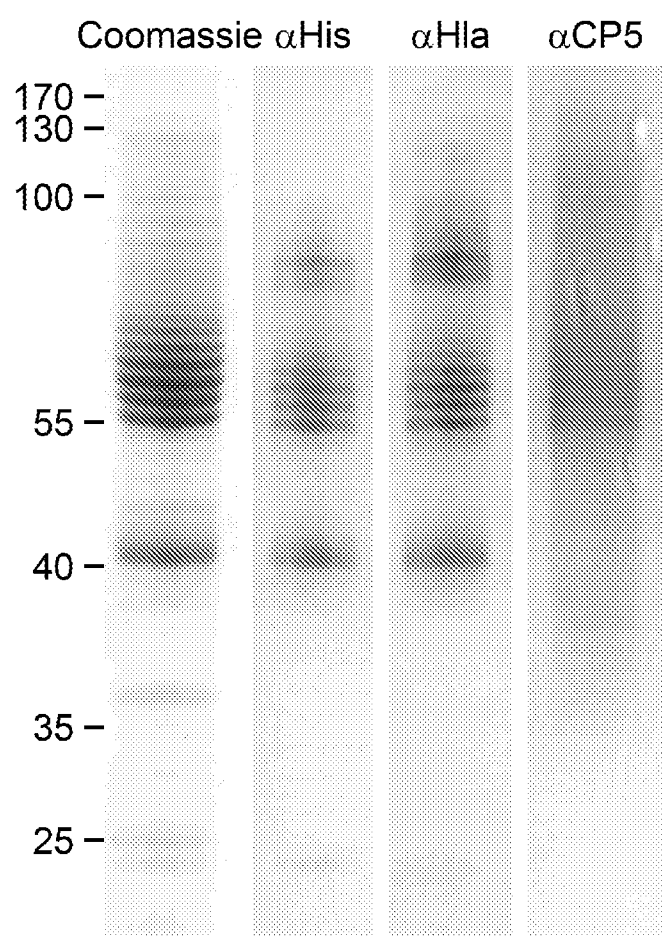
FIG. 14C shows the SDS PAGE analysis and immunodetection of purified CP5-Hla bioconjugate according to an embodiment of the present invention.

For glycosylation of Hla H35L site 130 *E. coli* cells (W3110 ΔwaaL ΔwecAwzzE ΔrmlB-wecG) comprising two expression plasmids: one for Hla H35L production (SEQ ID NO: 16), in which expression of the Hla H35L containing the N-terminal signal peptide for periplasmic secretion, one N-glycosylation site and a hexa HIS-tag for purification is under control of the ParaBAD promoter, and secondly one for expression of the CP5 chimeric cluster and pglB (SEQ ID NO.: 17) were used. This system corresponds to the beforehand optimized 2 plasmids expression system of CP5-EPA with an exchanged protein carrier expression plasmid. Cells were grown in a 12-L bioreactor in rich medium to an $OD_{600\ nm}$=30, expression of Hla was induced by the addition 0.2% arabinose. Cells were pelleted by centrifugation; the cells were washed and suspended in 0.2 vol sucrose buffer, pelleted, and lysed by osmotic shock. The spheroplasts were pelleted by centrifugation, and the periplasmic proteins in the supernatant were loaded on a $Ni^{2+}$ affinity chromatography. Glycosylated (CP5-Hla) and unglycosylated Hla were eluted from the affinity column by 0.5 M imidazole and loaded on an anionic exchange chromatography Proteins were eluted with a linear gradient from 0 to 0.7 M NaCl to separate CP5-Hla from Hla. The resulting protein was separated by SDS PAGE and stained by Coomassie, or transferred to nitrocellulose membranes and probed with either anti His, anti Hla, or anti CP5 antisera, as indicated (FIG. 14C). The results in FIG. 14C show the formation of glycoconjugate (CP5-Hla) by coomassie (left lane) and western blot using anti His (middle left lane) and anti Hla (middle right) and anti CP5 (right) antisera.

The identity of Hla H35L with an engineered glycosylation site 130 was confirmed by in-gel trypsinization and MALDI-MS/MS.

Figure 14D:
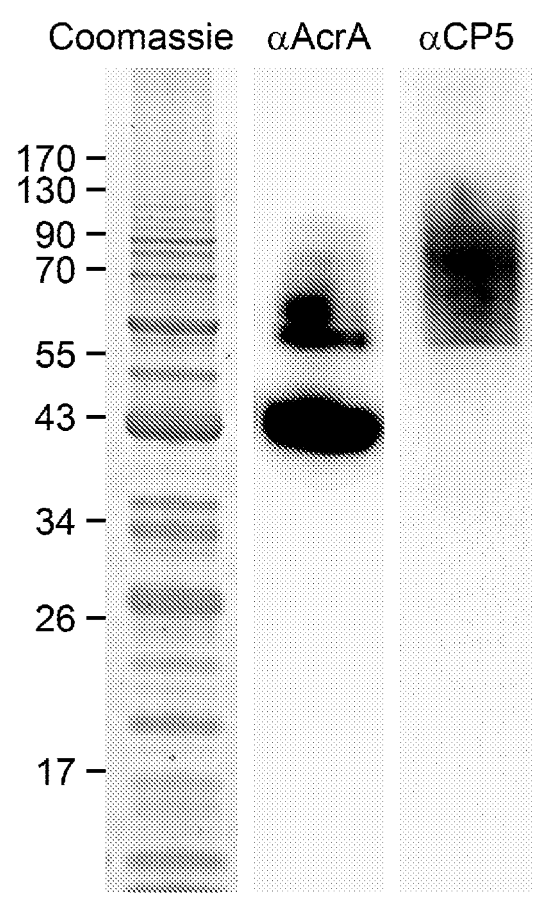
FIG. 14D presents the results of purified CP5-AcrA bioconjugate according to an embodiment of the present invention.

To further show that the carrier protein is exchangeable for glycosylation by CP5 and CP8, *C. jejuni* AcrA protein was used as a glycosylation acceptor (see FIG. 14D). Using the 3 plasmid system (SEQ ID NO: 3, SEQ ID NO: 15, and SEQ ID NO: 27), the production strain for this conjugate was W3110 ΔwaaL habouring the CP5 chimeric cluster (SEQ ID NO: 3), the PglB protein induced by IPTG (SEQ ID NO: 27) and the AcrA (SEQ ID NO: 15) under arabinose induction on separate plasmids. Cells were grown in a bioreactor with a starting volume of 7 L in semi-defined medium containing glycerol, peptone and yeast extract as C-sources. Cells were grown in batch or pulsed-batch mode to an $OD_{600\ nm}$ of 30, and expression of PglB and AcrA was induced by the addition of 1 mM IPTG and 10% arabinose. After induction, cells were further cultivated in fed-batch mode for a period 15 hours under oxygen-limiting conditions and collected by centrifugation. Cells were pelleted by centrifugation; the cells were washed and suspended in 0.2 vol sucrose buffer, pelleted, and lysed by osmotic shock. The spheroplasts were pelleted by centrifugation, and the periplasmic proteins were loaded on a $Ni^{2+}$ affinity chromatography. CP5-AcrA glycoproteins were eluted from the affinity column by 0.5 M imidazole. The purified protein was separated by SDS PAGE and stained by Coomassie, or transferred to nitrocellulose membranes and probed with either anti AcrA, or anti CP5 antisera, as indicated in FIG. 14D.

The insertion of the bacterial N-glycosylation sites in ClfA was performed as described in WO 2006/119987, generating SEQ ID NO: 10; SEQ ID NO: 11; SEQ ID NO: 12. The carrier proteins were expressed in *E. coli* cells from arabinose inducible promoters. The genes were designed to produce a N-terminal signal peptide for periplasmic secretion, several N-glycosylation sites and a hexa HIS-tag for purification. Purification was started from periplasmic extracts of *E. coli* cells.

Figure 14E:
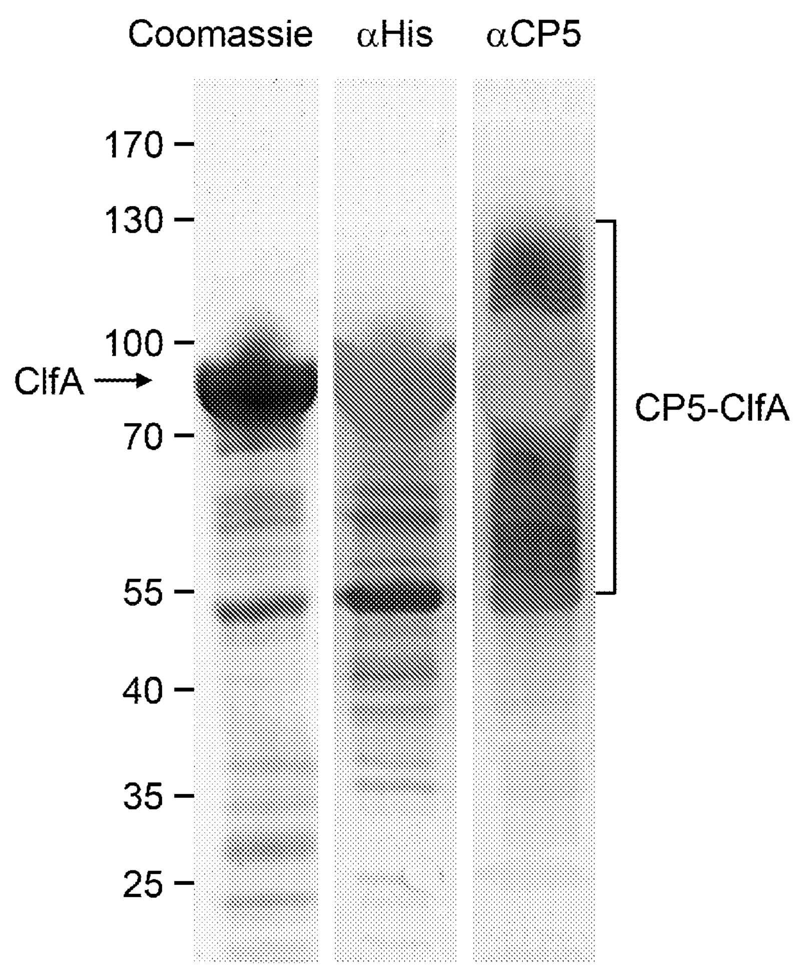
FIG. 14E presents the results of purified CP5-ClfA bioconjugate according to an embodiment of the present invention.

For glycosylation of ClfA 327 the beforehand optimized expression systems of CP5-EPA was employed. Using the 2 plasmid system (SEQ ID NO: 17 and SEQ ID NO: 11), *E. coli* cells (W3110 ΔwecAwzzE ΔrmlB-wecG ΔwaaL) comprising the CP5 chimeric cluster and pglB (constitutive expression cassette) as well as the expression plasmid for ClfA 327 (under control of the ParaBAD promoter) were grown in 1 L Erlenmeyer flasks in LB medium. An overnight culture was diluted to $OD_{600\ nm}$=0.05. At $OD_{600nm}$ around 0.5, ClfA expression was induced by addition of arabinose (0.2% final concentration). The cells were grown for 20 hours. Cells were pelleted by centrifugation; the cells were washed and suspended in 0.2 vol sucrose buffer, pelleted, and lysed by osmotic shock. The spheroplasts were pelleted by centrifugation, and the periplasmic proteins were loaded on a $Ni^{2+}$ affinity chromatography. ClfA-CP5 was eluted by 0.5M imidazole, was separated by SDS PAGE and stained by Coomassie, or transferred to nitrocellulose membranes and probed with either anti His, or anti CP5 antisera. FIG. 14E shows the results obtained using the ClfA variant with the glycosylation site inserted around amino acid position 327 of the protein (SEQ ID NO: 11). They show the formation of ClfA by Coomassie staining and anti His western blot, and glycoconjugate (CP5-ClfA) by western blot using anti CP5 antisera.

Example 7

Activity of CP5-EPA as Glycoconjugate Vaccine

W3110 ΔwaaL ΔwecAwzzECA::cat cells comprising CP5 chimeric cluster (SEQ ID NO: 3) with cap5K inside, the PglB protein (SEQ ID NO: 27) and EPA with signal 2 glycosylation sites on pEC415 (SEQ ID NO: 13) were grown in 1 L Erlenmeyer flasks in LB medium. An overnight culture was diluted to $OD_{600nm}$=0.05. At $OD_{600nm}$ around 0.5, EPA and PglB expression was induced by addition of arabinose (0.2% final concentration) and 1 mM IPTG, respectively. The cells were grown for 20 hours. Cells were pelleted by centrifugation; the cells were washed and suspended in 0.2 vol sucrose buffer, pelleted, and lysed by osmotic shock. The spheroplasts were pelleted by centrifugation, and the periplasmic proteins were loaded on a $Ni^{2+}$ affinity chromatography. Glycosylated and unglycosylated EPA were eluted from the affinity column by 0.5 M imidazole and loaded on a SourceQ anionic exchange column. Glycosylated EPA was separated from unglycosylated EPA by applying a gradient of increasing concentration of NaCl. Eluted protein amounts were determined by the BCA assay and based on the size of the bands obtained on SDS PAGE stained by Coomasie the theoretical mass of the sugar was calculated. Together with the protein determination, the amount of polysaccharide antigen was estimated in the preparation. This estimated quantification was confirmed by high mass maldi MS method (see FIG. 14A).

Figure 15A:
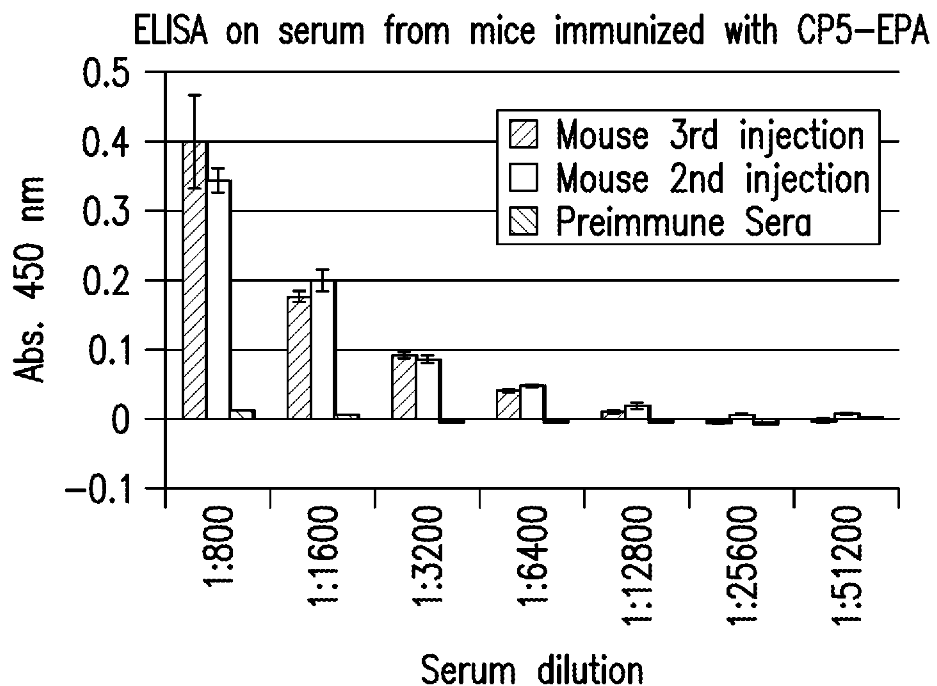
FIG. 15A depicts the specific anti CP5 antibodies raised in mice by CP5-EPA bioconjugate according to an embodiment of the present invention.

To measure the immunogenicity of CP5-EPA in living animals, 1 μg of the purified glycoconjugate was injected into mice by the IP (intra peritoneal) route in the presence of Aluminium hydroxide as adjuvant on days 1 (first injection), 21 (second injection), and 56 (third injection). After 35 and 61 days, which were two weeks after the second and third injections, respectively, the IgG response was measured by ELISA using a poly-L-lysine modified CP5 for coating (Gray, B. M. 1979. ELISA methodology for polysaccharide antigens: protein coupling of polysaccharides for adsorption to plastic tubes. J. Immunol. 28:187-192). Blood from mice immunized with CP5-bioconjugate was analyzed for specific IgG antibodies against CP5 capsular polysaccharide. FIG. 15A presents the IgG titers raised by CP5-EPA in mice. ELISA plates were coated with poly-L-lysine modified CP5, IgG response in mice immunized twice (second bar (empty) at each dilution) or three times (first bar (forward diagonals) at each dilution) with CP5-EPA was measured in triplicates. The signals obtained with the preimmune sera as control are indicated by the third bar (backward diagonals) at each dilution. The mice IgG response was measured with alkaline phosphatase-conjugated protein G. As shown in FIG. 15A, the CP5-EPA bioconjugate elicited a serum antibody titer of $6.4\times10^3$. The results presented in FIG. 15A show that CP5-EPA raises CP5 specific antibodies in mice. This experiment shows that the bioconjugate produced in *E. coli* is immunogenic in mice.

Figure 15B:
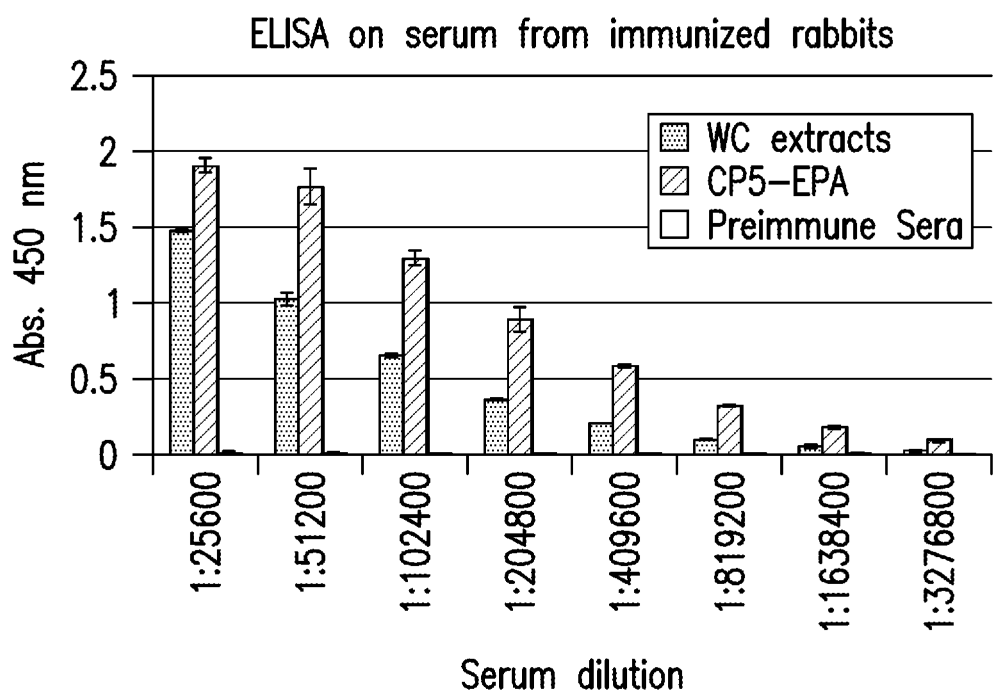
FIG. 15B depicts the specific anti CP5 antibodies raised in rabbit by CP5-EPA bioconjugate according to an embodiment of the present invention.

A similar experiment was performed in rabbits as the host organism. CP5-EPA (15 μg CP5) was injected into rabbits intra-dermal in the presence of Freund's complete adjuvant on day 1 and subcutaneously in the presence of Freund's incomplete adjuvant on days 20, and 40. After 61 days, the IgG response was measured by ELISA using a poly-L-lysine modified CP5 for coating (Gray, B. M. 1979. ELISA methodology for polysaccharide antigens: protein coupling of polysaccharides for adsorption to plastic tubes. J. Immunol. 28:187-192). FIG. 15B presents IgG titers raised by CP5-EPA in rabbits. The results presented in FIG. 15B show that CP5-EPA raises CP5 specific antibodies in rabbits. Immune response to CP5-EPA bioconjugate is the second bar (forward diagonals) at each dilution. Control sera include CP5-specific absorbed sera raised to killed *S. aureus* (WC extracts, first bar (dots) at each dilution) and preimmune serum (third bar (empty) at each dilution). Serum from rabbits immunized with various antigens was analyzed for specific antibodies to purified CP5. Plates were coated with poly-L-lysine modified CP5. The signals obtained with the preimmune sera as control are indicated by the third bar (backward diagonals) at each dilution. The rabbit IgG response was measured with alkaline phosphatase-conjugated protein G in triplicates. The CP5-EPA bioconjugate elicited a titer of $1\times10^6$, which was 4 times higher than the titer of control sera (prepared by immunization with whole killed *S. aureus* and then absorbed with Wood 46 and a trypsinized isogenic acapsular mutant, so that the antiserum was rendered CP5-specific). This experiment shows that the bioconjugate was able to elicit a high-titered CP5-specific IgG response.

Example 8

Functional Activities of CP5 Antibodies

In Vitro Activity

The rabbit polyclonal antiserum raised as described in Example 7 was purified by Protein A affinity column to enrich for IgG specific antibodies. IgG from rabbits immunized with *S. aureus* bioconjugate CP5-EPA was tested for functional activity in a classic in vitro opsonophagocytic killing assay (Thakker, M., J.-S. Park, V. Carey, and J. C. Lee. 1998. *Staphylococcus aureus* serotype 5 capsular polysaccharide is antiphagocytic and enhances bacterial virulence in a murine bacteremia model. Infect Immun 66:5183-5189). *S. aureus* was cultivated for 24 h on Columbia agar+2% NaCl. The bacteria were suspended in minimal essential medium+1% BSA (MEM-BSA). PMNs (polymorphonuclear neutrophils) were isolated from fresh human blood, washed, counted, and suspended in MEM-BSA. The purified IgG preparations from rabbits immunized with either *S. aureus* CP5-EPA or as control purified IgG preparations from rabbits immunized with *Shigella* O1-EPA that has been purified as described in WO 2009/104074 were added to the assay in serial 10-fold dilutions prepared in MEM-BSA. Guinea pig serum (Pel-Freez) was used as a C' source. Each assay (0.5 ml total volume) contained ~$5\times10^6$ PMNs, $1\times10^6$ CFU *S. aureus,* 0.5% to 1% guinea pig serum, and varying concentrations of IgG, ranging from 140 μg/ml to 1 μg/ml. Control samples contained 1) *S. aureus* incubated with C' and PMNs, but no antibody; 2) *S. aureus* incubated with IgG and C', but no PMNs; and 3) *S. aureus* alone. The samples were rotated end-over-end (12 rpm) for 2 h at 37° C. Sample dilutions were vortexed in sterile water, and bacterial killing was estimated by plating the diluted samples in duplicate on TSA. The percent killing was defined as the reduction in CFU/ml after 2 h compared with that at time zero.

Figure 16A:
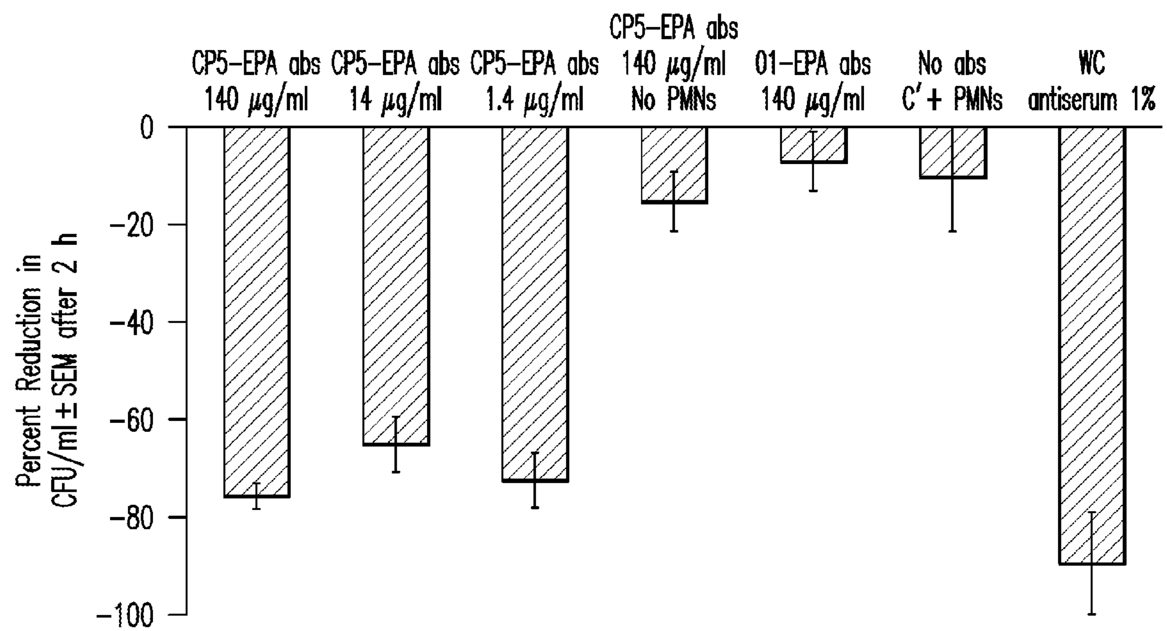
FIG. 16A illustrates in vitro opsonophagocytic activity (on *S. aureus* Reynolds) of CP5 specific antibodies raised by immunization of rabbits with CP5-EPA according to an embodiment of the present invention.

In the first set of experiments, the opsonophagocytic killing of the methicillin-sensitive *S. aureus* (MSSA) strain Reynolds, the prototype CP5 isolate, was tested, and the results are shown in FIG. 16A. Opsonic activity of antibodies to CP5-EPA raised in rabbit was tested against the *S. aureus* serotype 5 strain Reynolds. CP5-EPA antibodies were opsonic down to a concentration of 1.4 μg/ml, whereas O1-EPA antibodies showed little opsonic activity at 140 μg/ml. A positive control serum raised against *S. aureus* whole cell extracts (obtained from J. C. Lee at the Department of Medicine, Brigham and Women's Hospital, Harvard Medical School, Boston, Mass., USA) showed similar activity as the anti CP5-EPA serum (WC antiserum 1%).

As shown in FIG. 16A, between 65-75% of *S. aureus* Reynolds was killed by PMNs when incubated with antibodies to CP5-EPA and 1% guinea pig serum with complement activity. The antiserum was used at a final 1% in the assay, and 89% of the *S. aureus* inoculum was killed under these conditions. Little killing was observed when *S. aureus* was opsonized by C' alone (1% guinea pig serum) or antibodies and C' with no PMNs. The data shown are the means of 2 to 5 experiments. All samples graphed included guinea pig serum C', and no killing was observed in the absence of C'. Neither antibodies alone nor complement alone were opsonic, and this feature is characteristic of encapsulated bacterial pathogens. In contrast, antibodies elicited by the control vaccine (Shigella O1 antigen coupled to EPA) did not show opsonic activity, even in the presence of C'. As a positive control in this assay, we also tested CP5-specific rabbit antiserum (obtained from J. C. Lee at the Department of Medicine, Brigham and Women's Hospital, Harvard Medical School, Boston, Mass., USA). These data show that antibodies raised to the CP5-EPA bioconjugate showed opsonic activity against encapsulated *S. aureus* that is comparable to CP5 antibodies with documented opsonic activity (Thakker, M., J.-S. Park, V. Carey, and J. C. Lee. 1998. *Staphylococcus aureus* serotype 5 capsular polysaccharide is antiphagocytic and enhances bacterial virulence in a murine bacteremia model. Infect Immun 66:5183-5189).

Figure 16B:
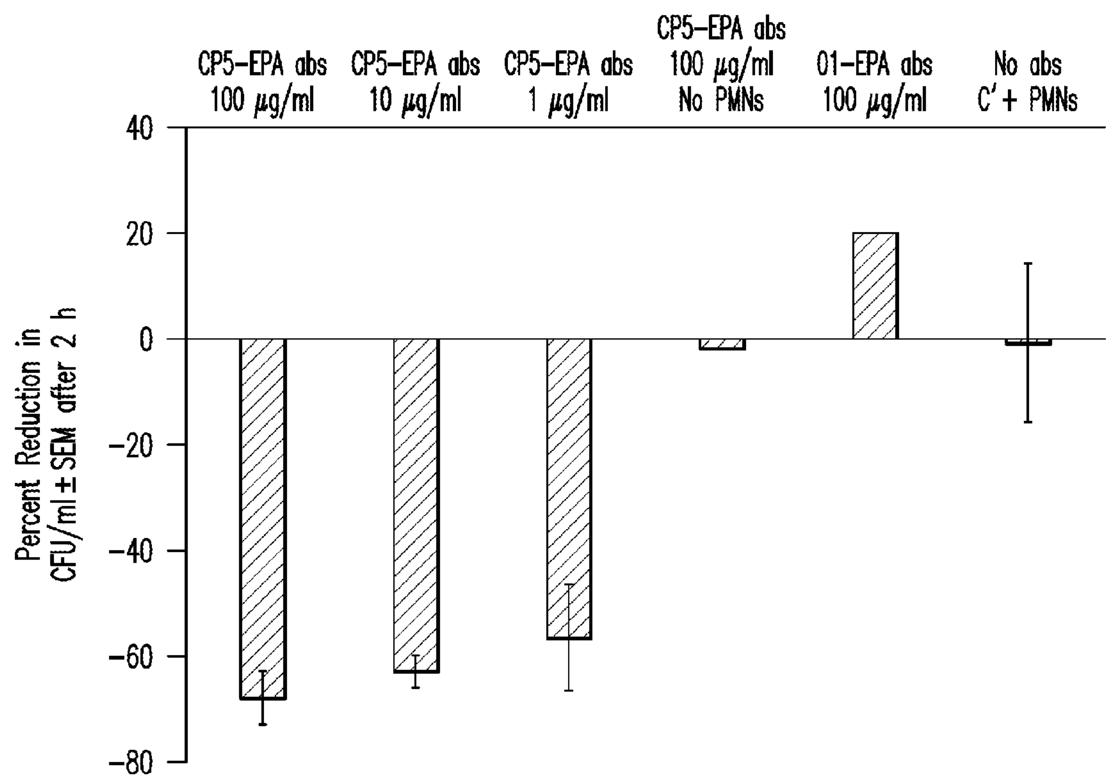
FIG. 16B illustrates in vitro opsonophagocytosis activity (on *S. aureus* USA 100) of CP5 specific antibodies raised by immunization of rabbits with CP5-EPA according to an embodiment of the present invention.

The opsonic activity of antibodies to CP5-EPA tested against the MRSA strain USA100 of CP5-EPA. FIG. 16B presents the results of the opsonic activity of IgG and C' tested against *S. aureus* strain USA100, a CP5+ isolate, and is called NRS382. The data shown are the means of 2 to 5 experiments. All samples graphed included guinea pig serum C', and no killing was observed in the absence of C'. As shown in FIG. 16B, ~60% of the USA100 inoculum was killed by PMNs incubated with 0.5% guinea pig complement and concentrations of CP5-EPA IgG ranging from 100 to 1 μg/ml. Minimal killing was observed in the absence of PMNs or when IgG was omitted from the assay. No killing was achieved when IgG raised to the O1-EPA conjugate vaccine was added to PMNs+C' (the bacteria multiplied in this sample). Little killing was observed when *S. aureus* was opsonized by C' alone or antibodies and C' with no PMNs. Thus, CP5-EPA antibodies were opsonic at concentrations ranging from 100 to 1 μg/ml, whereas O1-EPA antibodies showed little opsonic activity at 100 μg/ml. This experiment shows that CP5-EPA antibodies display opsonic activity against both MSSA and MRSA strains.

In Vivo Activity

To determine whether the opsonic activity of IgG raised to the bioconjugate CP5-EPA vaccine would predict protection in a mouse model of staphylococcal infection, passive immunization experiments were performed. In the initial studies, Swiss-Webster male mice (~6 wks of age) were injected IV (tail vein) with 1.4 to 2 mg IgG from rabbits immunized with CP5-EPA or *Shigella* O1-EPA. After 24 h, the mice were challenged by the intra-peritoneal (IP) route with ~$3.6\times10^7$ CFU *S. aureus* Reynolds. Bacteremia levels were measured 2 h after challenge to assess antibody-mediated clearance of the bacteremia. The lower limit of detection by culture was 5 CFU/ml blood. FIG. 17A show the resulting bacteremia levels. Each dot represents a quantitative blood culture performed by tail vein puncture on an individual mouse 2 h after bacterial inoculation. Horizontal lines represent median CFU/ml values. Empty circles are blood samples from mice that obtained anti CP5-EPA antibodies, black filled circles are samples from animals that got a control antibody preparation which was raised against EPA conjugated to a different glycan (*S. dysenteriae* O1). The results of FIG. 17A show that mice given CP5 antibodies showed a significant (P=0.0006 by Mann-Whitney analysis) reduction in bacteremia levels compared to mice given the O1-specific antibodies. In fact, the reduction in CFU/ml blood was 98% in mice passively immunized with the CP5-EPA vs. mice given O1-EPA IgG.

In subsequent passive immunization experiments, mice were challenged IP with a lower inoculum (~$5.5\times10^6$ CFU/mouse) of *S. aureus* Reynolds. Passive immunization with CP5-EPA antibodies was tested in mice challenged IP with 5–$6\times10^6$ CFU *S. aureus* Reynolds. Mice were injected intravenously (IV) with 2 mg CP5-EPA IgG or O1-EPA IgG 24 h before bacterial challenge. FIG. 17B shows the resulting bacteremia levels. Each dot represents a quantitative blood culture performed by tail vein puncture on an individual mouse 2 h after bacterial inoculation. Horizontal lines represent median CFU/ml values. Empty circles are blood samples from mice that obtained anti CP5-EPA antibodies, black filled circles are samples are from animal that got a control antibody preparation which was raised against EPA conjugated to a different glycan (*S. dysenteriae* O1). As shown in FIG. 17B, mice given 2 mg CP5-EPA IgG had significantly (P<0.0001 by Mann-Whitney analysis) lower bacteremia levels than animals given 2 mg of O1-EPA IgG. In fact, 6 of 7 mice passively immunized with CP5-EPA antibodies had sterile blood cultures (lower limit of detection 6 to 30 CFU/ml blood, depending on the blood volume collected and plated from each mouse). The reduction in bacteremia levels attributable to CP5 antibodies was 98%, compared to control mice given O1-EPA IgG.

To determine whether protection against bacteremia could be conferred by a lower level of IgG, a subsequent experiment was performed wherein mice were passively immunized by the IV route with 300 μg CP5-EPA or O1-EPA IgG. After 24 h, the mice were inoculated IP with $6\times10^6$ CFU *S. aureus* Reynolds. The lower limit of detection by culture was 13-67 CFU/ml blood. FIG. 17B shows the resulting bacteremia levels. Each dot represents a quantitative blood culture performed by tail vein puncture on an individual mouse 2 h after bacterial inoculation. Horizontal lines represent median CFU/ml values. Empty circles are blood samples from mice that obtained anti CP5-EPA antibodies, black filled circles are samples are from animal that got a control antibody preparation which was raised against EPA conjugated to a different glycan (*S. dysenteriae* O1). As in FIG. 17B, the results of FIG. 17C show CP5 antibody-mediated protection against bacteremia was achieved with this lower antibody dose. A 98% reduction in bacteremia levels was achieved by antibodies elicited by the CP5 bioconjugate vaccine, and 8 of 9 mice had sterile blood cultures compared to 0 of 8 mice given *Shigella* O1-EPA antibodies.

Example 9

Active Immunization in Mice

To show that vaccination of mice with the bioconjugate CP5-EPA mediates protection against bacterial challenge as in passive immunization assay, active immunization studies were performed.

CP5-EPA bioconjugate was produced in *E. coli* W3110 ΔwaaL ΔwecAwzzE::cat by co-expression of the chimeric CP5 gene cluster (SEQ ID NO: 3), PglB (SEQ ID NO: 27) from plasmid pEXT21 and EPA (containing two glycosylation sites, SEQ ID NO: 13) from separate plasmids. Cells were grown in a bioreactor with a starting volume of 7 L in semi-defined medium containing glycerol, peptone and yeast extract as C-sources. Cells were grown in batch or pulsed-batch mode to an $OD_{600\ nm}$ of 30, and expression of PglB and EPA was induced by the addition of 1 mM IPTG and 10% arabinose. After induction, cells were further cultivated in fed-batch mode for a period 15 hours under oxygen-limiting conditions and collected by centrifugation. The cells were washed and resuspended in 25% sucrose buffer at an $OD_{600\ nm}$=200, pelleted, and lysed by osmotic shock. The spheroplasts were pelleted by centrifugation, and the periplasmic proteins were loaded on a $Ni^{2+}$ affinity chromatography. Glycosylated and unglycosylated EPA were eluted from the affinity column by 0.5 M imidazole and loaded on a SourceQ anionic exchange column. Glycosylated EPA was separated from unglycosylated EPA by applying a gradient of increasing concentration of NaCl.

Figure 18:
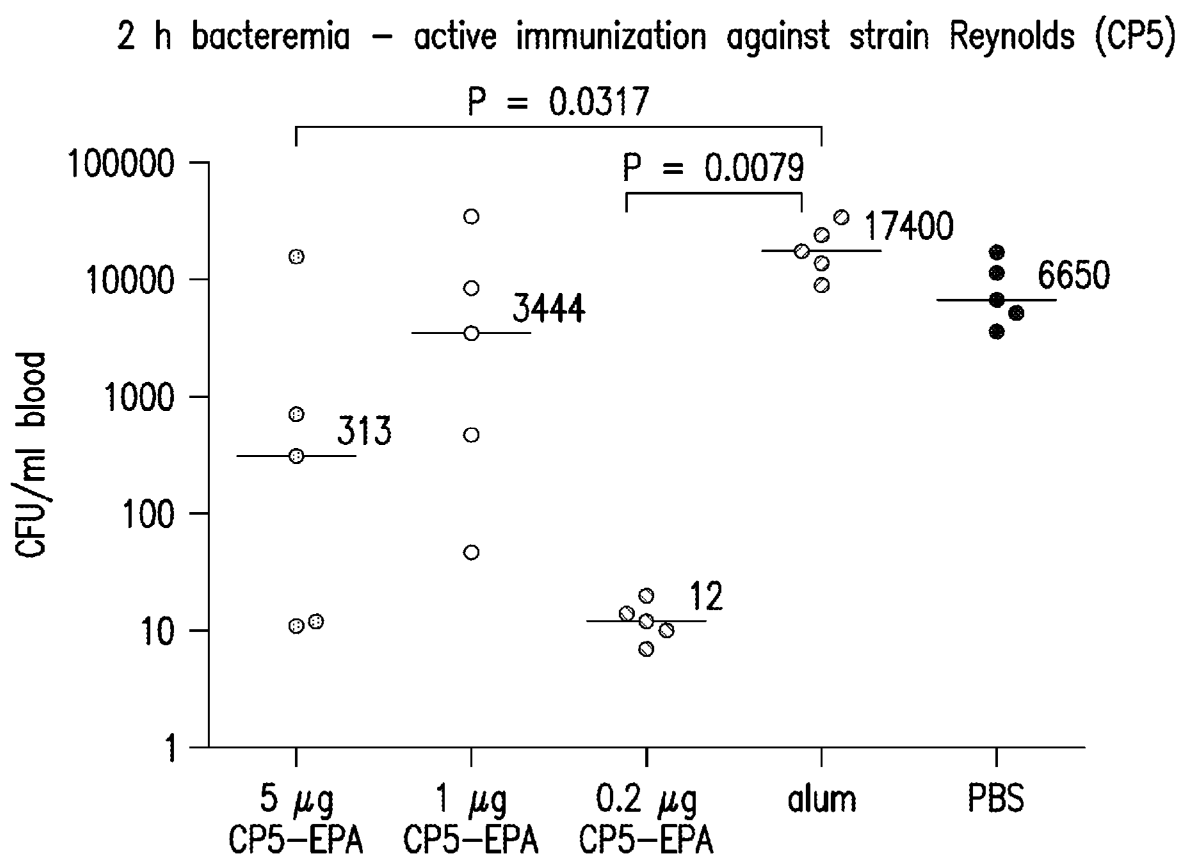
FIG. 18 depicts the results of an active immunization assay using different doses of CP5-EPA as vaccine according to an embodiment of the present invention and the mouse bacteremia model for challenge.

CP5-EPA is intended to be used as a conjugate vaccine to protect against CP5 *S. aureus* strains. To test whether such active immunization is functional, we immunized different groups of female Swiss Webster mice with three different doses of CP5-EPA and analyzed the immunization using a bacteremia model. Three doses were subcutaneously injected at days 0, 14 and 28. Mice were intra-peritoneally challenged at day 42 with *S. aureus* strain JL278, as shown in FIG. 18. Five groups of mice were immunized with three different doses of CP5-EPA as indicated below the x-axis (dotted circles; empty circles; and backward diagonals in circles). Two control groups received either adjuvants (forward diagonals in circles) or PBS (black filled circles) alone. Each dot represents a blood sample from a single mouse. The lowest dose of vaccine (0.2 μg) induced protection in all mice from the group. Two hours after challenge blood samples were analyzed for cfu formation and anti CP5 antibodies by ELISA using a poly-L-lysine modified CP5 for coating (Gray et al. (1979)). In all groups immunized with CP5-EPA, a mean reduction of cfu in blood was observed. However, only in the group which received the lowest dose of vaccine, there was a general protection from bacteremia in all five mice. Analysis of blood for anti CP5 antibodies resulted in a positive correlation of protection and mean ELISA titers in the different mouse groups. The results presented in FIG. 18 indicate that the antibodies induced the protection from bacteremia in immunized mice.

These studies indicate that the CP5-EPA bioconjugate vaccine induced antibodies that opsonized *S. aureus* for phagocytic killing by human PMNs and protected mice against bacteremia in positive and active immunization studies. These data provide strong evidence that the presented bioconjugate will protect against disease provoked by multiple *S. aureus* strains.

While this invention has been particularly shown and described with references to embodiments thereof, it will be understood by those skilled in the art that various changes in form and detail may be made therein without departing from the scope of the invention encompassed by the claims.

What is claimed is:

1. A Gram-negative host prokaryotic organism comprising:

(i) a nucleotide sequence encoding at least one glycosyltransferase from a Gram-positive bacterium, wherein said Gram-positive bacterium is a Staphylococcus aureus strain that expresses serotype 8 capsular polysaccharide;

(ii) a nucleotide sequence encoding at least one glycosyltransferase from a Gram-negative bacterium;

(iii) a nucleotide sequence encoding a carrier protein, wherein said carrier protein is genetically detoxified *Pseudomonas aeruginosa* Exotoxin, *Staphylococcus aureus* (*S. aureus*) alpha hemolysin, or *S. aureus* clumping factor A; and wherein said carrier protein comprises the amino acid sequence D/E-X-N-Z-S/T, wherein X and Z may be any natural amino acid except proline; and (iv) a nucleotide sequence encoding an oligosaccharyl transferase.

2. The host prokaryotic organism of claim 1, wherein said at least one glycosyltransferase from a Gram-negative bacterium is a *P. aeruginosa* glycosyltransferase.

3. The host prokaryotic organism of claim 1, wherein said carrier protein is genetically detoxified *P. aeruginosa* Exotoxin.

4. The host prokaryotic organism of claim 1, wherein said carrier protein is *S. aureus* alpha hemolysin.

5. The host prokaryotic organism of claim 1, wherein said carrier protein is *S. aureus* clumping factor A.

6. The host prokaryotic organism of claim 1, wherein said host organism is *E. coli*.

7. The host prokaryotic organism of claim 3, wherein said host organism is *E. coli*.

8. The host prokaryotic organism of claim 4, wherein said host organism is *E. coli*.

9. The host prokaryotic organism of claim 5, wherein said host organism is *E. coli*.

10. The host prokaryotic organism of claim 1, wherein said oligosaccharyl transferase is from *Campylobacter jejuni*.

11. The host prokaryotic organism of claim 6, wherein said oligosaccharyl transferase is from *Campylobacter jejuni*.

12. The host prokaryotic organism of claim 7, wherein said oligosaccharyl transferase is from *Campylobacter jejuni*.

13. The host prokaryotic organism of claim 8, wherein said oligosaccharyl transferase is from *Campylobacter jejuni*.

14. The host prokaryotic organism of claim 9, wherein said oligosaccharyl transferase is from *Campylobacter jejuni*.

15. A composition comprising the host prokaryotic organism of claim 1.

16. A composition comprising the host prokaryotic organism of claim 2.

17. A composition comprising the host prokaryotic organism of claim 12.

18. A composition comprising the host prokaryotic organism of claim 13.

19. A composition comprising the host prokaryotic organism of claim 14.

20. A method of producing a bioconjugate comprising a *S. aureus* Serotype 8 strain capsular polysaccharide linked to genetically detoxified *P. aeruginosa* Exotoxin, comprising producing in the host prokaryotic organism of claim 3 modified capsular polysaccharides on undecaprenol and linking said modified capsular polysaccharides to genetically detoxified *P. aeruginosa* Exotoxin.

21. A method of producing a bioconjugate comprising a *S. aureus* Serotype 8 strain capsular polysaccharide linked to *S. aureus* alpha hemolysin, comprising producing in the host prokaryotic organism of claim 4 modified capsular polysaccharides on undecaprenol and linking said modified capsular polysaccharides to *S. aureus* alpha hemolysin.

22. A method of producing a bioconjugate comprising a *S. aureus* Serotype 8 strain capsular polysaccharide linked to *S. aureus* clumping factor A, comprising producing in the host prokaryotic organism of claim 5 modified capsular polysaccharides on undecaprenol and linking said modified capsular polysaccharides to *P. aeruginosa* Exotoxin.

23. A *S. aureus* bioconjugate comprising, a genetically detoxified *P. aeruginosa* Exotoxin comprising an inserted consensus sequence D/E-X-N-Z-S/T, wherein X and Z may be any natural amino acid except proline; a *S. aureus* serotype 8 strain modified capsular polysaccharide linked to said consensus sequence; and optionally, a pharmaceutically acceptable carrier or adjuvant.

24. A *S. aureus* bioconjugate comprising, a *S. aureus* alpha hemolysin further comprising an inserted consensus sequence D/E-X-N-Z-S/T, wherein X and Z may be any natural amino acid except proline; a *S. aureus* serotype 8 strain modified capsular polysaccharide linked to said consensus sequence; and optionally, a pharmaceutically acceptable carrier or adjuvant.

25. A *S. aureus* bioconjugate comprising, a *S. aureus* clumping factor A comprising an inserted consensus sequence D/E-X-N-Z-S/T, wherein X and Z may be any natural amino acid except proline; a *S. aureus* serotype 8 strain modified capsular polysaccharide linked to said consensus sequence; and optionally, a pharmaceutically acceptable carrier or adjuvant.

* * * * *